(12) United States Patent
Chen et al.

(10) Patent No.: US 10,227,347 B2
(45) Date of Patent: Mar. 12, 2019

(54) PURINYL-N-HYDROXYL PYRIMIDINE FORMAMIDE DERIVATIVE, PREPARATION METHODS AND USES THEREOF

(71) Applicant: Guizhou Bailing Group Pharmaceutical CO., LTD., Anshun, Guizhou (CN)

(72) Inventors: Lijuan Chen, Sichuan (CN); Yuquan Wei, Sichuan (CN)

(73) Assignee: GUIZHOU BAILING GROUP PHARMACEUTICAL CO., LTD., Anshun, Guizhou (CN)

( * ) Notice: Subject to any disclaimer, the term of this patent is extended or adjusted under 35 U.S.C. 154(b) by 0 days.

(21) Appl. No.: 15/568,506

(22) PCT Filed: Apr. 12, 2016

(86) PCT No.: PCT/CN2016/079022
§ 371 (c)(1),
(2) Date: Oct. 23, 2017

(87) PCT Pub. No.: WO2016/169417
PCT Pub. Date: Oct. 27, 2016

(65) Prior Publication Data
US 2018/0134709 A1  May 17, 2018

(30) Foreign Application Priority Data
Apr. 21, 2015 (CN) .......................... 2015 1 0189476

(51) Int. Cl.
| C07D 473/34 | (2006.01) |
| A61K 31/52 | (2006.01) |
| A61K 31/5377 | (2006.01) |
| A61P 35/00 | (2006.01) |

(52) U.S. Cl.
CPC ............ *C07D 473/34* (2013.01); *A61K 31/52* (2013.01); *A61K 31/5377* (2013.01); *A61P 35/00* (2018.01); *Y02A 50/411* (2018.01)

(58) Field of Classification Search
CPC .................................................. C07D 473/34
See application file for complete search history.

(56) References Cited

U.S. PATENT DOCUMENTS

| 8,367,663 B2 | 2/2013 | Cai et al. |
| 8,461,157 B2 | 6/2013 | Cai et al. |
| 8,710,219 B2 | 4/2014 | Cai et al. |
| 8,906,909 B2 | 12/2014 | Cai et al. |
| 9,249,156 B2 | 2/2016 | Cai et al. |
| 9,657,032 B2 | 5/2017 | Cai et al. |
| 9,725,461 B2 | 8/2017 | Cai et al. |
| 2010/0222343 A1 | 9/2010 | Cai et al. |
| 2012/0088764 A1 | 4/2012 | Cai et al. |
| 2013/0090335 A1 | 4/2013 | Cai et al. |
| 2014/0155595 A1 | 6/2014 | Cai et al. |
| 2014/0243330 A1 | 8/2014 | Cai et al. |
| 2015/0086551 A1 | 3/2015 | Chen et al. |
| 2015/0203509 A1 | 7/2015 | Cai et al. |
| 2016/0185796 A1 | 6/2016 | Cai et al. |
| 2017/0304279 A1 | 10/2017 | Cai et al. |
| 2017/0362251 A1 | 12/2017 | Cai et al. |

FOREIGN PATENT DOCUMENTS

| CN | 102341108 A | 2/2012 |
| CN | 102970868 A | 3/2013 |
| CN | 103582483 A | 2/2014 |
| CN | 104066722 A | 9/2014 |

OTHER PUBLICATIONS

English Abstract of CN102970868, (2013).
International Search Report for corresponding PCT Application No. PCT/CN2016/079022, (dated 2016).

*Primary Examiner* — Bruck Kifle
(74) *Attorney, Agent, or Firm* — Caesar Rivise, PC

(57) ABSTRACT

The present invention relates to the field of the chemical medicines, and in particular, to purinyl-N-hydroxyl pyrimidine formamide derivatives, a preparation method therefor and a use thereof. The present invention provides a purinyl-N-hydroxyl pyrimidine formamide derivative having a structure represented by formula (I). The invention also provides a method for preparing said purinyl-N-hydroxyl pyrimidine formamide derivative and a use thereof. Purinyl-N-hydroxyl pyrimidine formamide derivative provided in the invention can be not only a PI3K and HDAC double-functional target kinase inhibitor, but also a PI3K or HDAC single target kinase inhibitor, thus providing new choice for preparing multi-target inhibitors.

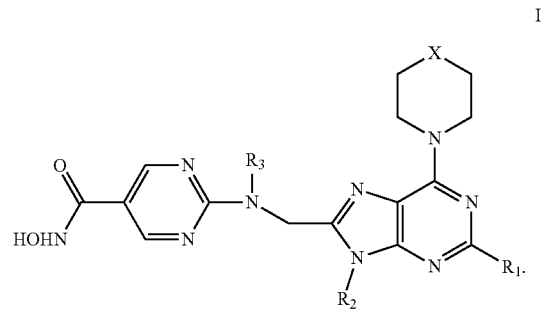

55 Claims, No Drawings

PURINYL-N-HYDROXYL PYRIMIDINE FORMAMIDE DERIVATIVE, PREPARATION METHODS AND USES THEREOF

CROSS-REFERENCE TO RELATED APPLICATIONS

This application is a U.S. National Phase Application of PCT/CN2016/079022, filed Apr. 12, 2016, which claims priority from CN 201510189476.9, filed Apr. 21, 2015, the contents of which applications are incorporated herein by reference in their entireties for all purposes.

TECHNICAL FIELD

The Invention relates to the field of chemical medicines, and particularly to a purinyl-N-hydroxyl pyrimidine formamide derivative, preparation methods and uses thereof.

BACKGROUND ART

Tumor is a kind of disease marked by cell malignant proliferation, having a complicated pathogenesis which often involves in heredity or epigenetic changes. The occurrence and development of tumor depend on a variety of receptors or signal transduction pathways, making the antineoplastic drugs which act on certain target point have to face following problems as: 1) The tumor cells cannot be fully killed; 2) it is easy to have drug resistance. Currently, although multi-drug combination has solved the above problems, it is likely to cause interactions between drugs, generating unpredictable adverse reactions; moreover, the usage of each drug in the combination is different from that for separate use. Compared with the drug combination, the multi-target drug can avoid interactions between drugs and have obviously better treatment effect than that of single-target drug.

In recent years, as the studies on malignant tumor are deepened constantly, more and more tumor signal pathways are found. Among which, the antineoplastic protocols with the signal transduction pathway mediated by PI3K as the target point gradually become a study hotspot. The important role of PI3K/Akt/mTOR signal pathway played in the occurrence and development of tumors has been proven in many studies and its function in lung cancer and liver cancer also has been reported.

Histone deacetylases (HDACs) are closely related to tumor; through deacetylation of histone N-lysine residues, gene transcription regulating and chromatin remodeling can be realized. In addition, HDACs can also catalyze non-histone deacetylation, such as p21, microtubulin, HSP90 (heat shock protein 90), etc. Inhibiting HDACs may induce cycle arrest, differentiation and apoptosis of tumor cells.

PI3K protein kinase and HDAC are the most important target points for tumor cell survival; HDAC inhibitor may have inhibition effect on tumor cell messenger multiple target points through epigenetic regulatory mechanism. The significant anti-cancer effect of PI3K inhibitor and HDAC inhibitor has been verified clinically. Multiple HDAC inhibitors as vorinostat (SAHA), panobinostat (LBH589) and chidamide have come into the market upon approval.

Based on the structure characteristics of PI3K kinase inhibitor GDC-0941, Qian C G et al. used the method of pharmacophore splicing, i.e., splicing the pharmacophores of PI3K kinase inhibitor and HDACIs inhibitor into a molecule. Through a great deal of in vivo/in vitro screening, the most preferred compound CUDC-907 is found. It can potently inhibit PI3Ks enzyme of Type I and HDAC enzyme of Type I & II, and its inhibition values to activities of HDAC1, HDAC2, HDAC3, HDAC8, HDAC6, HDAC10, HDAC11, PI3Kα, PI3Kβ, PI3Kγ and PI3Kδ are respectively 1.7, 5.0, 1.8, 191, 27, 2.8, 5.4, 19, 54, 39 and 311 nM[11]. The subsequent pharmacology experiment shows that, multiple signal pathways are decreased by inhibiting HDAC through CUDC-907 and the tumor cell growth is thus inhibited. For its favorable subsequent performance, Curis declared on Apr. 6, 2015 that FDA has granted CUDC-907 the qualification of orphan drug for treating diffuse large b-cell lymphoma. Such progress also promotes and encourages the research and development of DAC-kinase multi-target inhibitors.

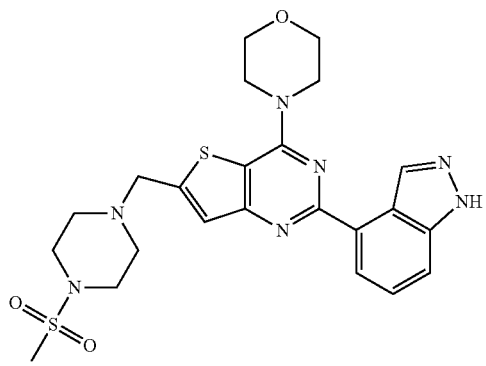

GDC-0941

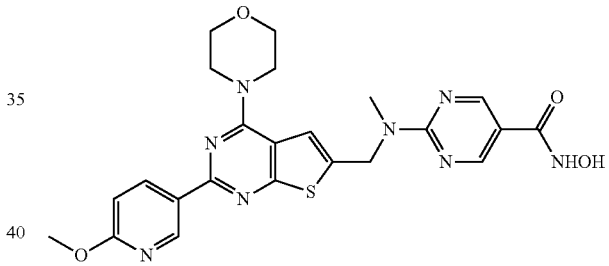

CUDC-907

However, currently there are no related reports to difunctional kinase inhibitors having the biochemical structure of purinyl-N-hydroxyl pyrimidine formamide derivative.

SUMMARY OF THE INVENTION

The Invention provides a purinyl-N-hydroxyl pyrimidine formamide derivative having PI3K and HDAC difunctional targets.

Said purinyl-N-hydroxyl pyrimidine formamide derivative, the structure of which is as shown in Formula I:

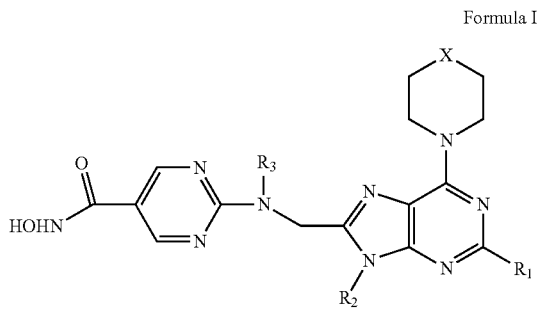

Formula I wherein, X is O or N—R'; R' is —H, $C_1$-$C_4$ alkyl, $C_1$-$C_4$ alkoxy or an alkyl substituted by $C_1$-$C_4$ hydroxy;

$R_1$ is $C_1$-$C_4$ alkyl, $C_1$-$C_4$ alkoxy, —OH, halogen, $C_3$-$C_8$ cycloalkyl, —$NH_2$,

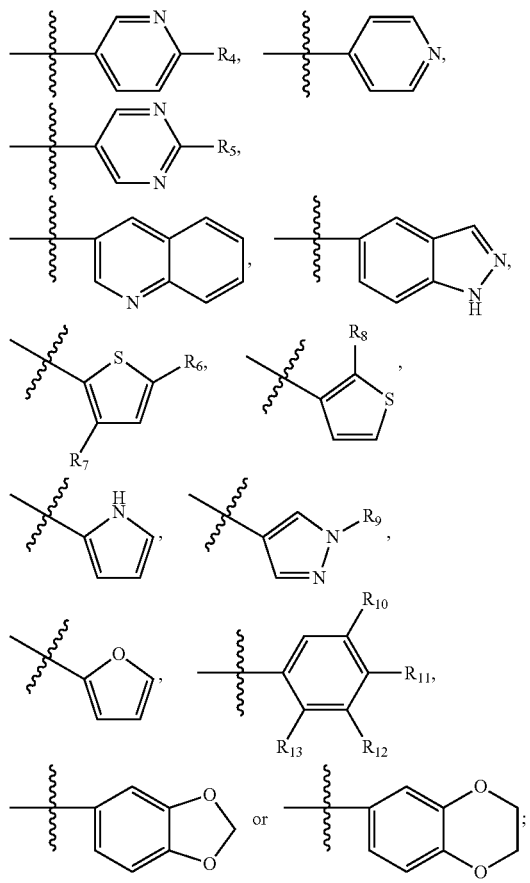

$R_2$ and $R_3$ are independently —H, $C_1$-$C_4$ alkyl, $C_1$-$C_4$ alkoxy, —OH, halogen or $C_3$-$C_8$ cycloalkyl;

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

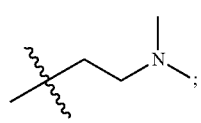

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

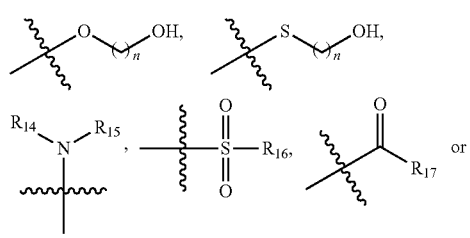

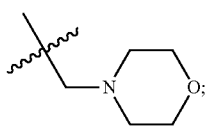

$R_{14}$ and $R_{15}$ are independently —H, $C_1$-$C_4$ alkyl, $C_1$-$C_6$ alkenyl,

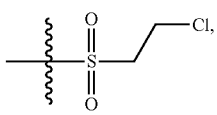 [SMILES: *S(=O)(=O)CCCl]

t-butyloxycarboryl,

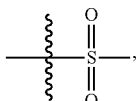

$C_1$-$C_4$ alkoxy or halogen;

$R_{16}$ is $C_1$-$C_4$ alkyl, $C_1$-$C_4$ alkoxy, halogen,

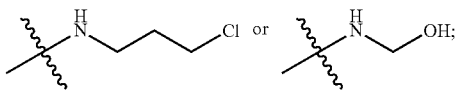

$R_{17}$ is —$NH_2$,

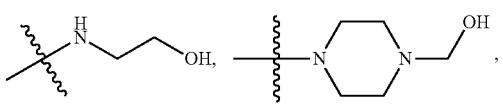 [SMILES: *NCCO ; *N1CCN(CO)CC1 ; ","]

—OH or halogen.

As a preferred scheme of the Invention, X is O or N—R'; R' is —H or an alkyl substituted $C_1$-$C_4$ hydroxy; $R_1$ is $C_1$-$C_4$ alkyl, $C_1$-$C_4$ alkoxy, —OH, halogen, $C_3$-$C_8$ cycloalkyl, —$NH_2$,

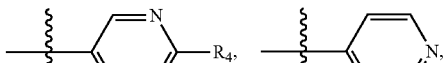
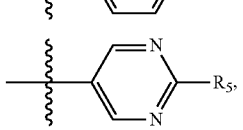
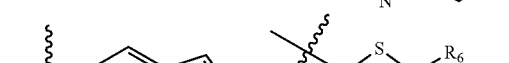
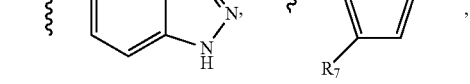

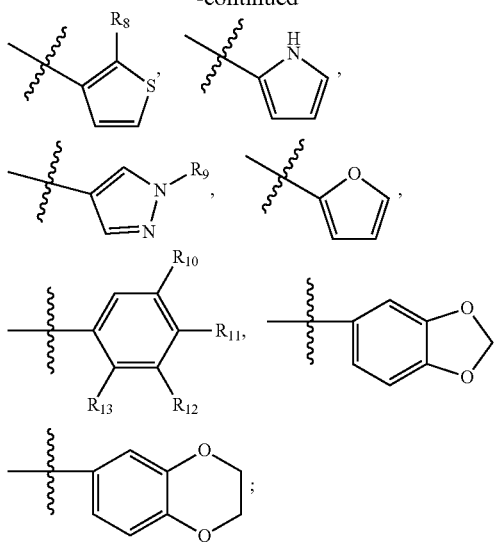

$R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

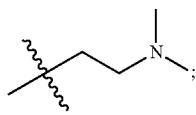

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

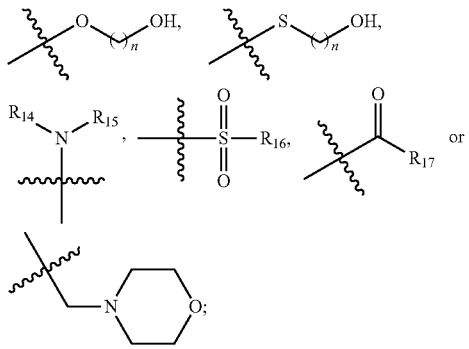

n=1-4; $R_{14}$ and $R_{15}$ are independently —H, $C_1$-$C_4$ alkyl, $C_1$-$C_6$ alkenyl,

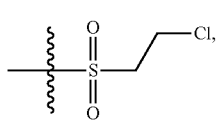 [SMILES: *S(=O)(=O)CCCl]

t-butyloxycarboryl,

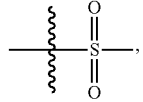

$C_1$-$C_4$ alkoxy or halogen; $R_{16}$ is $C_1$-$C_4$ alkyl, $C_1$-$C_4$ alkoxy, halogen,

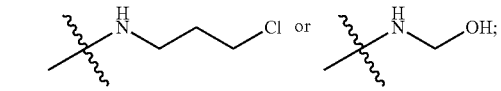

$R_{17}$ is —NH$_2$,

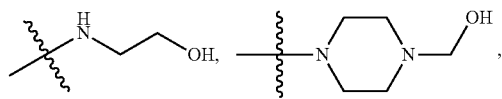

—OH or halogen.

Preferably, $R_1$ is halogen, $C_3$-$C_8$ cycloalkyl, —NH$_2$,

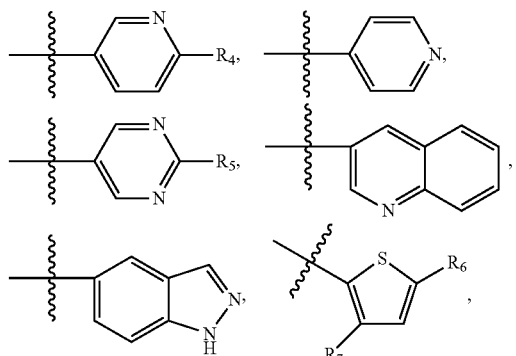

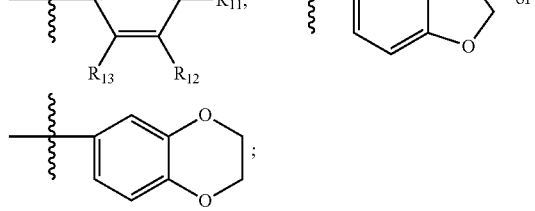

X is O or N—R'; R' is —H or an alkyl substituted by $C_1$-$C_4$ hydroxy; $R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

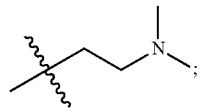

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

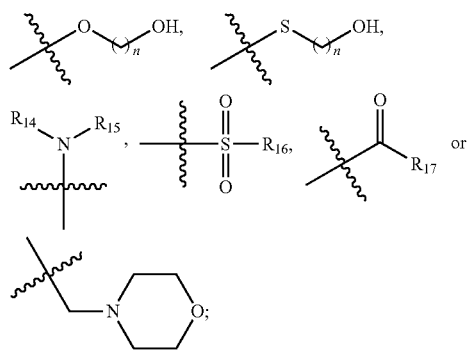

n=1-4; $R_{14}$ and $R_{15}$ are independently —H, $C_1$-$C_4$ alkyl, $C_1$-$C_6$ alkenyl,

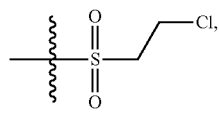

t-butyloxycarboryl,

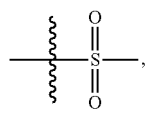 [SMILES: *S(C)(=O)=O]

$C_1$-$C_4$ alkoxy or halogen; $R_{16}$ is $C_1$-$C_4$ alkyl, $C_1$-$C_4$ alkoxy, halogen

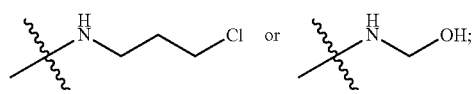

$R_{17}$ is —$NH_2$,

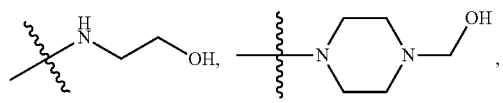

—OH or halogen.

More preferably, $R_1$ is halogen,

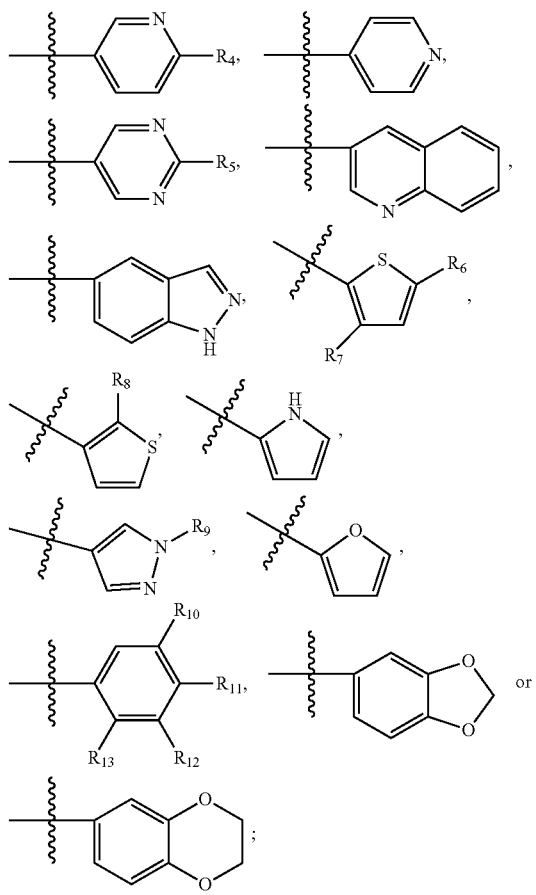

X is O or N—R'; R' is —H or an alkyl substituted by $C_1$-$C_4$ hydroxy; $R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

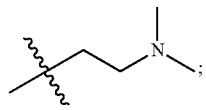 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

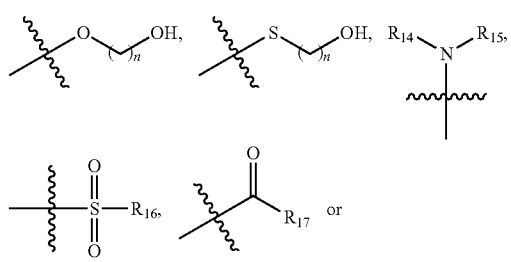

-continued

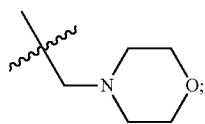

n=1-4; $R_{14}$ and $R_{15}$ are independently —H, $C_1$-$C_4$ alkyl, $C_1$-$C_6$ alkenyl,

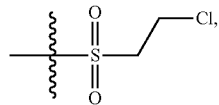 [SMILES: *S(=O)(=O)CCCl]

t-butyloxycarboryl,

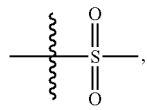

$C_1$-$C_4$ alkoxy or halogen; $R_{16}$ is $C_1$-$C_4$ alkyl, $C_1$-$C_4$ alkoxy, halogen,

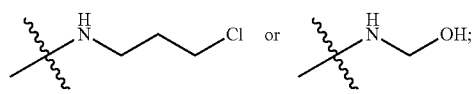

$R_{17}$ is —NH$_2$,

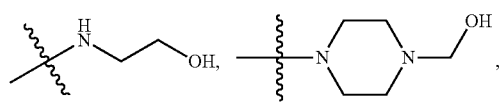

—OH or halogen.

More preferably, $R_1$ is —Cl,

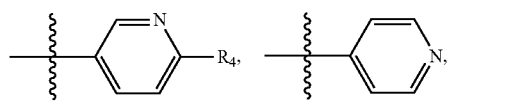

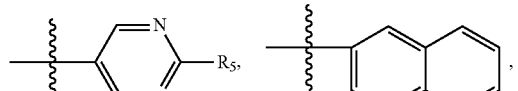

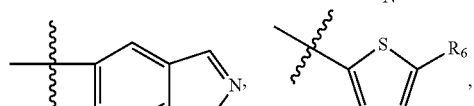

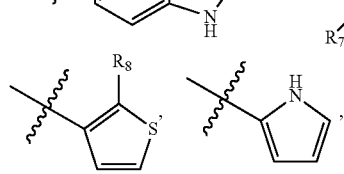

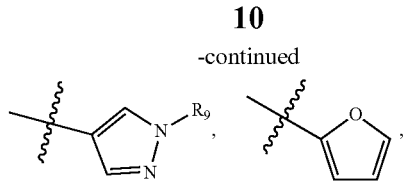

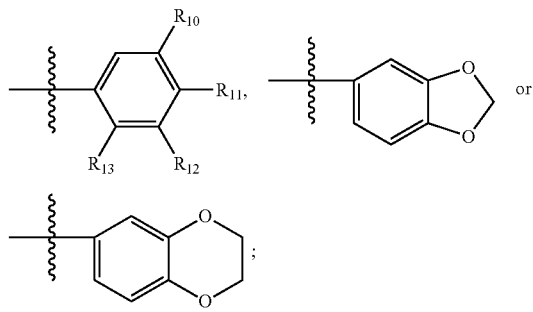

X is O or N—R'; R' is —H or an alkyl substituted by $C_1$-$C_4$ hydroxy; $R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

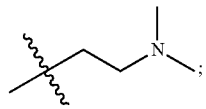 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

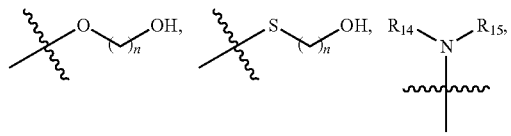

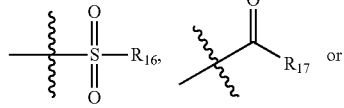

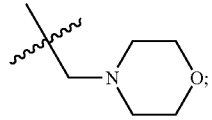

n=1-4; $R_{14}$ and $R_{15}$ are independently —H, $C_1$-$C_4$ alkyl, $C_1$-$C_6$ alkenyl,

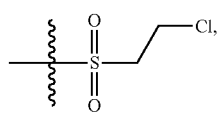 [SMILES: *S(=O)(=O)CCCl]

t-butyloxycarboryl,

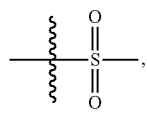

$C_1$-$C_4$ alkoxy or halogen; $R_{16}$ is $C_1$-$C_4$ alkyl, $C_1$-$C_4$ alkoxy, halogen,

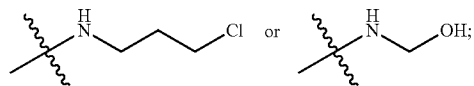

$R_{17}$ is —$NH_2$,

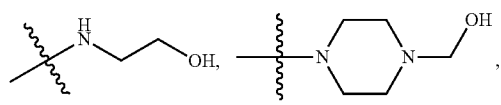

—OH or halogen.

Preferably, $R_2$ and $R_3$ are independently —H, $C_1$-$C_4$ alkyl, $C_1$-$C_4$ alkoxy or $C_3$-$C_8$ cycloalkyl; X is O or N—R'; R' is —H or an alkyl substituted by $C_1$-$C_4$ hydroxy; $R_1$ is halogen,

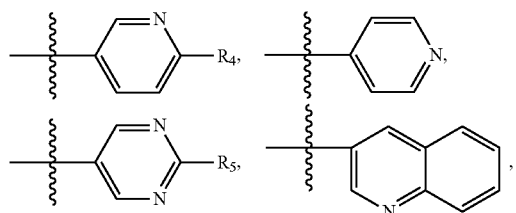

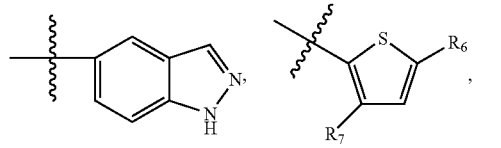

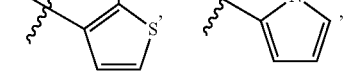

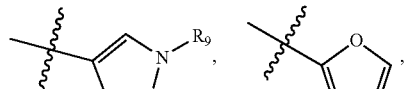

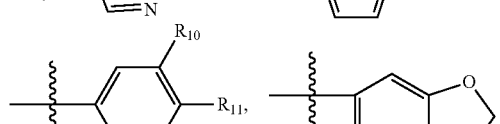

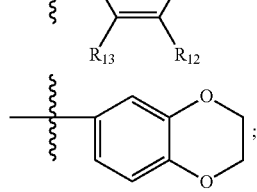

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

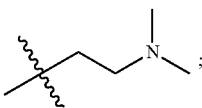

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

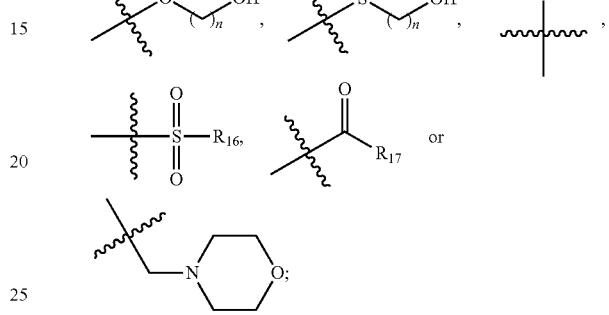

n=1-4; $R_{14}$ and $R_{15}$ are independently —H, $C_1$-$C_4$ alkyl, $C_1$-$C_6$ alkenyl,

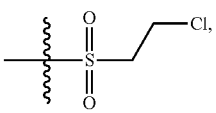 [SMILES: *S(=O)(=O)CCCl]

t-butyloxycarboryl,

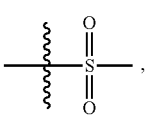

$C_1$-$C_4$ alkoxy or halogen; $R_{16}$ is $C_1$-$C_4$ alkyl, $C_1$-$C_4$ alkoxy, halogen,

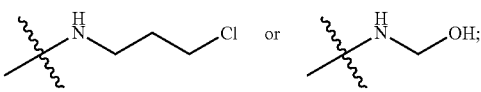

$R_{17}$ is —$NH_2$,

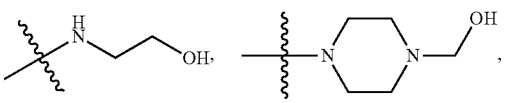 [SMILES: *NCCO ; *N1CCN(CO)CC1]

—OH or halogen.

More preferably, $R_2$ and $R_3$ are independently —H, $C_1$-$C_4$ alkyl or $C_3$-$C_8$ cycloalkyl; X is O or N—R'; R' is —H or an alkyl substituted by $C_1$-$C_4$ hydroxy; $R_1$ is halogen,

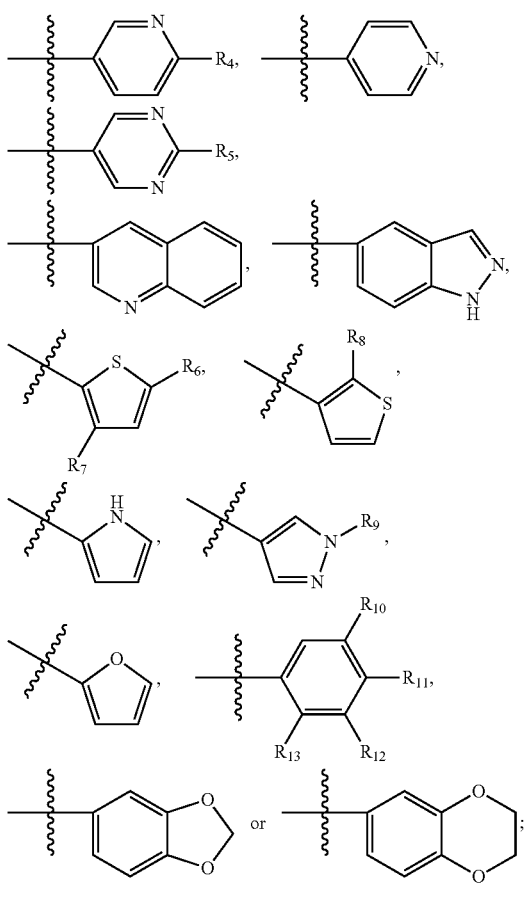

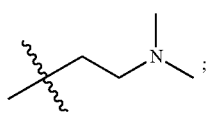 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

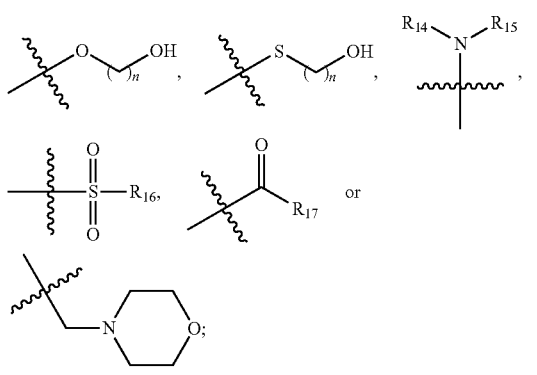

n=1-4; $R_{14}$ and $R_{15}$ are independently —H, $C_1$-$C_4$ alkyl, $C_1$-$C_6$ alkenyl,

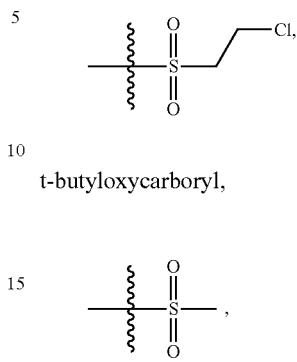

t-butyloxycarboryl, $C_1$-$C_4$ alkoxy or halogen; $R_{16}$ is $C_1$-$C_4$ alkyl, $C_1$-$C_4$ alkoxy, halogen,

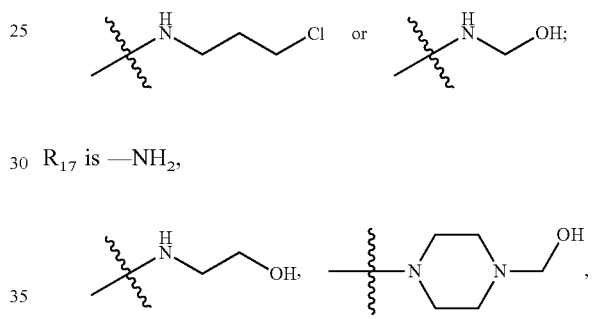

$R_{17}$ is —$NH_2$,

—OH or halogen.

More preferably, $R_2$ and $R_3$ are independently —H, $C_1$-$C_4$ alkyl or cyclopentyl alkyl; X is O or N—R'; R' is —H or an alkyl substituted by $C_1$-$C_4$ hydroxy; $R_1$ is halogen,

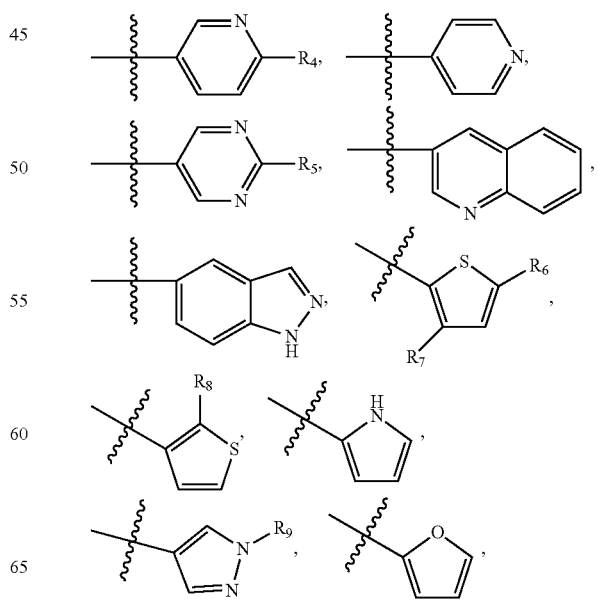

-continued

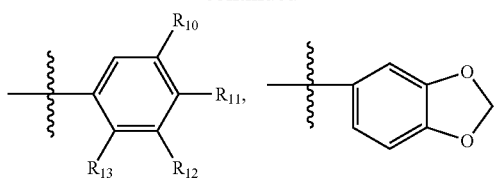

R$_4$-R$_9$ are independently —H, C$_1$-C$_4$ alkyl, C$_1$-C$_4$ alkoxy, —OH, halogen, C$_3$-C$_8$ naphthenic base, —NH$_2$, —COOH, C$_1$-C$_4$ alkyl amino or

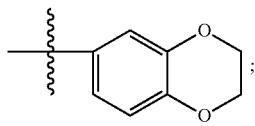

R$_{10}$-R$_{13}$ are independently —H, C$_1$-C$_4$ alkyl, C$_1$-C$_4$ alkoxy, —OH, —CF$_3$, halogen, C$_3$-C$_8$ naphthenic base, —NH$_2$, an alkyl substituted by C$_1$-C$_4$ hydroxy,

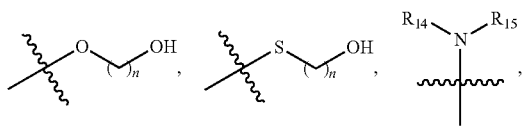

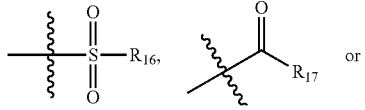

n=1-4; R$_{14}$ and R$_{15}$ are independently —H, C$_1$-C$_4$ alkyl, C$_1$-C$_6$ alkenyl,

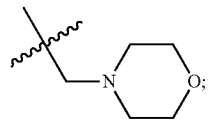

t-butyloxycarboryl,

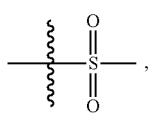

C$_1$-C$_4$ alkoxy or halogen; R$_{16}$ is C$_1$-C$_4$ alkyl, C$_1$-C$_4$ alkoxy, halogen,

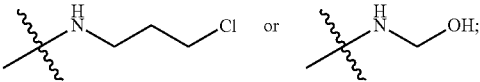

R$_{17}$ is —NH$_2$,

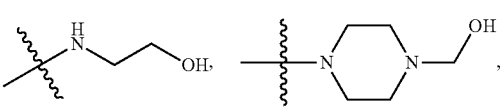 [SMILES: *NCCO ; *N1CCN(CO)CC1]

—OH or halogen.

More preferably, R$_4$-R$_9$ are independently —H, C$_1$-C$_4$ alkyl, C$_1$-C$_4$ alkoxy, C$_3$-C$_8$ cycloalkyl, —NH$_2$, —COOH, C$_1$-C$_4$ alkyl amino or

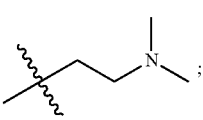

X is O or N—R'; R' is —H or an alkyl substituted by C$_1$-C$_4$ hydroxy; R$_1$ is halogen,

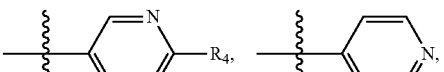

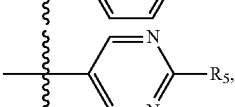

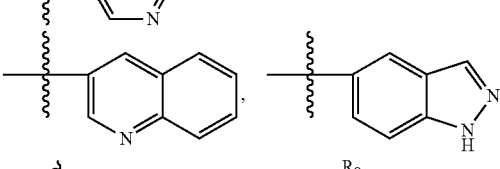

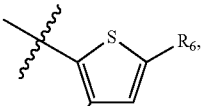

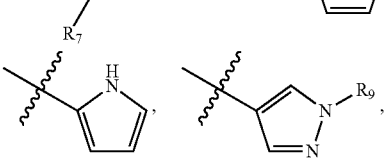

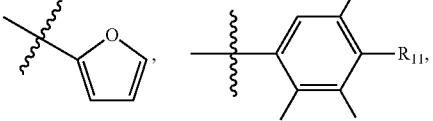

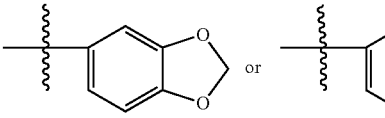

R$_2$ and R$_3$ are independently —H, C$_1$-C$_4$ alkyl or C$_3$-C$_8$ cycloalkyl; R$_{10}$-R$_{13}$ are independently —H, C$_1$-C$_4$ alkyl, C$_1$-C$_4$ alkoxy, —OH, —CF$_3$, halogen, C$_3$-C$_8$ cycloalkyl, —NH$_2$, an alkyl substituted by C$_1$-C$_4$ hydroxy,

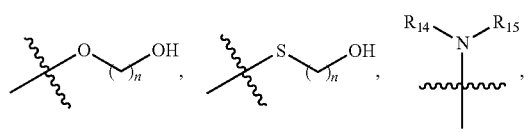

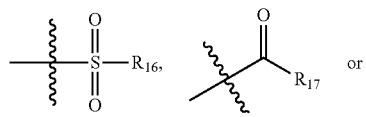

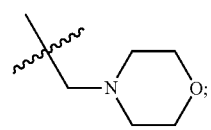

n=1-4; $R_{14}$ and $R_{15}$ are independently —H, $C_1$-$C_4$ alkyl, $C_1$-$C_6$ alkenyl,

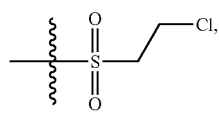 [SMILES: *S(=O)(=O)CCCl]

t-butyloxycarboryl,

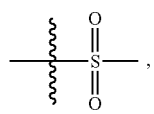 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

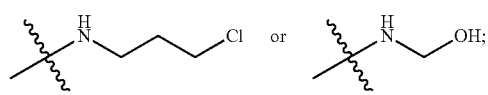

$R_{17}$ is —$NH_2$,

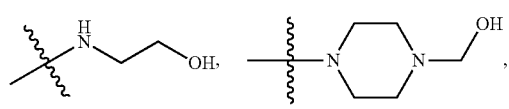 [SMILES: *NCCO ; *N1CCN(CO)CC1]

—OH or halogen.

More preferably, $R_4$-$R_9$ are independently —H, $C_1$-$C_4$ alkyl, $C_1$-$C_4$ alkoxy, —$NH_2$, —COOH, $C_1$-$C_4$ alkyl amino or

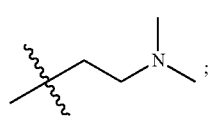 [SMILES: *CCN(C)C]

X is O or N—R'; R' is —H or an alkyl substituted by $C_1$-$C_4$ hydroxy; $R_1$ is halogen,

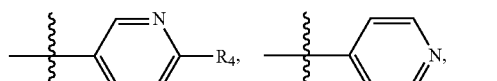

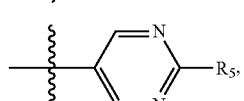

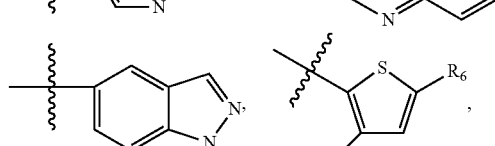

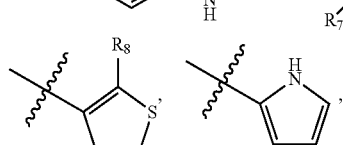

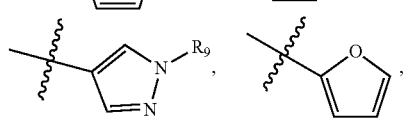

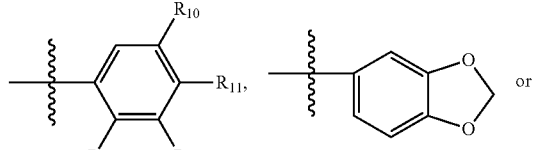

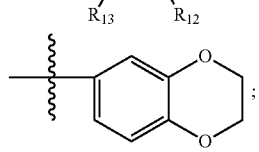

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

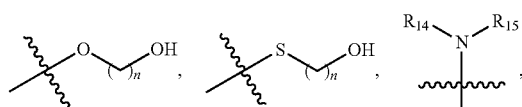

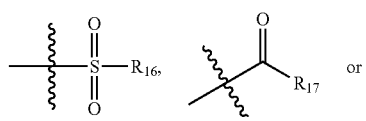

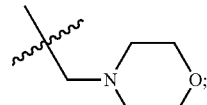

n=1-4; $R_{14}$ and $R_{15}$ are independently —H, $C_1$-$C_4$ alkyl, $C_1$-$C_6$ alkenyl,

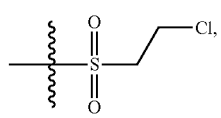 [SMILES: *S(=O)(=O)CCCl]

t-butyloxycarboryl,

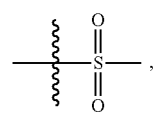 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

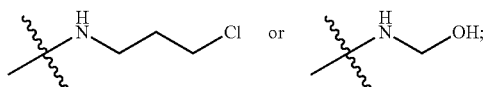

$R_{17}$ is —$NH_2$,

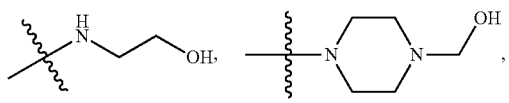

—OH or halogen.

More preferably, $R_4$-$R_9$ are independently —H, $C_1$-$C_4$ alkyl, methoxyl, —$NH_2$, —COOH, methylamino or

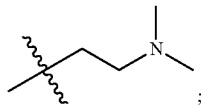 [SMILES: *CCN(C)C]

X is O or N—R'; R' is —H or an alkyl substituted by $C_1$-$C_4$ hydroxy; $R_1$ is halogen,

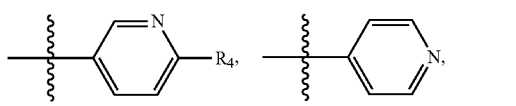

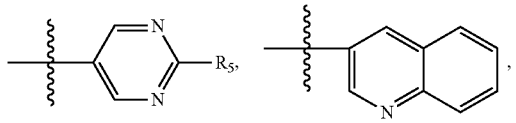

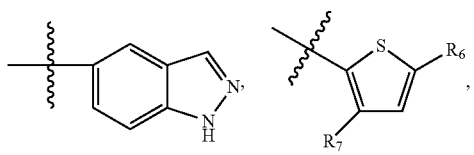

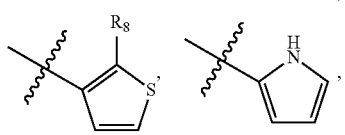

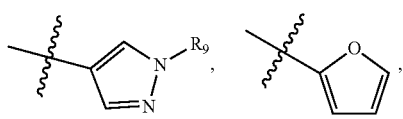

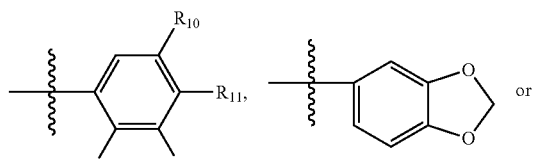

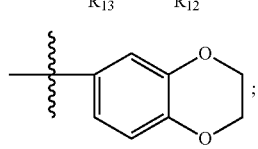

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

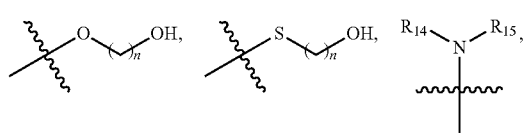

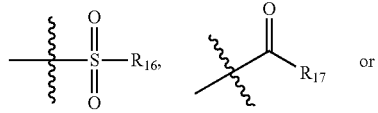

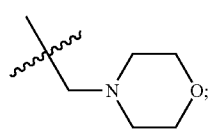

n=1-4; $R_{14}$ and $R_{15}$ are independently —H, $C_1$-$C_4$ alkyl, $C_1$-$C_6$ alkenyl,

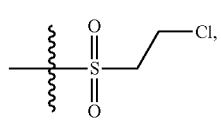 [SMILES: *S(=O)(=O)CCCl]

t-butyloxycarboryl,

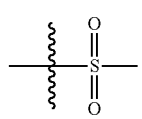

$C_1$-$C_4$ alkoxy or halogen; $R_{16}$ is $C_1$-$C_4$ alkyl, $C_1$-$C_4$ alkoxy, halogen,

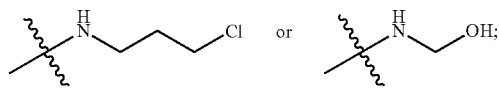

$R_{17}$ is —NH$_2$,

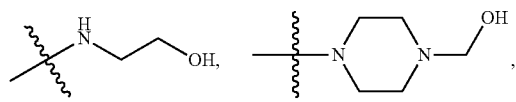

—OH or halogen.

Preferably, $R_{10}$-$R_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

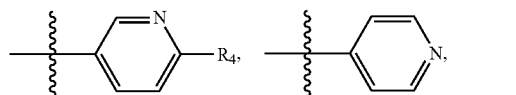

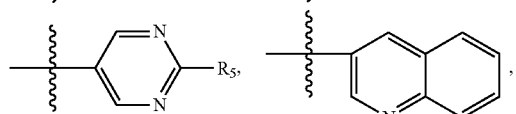

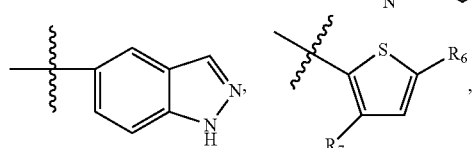

n=1-4; X is O or N—R'; R' is —H or an alkyl substituted by C$_1$-C$_4$ hydroxy; $R_1$ is halogen,

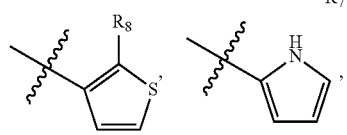

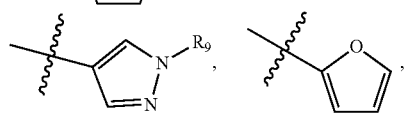

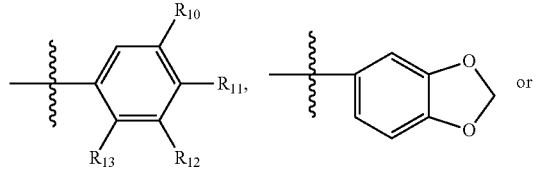

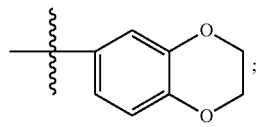;

$R_2$ and $R_3$ are independently —H, C$_1$-C$_4$ alkyl or C$_3$-C$_8$ cycloalkyl; $R_4$-$R_9$ are independently —H, C$_1$-C$_4$ alkyl, C$_1$-C$_4$ alkoxy, —NH$_2$, —COOH, C$_1$-C$_4$ alkyl amino or

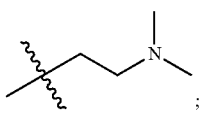;

$R_{14}$ and $R_{15}$ are independently —H, C$_1$-C$_4$ alkyl, C$_1$-C$_6$ alkenyl,

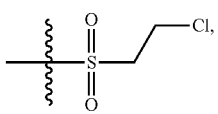

t-butyloxycarboryl,

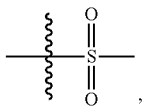,

C$_1$-C$_4$ alkoxy or halogen; $R_{16}$ is C$_1$-C$_4$ alkyl, C$_1$-C$_4$ alkoxy, halogen,

$R_{17}$ is —NH$_2$,

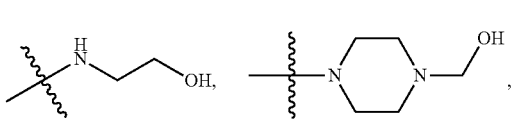

—OH or halogen.

More preferably, $R_{10}$-$R_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

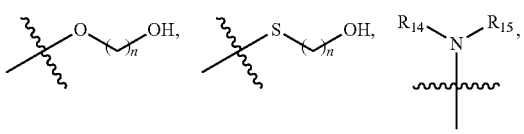

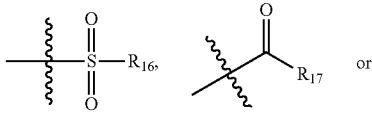

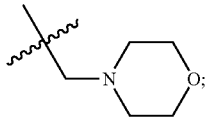

n=1 or 2; X is O or N—R'; R' is —H or an alkyl substituted by $C_1$-$C_4$ hydroxy; $R_1$ is halogen,

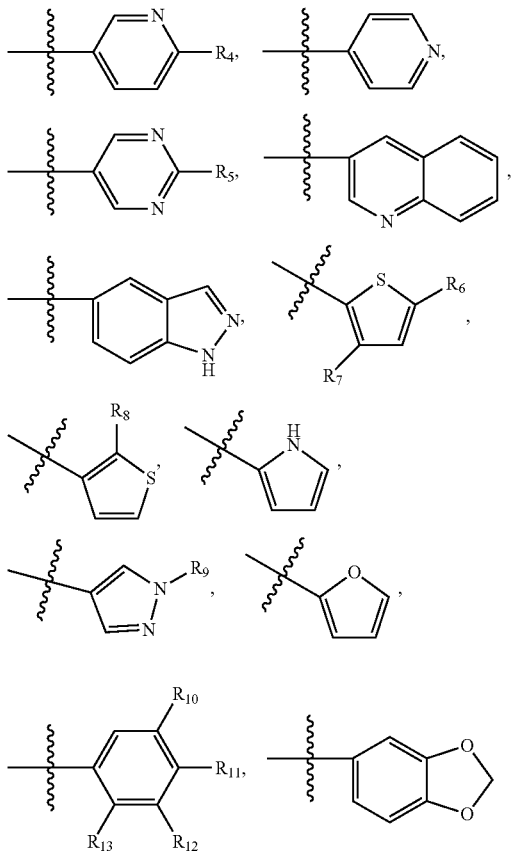

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

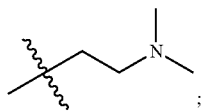 [SMILES: *CCN(C)C]

$R_{14}$ and $R_{15}$ are independently —H, $C_1$-$C_4$ alkyl, $C_1$-$C_6$ alkenyl,

t-butyloxycarboryl,

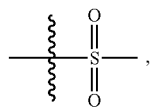 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

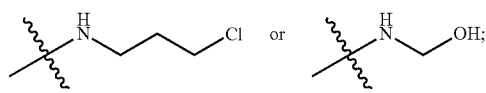

$R_{17}$ is —$NH_2$,

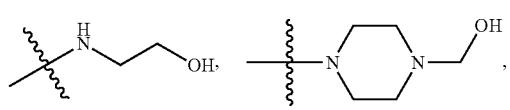

—OH or halogen.

Preferably, $R_{14}$ and $R_{15}$ are independently —H, $C_1$-$C_4$ alkyl, $C_1$-$C_6$ alkenyl,

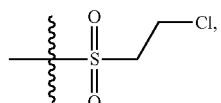

t-butyloxycarboryl,

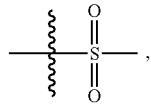 [SMILES: *S(C)(=O)=O]

$C_1$-$C_4$ alkoxy or halogen; X is O or N—R'; R' is —H or an alkyl substituted by $C_1$-$C_4$ hydroxy; $R_1$ is halogen,

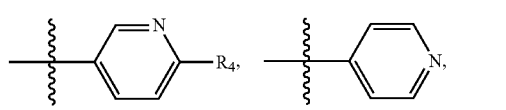

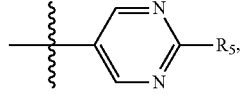

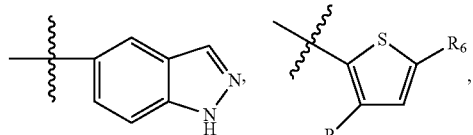

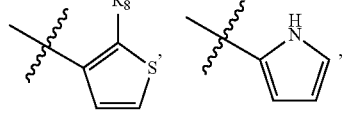

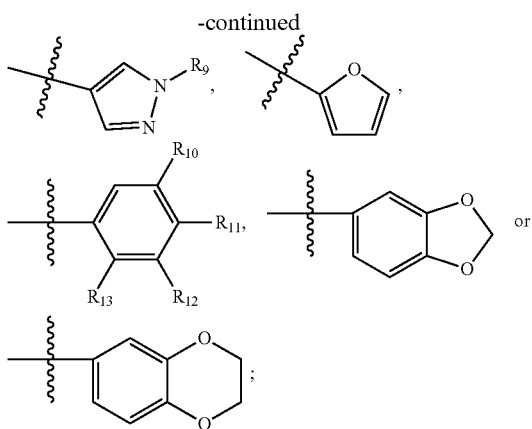

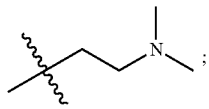 [SMILES: *CCN(C)C]

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

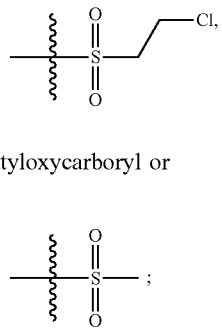

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

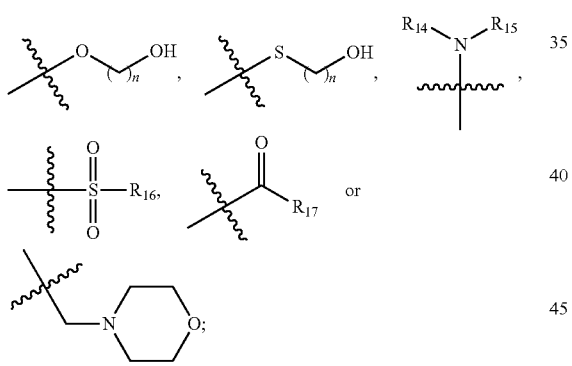

n=1-4; $R_{16}$ is $C_1$-$C_4$ alkyl, $C_1$-$C_4$ alkoxy, halogen,

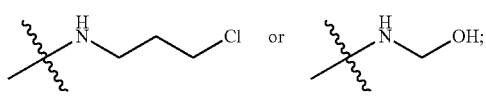

$R_{17}$ is —$NH_2$,

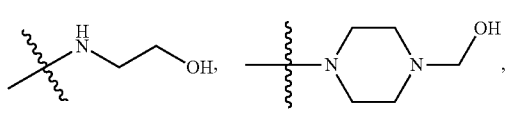

—OH or halogen.

More preferably, $R_{14}$ and $R_{15}$ are independently —H, $C_1$-$C_4$ alkyl, $C_1$-$C_6$ alkenyl,

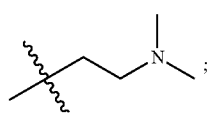

t-butyloxycarboryl or

[sulfonyl structure];

X is O or N—R'; R' is —H or an alkyl substituted by $C_1$-$C_4$ hydroxy; $R_1$ is halogen,

[pyridine, pyridine, pyrimidine, quinoline, indazole, thiophene, thiophene, pyrrole, pyrazole, furan, substituted phenyl, benzodioxole, benzodioxane structures with $R_4$–$R_{13}$];

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

[dimethylaminoethyl structure];

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

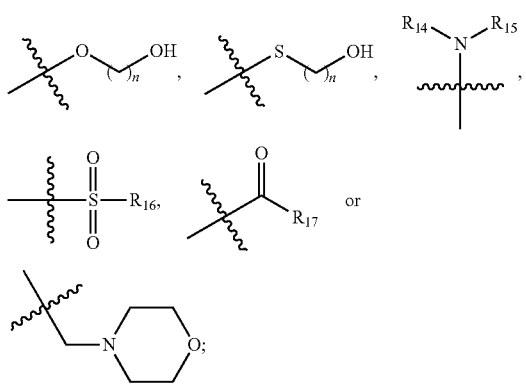

n=1-4; $R_{16}$ is $C_1$-$C_4$ alkyl, $C_1$-$C_4$ alkoxy, halogen,

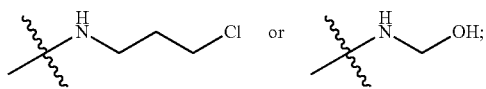

$R_{17}$ is —$NH_2$,

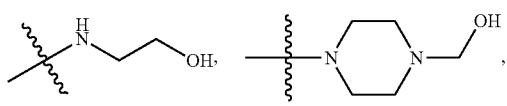

—OH or halogen.

Preferably, $R_{16}$ is $C_1$-$C_4$ alkyl,

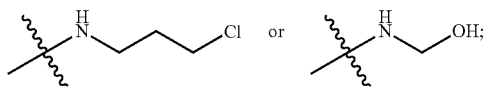

X is O or N—R'; R' is —H or an alkyl substituted by $C_1$-$C_4$ hydroxy; $R_1$ is halogen,

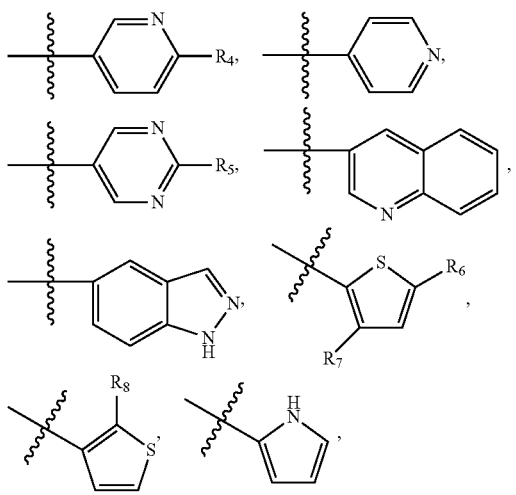

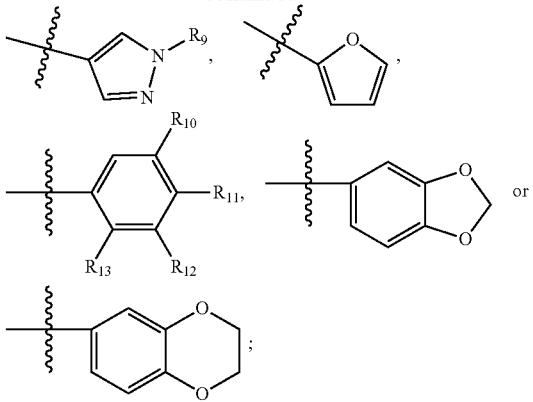

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

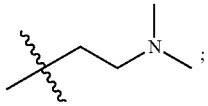 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

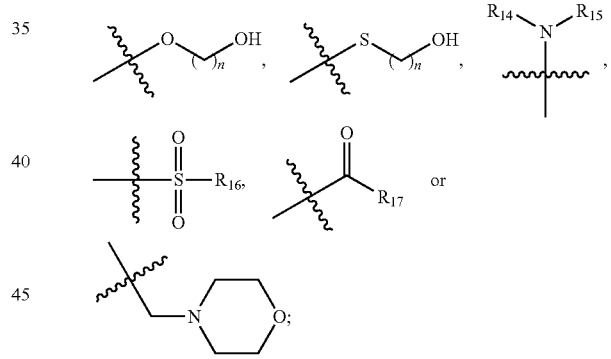

n=1-4; $R_{14}$ and $R_{15}$ are independently —H, $C_1$-$C_4$ alkyl, $C_1$-$C_6$ alkenyl,

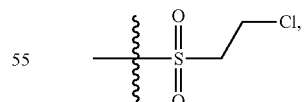

t-butyloxycarboryl or

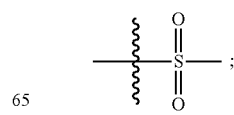

$R_{17}$ is —$NH_2$,

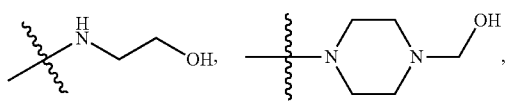

—OH or halogen.

More preferably, X is O or N—R'; R' is —H or an alkyl substituted by $C_1$-$C_4$ hydroxy; $R_1$ is halogen,

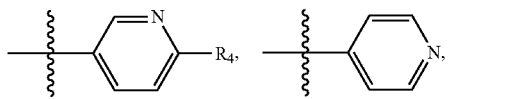

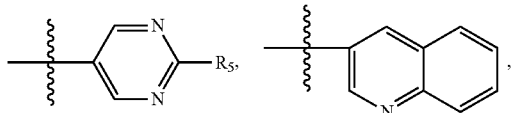

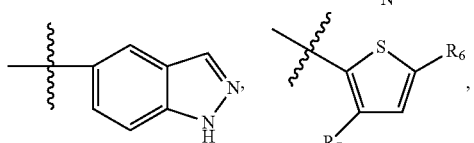

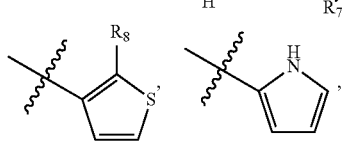

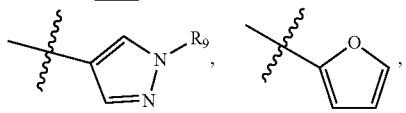

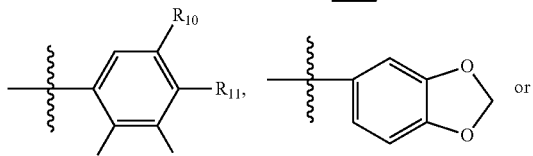

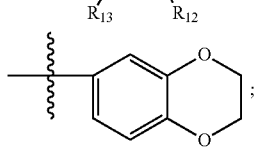

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

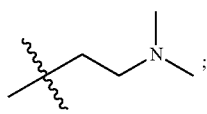 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

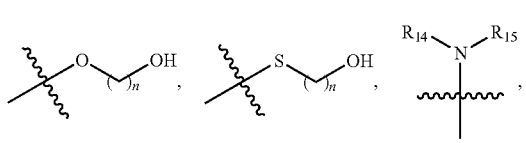

-continued

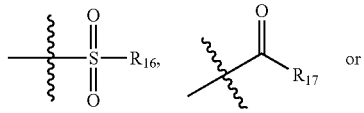

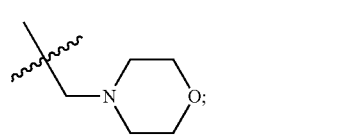

n=1-4; $R_{14}$ and $R_{15}$ are independently —H, $C_1$-$C_4$ alkyl, $C_1$-$C_6$ alkenyl,

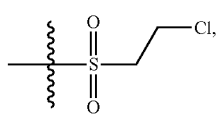 [SMILES: *S(=O)(=O)CCCl]

t-butyloxycarboryl or

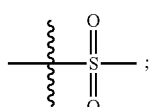

$R_{16}$ is $C_1$-$C_4$ alkyl,

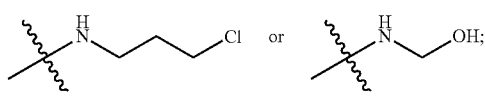

$R_{17}$ is —$NH_2$,

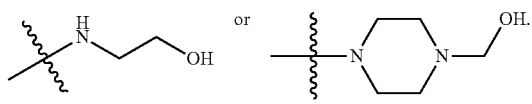 [SMILES: *NCCO ; "or" ; *N1CCN(CO)CC1]

Most preferably, X is O or N—R'; R' is —H or hydroxy ethyl; $R_1$ is —Cl,

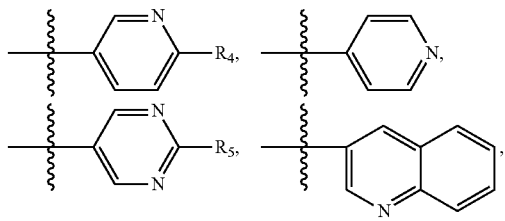

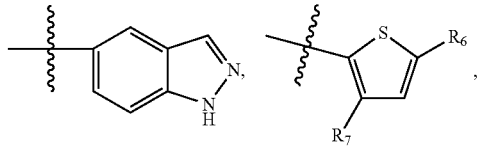

-continued

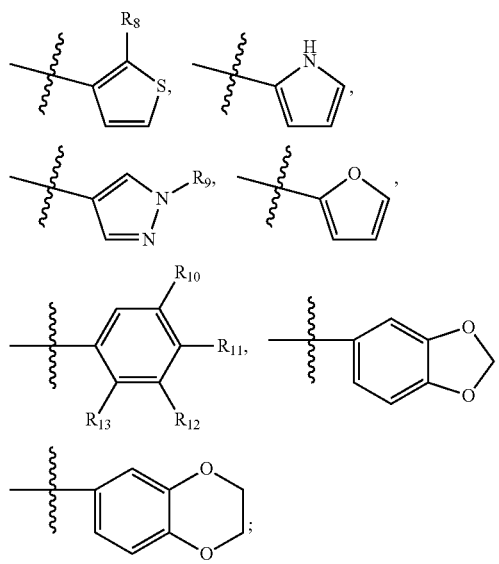

$R_2$ and $R_3$ are independently —H, $C_1$-$C_4$ alkyl or cyclopentyl alkyl; $R_4$-$R_9$ are independently —H, $C_1$-$C_4$ alkyl, methoxy, —NH$_2$, —COOH, methylamino or

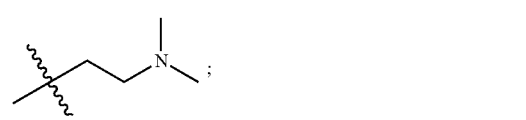 [SMILES: *CCN(C)C]

$R_{10}$-$R_{13}$ are independently —H, $C_1$-$C_4$ alkyl, methoxy, —OH, —CF$_3$, —Cl, —NH$_2$, an alkyl substituted by $C_1$-$C_4$ hydroxy,

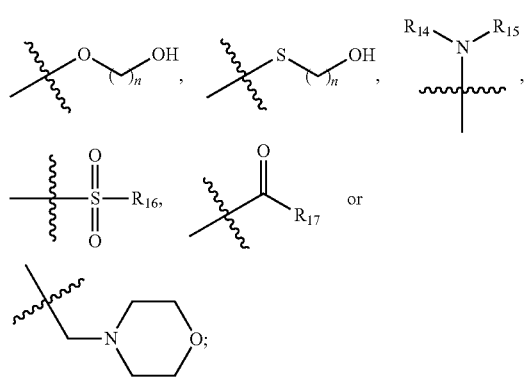

n=1 or 2; $R_{14}$ and $R_{15}$ are independently —H, $C_1$-$C_4$ alkyl, $C_1$-$C_6$ alkenyl,

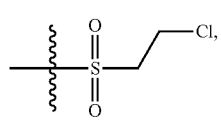

t-butyloxycarboryl or

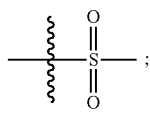 [SMILES: *S(C)(=O)=O]

$R_{16}$ is $C_1$-$C_4$ alkyl,

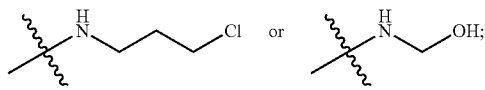

$R_{17}$ is —NH$_2$,

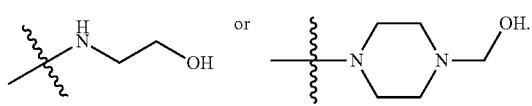 [SMILES: *NCCO ; "or" ; *N1CCN(CO)CC1]

Said purinyl-N-hydroxyl pyrimidine formamide derivative, when X is O, the structure of which is as shown in Formula II:

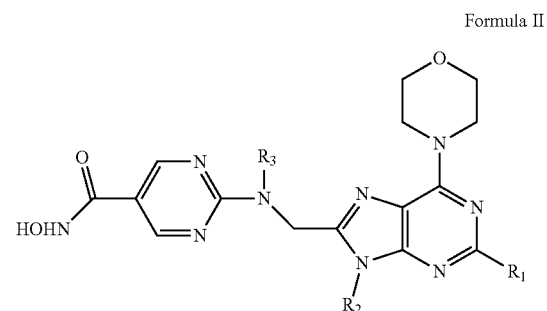

Formula II wherein, $R_1$ is $C_1$-$C_4$ alkyl, $C_1$-$C_4$ alkoxy, —OH, halogen, $C_3$-$C_8$ cycloalkyl, —NH$_2$,

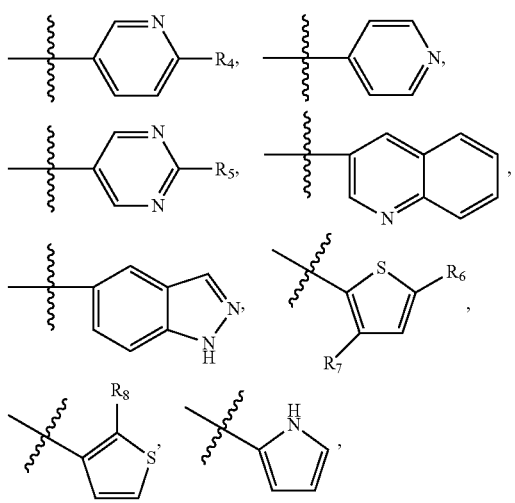

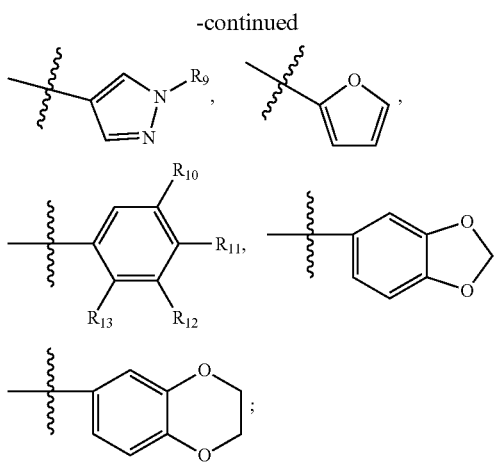

$R_2$ and $R_3$ are independently —H, $C_1$-$C_4$ alkyl, $C_1$-$C_4$ alkoxy, —OH, halogen or $C_3$-$C_8$ cycloalkyl;

$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

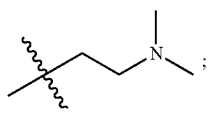 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

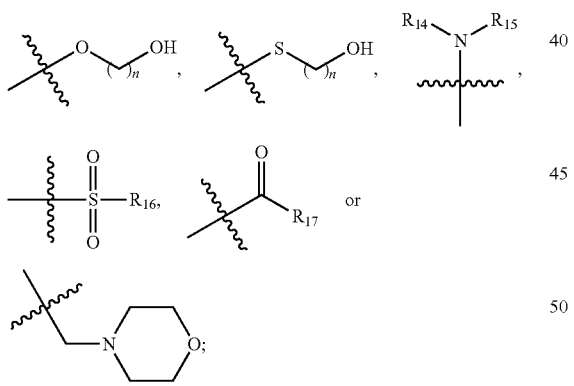

n=1-4;

$R_{14}$ and $R_{15}$ are independently —H, $C_1$-$C_4$, alkyl, $C_1$-$C_6$ alkenyl,

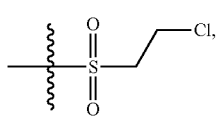

t-butyloxycarboryl,

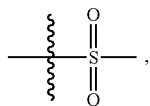 [SMILES: *S(C)(=O)=O]

$C_1$-$C_4$ alkoxy or halogen;

$R_{16}$ is $C_1$-$C_4$ alkyl, $C_1$-$C_4$ alkoxy, halogen,

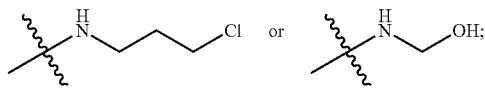

$R_{17}$ is —NH$_2$,

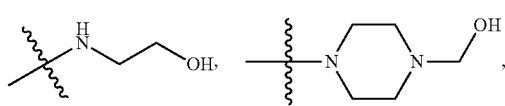 [SMILES: *NCCO ; *N1CCN(CO)CC1]

—OH or halogen.

As a preferred scheme of the Invention, $R_1$ is halogen, $C_3$-$C_8$ cycloalkyl, —NH$_2$,

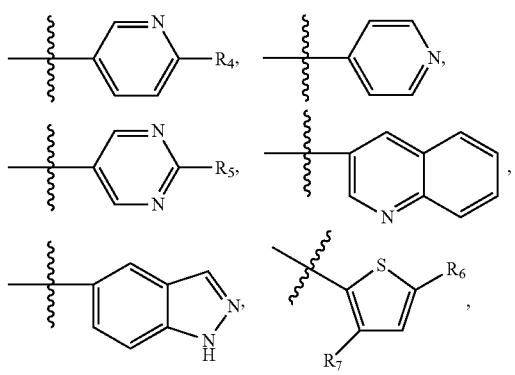

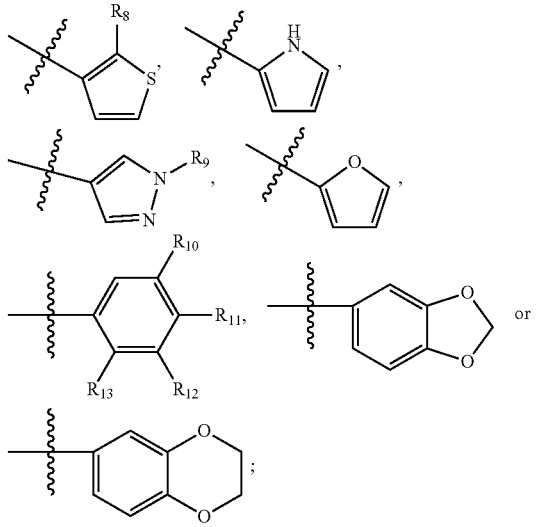

$R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

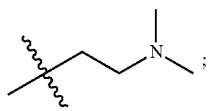 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

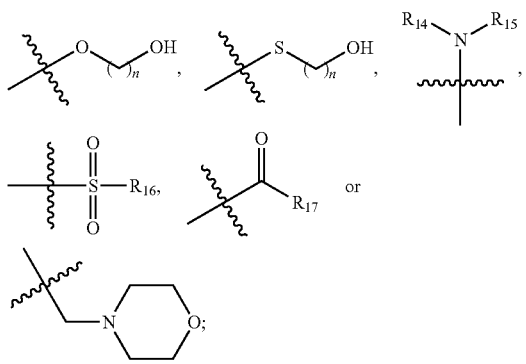

n=1-4; $R_{14}$ and $R_{15}$ are independently —H, $C_1$-$C_4$ alkyl, $C_1$-$C_6$ alkenyl,

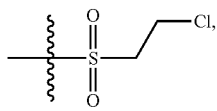 [SMILES: *S(=O)(=O)CCCl]

t-butyloxycarboryl,

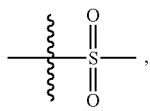 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

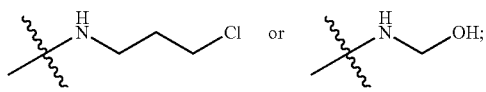

$R_{17}$ is —$NH_2$,

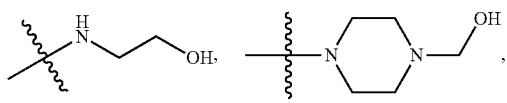 [SMILES: *NCCO ; *N1CCN(CO)CC1]

—OH or halogen.

Preferably, $R_1$ is halogen,

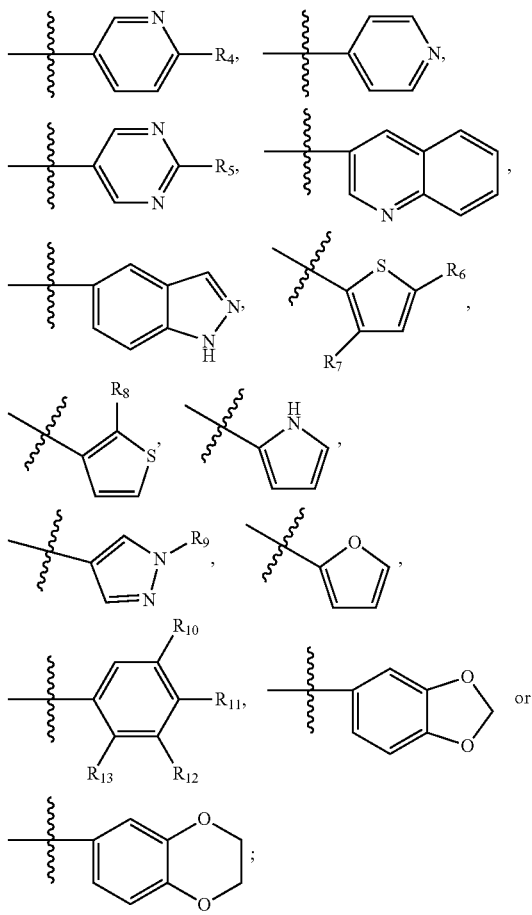

$R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

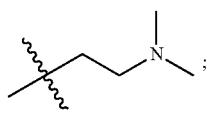

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

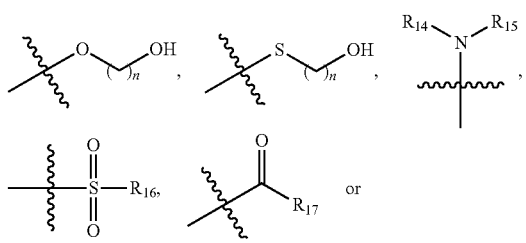

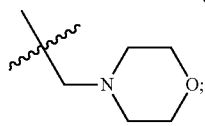

n=1-4; R$_{14}$ and R$_{15}$ are independently —H, C$_1$-C$_4$ alkyl, C$_1$-C$_6$ alkenyl,

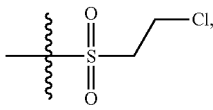 [SMILES: *S(=O)(=O)CCCl]

t-butyloxycarboryl,

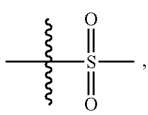 [SMILES: *S(C)(=O)=O]

C$_1$-C$_4$ alkoxy or halogen; R$_{16}$ is C$_1$-C$_4$ alkyl, C$_1$-C$_4$ alkoxy, halogen,

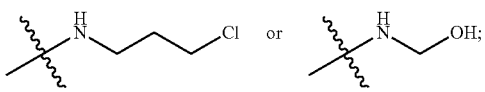

R$_{17}$ is —NH$_2$,

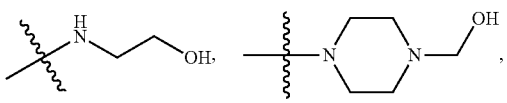

—OH or halogen.

More preferably, R$_1$ is —Cl,

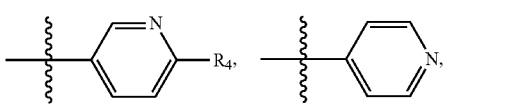
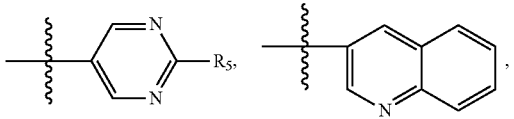
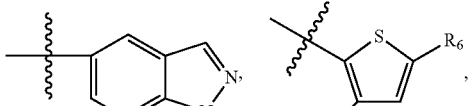
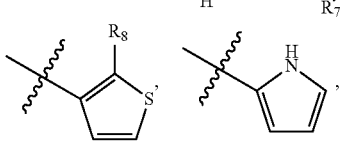

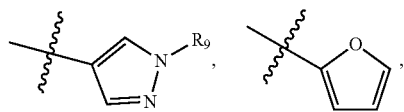
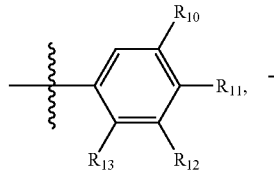

R$_2$ and R$_3$ are independently —H, C$_1$-C$_4$ alkyl, C$_1$-C$_4$ alkoxy, —OH, halogen or C$_3$-C$_8$ cycloalkyl; R$_4$-R$_9$ are independently —H, C$_1$-C$_4$ alkyl, C$_1$-C$_4$ alkoxy, —OH, halogen, C$_3$-C$_8$ cycloalkyl, —NH$_2$, —COOH, C$_1$-C$_4$ alkyl amino or

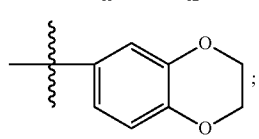

R$_{10}$-R$_{13}$ are independently —H, C$_1$-C$_4$ alkyl, C$_1$-C$_4$ alkoxy, —OH, —CF$_3$, halogen, C$_3$-C$_8$ cycloalkyl, —NH$_2$, an alkyl substituted by C$_1$-C$_4$ hydroxy,

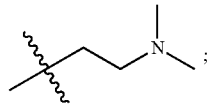 [SMILES: *CCN(C)C]
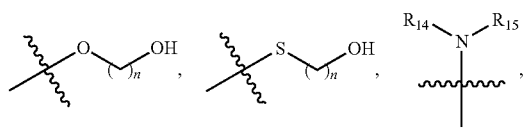
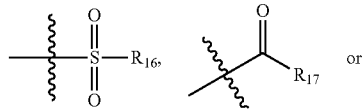

n=1-4; R$_{14}$ and R$_{15}$ are independently —H, C$_1$-C$_4$ alkyl, C$_1$-C$_6$ alkenyl,

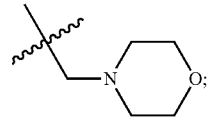

t-butyloxycarboryl,

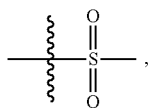

$C_1$-$C_4$ alkoxy or halogen; $R_{16}$ is $C_1$-$C_4$ alkyl, $C_1$-$C_4$ alkoxy, halogen,

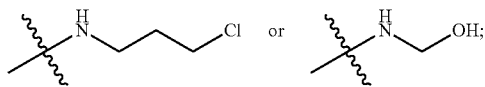

$R_{17}$ is —$NH_2$,

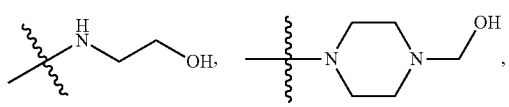

—OH or halogen.

Preferably, $R_2$ and $R_3$ are independently —H, $C_1$-$C_4$ alkyl, $C_1$-$C_4$ alkoxy or $C_3$-$C_8$ cycloalkyl; $R_1$ is halogen,

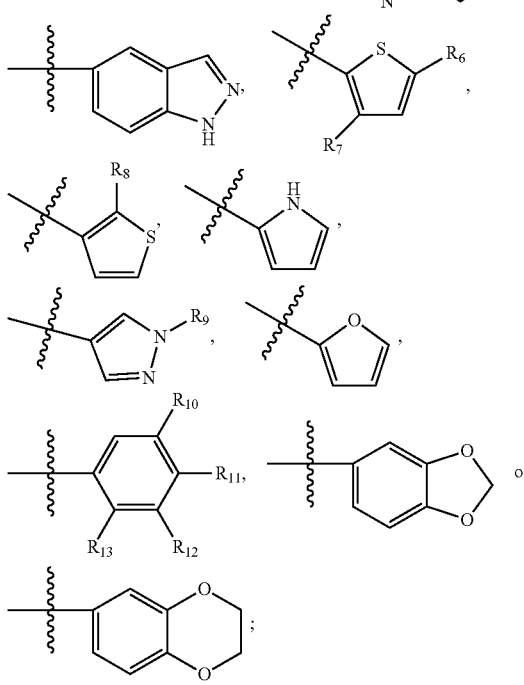

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

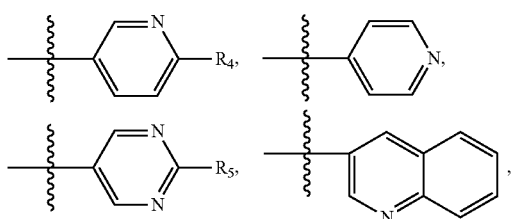

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

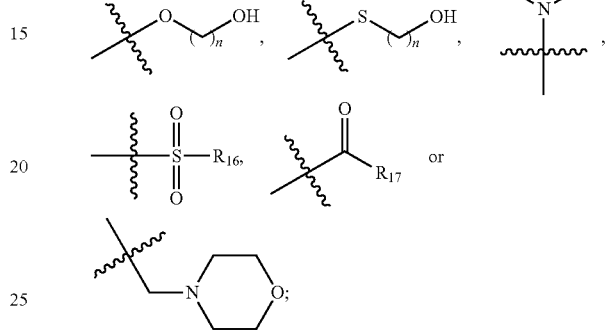

n=1-4; $R_{14}$ and $R_{15}$ are independently —H, $C_1$-$C_4$ alkyl, $C_1$-$C_6$ alkenyl,

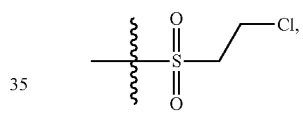

t-butyloxycarboryl,

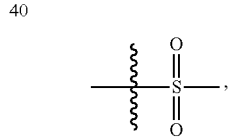

$C_1$-$C_4$ alkoxy or halogen; $R_{16}$ is $C_1$-$C_4$ alkyl, $C_1$-$C_4$ alkoxy, halogen,

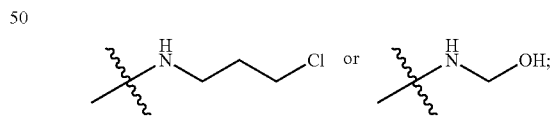

$R_{17}$ is —$NH_2$,

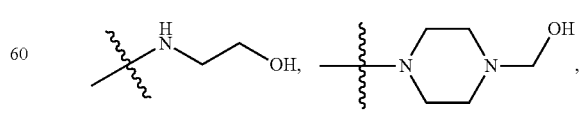

—OH or halogen.

More preferably, $R_2$ and $R_3$ are independently —H, $C_1$-$C_4$ alkyl or $C_3$-$C_8$ cycloalkyl; $R_1$ is halogen,

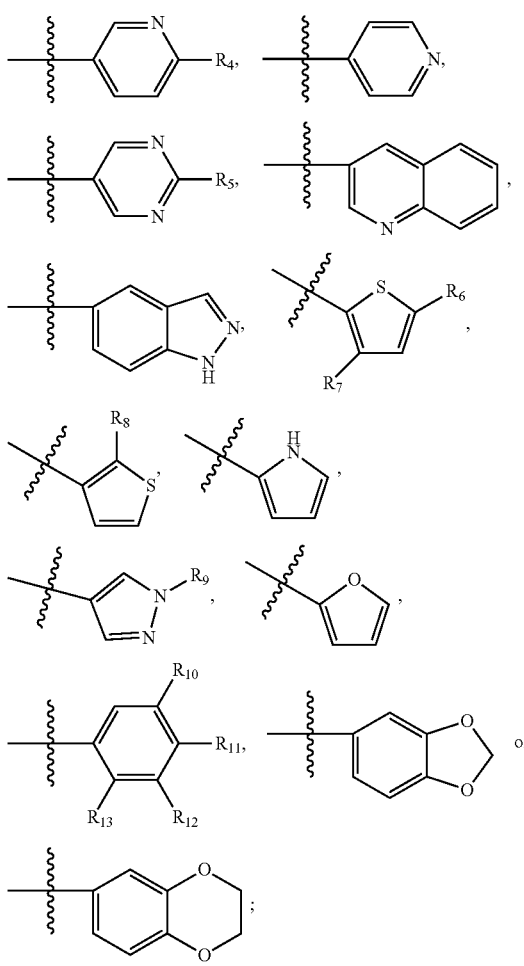

$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

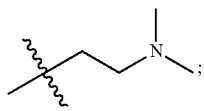

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

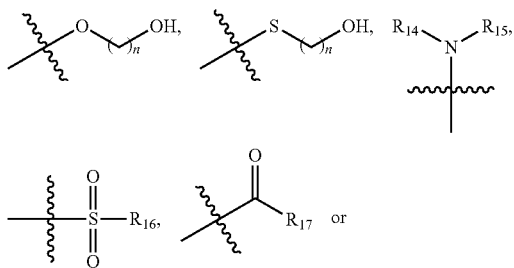

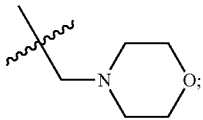

n=1-4; $R_{14}$ and $R_{15}$ are independently —H, $C_1$-$C_4$ alkyl, $C_1$-$C_6$ alkenyl,

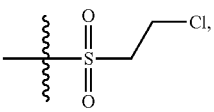

t-butyloxycarboryl,

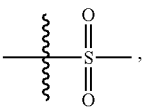

$C_1$-$C_4$ alkoxy or halogen; $R_{16}$ is $C_1$-$C_4$ alkyl, $C_1$-$C_4$ alkoxy, halogen

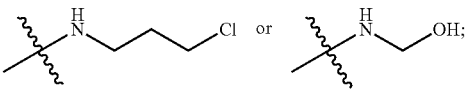

$R_{17}$ is —NH$_2$,

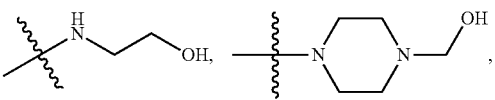 [SMILES: *NCCO ; *N1CCN(CO)CC1]

—OH or halogen.

More preferably, $R_2$ and $R_3$ are independently —H, $C_1$-$C_4$ alkyl or cyclopentyl alkyl; $R_1$ is halogen,

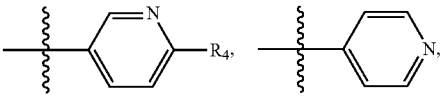

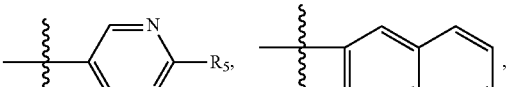

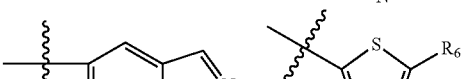

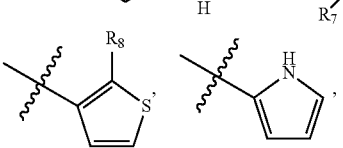

-continued

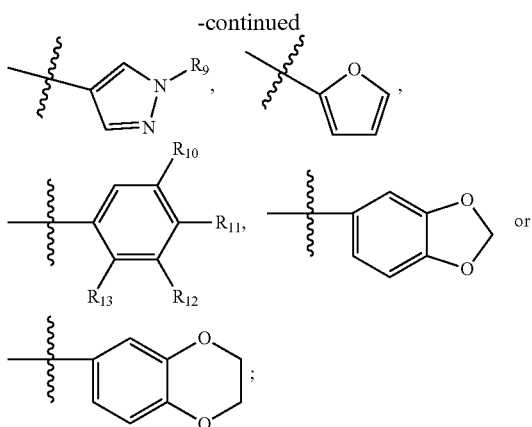

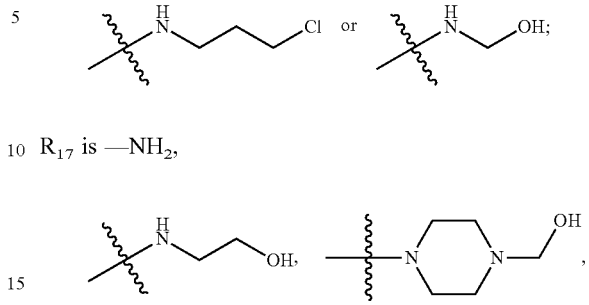

$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

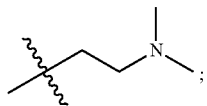 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

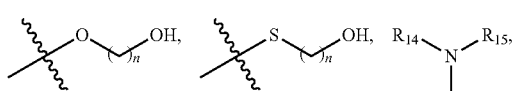

n=1-4; $R_{14}$ and $R_{15}$ are independently —H, $C_1$-$C_4$ alkyl, $C_1$-$C_6$ alkenyl,

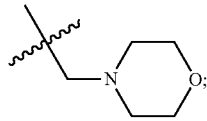

t-butyloxycarboryl,

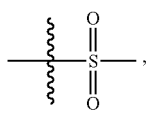

$C_1$-$C_4$ alkoxy or halogen; $R_{16}$ is $C_1$-$C_4$ alkyl, $C_1$-$C_4$ alkoxy, halogen,

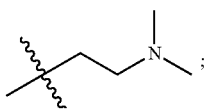 [SMILES: *CCN(C)C]

$R_{17}$ is —NH$_2$,

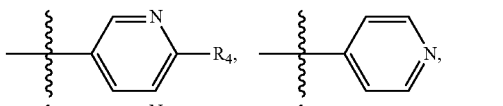

—OH or halogen.

Preferably, $R_4$-$R_9$ are independently —H, $C_1$-$C_4$ alkyl, $C_1$-$C_4$ alkoxy, $C_3$-$C_8$ cycloalkyl, —NH$_2$, —COOH, $C_1$-$C_4$ alkyl amino or

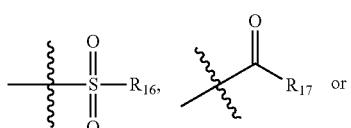

$R_1$ is halogen,

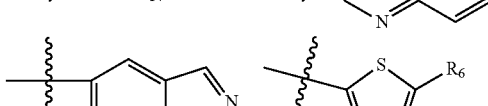

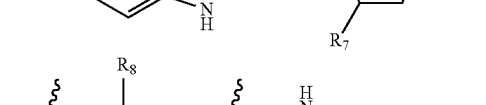

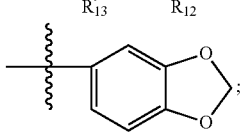

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

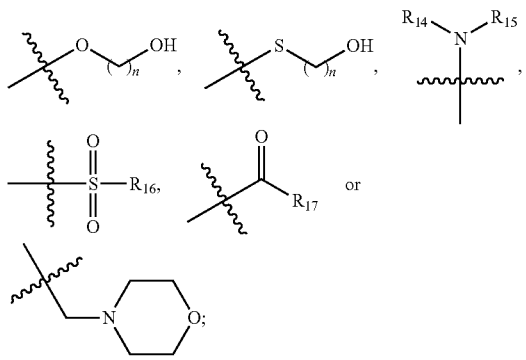

n=1-4; $R_{14}$ and $R_{15}$ are independently —H, $C_1$-$C_4$ alkyl, $C_1$-$C_6$ alkenyl,

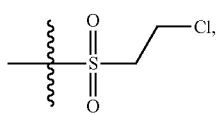 [SMILES: *S(=O)(=O)CCCl]

t-butyloxycarboryl,

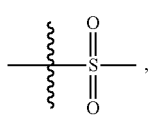 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

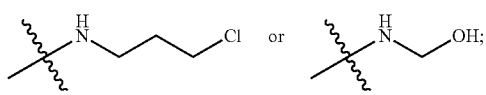

$R_{17}$ is —NH$_2$,

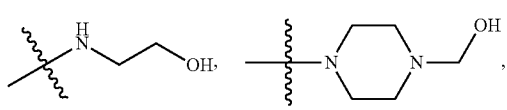

—OH or halogen.

More preferably, $R_4$-$R_9$ are independently —H, $C_1$-$C_4$ alkyl, $C_1$-$C_4$ alkoxy, —NH$_2$, —COOH, $C_1$-$C_4$ alkyl amino or

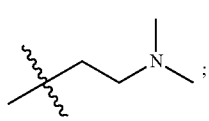 [SMILES: *CCN(C)C]

$R_1$ is halogen,

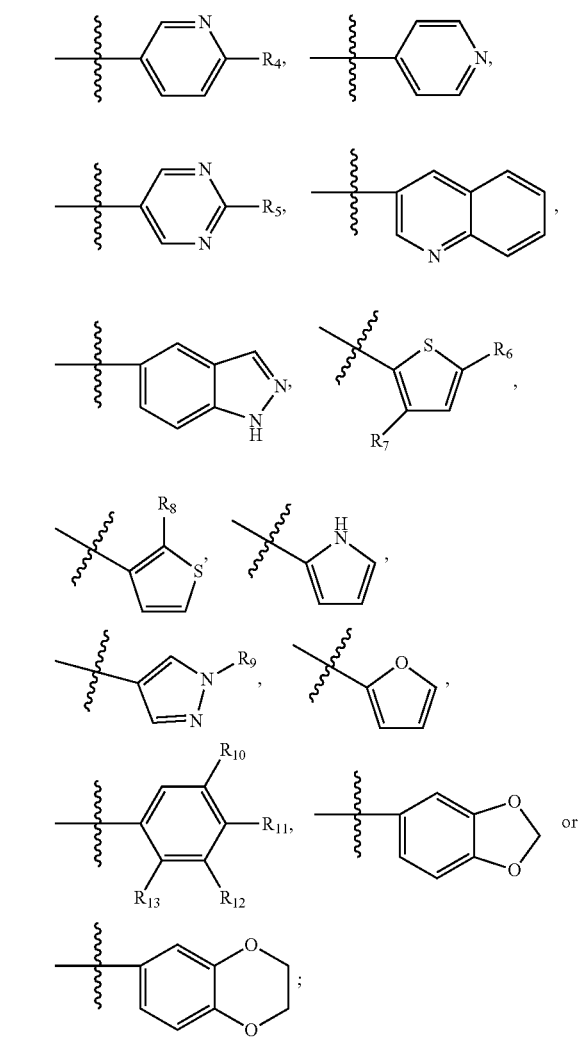

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

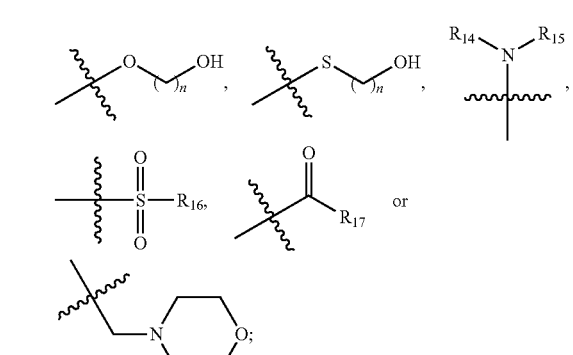

n=1-4; $R_{14}$ and $R_{15}$ are independently —H, $C_1$-$C_4$ alkyl, $C_1$-$C_6$ alkenyl,

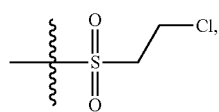 [SMILES: *S(=O)(=O)CCCl]

t-butyloxycarboryl,

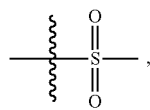 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

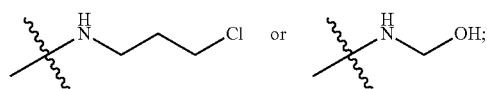

$R_{17}$ is —$NH_2$,

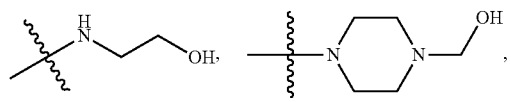

—OH or halogen.

More preferably, $R_4$-$R_9$ are independently —H, $C_1$-$C_4$ alkyl, methoxy, —$NH_2$, —COOH, methylamino or

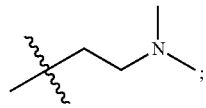 [SMILES: *CCN(C)C]

$R_1$ is halogen,

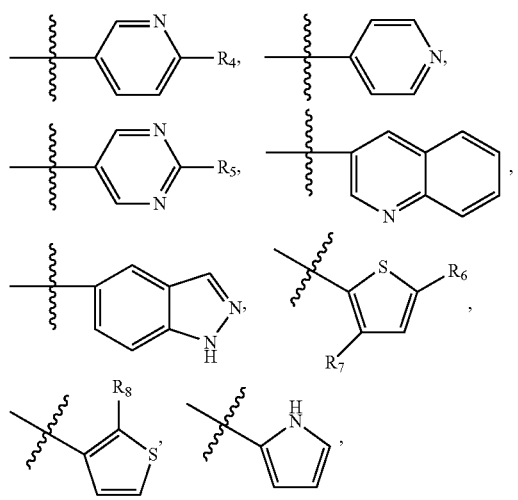

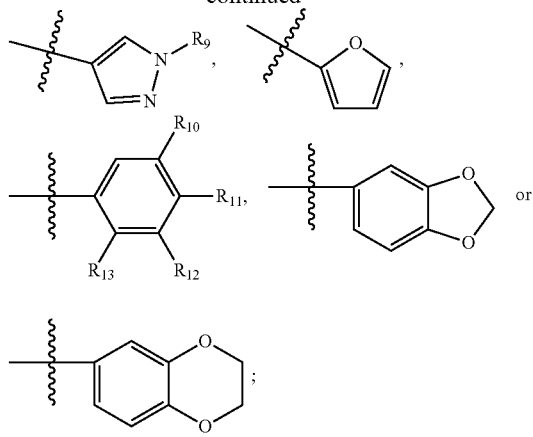

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

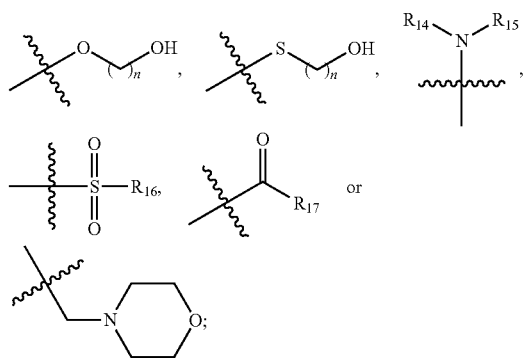

n=1-4; $R_{14}$ and $R_{15}$ are independently —H, $C_1$-$C_4$ alkyl, $C_1$-$C_6$ alkenyl,

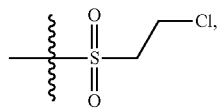

t-butyloxycarboryl,

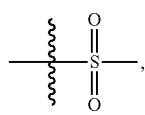

$C_1$-$C_4$ alkoxy or halogen; $R_{16}$ is $C_1$-$C_4$ alkyl, $C_1$-$C_4$ alkoxy, halogen,

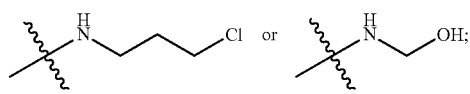

$R_{17}$ is —$NH_2$,

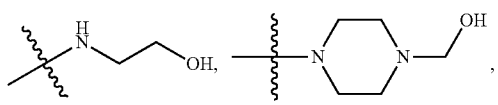

Preferably, $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

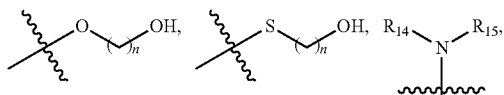

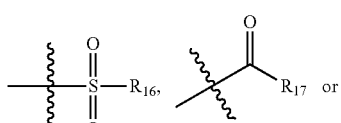

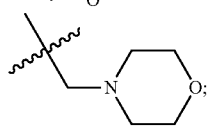

n=1-4; $R_1$ is halogen,

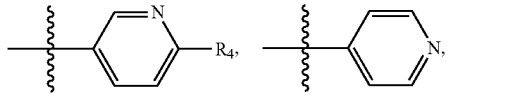

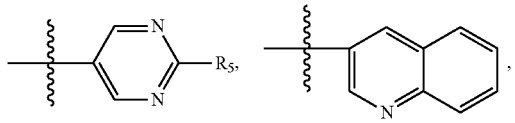

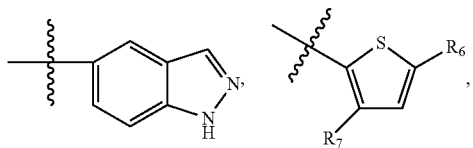

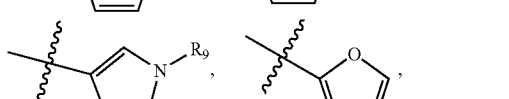

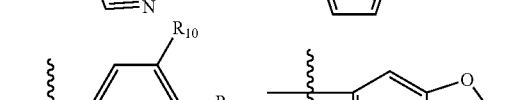

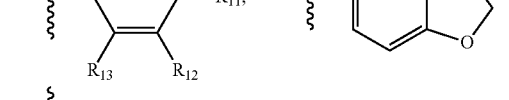

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

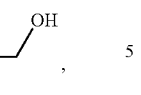

$R_{14}$ and $R_{15}$ are independently —H, $C_1$-$C_4$ alkyl, $C_1$-$C_6$ alkenyl,

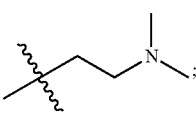 [SMILES: *CCN(C)C]

t-butyloxycarboryl,

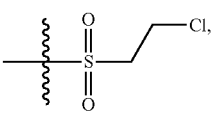 [SMILES: *S(=O)(=O)CCCl]

$C_1$-$C_4$ alkoxy or halogen; $R_{16}$ is $C_1$-$C_4$ alkyl, $C_1$-$C_4$ alkoxy, halogen,

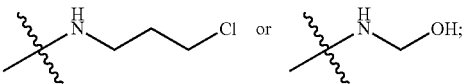

$R_{17}$ is —$NH_2$,

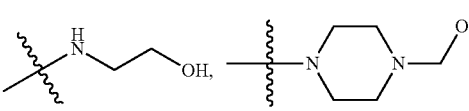

—OH or halogen.

More preferably, $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

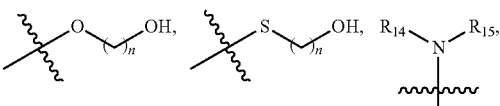

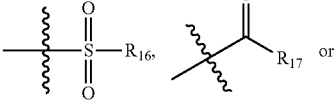

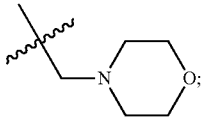

n=1 or 2; $R_1$ is halogen,

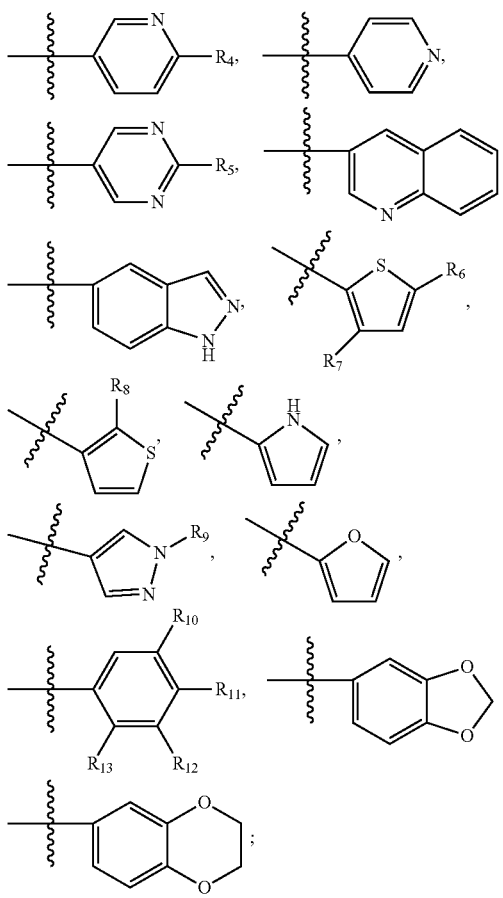

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —NH$_2$, —COOH, $C_1$-$C_4$ alkyl amino or

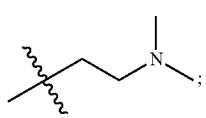 [SMILES: *CCN(C)C]

$R_{14}$ and $R_{15}$ are independently —H, $C_1$-$C_4$ alkyl, $C_1$-$C_6$ alkenyl,

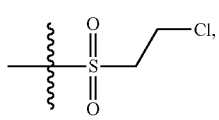 [SMILES: *S(=O)(=O)CCCl]

t-butyloxycarboryl,

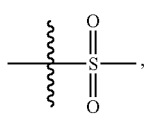 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

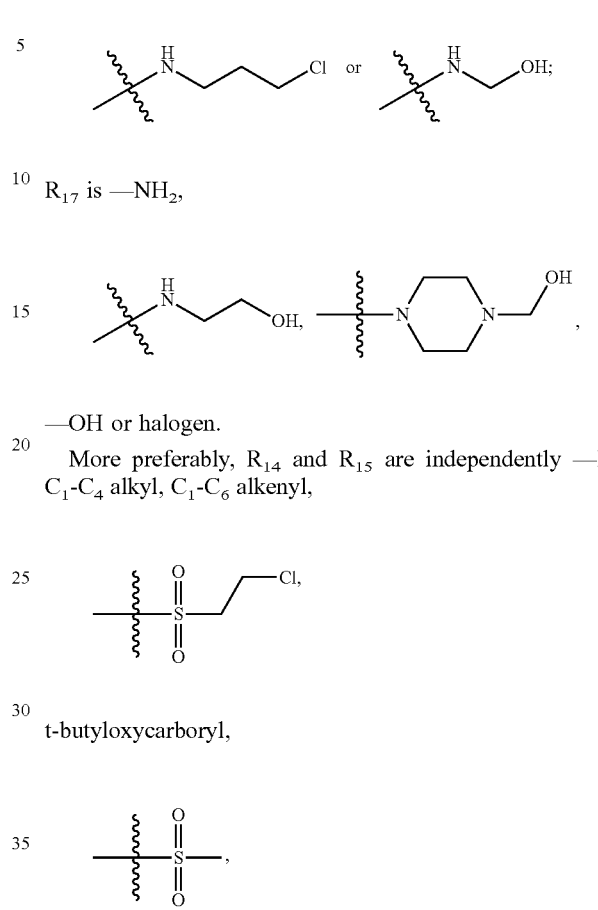

—OH or halogen.

More preferably, $R_{14}$ and $R_{15}$ are independently —H, $C_1$-$C_4$ alkyl, $C_1$-$C_6$ alkenyl,

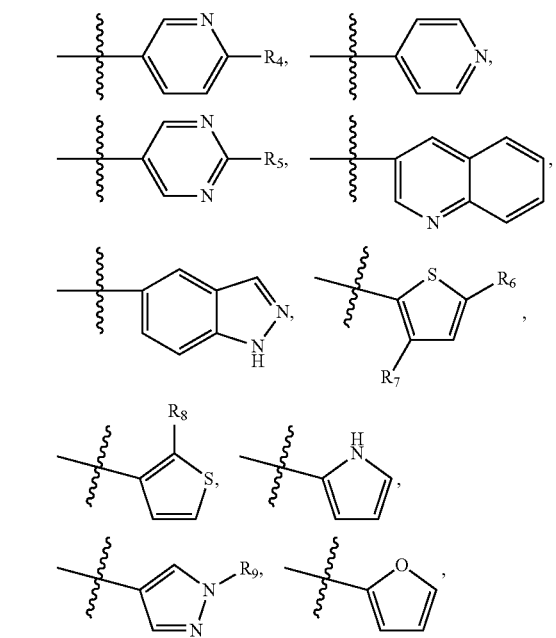

$C_1$-$C_4$ alkoxy or halogen; $R_1$ is halogen,

-continued

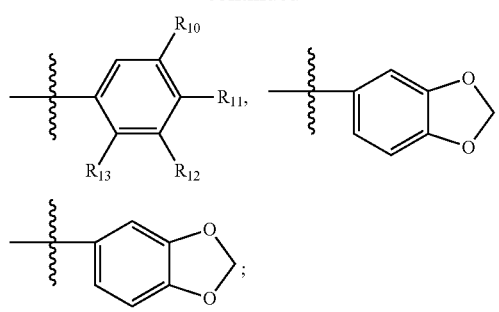

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —NH$_2$, —COOH, $C_1$-$C_4$ alkyl amino or

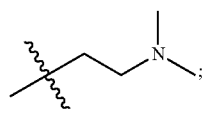 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, —NH$_2$, an alkyl substituted by $C_1$-$C_4$ hydroxy,

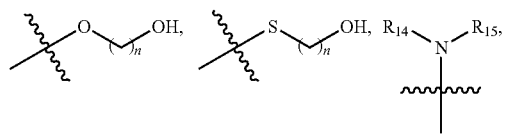

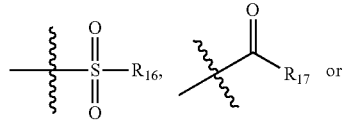

n=1-4; $R_{16}$ is $C_1$-$C_4$ alkyl, $C_1$-$C_4$ alkoxy, halogen,

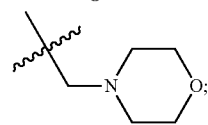

$R_{17}$ is —NH$_2$,

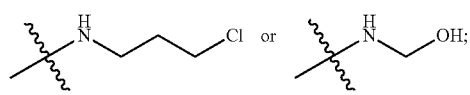

—OH or halogen.

More preferably, $R_{14}$ and $R_{15}$ are independently —H, $C_1$-$C_4$ alkyl, $C_1$-$C_6$ alkenyl,

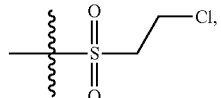

t-butyloxycarboryl or

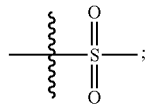 [SMILES: *S(C)(=O)=O]

$R_1$ is halogen,

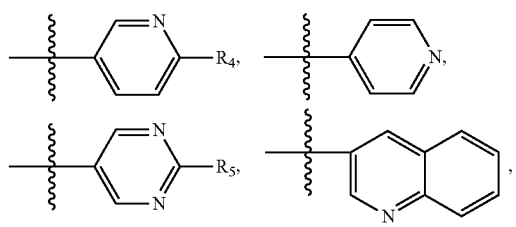

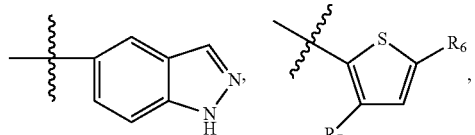

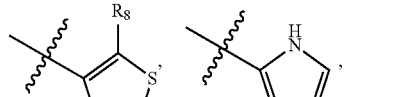

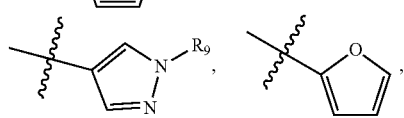

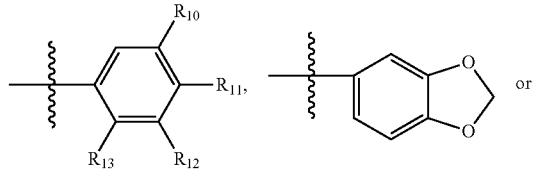

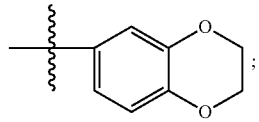

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —NH$_2$, —COOH, $C_1$-$C_4$ alkyl amino or

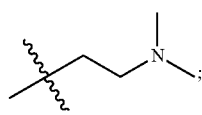 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, —NH$_2$, an alkyl substituted by $C_1$-$C_4$ hydroxy,

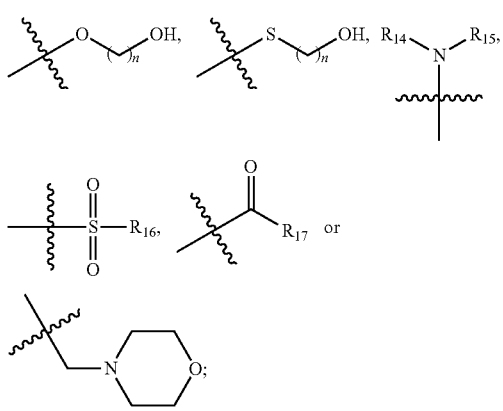

n=1-4; R$_{16}$ is C$_1$-C$_4$ alkyl, C$_1$-C$_4$ alkoxy, halogen,

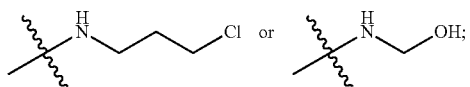

R$_{17}$ is —NH$_2$,

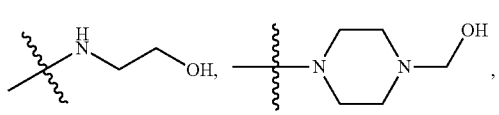

—OH or halogen.

Preferably, R$_{16}$ is C$_1$-C$_4$ alkyl,

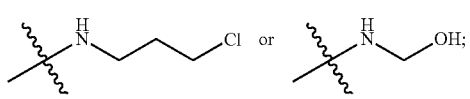

R$_1$ is halogen,

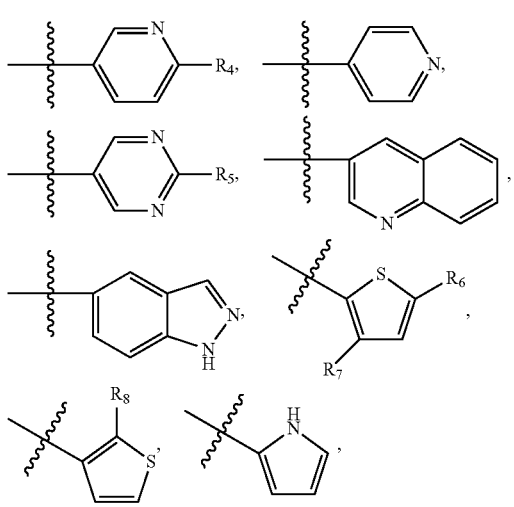

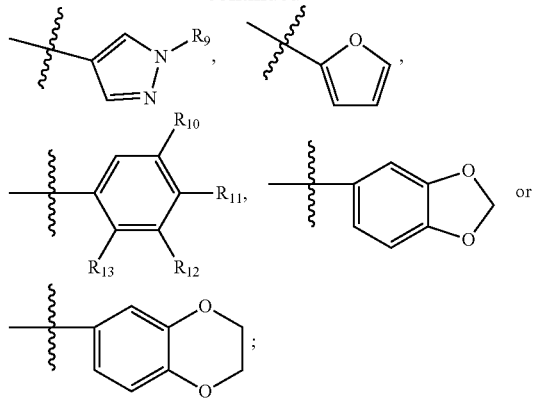

R$_2$ and R$_3$ are independently —H, C$_1$-C$_4$ alkyl or C$_3$-C$_8$ cycloalkyl; R$_4$-R$_9$ are independently —H, C$_1$-C$_4$ alkyl, C$_1$-C$_4$ alkoxy, —NH$_2$, —COOH, C$_1$-C$_4$ alkyl amino or

R$_{10}$-R$_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

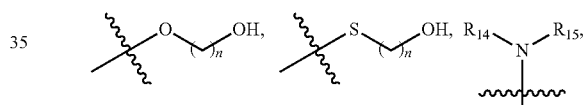

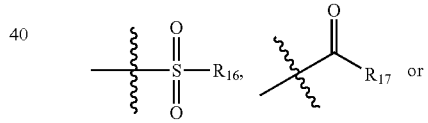

n=1-4; R$_{14}$ and R$_{15}$ are independently —H, C$_1$-C$_4$ alkyl, C$_1$-C$_6$ alkenyl,

t-butyloxycarboryl or

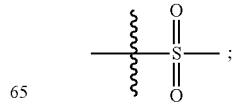

$R_{17}$ is —$NH_2$,

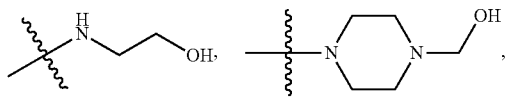

—OH or halogen.

More preferably, $R_1$ is halogen,

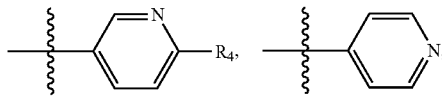

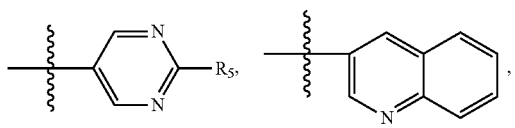

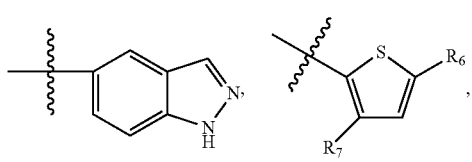

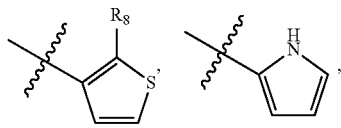

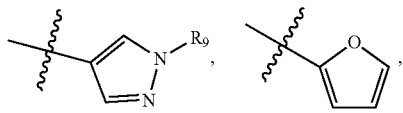

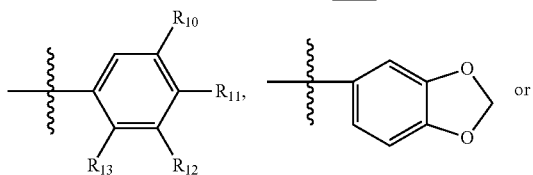

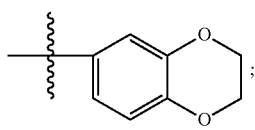

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

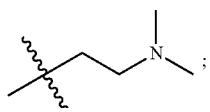 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

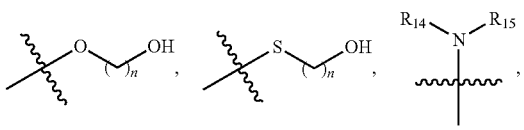

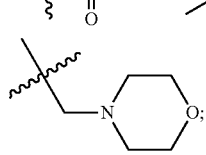

n=1-4; $R_{14}$ and $R_{15}$ are independently —H, $C_1$-$C_4$ alkyl, $C_1$-$C_6$ alkenyl,

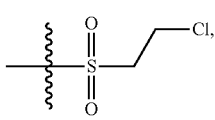 [SMILES: *S(=O)(=O)CCCl]

t-butyloxycarboryl or

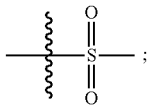 [SMILES: *S(C)(=O)=O]

$R_{16}$ is $C_1$-$C_4$ alkyl,

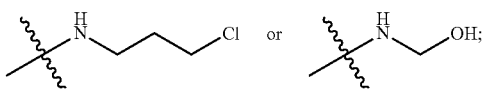

$R_{17}$ is —$NH_2$,

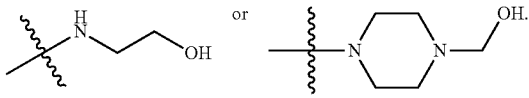

Most preferably, $R_1$ is —Cl,

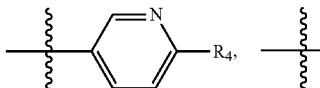

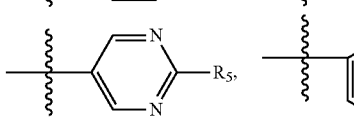

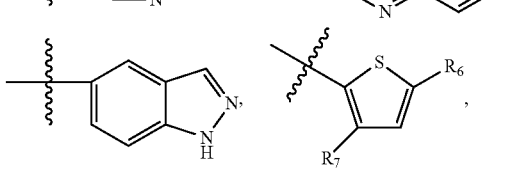

-continued

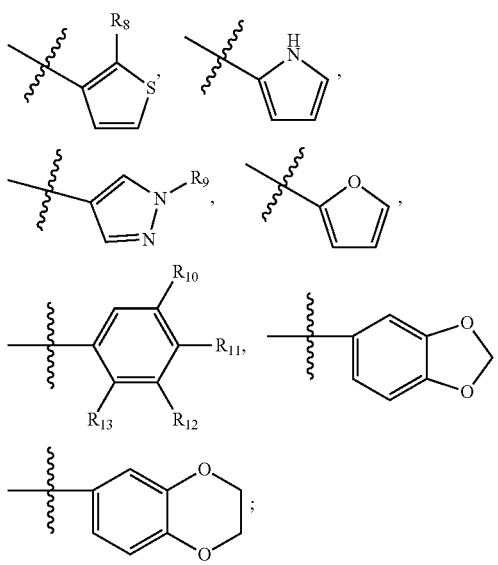

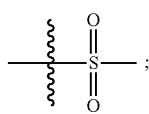 [SMILES: *S(C)(=O)=O]

$R_{16}$ is $C_1$-$C_4$ alkyl,

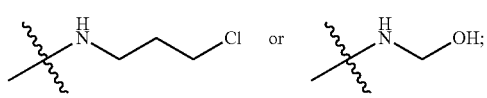

$R_{17}$ is —$NH_2$,

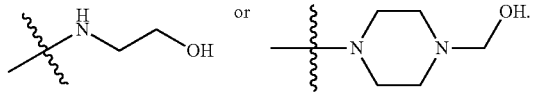

$R_2$ and $R_3$ are independently —H, $C_1$-$C_4$ alkyl or cyclopentyl alkyl; $R_4$-$R_9$ are independently —H, $C_1$-$C_4$ alkyl, methoxy, —$NH_2$, —COOH, methylamino or

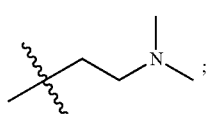 [SMILES: *CCN(C)C]

$R_{10}$-$R_{13}$ are independently —H, $C_1$-$C_4$ alkyl, methoxy, —OH, —$CF_3$, —Cl, —$NH_2$, an alkyl substituted by $C_1$-$C_4$ hydroxy,

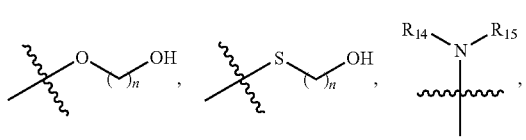

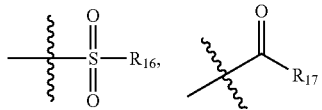

n=1 or 2; $R_{14}$ and $R_{15}$ are independently —H, $C_1$-$C_4$ alkyl, $C_1$-$C_6$ alkenyl,

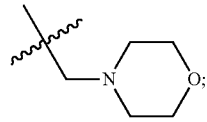

t-butyloxycarboryl or

Said purinyl-N-hydroxyl pyrimidine formamide derivative, when X is O and $R_2$ is methyl, the structure of which is as shown in Formula III:

Formula III

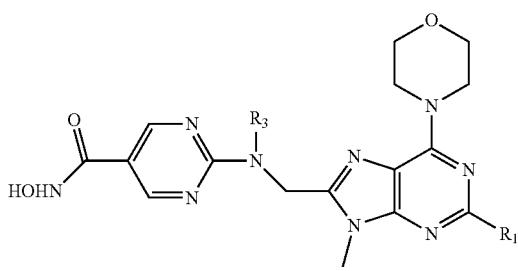

wherein, $R_1$ is $C_1$-$C_4$ alkyl, $C_1$-$C_4$ alkoxy, —OH, halogen, $C_3$-$C_8$ cycloalkyl, —$NH_2$,

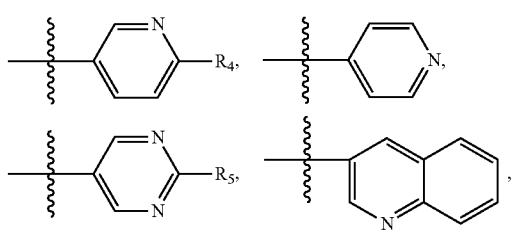

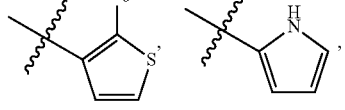

-continued

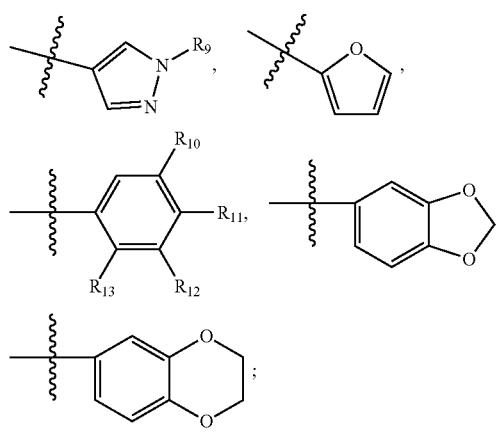

R₃ is —H, C₁-C₄ alkyl, C₁-C₄ alkoxy, —OH, halogen or C₃-C₈ cycloalkyl;

R₄-R₉ are independently —H, C₁-C₄ alkyl, C₁-C₄ alkoxy, —OH, halogen, C₃-C₈ cycloalkyl, —NH₂, —COOH, C₁-C₄ alkyl amino or

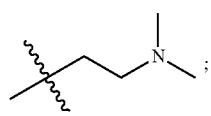

R₁₀-R₁₃ are independently —H, C₁-C₄ alkyl, C₁-C₄ alkoxy, —OH, —CF₃, halogen, C₃-C₈ cycloalkyl, —NH₂, an alkyl substituted by C₁-C₄ hydroxy,

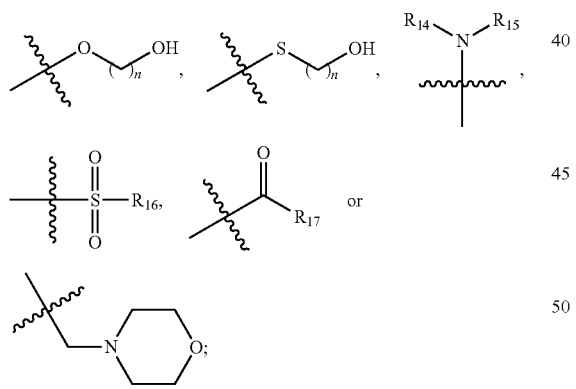

n=1-4;

R₁₄ and R₁₅ are independently —H, C₁-C₄ alkyl, C₁-C₆ alkenyl,

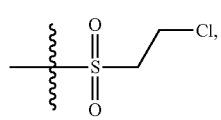 [SMILES: *S(=O)(=O)CCCl]

t-butyloxycarboryl,

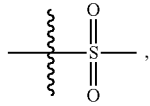 [SMILES: *S(C)(=O)=O]

C₁-C₄ alkoxy or halogen;

R₁₆ is C₁-C₄ alkyl, C₁-C₄ alkoxy, halogen,

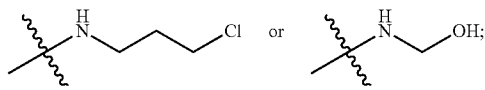

R₁₇ is —NH₂,

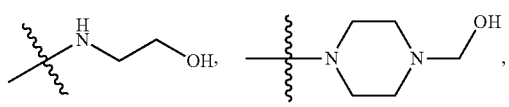 [SMILES: *NCCO ; *N1CCN(CO)CC1]

—OH or halogen.

As a preferred scheme of the Invention, R₁ is halogen, C₃-C₈ cycloalkyl, —NH₂,

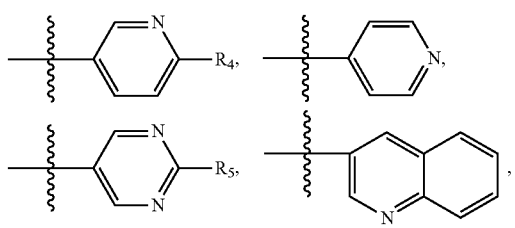

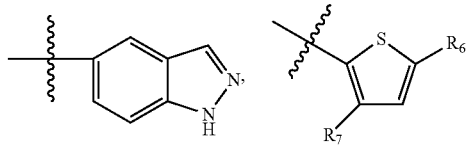

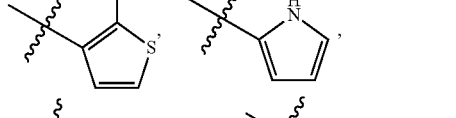

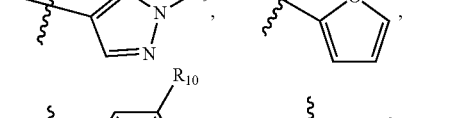

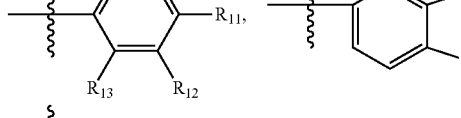

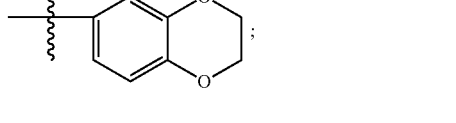

R₃ is —H, C₁-C₄ alkyl, C₁-C₄ alkoxy, —OH, halogen or C₃-C₈ cycloalkyl; R₄-R₉ are independently —H, C₁-C₄ alkyl, C₁-C₄ alkoxy, —OH, halogen, C₃-C₈ cycloalkyl, —NH₂, —COOH, C₁-C₄ alkyl amino or

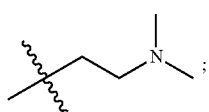

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

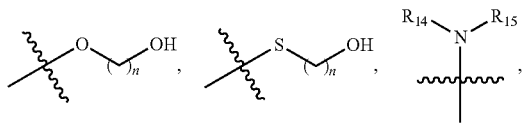

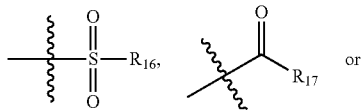

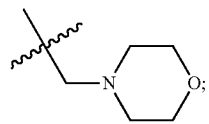

n=1-4; $R_{14}$ and $R_{15}$ are independently —H, $C_1$-$C_4$ alkyl, $C_1$-$C_6$ alkenyl,

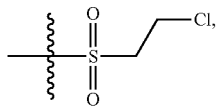

t-butyloxycarboryl,

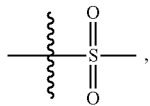 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

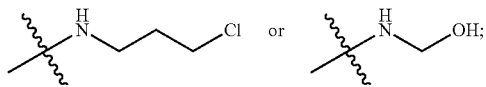

$R_{17}$ is —NH$_2$,

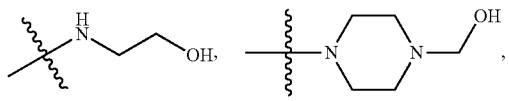

—OH or halogen.

Preferably, $R_1$ is halogen,

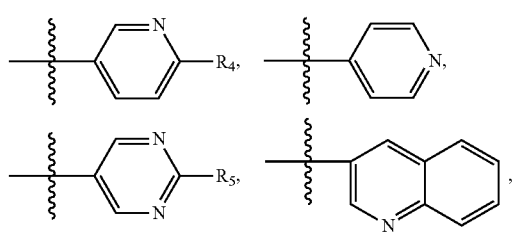

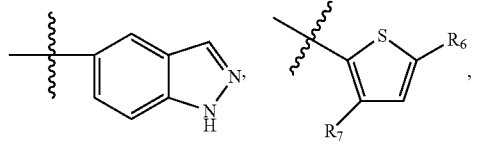

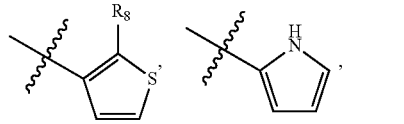

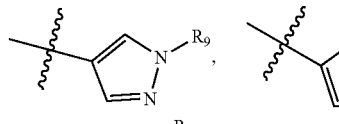

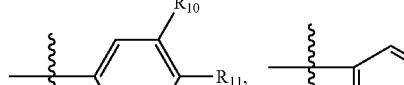

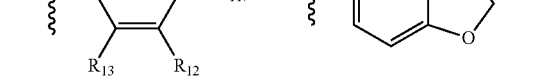

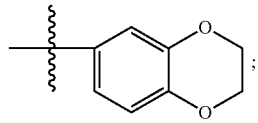

$R_3$ is —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

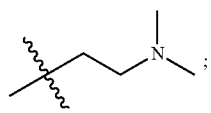

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

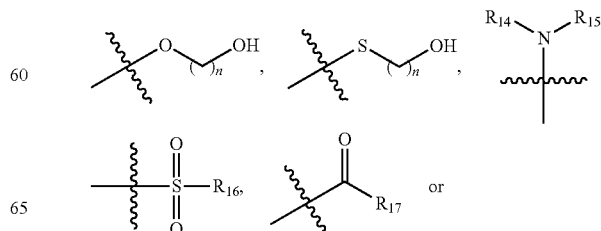

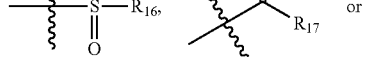

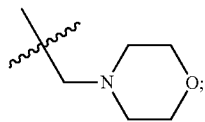

n=1-4; R$_{14}$ and R$_{15}$ are independently —H, C$_1$-C$_4$ alkyl, C$_1$-C$_6$ alkenyl,

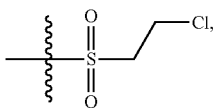

t-butyloxycarboryl,

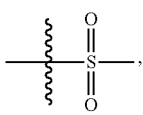 [SMILES: *S(C)(=O)=O]

C$_1$-C$_4$ alkoxy or halogen; R$_{16}$ is C$_1$-C$_4$ alkyl, C$_1$-C$_4$ alkoxy, halogen,

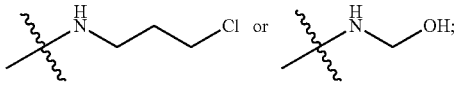

R$_{17}$ is —NH$_2$,

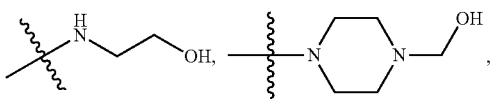

—OH or halogen.

More preferably, R$_1$ is —Cl,

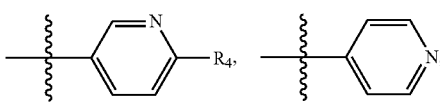

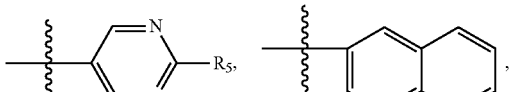

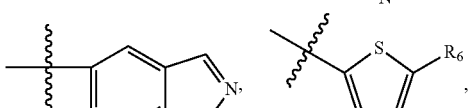

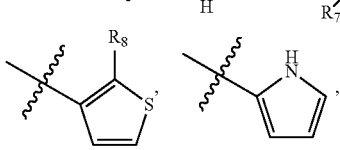

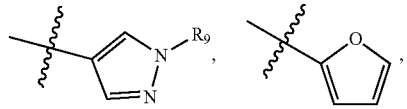

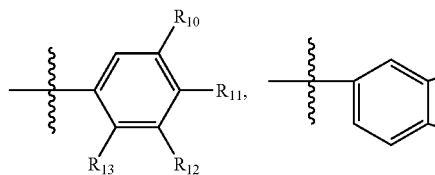

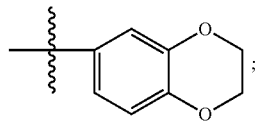

R$_3$ is —H, C$_1$-C$_4$ alkyl, C$_1$-C$_4$ alkoxy, —OH, halogen or C$_3$-C$_8$ cycloalkyl; R$_4$-R$_9$ are independently —H, C$_1$-C$_4$ alkyl, C$_1$-C$_4$ alkoxy, —OH, halogen, C$_3$-C$_8$ cycloalkyl, —NH$_2$, —COOH, C$_1$-C$_4$ alkyl amino or

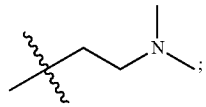 [SMILES: *CCN(C)C]

R$_{10}$-R$_{13}$ are independently —H, C$_1$-C$_4$ alkyl, C$_1$-C$_4$ alkoxy, —OH, —CF$_3$, halogen, C$_3$-C$_8$ cycloalkyl, —NH$_2$, an alkyl substituted by C$_1$-C$_4$ hydroxy,

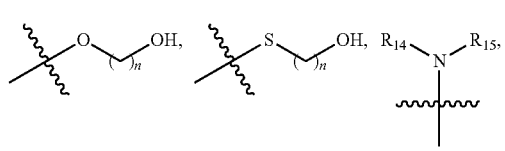

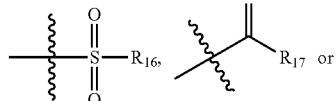

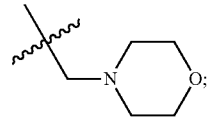

n=1-4; R$_{14}$ and R$_{15}$ are independently —H, C$_1$-C$_4$ alkyl, C$_1$-C$_6$ alkenyl,

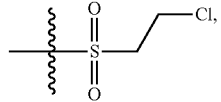 [SMILES: *S(=O)(=O)CCCl]

t-butyloxycarboryl,

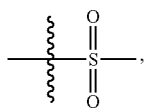 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

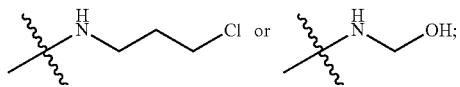

$R_{17}$ is —$NH_2$,

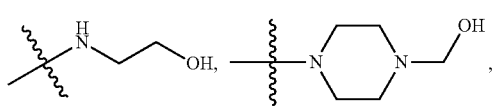

—OH or halogen.

Preferably, $R_3$ is —H, $C_1$-$C_4$ alkyl, $C_1$-$C_4$ alkoxy or $C_3$-$C_8$ cycloalkyl; $R_1$ is halogen,

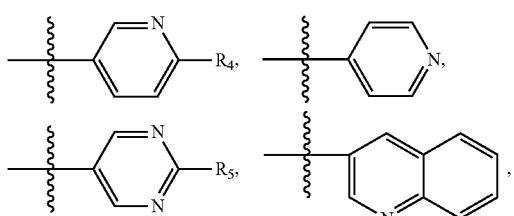

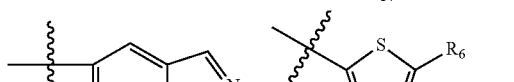

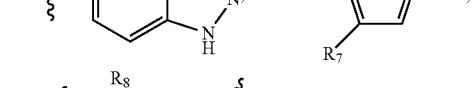

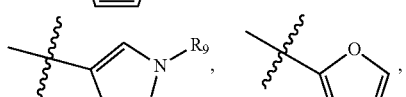

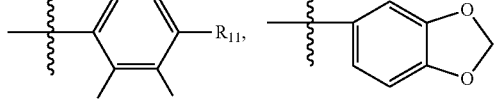

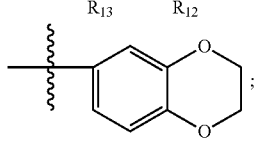

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

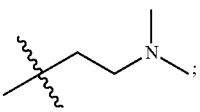 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

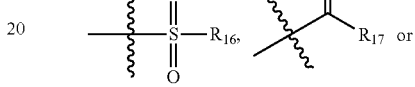

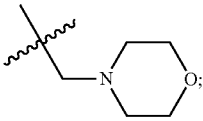

n=1-4; $R_{14}$ and $R_{15}$ are independently —H, $C_1$-$C_4$ alkyl, $C_1$-$C_6$ alkenyl,

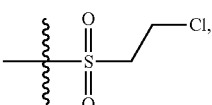

t-butyloxycarboryl,

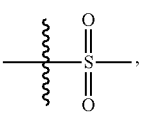

$C_1$-$C_4$ alkoxy or halogen; $R_{16}$ is $C_1$-$C_4$ alkyl, $C_1$-$C_4$ alkoxy, halogen,

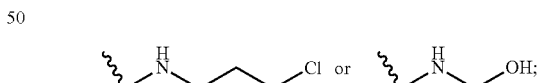

$R_{17}$ is —$NH_2$,

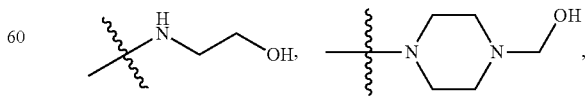

—OH or halogen.

More preferably, $R_3$ is —H, $C_1$-$C_4$ alkyl or $C_3$-$C_8$ cycloalkyl; $R_1$ is halogen,

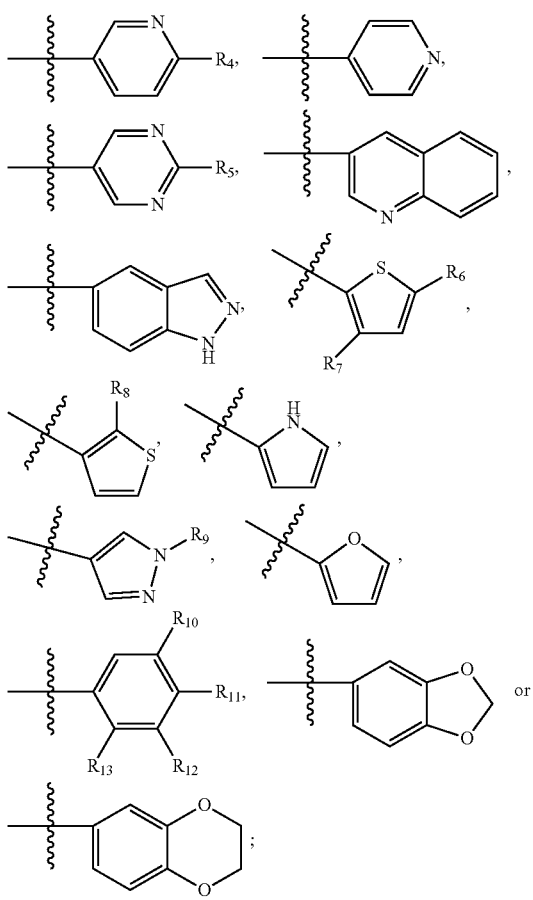

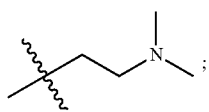 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

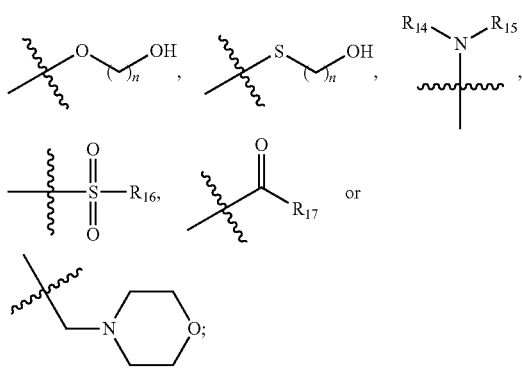

n=1-4; $R_{14}$ and $R_{15}$ are independently —H, $C_1$-$C_4$ alkyl, $C_1$-$C_6$ alkenyl,

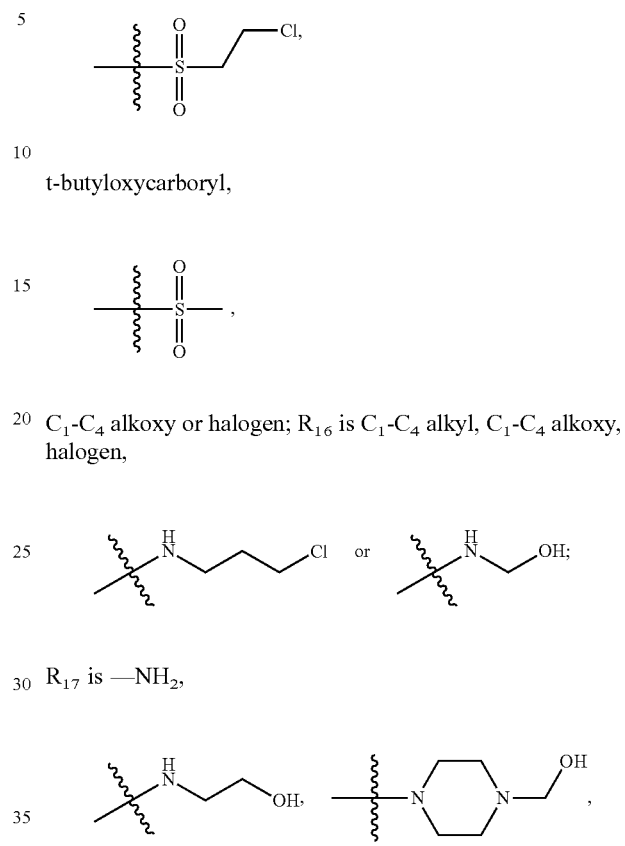

t-butyloxycarboryl, $C_1$-$C_4$ alkoxy or halogen; $R_{16}$ is $C_1$-$C_4$ alkyl, $C_1$-$C_4$ alkoxy, halogen, $R_{17}$ is —$NH_2$, —OH or halogen.

More preferably, $R_3$ is —H or $C_1$-$C_4$ alkyl; $R_1$ is halogen,

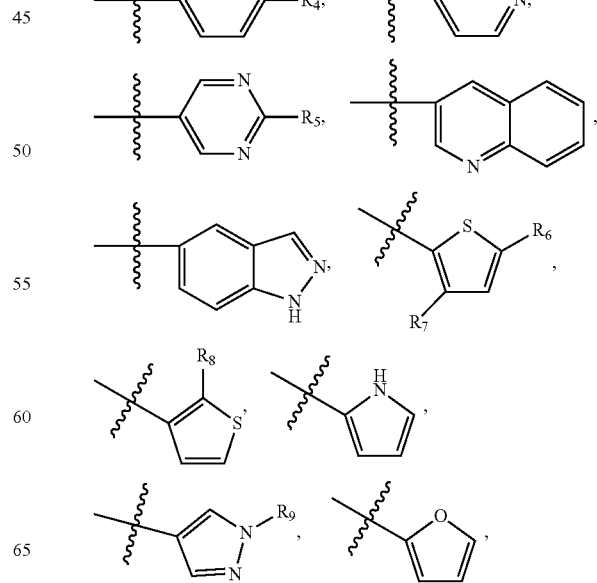

-continued

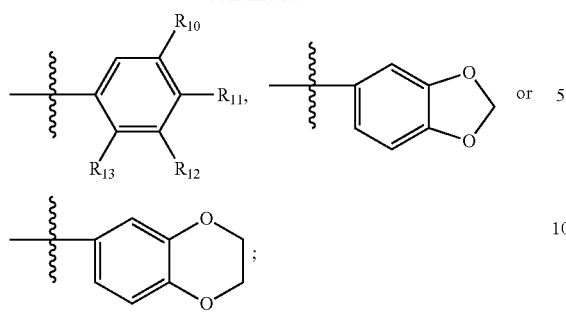

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

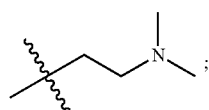 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

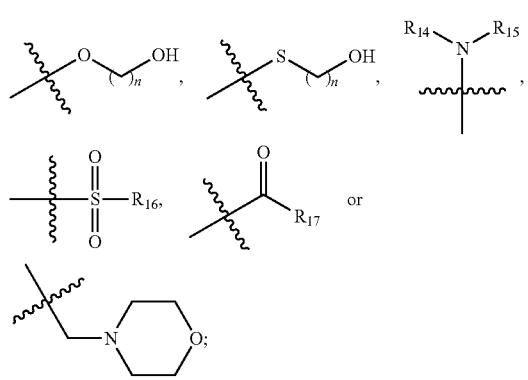

n=1-4; $R_{14}$ and $R_{15}$ are independently —H, $C_1$-$C_4$ alkyl, $C_1$-$C_6$ alkenyl,

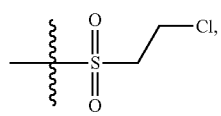

t-butyloxycarboryl,

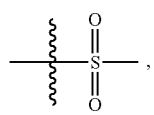 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

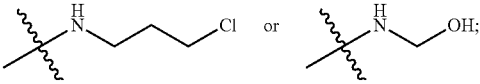

$R_{17}$ is —$NH_2$,

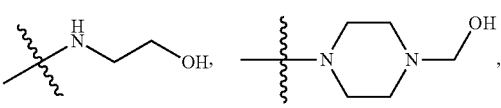

—OH or halogen.

Preferably, $R_4$-$R_9$ are independently —H, $C_1$-$C_4$ alkyl, $C_1$-$C_4$ alkoxy, $C_3$-$C_8$ cycloalkyl, —$NH_2$, —COOH, $C_1$-$C_4$ alkyl amino or

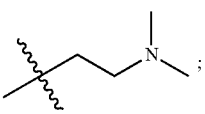 [SMILES: *CCN(C)C]

$R_1$ is halogen,

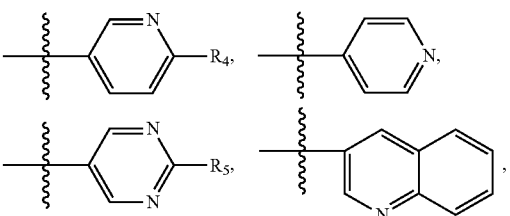

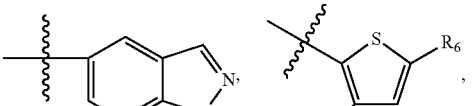

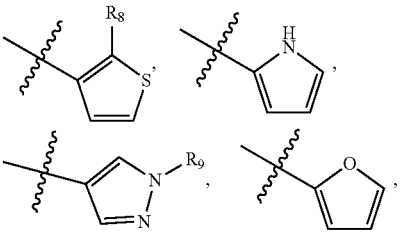

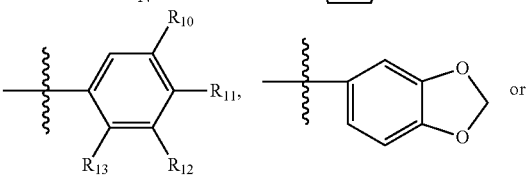

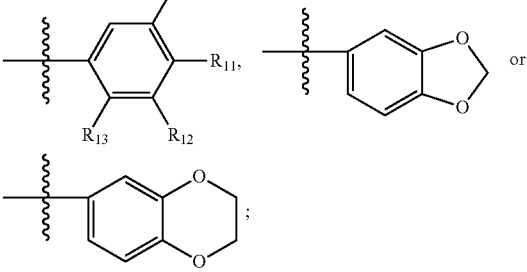

$R_3$ is —H or $C_1$-$C_4$ alkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

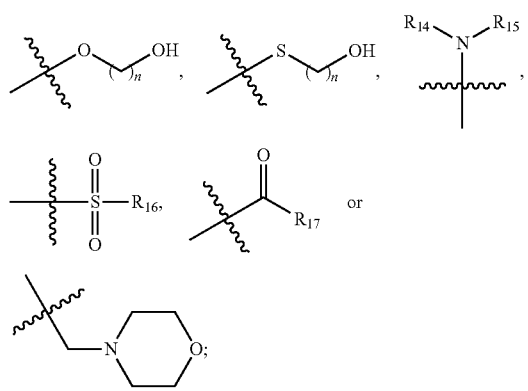

n=1-4; $R_{14}$ and $R_{15}$ are independently —H, $C_1$-$C_4$ alkyl, $C_1$-$C_6$ alkenyl,

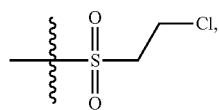 [SMILES: *S(=O)(=O)CCCl]

t-butyloxycarboryl,

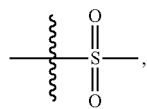 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

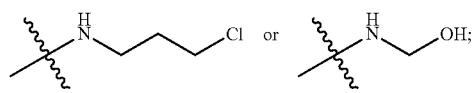

$R_1$ is —$NH_2$,

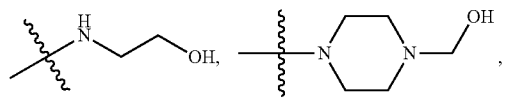

—OH or halogen.

More preferably, $R_4$-$R_9$ are independently —H, $C_1$-$C_4$ alkyl, $C_1$-$C_4$ alkoxy, —$NH_2$, —COOH, $C_1$-$C_4$ alkyl amino or

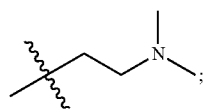 [SMILES: *CCN(C)C]

$R_1$ is halogen,

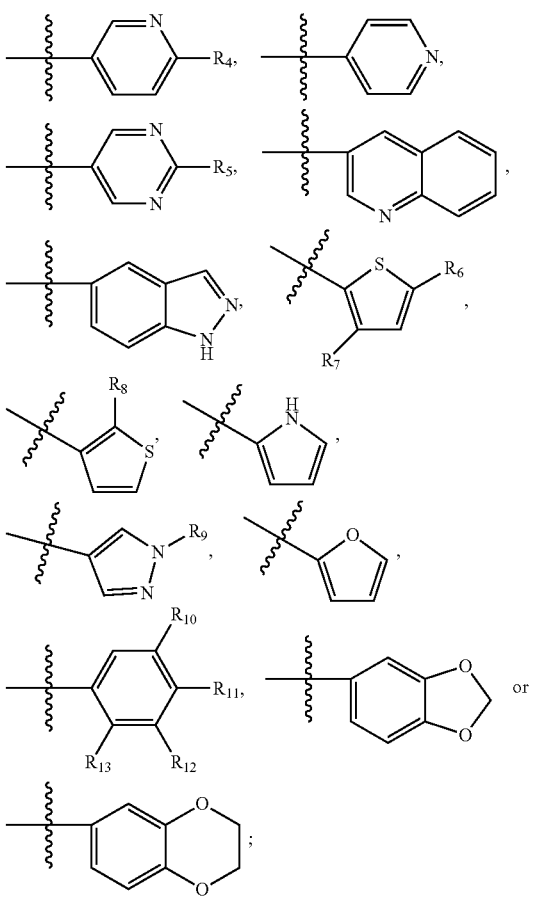

$R_3$ is —H or $C_1$-$C_4$ alkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

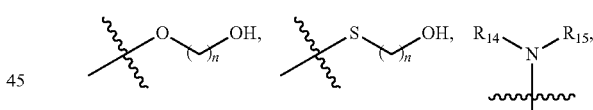

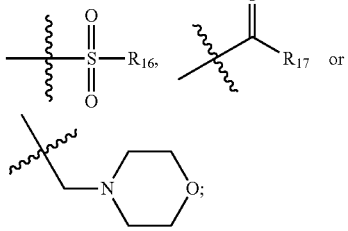

n=1-4; $R_{14}$ and $R_{15}$ are independently —H, $C_1$-$C_4$ alkyl, $C_1$-$C_6$ alkenyl, t-butyloxycarboryl,

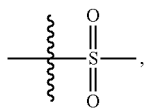 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

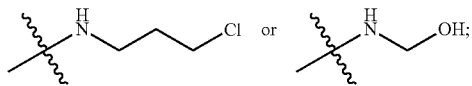

$R_{17}$ is —$NH_2$,

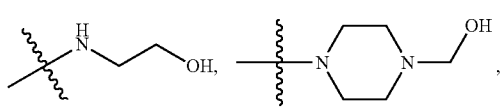

—OH or halogen.

More preferably, $R_4$-$R_9$ are independently —H, $C_1$-$C_4$ alkyl, methoxy, —$NH_2$, —COOH, methylamino or

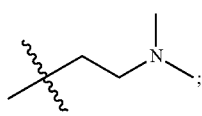

$R_1$ is halogen,

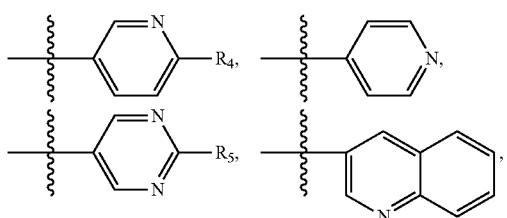

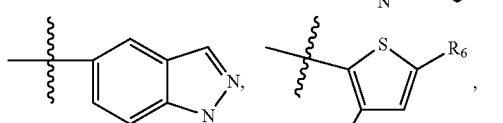

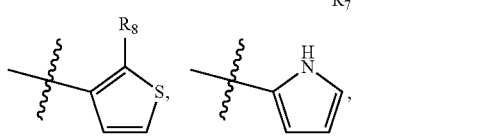

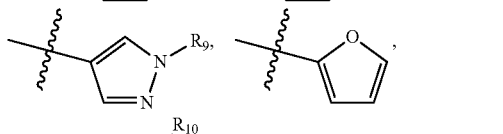

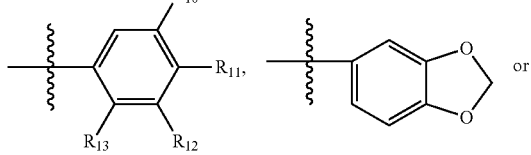

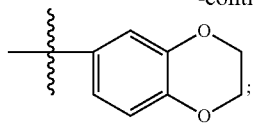

$R_3$ is —H or $C_1$-$C_4$ alkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

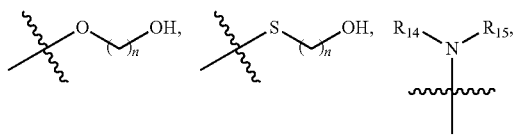

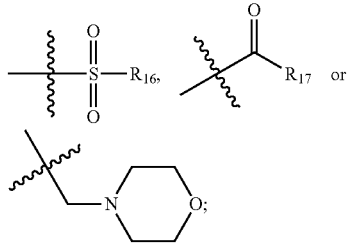

n=1-4; $R_{14}$ and $R_{15}$ are independently —H, $C_1$-$C_4$ alkyl, $C_1$-$C_6$ alkenyl,

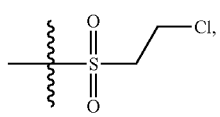 [SMILES: *S(=O)(=O)CCCl]

t-butyloxycarboryl,

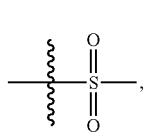

$C_1$-$C_4$ alkoxy or halogen; $R_{16}$ is $C_1$-$C_4$ alkyl, $C_1$-$C_4$ alkoxy, halogen

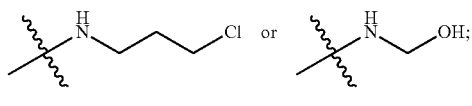

$R_{17}$ is —$NH_2$,

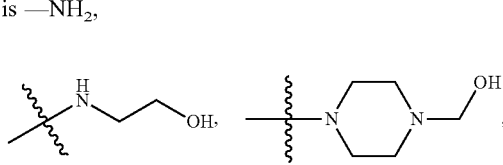

—OH or halogen.

Preferably, $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

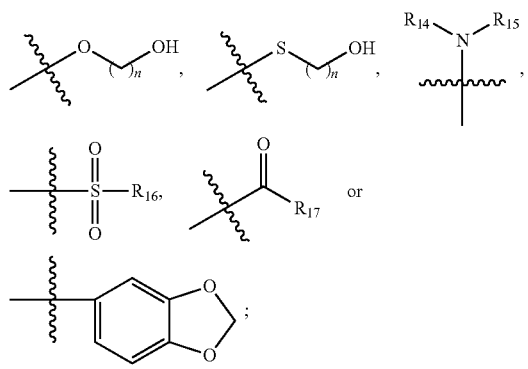

n=1-4; R₁ is halogen,

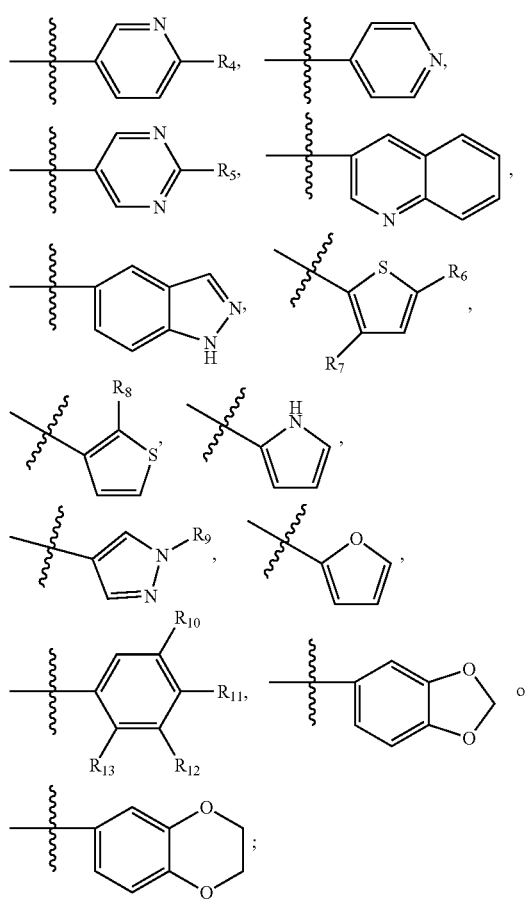

R₃ is —H or $C_1$-$C_4$ alkyl; R₄-R₉ are independently —H, $C_1$-$C_4$ alkyl, $C_1$-$C_4$ alkoxy, —NH₂, —COOH, $C_1$-$C_4$ alkyl amino or

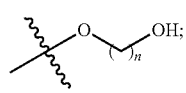

R₁₄ and R₁₅ are independently —H, $C_1$-$C_4$ alkyl, $C_1$-$C_6$ alkenyl,

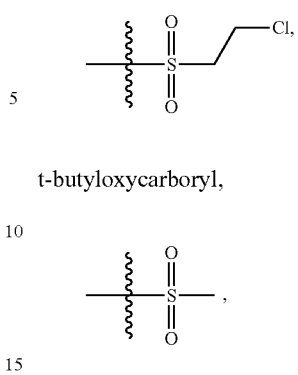

t-butyloxycarboryl,

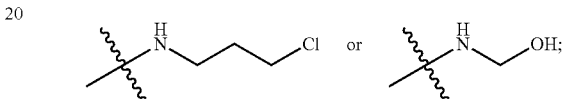

$C_1$-$C_4$ alkoxy or halogen; R₁₆ is $C_1$-$C_4$ alkyl, $C_1$-$C_4$ alkoxy, halogen,

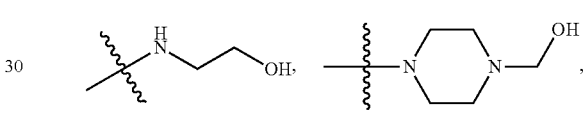

R₁₇ is —NH₂,

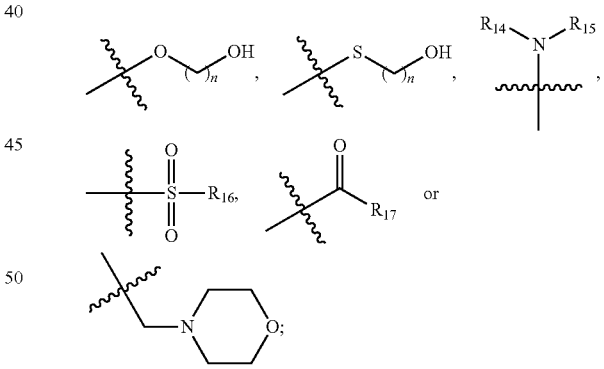

—OH or halogen.

More preferably, R₁₀-R₁₃ are independently —H, $C_1$-$C_4$ alkyl, $C_1$-$C_4$ alkoxy, —OH, —CF₃, halogen, —NH₂, an alkyl substituted by $C_1$-$C_4$ hydroxy,

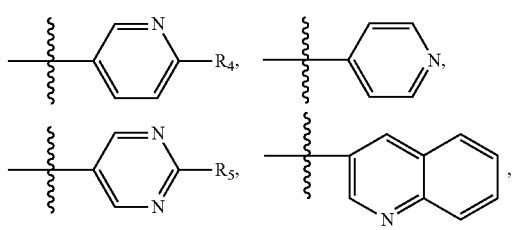

n=1 or 2; R₁ is halogen,

-continued

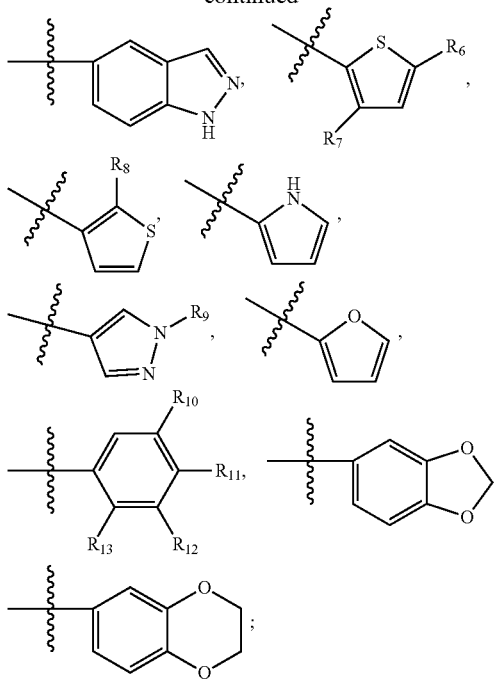

$R_3$ is —H or $C_1$-$C_4$ alkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

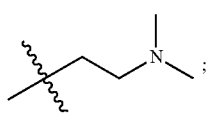

$R_{14}$ and $R_{15}$ are independently —H, $C_1$-$C_4$ alkyl, $C_1$-$C_6$ alkenyl,

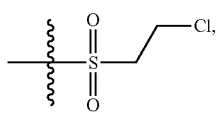

t-butyloxycarboryl,

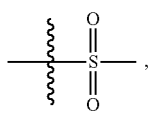 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

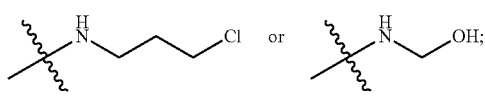

$R_{17}$ is —$NH_2$,

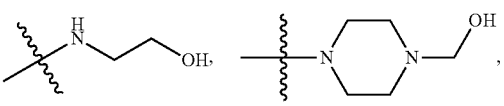 [SMILES: *NCCO ; *N1CCN(CO)CC1]

—OH or halogen.

Preferably, $R_{14}$ and $R_{15}$ are independently —H, $C_1$-$C_4$ alkyl, $C_1$-$C_6$ alkenyl,

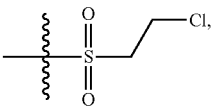

t-butyloxycarboryl,

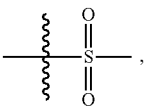 [SMILES: *S(C)(=O)=O]

$C_1$-$C_4$ alkoxy or halogen; $R_1$ is halogen,

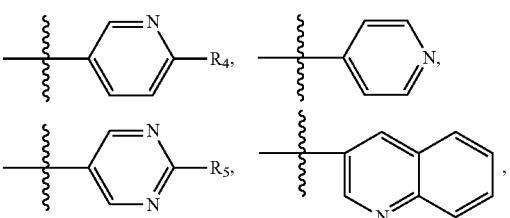

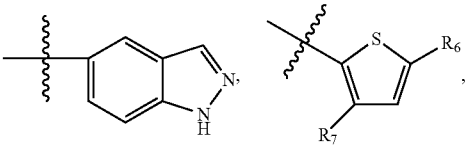

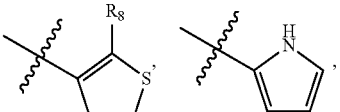

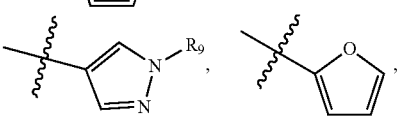

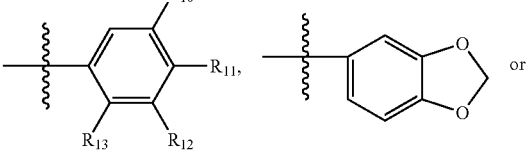

$R_3$ is —H or $C_1$-$C_4$ alkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

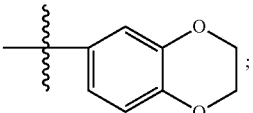

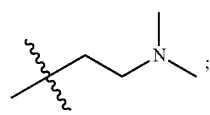 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

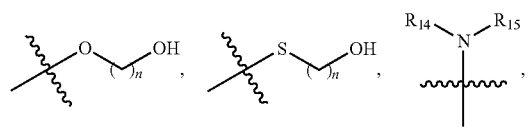

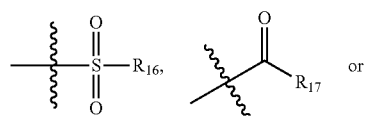

n=1-4; $R_{16}$ is $C_1$-$C_4$ alkyl, $C_1$-$C_4$ alkoxy, halogen,

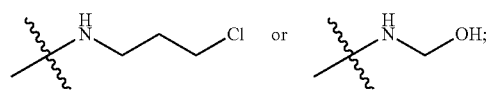

$R_{17}$ is —$NH_2$,

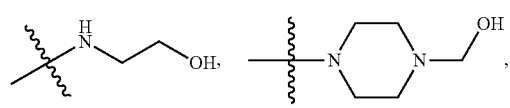 [SMILES: *NCCO ; *N1CCN(CO)CC1]

—OH or halogen.

More preferably, $R_{14}$ and $R_{15}$ are independently —H, $C_1$-$C_4$ alkyl, $C_1$-$C_6$ alkenyl,

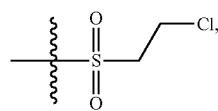 [SMILES: *S(=O)(=O)CCCl]

t-butyloxycarboryl or

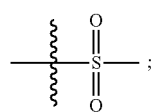 [SMILES: *S(C)(=O)=O]

$R_1$ is halogen,

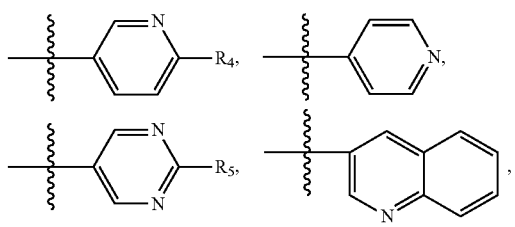

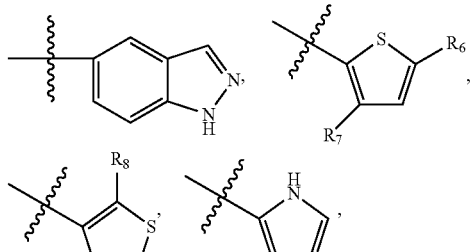

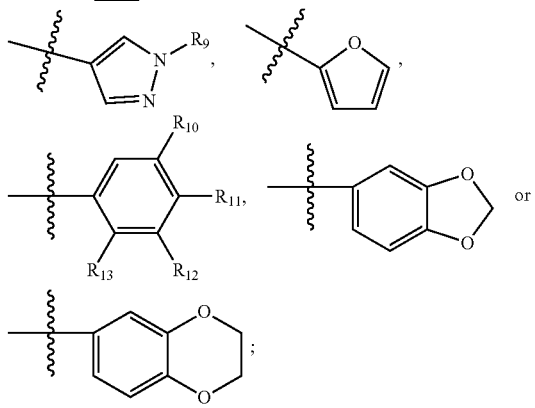

$R_3$ is —H or $C_1$-$C_4$ alkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

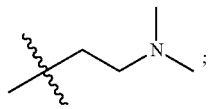 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

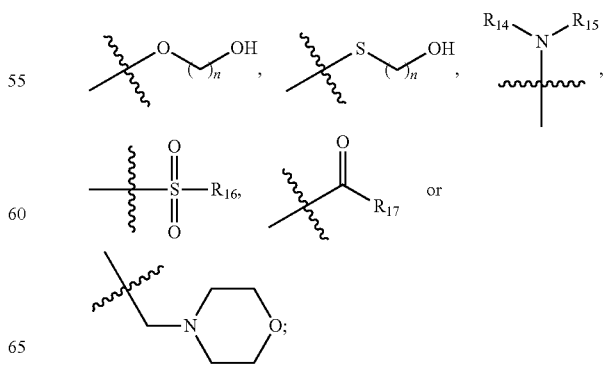

n=1-4; $R_{16}$ is $C_1$-$C_4$ alkyl, $C_1$-$C_4$ alkoxy, halogen,

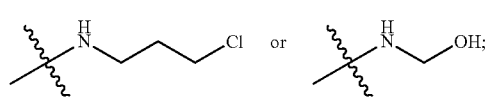

R$_{17}$ is —NH$_2$,

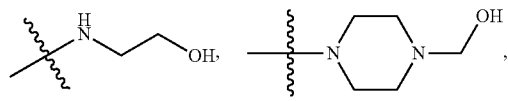

—OH or halogen.

Preferably, R$_{16}$ is C$_1$-C$_4$ alkyl,

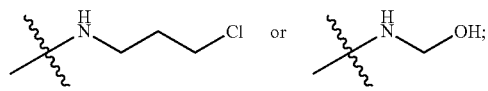

R$_1$ is halogen,

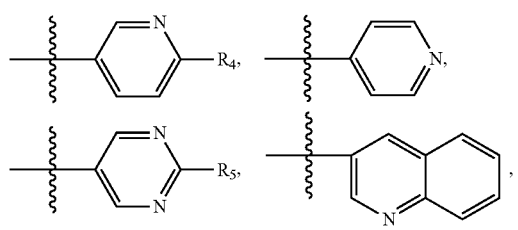

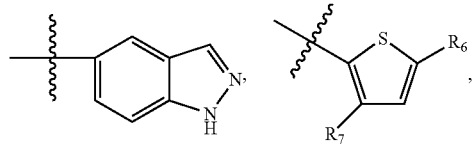

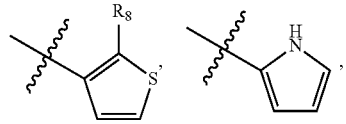

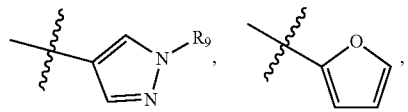

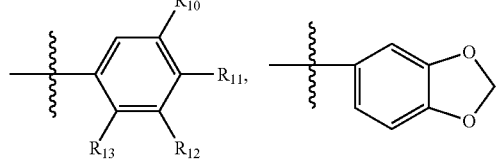

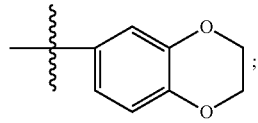

R$_3$ is —H or C$_1$-C$_4$ alkyl; R$_4$-R$_9$ are independently —H, C$_1$-C$_4$ alkyl, C$_1$-C$_4$ alkoxy, —NH$_2$, —COOH, C$_1$-C$_4$ alkyl amino or

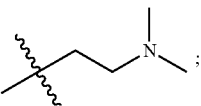

R$_{10}$-R$_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

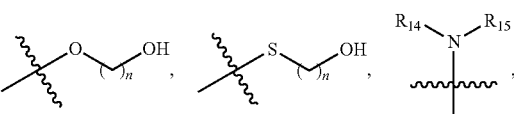

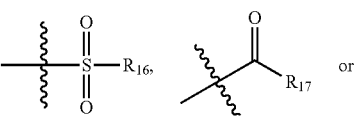

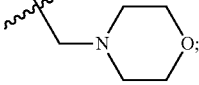

n=1-4; R$_{14}$ and R$_{15}$ are independently —H, C$_1$-C$_4$ alkyl, C$_1$-C$_6$ alkenyl,

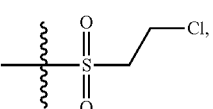

t-butyloxycarboryl or

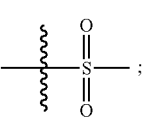

R$_{17}$ is —NH$_2$,

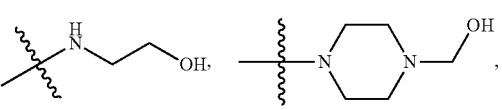

—OH or halogen.

More preferably, R$_1$ is halogen,

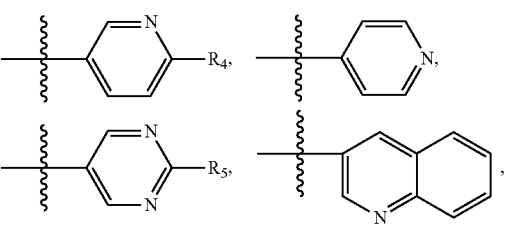

-continued
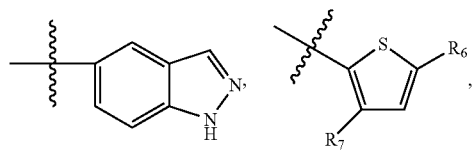
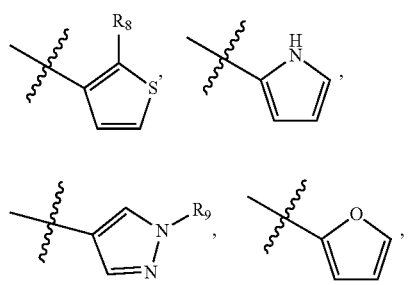
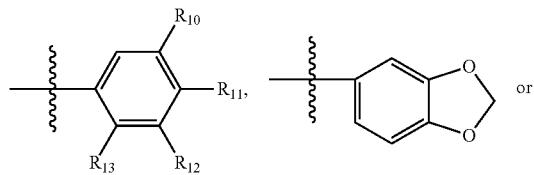
R₃ is —H or C₁-C₄ alkyl; R₄-R₉ are independently —H, C₁-C₄ alkyl, C₁-C₄ alkoxy, —NH₂, —COOH, C₁-C₄ alkyl amino or
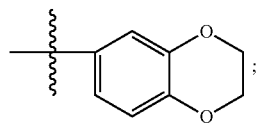
R₁₀-R₁₃ are independently —H, C₁-C₄ alkyl, C₁-C₄ alkoxy, —OH, —CF₃, halogen, —NH₂, an alkyl substituted by C₁-C₄ hydroxy,
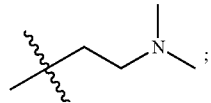 [SMILES: *CCN(C)C]
n=1-4; R₁₄ and R₁₅ are independently —H, C₁-C₄ alkyl, C₁-C₆ alkenyl,
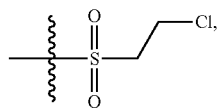
t-butyloxycarboryl or
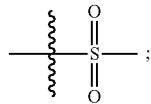 [SMILES: *S(C)(=O)=O]
R₁₆ is C₁-C₄ alkyl,
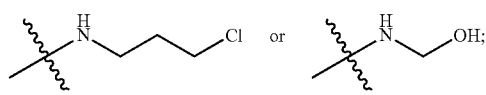
R₁₇ is —NH₂,
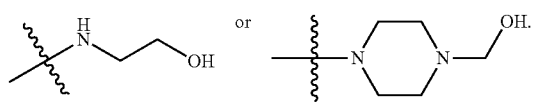
Most preferably, R₁ is —Cl,
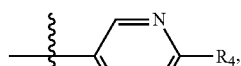 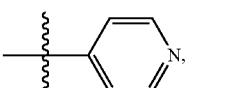
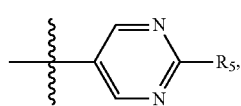 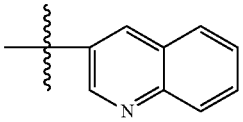
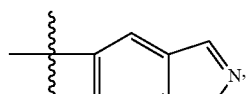 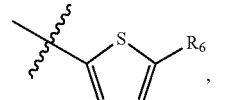
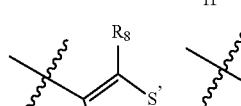 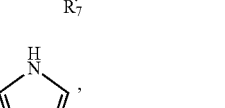
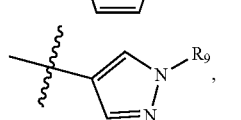 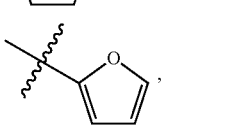
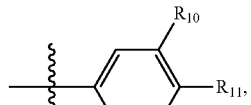 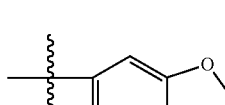 or
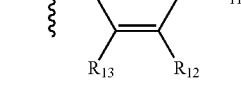 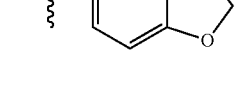

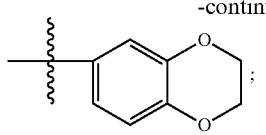

$R_3$ is —H or $C_1$-$C_4$ alkyl; $R_4$-$R_9$ are independently —H, $C_1$-$C_4$ alkyl, methoxy, —NH$_2$, —COOH, methylamino or

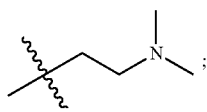 [SMILES: *CCN(C)C]

$R_{10}$-$R_{13}$ are independently —H, $C_1$-$C_4$ alkyl, methoxy, —OH, —CF$_3$, —Cl, —NH$_2$, an alkyl substituted by $C_1$-$C_4$ hydroxy,

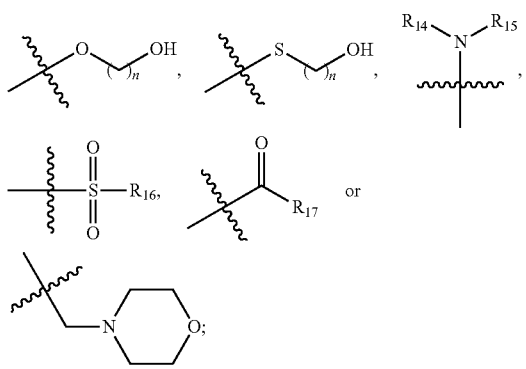

n=1 or 2; $R_{14}$ and $R_{15}$ are independently —H, $C_1$-$C_4$ alkyl, $C_1$-$C_6$ alkenyl,

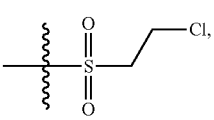 [SMILES: *S(=O)(=O)CCCl]

t-butyloxycarboryl or

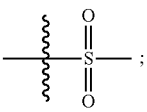 [SMILES: *S(C)(=O)=O]

$R_{16}$ is $C_1$-$C_4$ alkyl,

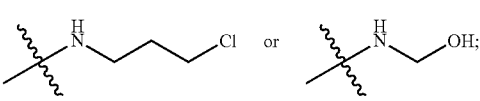

$R_{17}$ is —NH$_2$,

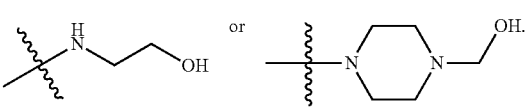 [SMILES: *NCCO ; "or" ; *N1CCN(CO)CC1]

Said purinyl-N-hydroxyl pyrimidine formamide derivative, the structures of which are shown as follows:

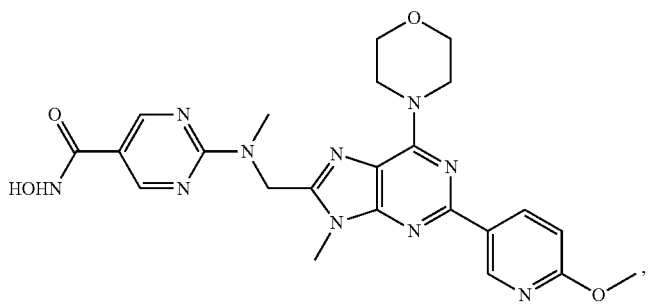

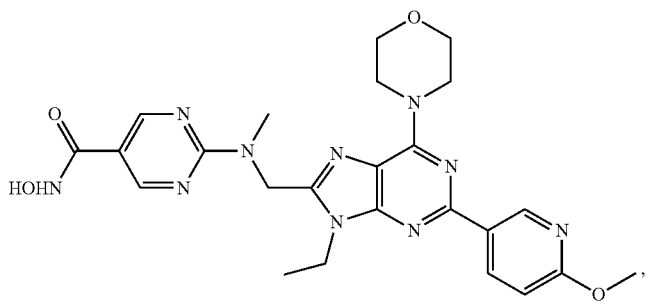

-continued
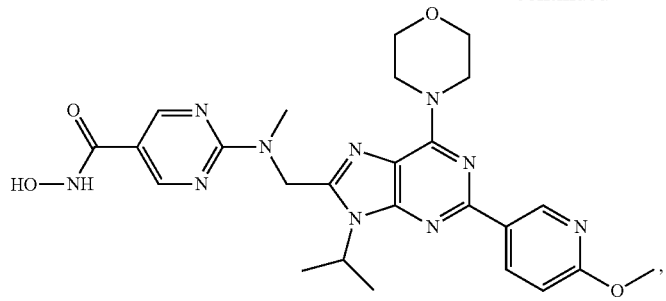
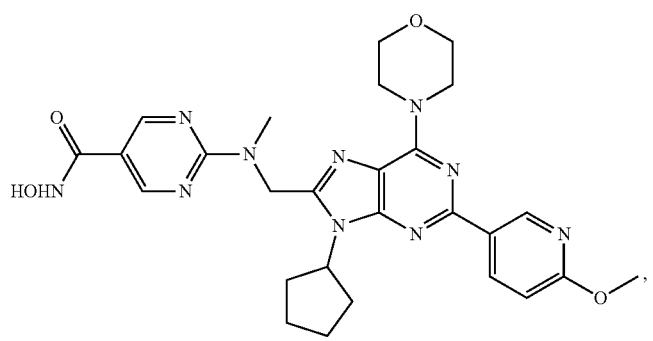
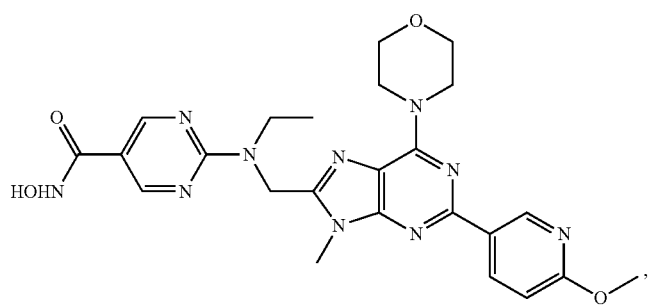
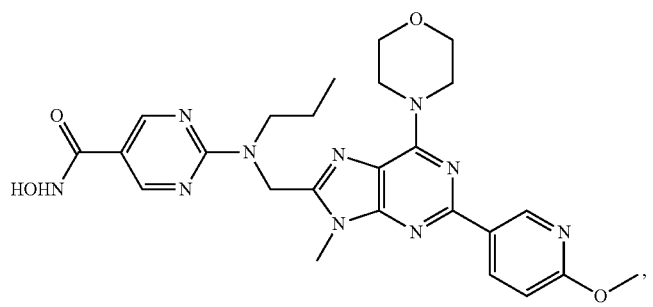
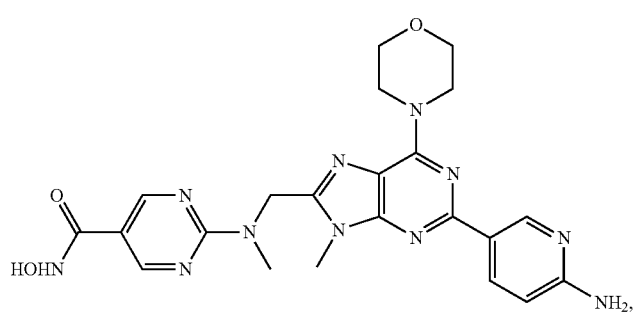

-continued
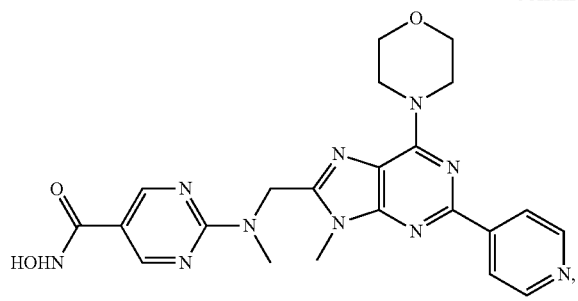
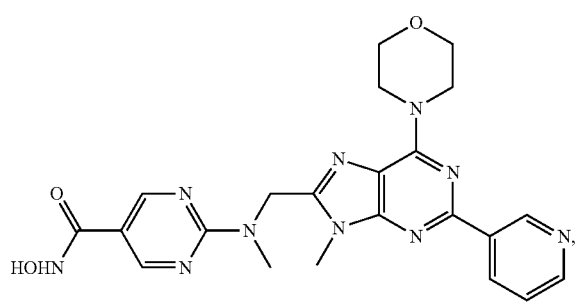
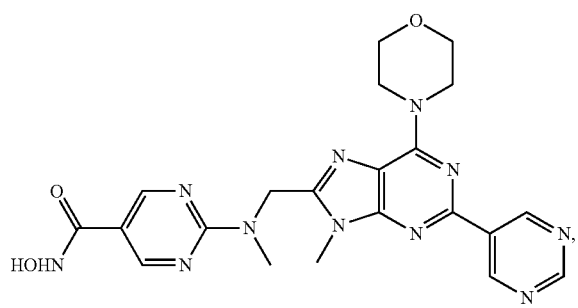
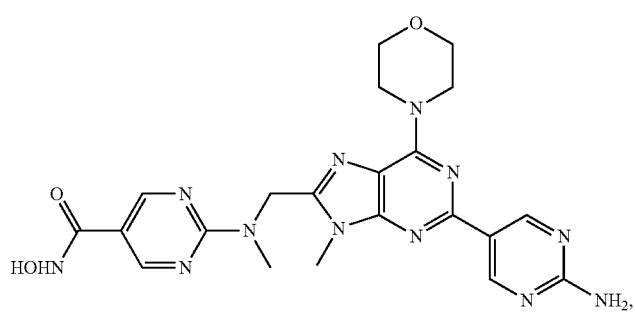
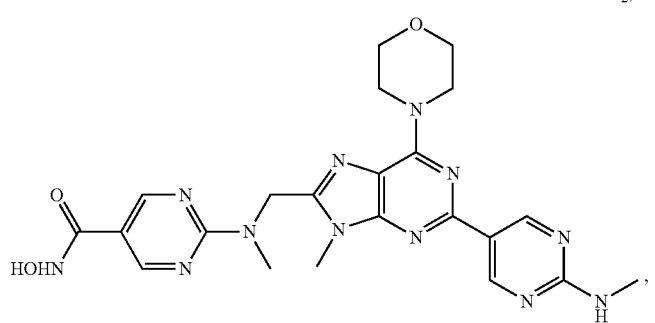

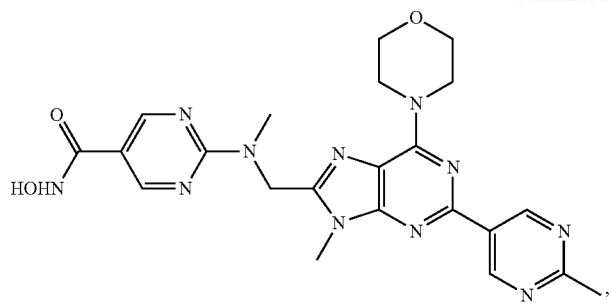
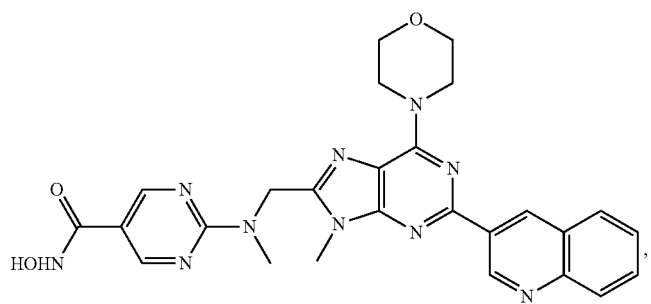
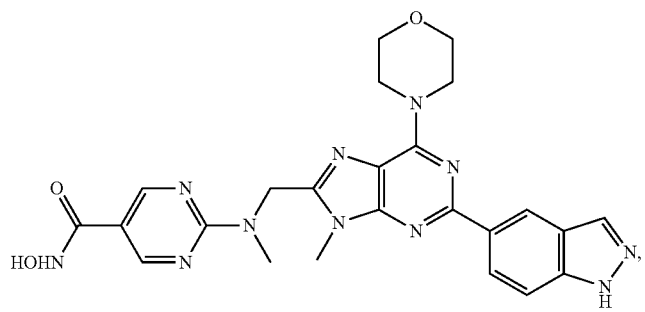
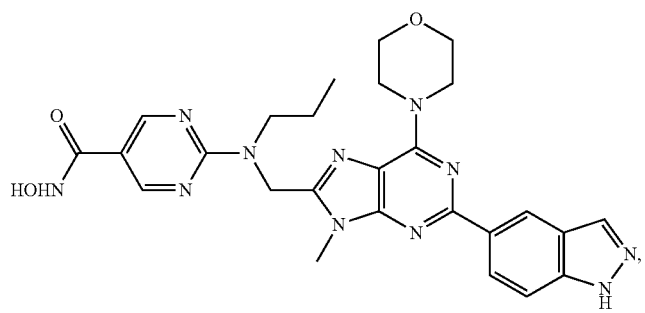
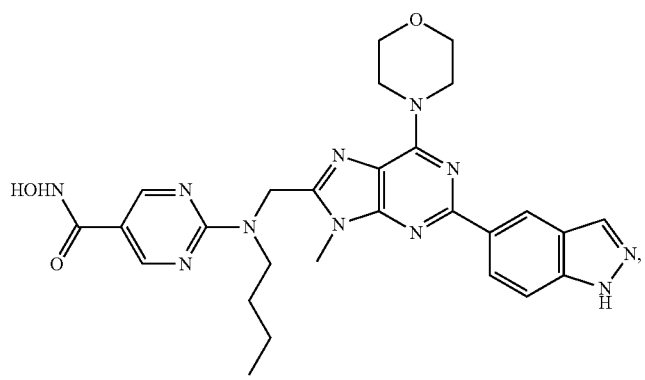

-continued
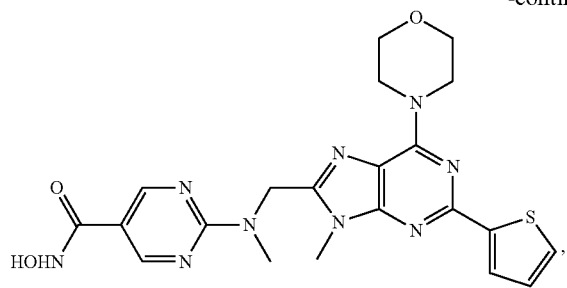
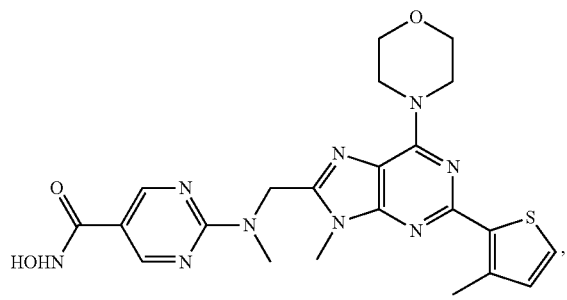
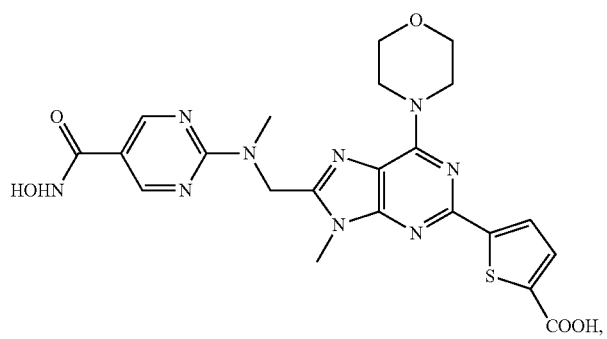
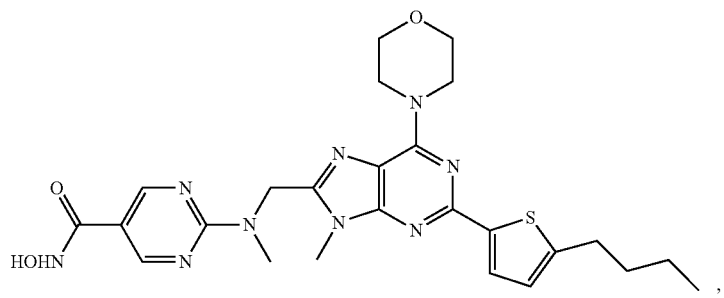
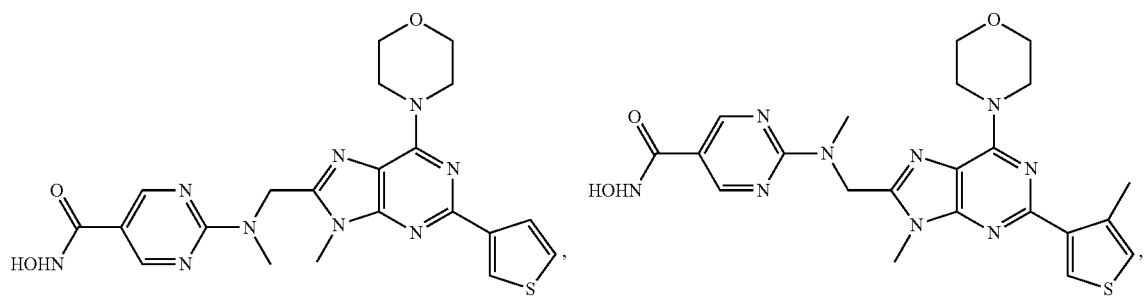

-continued
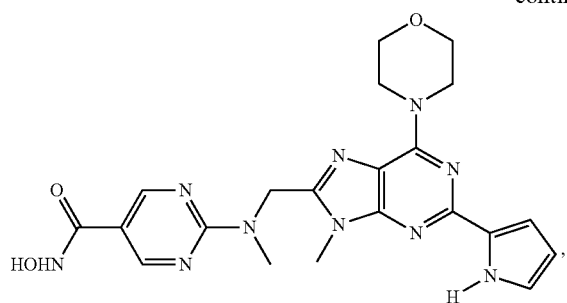
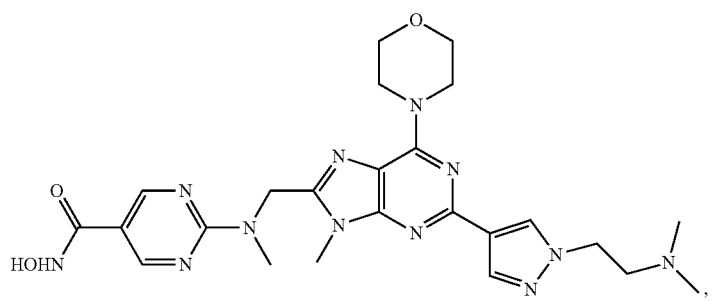
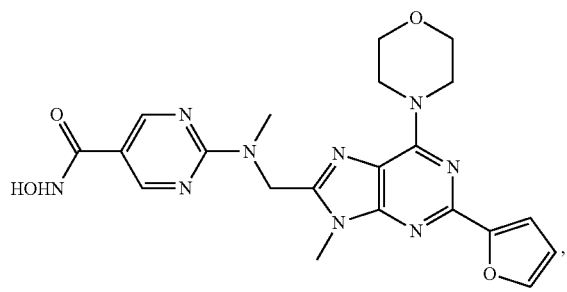
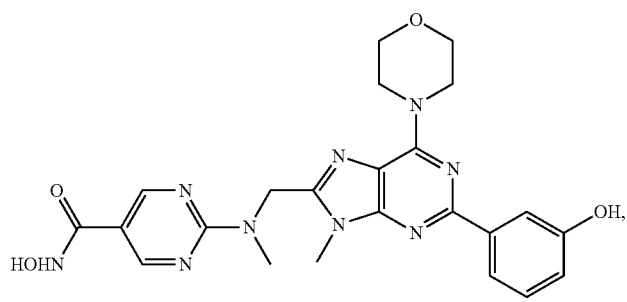
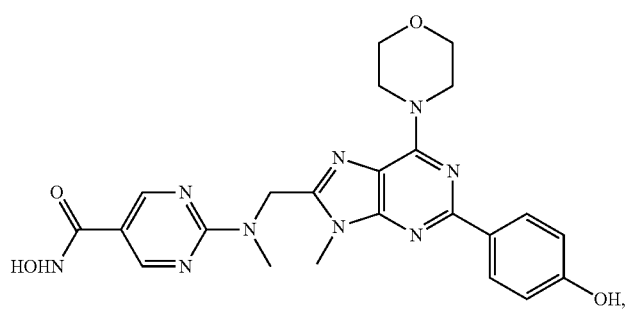

-continued
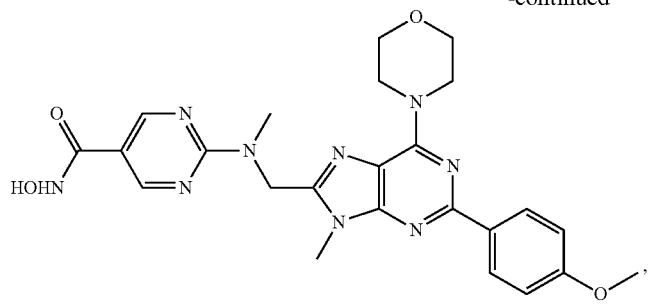
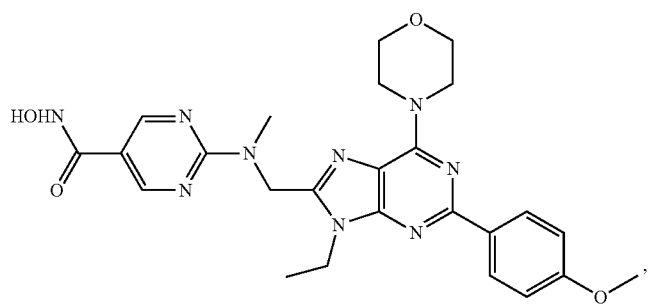
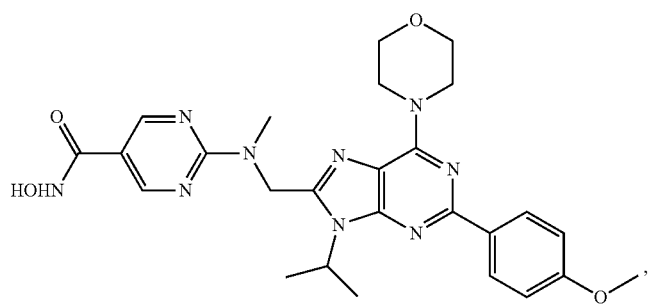
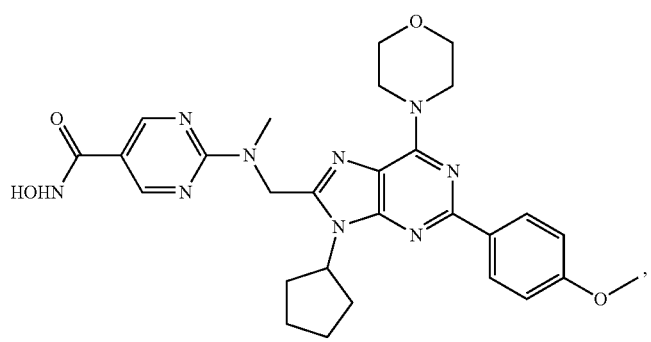
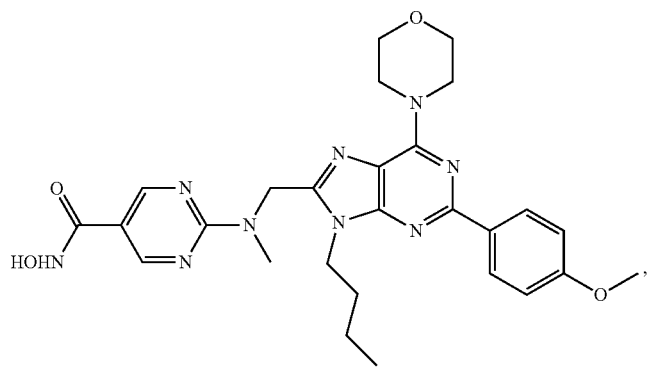

-continued
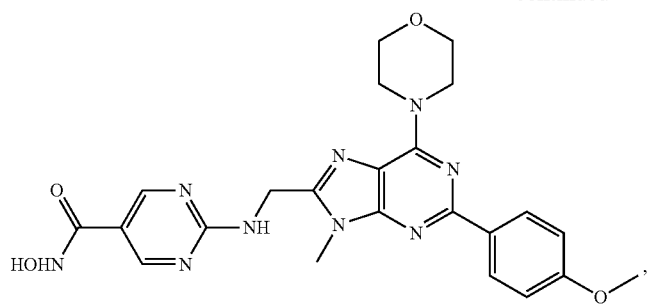
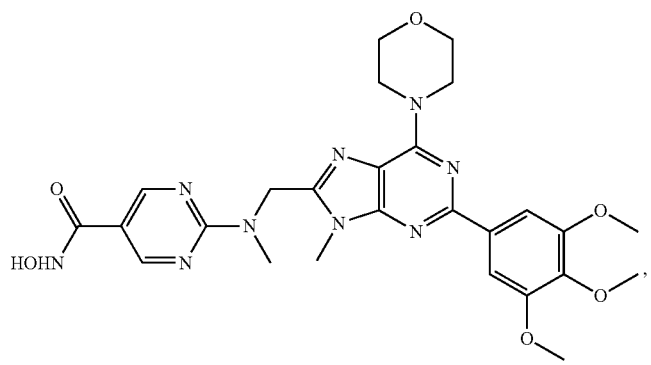
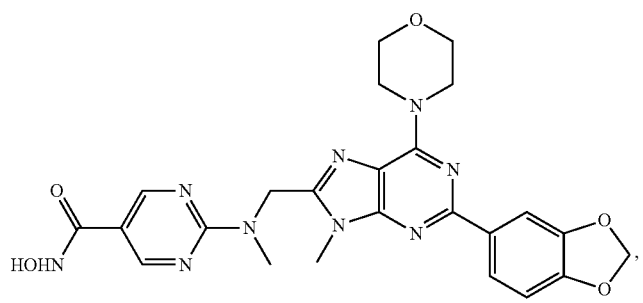
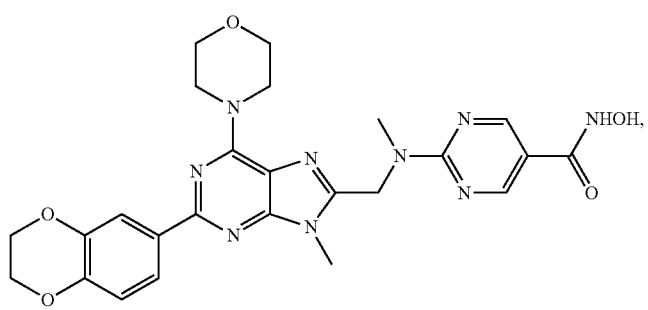
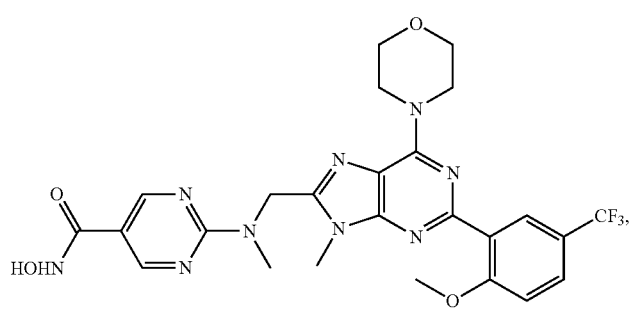

-continued
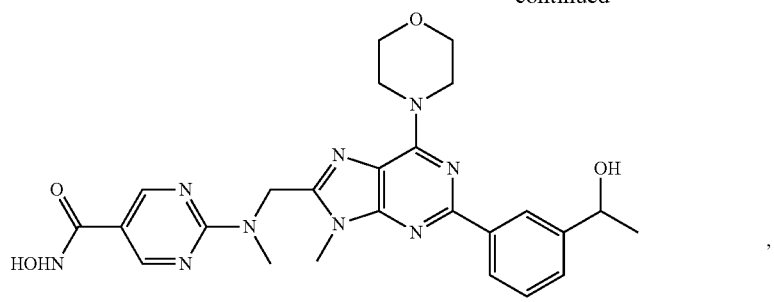
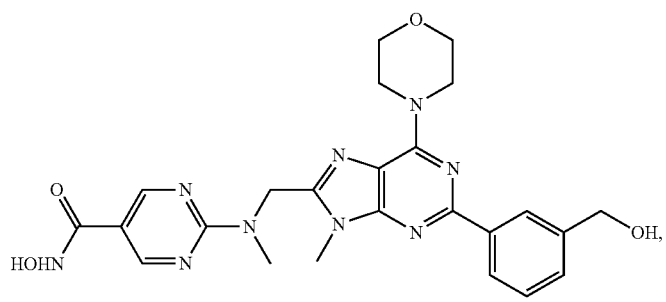
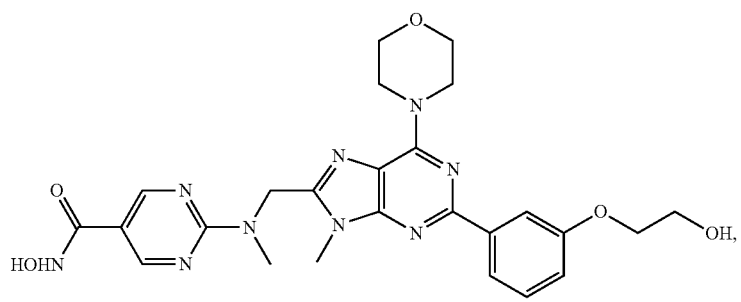
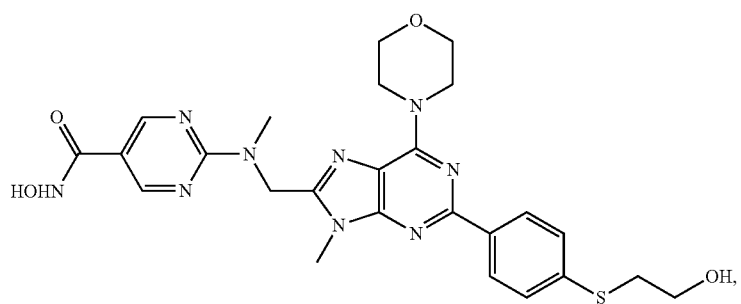
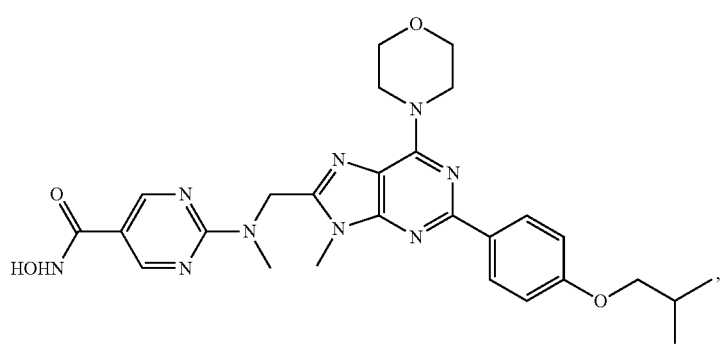

-continued
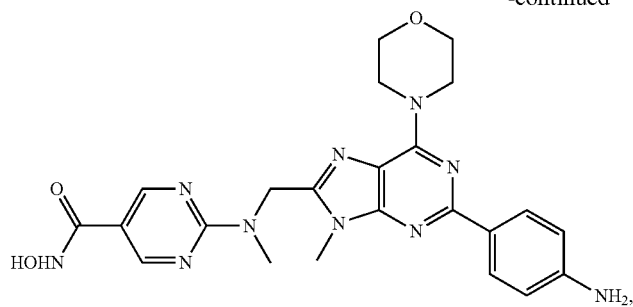
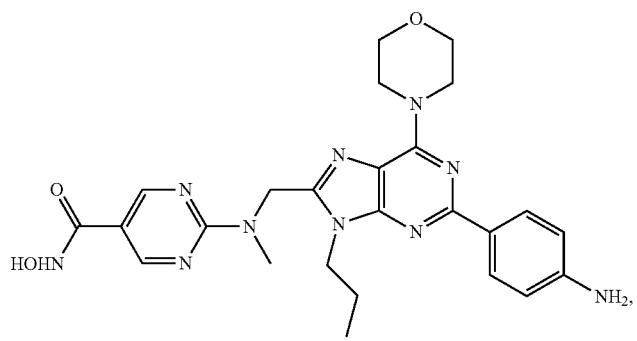
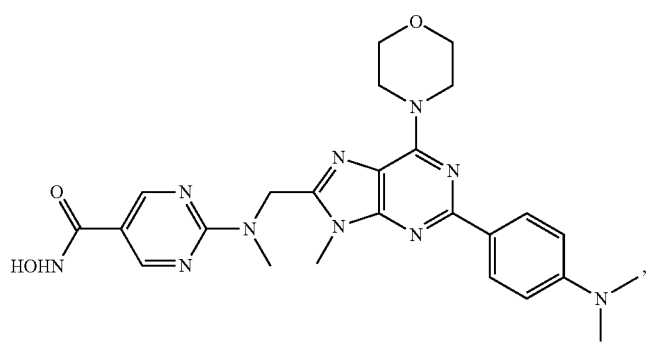
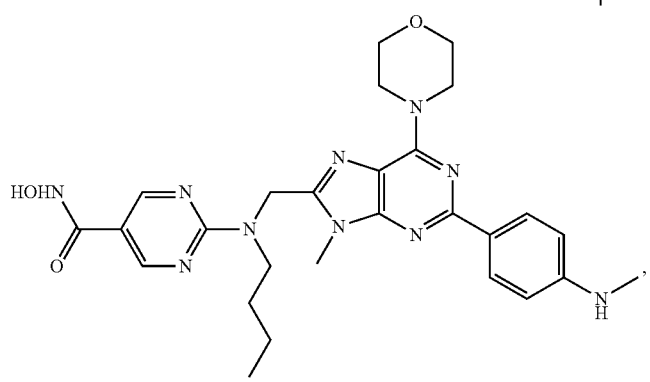
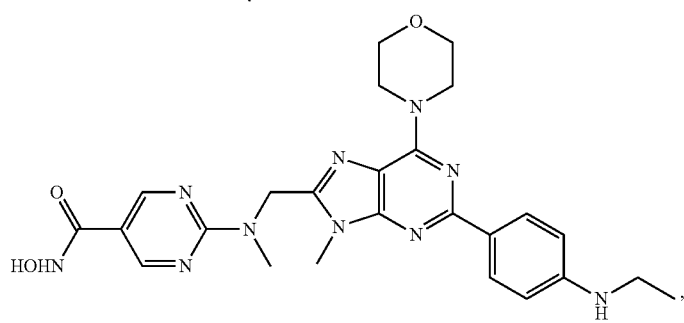

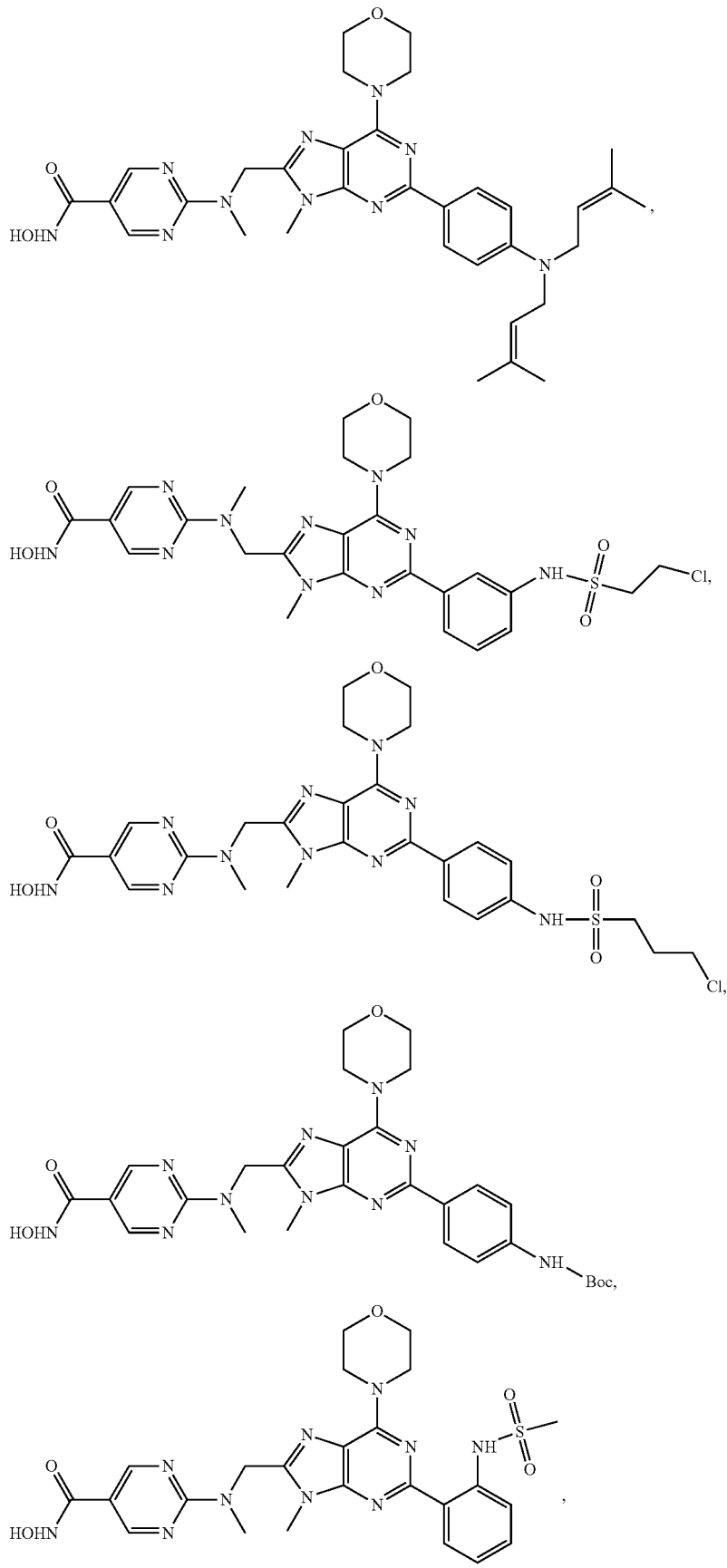

-continued
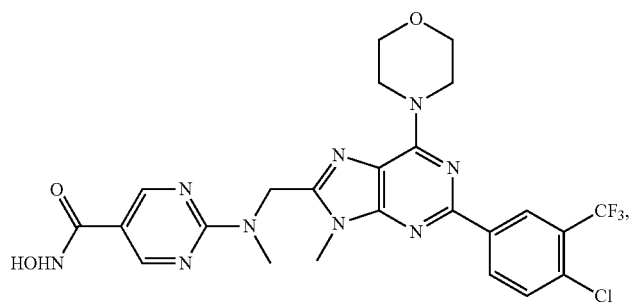
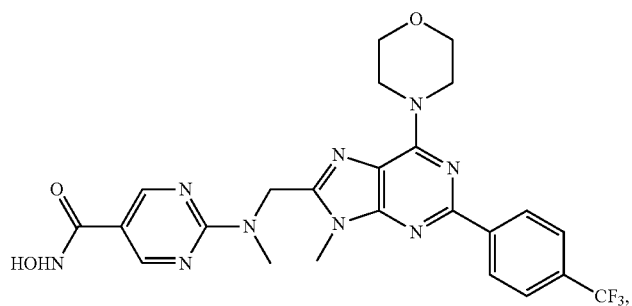
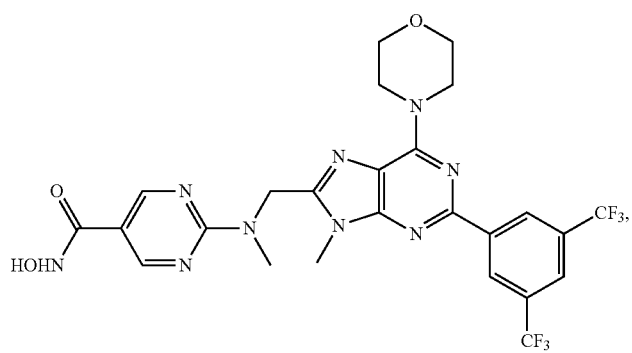
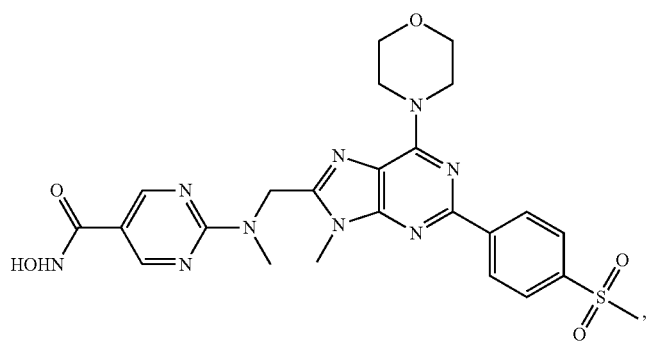

-continued
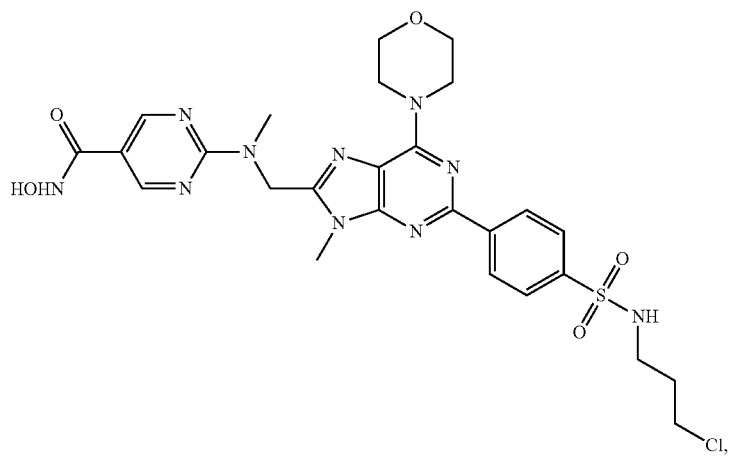
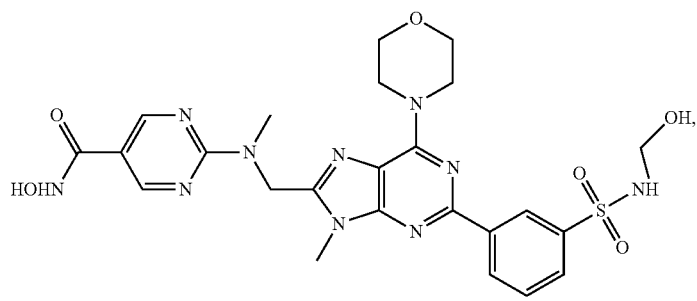
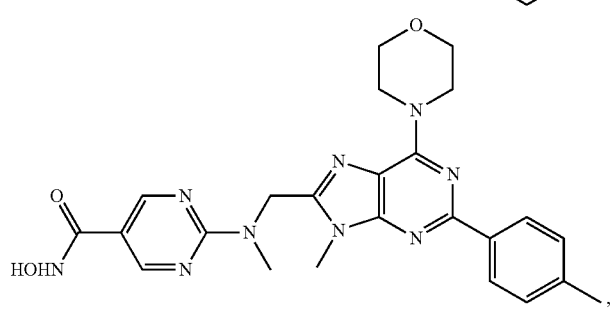
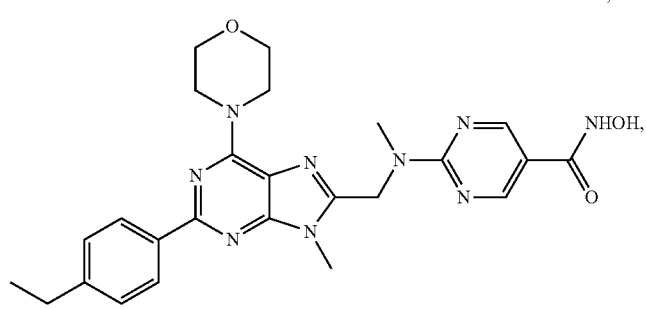
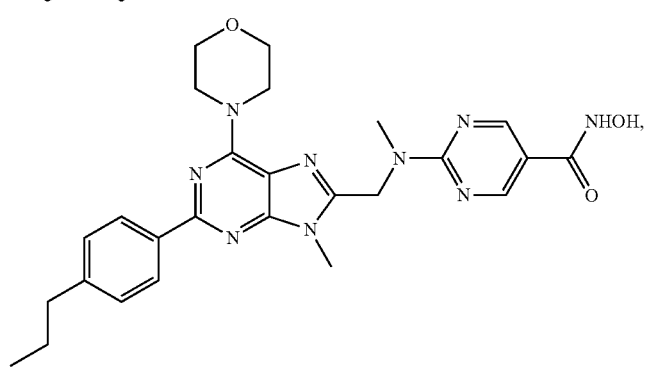

-continued
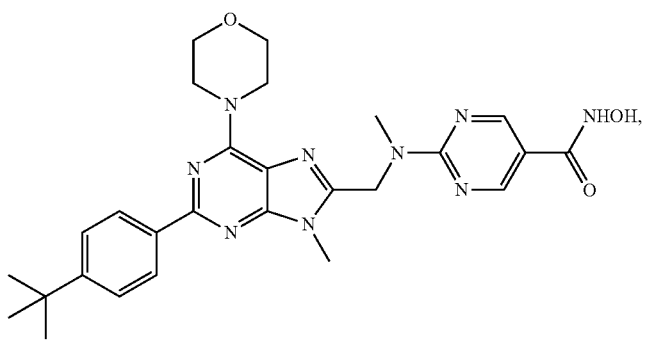
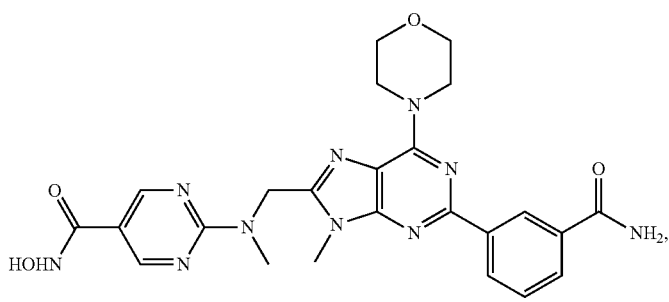
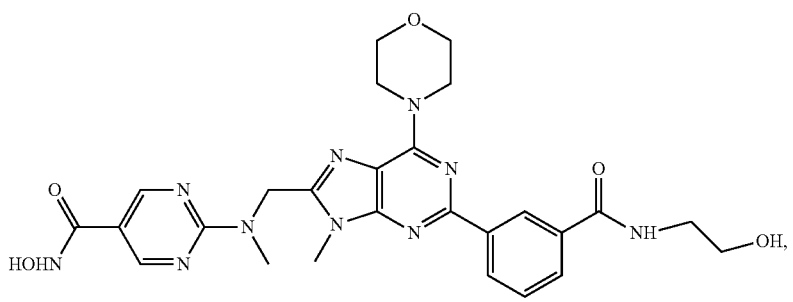
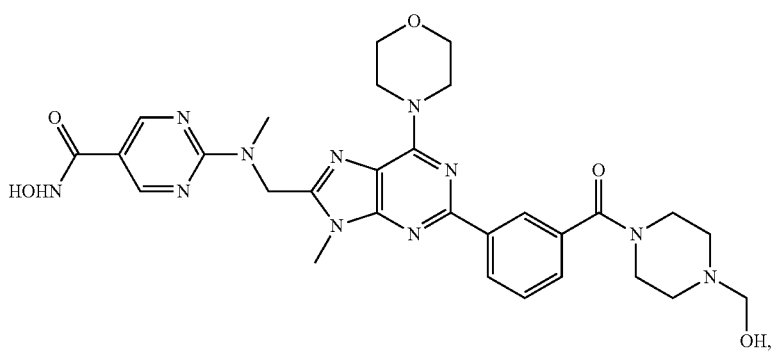
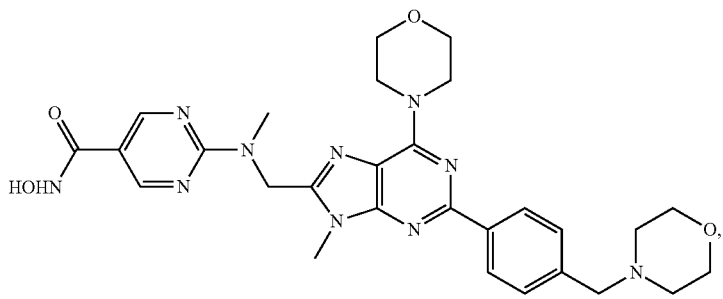

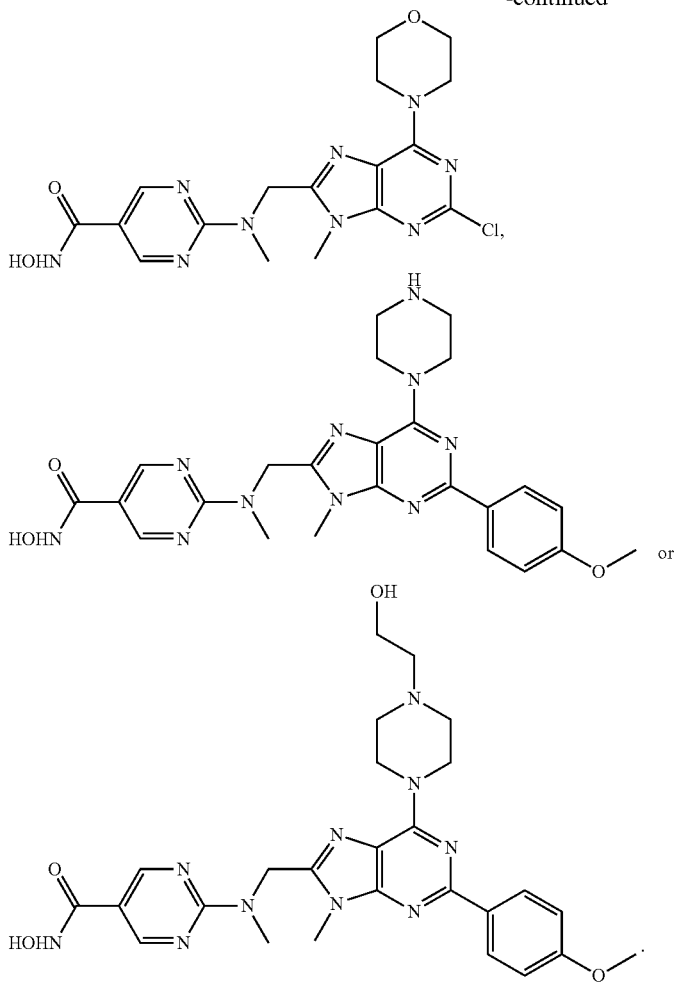
The Invention also provides preparation methods of said purinyl-N-hydroxyl pyrimidine formamide derivative, the synthetic route of which is as follows:
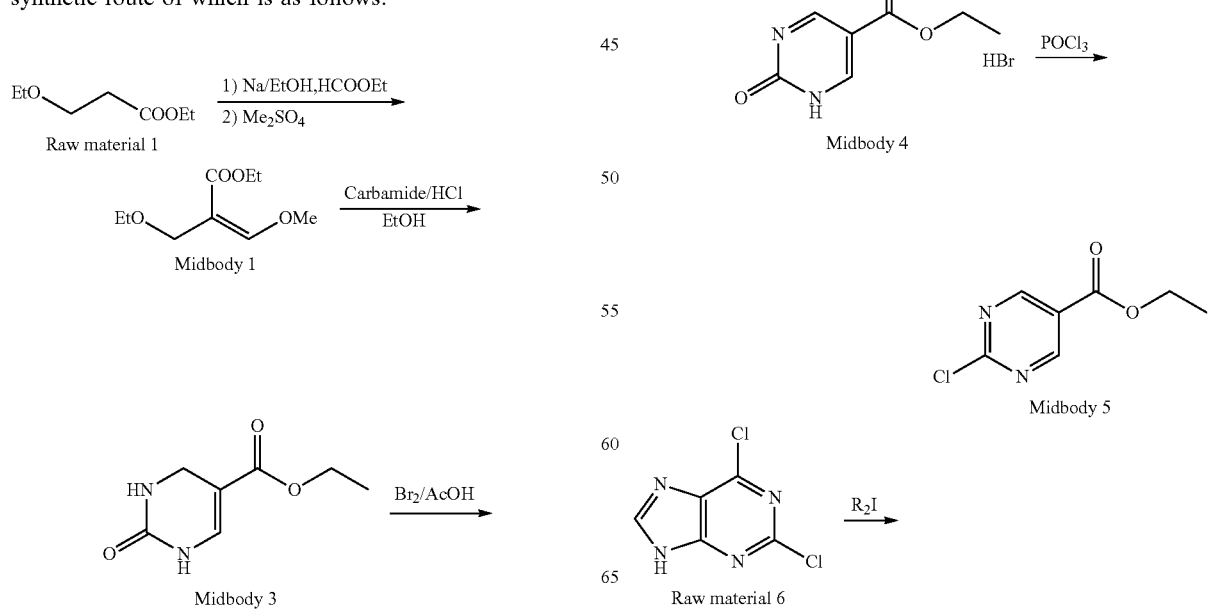

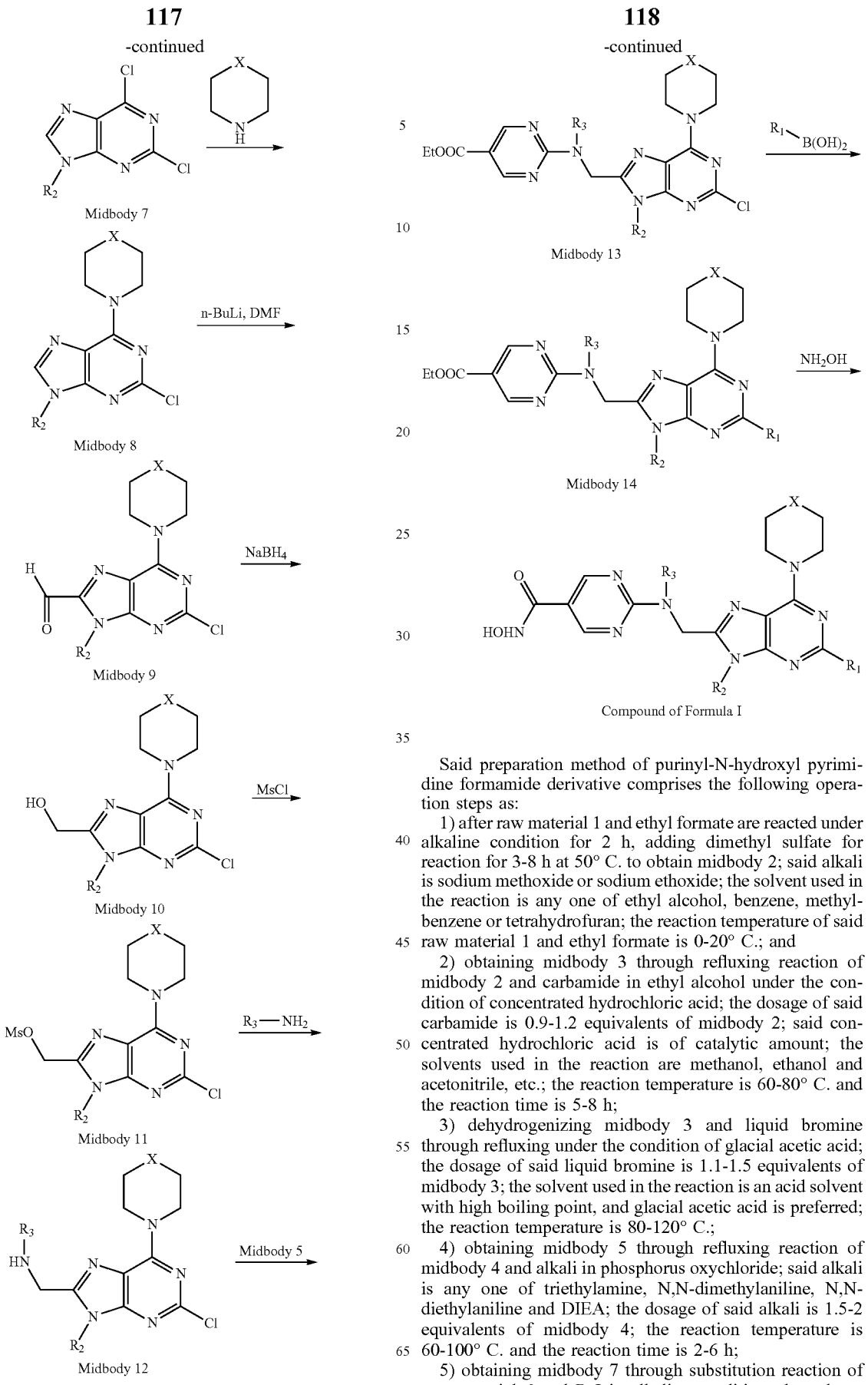

Said preparation method of purinyl-N-hydroxyl pyrimidine formamide derivative comprises the following operation steps as:

1) after raw material 1 and ethyl formate are reacted under alkaline condition for 2 h, adding dimethyl sulfate for reaction for 3-8 h at 50° C. to obtain midbody 2; said alkali is sodium methoxide or sodium ethoxide; the solvent used in the reaction is any one of ethyl alcohol, benzene, methylbenzene or tetrahydrofuran; the reaction temperature of said raw material 1 and ethyl formate is 0-20° C.; and 2) obtaining midbody 3 through refluxing reaction of midbody 2 and carbamide in ethyl alcohol under the condition of concentrated hydrochloric acid; the dosage of said carbamide is 0.9-1.2 equivalents of midbody 2; said concentrated hydrochloric acid is of catalytic amount; the solvents used in the reaction are methanol, ethanol and acetonitrile, etc.; the reaction temperature is 60-80° C. and the reaction time is 5-8 h;

3) dehydrogenizing midbody 3 and liquid bromine through refluxing under the condition of glacial acetic acid; the dosage of said liquid bromine is 1.1-1.5 equivalents of midbody 3; the solvent used in the reaction is an acid solvent with high boiling point, and glacial acetic acid is preferred; the reaction temperature is 80-120° C.;

4) obtaining midbody 5 through refluxing reaction of midbody 4 and alkali in phosphorus oxychloride; said alkali is any one of triethylamine, N,N-dimethylaniline, N,N-diethylaniline and DIEA; the dosage of said alkali is 1.5-2 equivalents of midbody 4; the reaction temperature is 60-100° C. and the reaction time is 2-6 h;

5) obtaining midbody 7 through substitution reaction of raw material 6 and R$_2$I in alkaline condition; the solvent used in the reaction is any one of acetone, acetonitrile or DMF (N,N-dimethylformamide); the dosage of $R_2I$ is 2-3 equivalents of raw material 6; said alkali is any one of cesium carbonate, potassium carbonate, NaOH and KOH; the dosage of said alkali is 1.5-2 equivalents of raw material 6; the reaction temperature is 25-80° C. and the reaction time is 0.5-2 h;

6) obtaining midbody 8 through the reaction of midbody 7 and

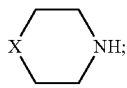

the solvent used in the reaction is an organic alcoholic solvent containing less than 6 carbons, such as methanol and ethanol; the dosage of

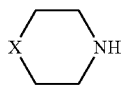

is 1.5-2 equivalents of midbody 7;

7) obtaining midbody 9 by adding DMF for 1-3 h's reaction after 2-3 h's reaction of midbody 8 and n-butyllithium in THF (tetrahydrofuran); the dosage of said n-butyllithium is 1.6 equivalents of midbody 8; the temperature for the reaction of midbody 9 and n-butyllithium is −78-−40° C.; the dosage of DMF is 2 equivalents of midbody 8;

8) obtaining midbody 10 through the reaction of midbody 9 and reductant; the solvent used in the reaction is any one of THF, ethanol or methanol; said reductant is $LiAlH_4$ or $NaBH_4$, the dosage of which is 2-3 equivalents of midbody 9; the reaction temperature is 0-25° C.;

9) obtaining midbody 11 through the reaction of midbody 10 and methane sulfonyl chloride under alkaline condition; the solvent used in the reaction is THF or $CH_2Cl_2$ (dichloromethane); the alkali is triethylamine or DIEA, the dosage of which is 2-3 equivalents of midbody 10; the dosage of methane sulfonyl chloride is 1.5-2 equivalents of midbody 10; the reaction temperature is 0-25° C.;

10) obtaining midbody 12 through the reaction of midbody 11 and $R_3$—$NH_2$; the solvent used in the reaction is ethanol or methanol; the dosage of $R_3$—$NH_2$ is 1.5-2 equivalents of midbody 11; the reaction temperature is 0-25° C. and the reaction time is 1-5 h;

11) obtaining midbody 13 through the reaction of midbody 12 and midbody 5 under alkaline condition; the solvent used in the reaction is at least one of acetonitrile, ethyl alcohol or dichloromethane; the dosage of midbody 5 is 1.1-1.2 equivalents of midbody 12;

12) obtaining midbody 14 through the coupled reaction of midbody 13 and $R_1$—$B(OH)_2$ catalyzed by Pd; the solvent used in the reaction is a mixed solution of methylbenzene ethyl alcohol and water at a volume ratio of 7:3:2; inorganic alkli should be added in the reaction, the dosage of which is 1.5-2 equivalents of midbody 13; said inorganic alkli is any one of sodium bicarbonate, sodium carbonate, cesium carbonate, NaOH or KOH; said Pd catalyst is any one of tetrakis triphenylphosphine palladium, [1,1'-bis(diphenylphosphine)ferrocene]palladium dichloride or palladium acetate, the dosage of which is catalyze equivalent; the reaction temperature is 80-100° C. and the reaction time is 5-8 h;

13) Obtaining the compound of Formula I through the reaction of midbody 14 and hydroxylamine; the solvent used in the reaction is a mixed solution of methanol and dichloromethane; the concentration of said hydroxylamine is 4N; the reaction temperature is ambient temperature and the reaction time is 1-8 h.

Wherein, X is O or N—R'; R' is —H, $C_1$-$C_4$ alkyl, $C_1$-$C_4$ alkoxy or an alkyl substituted by $C_1$-$C_4$ hydroxy;

$R_1$ is $C_1$-$C_4$ alkyl, $C_1$-$C_4$ alkoxy, —OH, halogen, $C_3$-$C_8$ cycloalkyl, —$NH_2$,

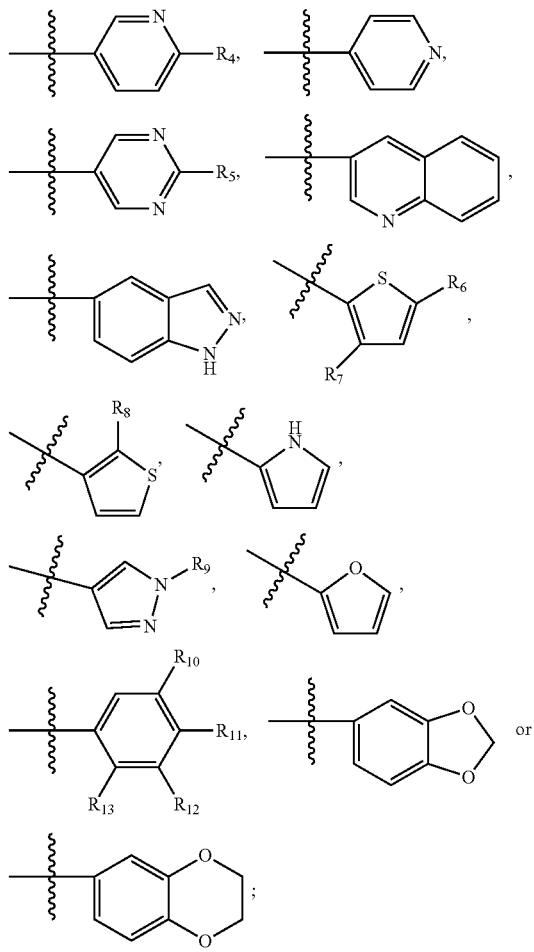

$R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

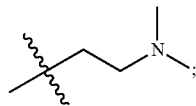

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

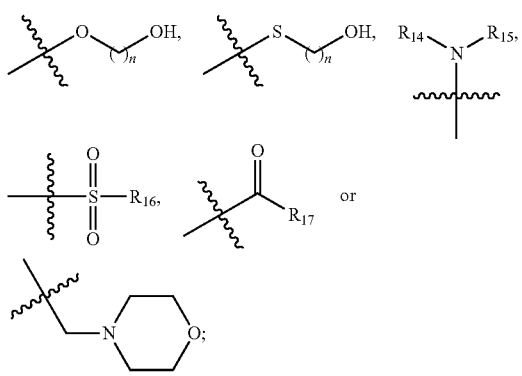

n=1-4; $R_{14}$ and $R_5$ are independently —H, $C_1$-$C_4$ alkyl, $C_1$-$C_6$ alkenyl,

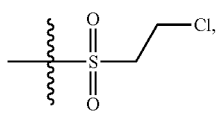 [SMILES: *S(=O)(=O)CCCl]

t-butyloxycarboryl,

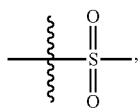

$C_1$-$C_4$ alkoxy or halogen; $R_{16}$ is $C_1$-$C_4$ alkyl, $C_1$-$C_4$ alkoxy, halogen,

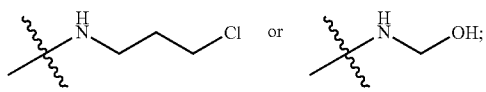

$R_{17}$ is —$NH_2$,

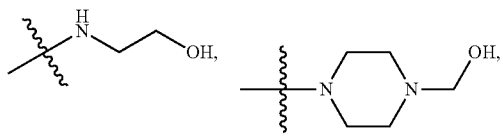 [SMILES: *NCCO ; *N1CCN(CO)CC1]

—OH or halogen.

The purinyl-N-hydroxyl pyrimidine formamide derivative of the Invention comprises its tautomer, stereoisomer and mixtures of all proportions, and also comprises the compound substituted by its isotope.

The Invention also provides a pharmaceutically acceptable salt of said purinyl-N-hydroxyl pyrimidine formamide derivative. Wherein, acid addition salt refers to that the salt is obtained through the reaction of free alkali of the parent compound and inorganic acid or organic acid. Inorganic acid comprises hydrochloric acid, hydrobromic acid, nitric acid, phosphoric acid, metaphosphoric acid, sulfuric acid, sulphurous acid and perchloric acid, etc. Organic acid comprises acetic acid, propionic acid, crylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfonic acid, naphthalene-2-sulfonic acid, p-toluenesulfonic acid, salicylic acid, tartaric acid, citric acid, lactic acid, mandelic acid, succinic acid and malonic acid, etc.

The term "pharmaceutically acceptable" used in the Invention refers to that in the scope of reasonable medical judgment, something applies to contacting tissues of human and other mammals without any undue toxicity, stimulus or anaphylactic reaction, and can directly or indirectly provide the compound of the Invention or a prodrug of such compound while drugs are administrated to a receptor.

The Invention also provides a pharmaceutically acceptable hydrate of said purinyl-N-hydroxyl pyrimidine formamide derivative. The term "hydrate" refers to a compound of water that is combined with chemometry or non-stoichiometry through the acting force between noncovalent molecules.

The Invention also provides a pharmaceutically acceptable polymorphic substance of said purinyl-N-hydroxyl pyrimidine formamide derivative. The term "polymorphic substance" refers to the solid crystal of a compound or its composite, which can be represented by physical methods, such as X-ray powder diffraction pattern or infrared spectroscopy.

The Invention also provides a pharmaceutically acceptable pharmaceutical composition of said purinyl-N-hydroxyl pyrimidine formamide derivative; such pharmaceutical composition is prepared by the purinyl-N-hydroxyl pyrimidine formamide derivative shown in Formulas I-III and its salt or hydrate with pharmaceutically acceptable auxiliary ingredients. Said auxiliary ingredients are cyclodextrin, arginine or meglumine. Said cyclodextrin is selected from α-cyclodextrins, β-cyclodextrins, γ-cyclodextrins, ($C_{1-4}$ alkyl)-α-cyclodextrins, ($C_{1-4}$ alkyl)-β-cyclodextrins, ($C_{1-4}$ alkyl)-γ-cyclodextrins, (hydroxyl-$C_{1-4}$ alkyl)-α-cyclodextrins, (hydroxyl-$C_{1-4}$ alkyl)-β-cyclodextrins, (hydroxyl-$C_{1-4}$ alkyl)-γ-cyclodextrins, (carboxyl-$C_{1-4}$ alkyl)-α-cyclodextrins, (carboxyl-$C_{1-4}$ alkyl)-β-cyclodextrins, (carboxyl-$C_{1-4}$ alkyl)-γ-cyclodextrins, carbohydrate ether of α-cyclodextrins, carbohydrate ether of β-cyclodextrins, carbohydrate ether of γ-cyclodextrins, sulfobutyl ether of α-cyclodextrins, sulfobutyl ether of β-cyclodextrins and sulfobutyl ether of γ-cyclodextrins. Said auxiliary ingredients also comprise pharmaceutically acceptable carrier, adjuvant or agent. The pharmaceutically acceptable pharmaceutical composition also comprises ion exchanger, aluminium oxide, aluminium stearate, lecithin; the buffer substance comprises phosphate, glycine, arginine and sorbic acid, etc.

Said pharmaceutical composition can be in either liquid or solid form. Wherein, said liquid form can be the form of aqueous solution; said solid form can be the form of powder, particle, tablet or lyophilized powder. The pharmaceutical composition also comprises water for injection, saline solution, glucose aqueous solution, saline for injection/infusion, glucose for injection/infusion, Ringer's solution or Ringer's solution containing lactate.

Uses of the purinyl-N-hydroxyl pyrimidine formamide derivative shown in Formulas I-III and its salt, hydrate or pharmaceutical composition in preparing PI3K inhibitor.

Uses of the purinyl-N-hydroxyl pyrimidine formamide derivative shown in Formulas I-III and its salt, hydrate or pharmaceutical composition in preparing HDAC inhibitor.

Uses of the purinyl-N-hydroxyl pyrimidine formamide derivative shown in Formulas I-III and its salt, hydrate or pharmaceutical composition in preparing antineoplastic drugs.

The Invention also provides uses of the purinyl-N-hydroxyl pyrimidine formamide derivative shown in Formulas I-III and its salt, hydrate or pharmaceutical composition in preparing oral or intravenous injection preparations. Said oral or intravenous injection preparations comprise at least one urinyl-N-hydroxyl pyrimidine formamide derivative shown in Formulas I-III and its salt, hydrate or pharmaceutical composition, and any excipients and/or adjuvants.

The purinyl-N-hydroxyl pyrimidine formamide derivative provided in the Invention can be not only a kinase inhibitor with PI3K and HDAC difunctional targets, but also a kinase inhibitor with single PI3K or HDAC functional target, thus providing a new choice for preparing antineoplastic drugs.

DETAILED DESCRIPTION OF THE PREFERRED EMBODIMENTS

Embodiment 1 Synthesis of 2-chloropyrimidine-5-carboxylic acid ethyl ester (midbody 5)

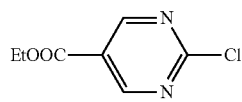

Adding sodium (13.8 g) into the mixture of benzene (300 mL) and ethyl alcohol (27 g); slowly adding the mixture of ethyl formate (45 g, 0.61 mol) and ethyl 3-ethoxypropionate (44 g, 0.3 mol) into above-mentioned mixture at 0° C. Stirring the obtained reaction mixture for 2 h, then adding dimethyl sulfate (76 g, 0.61 mol) and stirring for 3 h at 50° C.; filtering the mixture and washing the filtrate with water; separating and extracting the organic layer, drying it with anhydrous sodium sulfate, filtering and evaporating it to obtain a residue for distillation under vacuum condition, then the midbody 2 is obtained; said compound can be directly used in the following steps without further purification.

Heating up overnight the ethanol (300 mL) mixture of midbody 2 (21.4 g, 0.11 mol), carbamide (5.7 g, 0.095 mol), concentrated hydrochloric acid and ethanol (36%-38%, 5 mL) in the state of refluxing; recrystallizing said residue in ethanol after evaporation to obtain a colorless prismatic midbody 3 (7.8 g, 65%).

Heating up the acetic acid solution (55 mL) of midbody 3 (2.5 g, 14.7 mmol) and bromine (2.4 g, 15 mmol) for 1.5 h in the state of refluxing; removing said solvent to obtain coarse midbody 4 (3.6 g, 99%), which can be directly used in the following steps without further purification.

Heating up the mixture of midbody 4 (3.6 g, 21 mmol), phosphorus oxychloride (25 mL) and N,N-dimethylaniline (2.5 mL) for 1.5 h in the state of refluxing; removing said solvent and then adding ice water (10 mL) into said residue; adding said mixture into 2N sodium hydroxide (90 mL) and extracting it with ethyl acetate. Evaporating the organic layer for purification through column chromatography (developing solvent petroleum ether:ethyl acetate=20:1) to obtain midbody 5 (1.2 g, 30%).

Embodiment 2 2-(((2-chlorine-9-methyl-6-morpholine-9H-purine-8-yl))methyl(methyl)amino)pyrimidine-5-carboxylic acid ethyl ester (midbody 13-1)

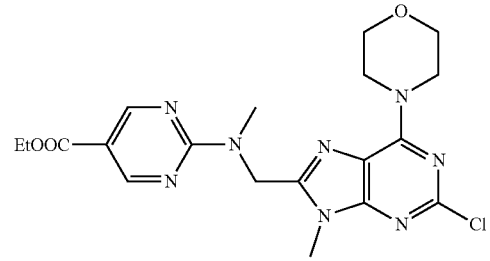 [SMILES: CCOC(=O)c1cnc(N(C)Cc2nc3c(N4CCOCC4)nc(Cl)nc3n2C)nc1]

Adding midbody 12-1 (1-(2-chlorine-9-methyl-6-morpholine-9H-purine-8-yl)-N-methyl methylamine and midbody 5 into acetonitrile mixture as per the equivalent of 1:1 and slowly adding N,N-diisopropylethylamine for overnight reaction; then dissolving out the product from acetonitrile, filtering it to obtain the crude product, then wash it with ethyl acetate and dry it to obtain the target midbody 13-1.

Embodiment 3 Synthesis of 2-(((2-(6-methoxypyridine-3-yl)-9-methyl-6-morpholine-9H-purine-8-yl))methyl(methyl)amino)-N-hydroxyl pyrimidine-5-formamide (Compound CLJ-1)

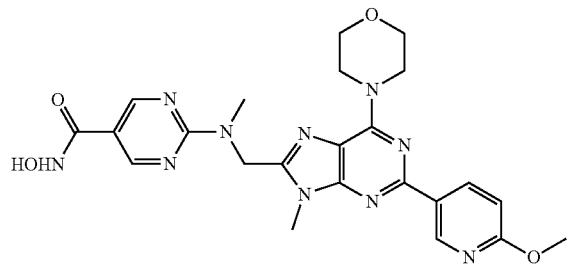

Adding midbody 13-1, 6-methoxypyridine-3-boronic acid and PdCl$_2$ (dppf) in a reaction flask; vacuumizing it and inletting nitrogen; adding 20 mL solution of methylbenzene:ethyl alcohol=1:1 and 2 mL Na$_2$CO$_3$ aqueous solution of 2 mol/L in sequence; heating up to 80° C. for overnight reaction. Conducting suction filtration with kieselguhr after complete reaction; reducing pressure, removing the solvent and conducting silicagel column chromatography (developing solvent petroleum ether:ethyl acetate=2:1) to obtain the key midbody 14-1.

In the meanwhile, adding methanol solution of potassium hydroxide in the methanol stirring solution of hydroxylamine hydrochloride at 0° C.; then stirring the mixture for 30 min at 0° C. and allowing it to stay at low temperature; separating the obtained sediment and preparing the solution into free hydroxylamine.

Adding midbody 14-1 into the free hydroxylamine solution and stirring it for 1 h; then adding water in the reaction mixture after the reaction and adjusting the PH value to 7-8; filtering it after some solid is dissolved out and cleaning the filter cake with methyl alcohol and dichloromethane to obtain the target compound CLJ-1.

LCMS: 507.2[M+1]⁺. ¹H-NMR (400 MHz, DMSO-d6) δ: 3.23 (s, 3H), 3.71-3.77 (m, 4H), 3.76 (s, 3H), 3.92 (s, 3H), 4.21-4.27 (br, 4H), 5.17 (s, 2H), 6.91 (d, J=8.4 Hz, 1H), 8.58 (d, J=8.4 Hz, 1H), 8.72 (s, 2H), 9.14 (s, 1H).

Embodiment 4 Synthesis of 2-(((9-ethyl-2(6-methoxyl 3-pyridyl)-6-morpholino-9H-purine-8-yl))methyl(methyl)amino)-N-hydroxyl pyrimidine-5-formamide (Compound CLJ-2)

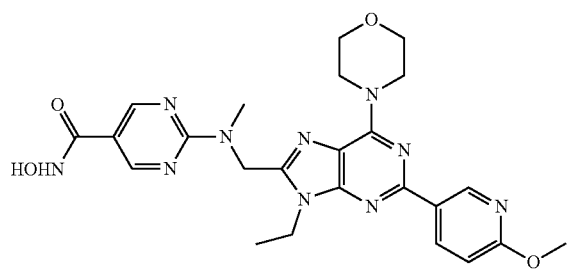

The synthesis method is the same as that of Embodiment 3, except that methyl iodide is replaced by ethyl iodide in step 5 of the reaction; the sum yield of the final two steps is 41%.

LCMS: 521.3[M+1]⁺. ¹H-NMR (400 MHz, DMSO-d6) δ:1.19 (t, J=7.0 Hz, 3H), 3.71-3.82 (m, 4H), 4.21-4.29 (br, 4H), 5.17 (s, 2H), 6.91 (d, 1H, J=8.4 Hz), 8.58 (d, 1H, J=8.4 Hz), 8.72 (s, 2H), 9.14 (s, 1H).

Embodiment 5 Synthesis of 2-(((9-isopropyl-2-(6-methoxyl-3-pyridyl)-6-morpholino-9H-purine-8-yl))methyl(methyl)amino)-N-hydroxyl pyrimidine-5-formamide (Compound CLJ-3)

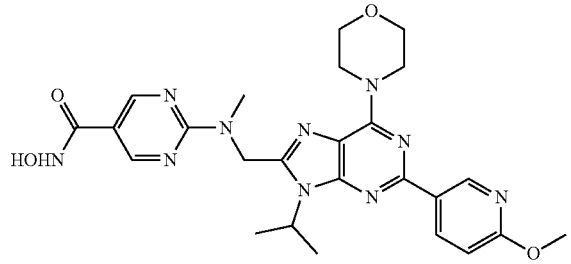

The synthesis method is the same as that of Embodiment 3, except that methyl iodide is replaced by 2-iodopropane in step 5 of the reaction; the sum yield of the final two steps is 42%.

LCMS: 534.3[M+1]⁺. ¹H-NMR (400 MHz, DMSO-d6) δ:1.61 (d, 6H, J=6.8 Hz), 3.17 (s, 3H), 3.68-3.75 (br, 4H), 3.92 (s, 3H), 4.19-4.28 (br, 4H), 4.78-4.87 (m, 1H), 5.18 (s, 2H), 6.91 (d, 1H, J=8.4 Hz), 8.55 (dd, 1H, J=8.4 Hz, J=2.4 Hz), 8.71 (s, 2H), 9.12 (s, 1H).

Embodiment 6 Synthesis of 2-(((9-cyclopentyl-2-(6-methoxyl-3-pyridyl)-6-morpholino-9H-purine-8-yl))methyl(meth yl)amino)-N-hydroxyl pyrimidine-5-formamide (Compound CLJ-4)

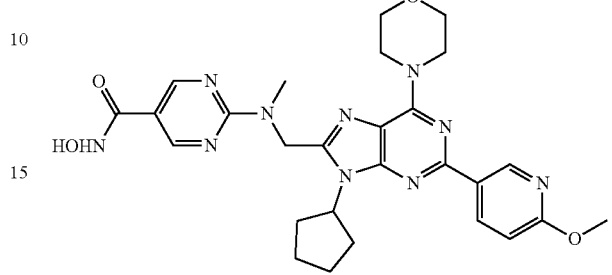

The synthesis method is the same as that of Embodiment 3, except that methyl iodide is replaced by iodocyclopentane in step 5 of the reaction; the sum yield of the final two steps is 48%.

LCMS: 561.3 [M+1]+. ¹H-NMR (400 MHz, DMSO-d6) δ: 1.54-1.64 (m, 2H), 1.84-1.98 (m, 2H), 2.00-2.09 (m, 2H), 2.30-2.40 (m, 2H), 3.18 (s, 3H), 3.66-3.74 (m, 4H), 4.17-4.29 (br, 4H), 4.87-4.97 (m, 1H), 5.20 (s, 2H), 6.92 (d, 1H, J=8.8 Hz), 8.52 (dd, 1H, J=8.8, 2.0 Hz), 8.73 (s, 2H), 9.06 (s, 1H), 9.10 (d, 1H, J=2.0 Hz), 11.13 (s, 1H).

Embodiment 7 Synthesis of N-hydroxy-2-(((2-(6-methoxyl-3-pyridyl)-9-methyl-6-morpholine-9H-purine-8-yl))methyl(ethyl)amino)pyrimidine-5-formamide (Compound CLJ-5)

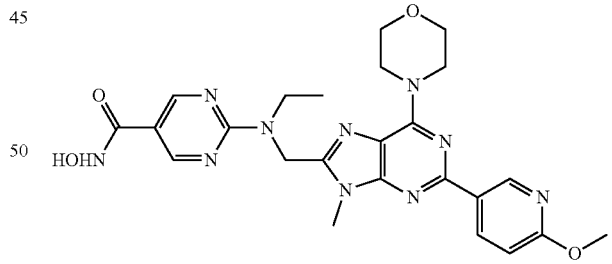

The synthesis method is the same as that of Embodiment 3, except that methylamine is replaced by ethamine in step 9 of the reaction; the sum yield of the final two steps is 33%.

LCMS: 521.3[M+1]⁺. ¹H-NMR (400 MHz, DMSO-d6) δ: 1.02 (t, 3H, J=4.8 Hz), 3.23 (q, 3H, J=4.8 Hz), 3.64-3.71 (m, 4H), 3.76 (s, 3H), 3.92 (s, 3H), 4.21-4.29 (br, 4H), 5.17 (s, 2H), 6.91 (d, 1H, J=8.4 Hz), 8.58 (d, 1H, J=8.4 Hz), 8.72 (s, 2H), 9.14 (s, 1H).

Embodiment 8 Synthesis of N-hydroxy-2-(((2-(6-methoxyl-3-pyridyl)-9-methyl-6-morpholine-9H-purine-8-yl))methyl(propyl)amino)pyrimidine-5-formamide (Compound CLJ-6)

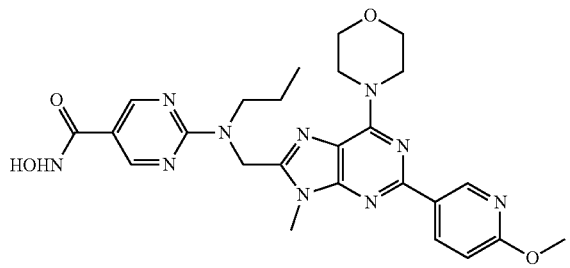

The synthesis method is the same as that of Embodiment 3, except that methylamine is replaced by propylammonia in step 9 of the reaction; the sum yield of the final two steps is 33%.

LCMS: 535.3[M+1]$^+$. $^1$H-NMR (400 MHz, DMSO-d6) δ: 0.90 (t, 4.8 Hz, 3H), 1.57-1.63 (m, 2H), 3.49 (t, J=4.8 Hz, 2H), 3.71-3.78 (m, 4H), 3.76 (s, 3H), 3.92 (s, 3H), 4.21-4.27 (br, 4H), 5.17 (s, 2H), 6.91 (d, J=8.4 Hz, 1H), 8.58 (d, J=8.4 Hz, 1H), 8.72 (s, 2H), 9.14 (s, 1H).

Embodiment 9 Synthesis of 2-(((2-(p-amino-3-pyridyl)-9-methyl-6-morpholine-9H-purine-8-yl))methyl(methyl)amino)-N-hydroxyl pyrimidine-5-formamide (Compound CLJ-7)

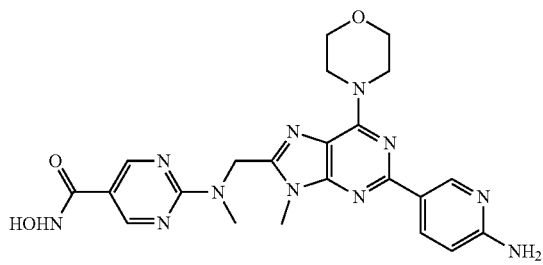

The synthesis method is the same as that of Embodiment 3, except that 6-methoxypyridine-3-boronic acid is replaced by p-6-aminopyridine boronic acid; the sum yield of the final two steps is 49%.

LCMS: 492.5 [M+1]$^+$. $^1$H-NMR (400 MHz, DMSO-d6) δ: 3.14 (s, 3H), 3.65-3.82 (m, 7H), 4.12-4.30 (br, 4H), 5.13 (s, 2H), 6.33 (s, 2H), 6.49 (d, J=8.4 Hz, 1H), 8.29 (d, J=8.4 Hz, 1H), 8.66 (s, 2H), 8.93 (s, 1H).

Embodiment 10 Synthesis of 2-(((2-(4-pyridyl)-9-methyl-6-morpholine-9H-purine-8-yl))methyl(methyl)amino)-N-hydroxyl pyrimidine-5-formamide (Compound CLJ-8)

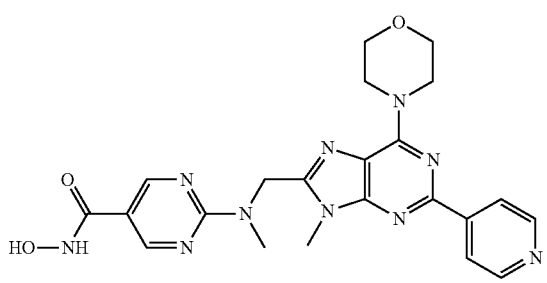 [SMILES: CN(Cc1nc2c(N3CCOCC3)nc(-c3ccncc3)nc2n1C)c1ncc(C(=O)NO)cn1]

The synthesis method is the same as that of Embodiment 3, except that 6-methoxypyridine-3-boronic acid is replaced by 4-pyridine boronic acid; the sum yield of the two steps is 30%.

LCMS: 574.3[M+1]$^+$. $^1$H-NMR (400 MHz, DMSO-d6) δ: 3.24 (s, 3H), 3.72-3.80 (br, 4H), 3.80 (s, 3H), 3.84 (s, 3H), 4.25 (s, 4H), 5.20 (s, 2H), 8.26 (s, 2H), 8.71-8.78 (m, 4H), 9.05 (s, 1H), 11.07 (s, 1H).

Embodiment 11 Synthesis of 2-(((2-(3-pyridyl)-9-methyl-6-morpholine-9H-purine-8-yl))methyl(methyl)amino)-N-hydroxyl pyrimidine-5-formamide (Compound CLJ-9)

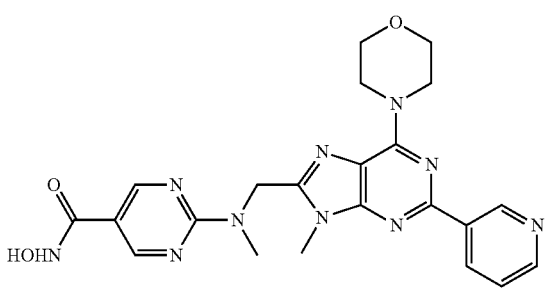

The synthesis method is the same as that of Embodiment 3, except that 6-methoxypyridine-3-boronic acid is replaced by 3-pyridine boronic acid; the sum yield of the two steps is 33%.

LCMS: 477.5 [M+1]$^+$. $^1$H-NMR (400 MHz, DMSO-d6) δ: 3.23 (s, 1H), 3.68-3.75 (m, 4H), 3.79 (s, 3H), 4.17-4.32 (br, 4H), 7.45-7.51 (m, 1H), 8.60-8.68 (m, 2H), 8.72 (s, 2H), 9.53 (s, 1H).

Embodiment 12 Synthesis of 2-(((2-(pyrimidine-5-yl)-9-methyl-6-morpholine-9H-purine-8-yl))methyl(methyl)amino)-N-hydroxyl pyrimidine-5-formamide (Compound CLJ-10)

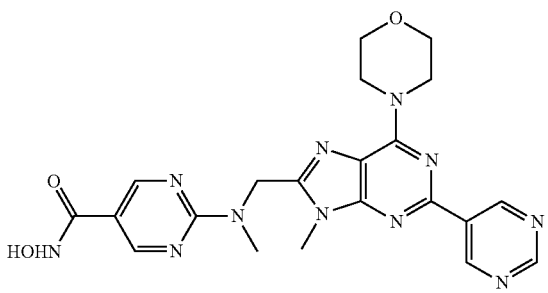

The operation is the same as that of Embodiment 3, except that 6-methoxypyridine-3-boronic acid is replaced by pyrimidine-5-boronic acid; the sum yield of the two steps is 35%.

LCMS: 478.3[M+1]$^+$. $^1$H-NMR (400 MHz, DMSO-d6) δ: 3.25 (s, 3H), 3.72-3.78 (br, 4H), 3.80 (s, 3H), 4.25-4.32 (br, 4H), 5.19 (s, 2H), 8.72 (s, 2H), 9.26 (s, 1H), 9.62 (s, 2H).

Embodiment 13 Synthesis of 2-(((2-(2-aminopyrimidine-5-yl)-9-methyl-6-morpholine-9H-purine-8-yl))methyl(methyl) amino)-N-hydroxyl pyrimidine-5-formamide (Compound CLJ-11)

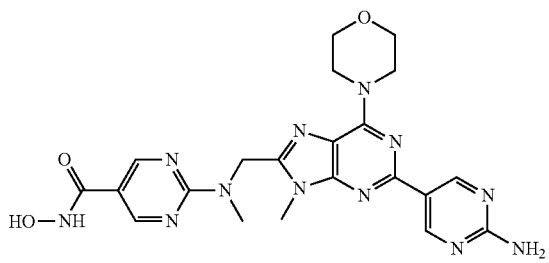 [SMILES: CN(Cc1nc2c(N3CCOCC3)nc(-c3cnc(N)nc3)nc2n1C)c1ncc(C(=O)NO)cn1]

The synthesis method is the same as that of Embodiment 3, except that 6-methoxypyridine-3-boronic acid is replaced by 2-aminopyrimidine-5-boronic acid; the sum yield of the two steps is 42%.

LCMS: 493.2[M+1]$^+$. $^1$H-NMR (400 MHz, DMSO-d6) δ: 3.22 (s, 3H), 3.71-3.82 (m, 7H), 4.20-4.28 (br, 4H), 5.16 (s, 2H), 7.03 (s, 2H), 8.73 (s, 2H), 9.11 (s, 2H).

Embodiment 14 Synthesis of 2-(((2-(4-amine methylpyrimidine)-9-methyl-6-morpholine-9H-purine-8-yl))methyl(methyl)amino)-N-hydroxyl pyrimidine-5-formamide (Compound CLJ-12)

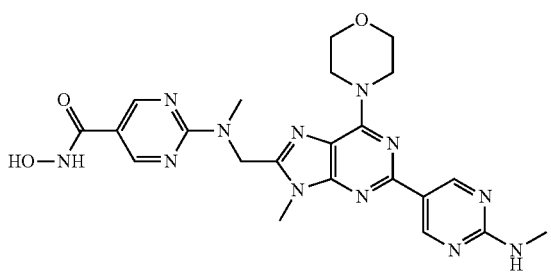 [SMILES: CNc1ncc(-c2nc(N3CCOCC3)c3nc(CN(C)c4ncc(C(=O)NO)cn4)n(C)c3n2)cn1]

The synthesis method is the same as that of Embodiment 3, except that the 6-methoxypyridine-3-boronic acid is replaced by 4-amine methylpyrimidine boronic acid; the sum yield of the two steps is 33%.

LCMS: 507.3[M+1]$^+$. $^1$H-NMR (400 MHz, DMSO-d6) δ: 2.92 (s, 3H), 3.22 (s, 3H), 3.71-3.80 (m, 7H), 4.20-4.28 (br, 4H), 5.16 (s, 2H), 7.03 (s, 2H), 8.73 (s, 2H), 9.11 (s, 2H).

Embodiment 15 Synthesis of 2-(((2-(4-methylpyrimidine)-9-methyl-6-morpholine-9H-purine-8-yl))methyl(methyl)amino)-N-hydroxyl pyrimidine-5-formamide (Compound CLJ-13)

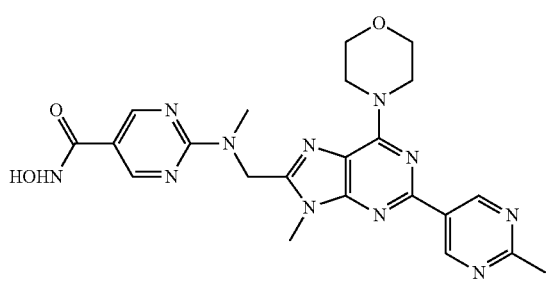

The synthesis method is the same as that of Embodiment 3, except that 6-methoxypyridine-3-boronic acid is replaced by 4-methoxypyridine boronic acid; the sum yield of the two steps is 32%.

LCMS: 492.3[M+1]$^+$. $^1$H-NMR (400 MHz, DMSO-d6) δ: 2.45 (s, 2H), 3.22 (s, 3H), 3.71-3.80 (m, 7H), 4.20-4.28 (br, 4H), 5.16 (s, 2H), 8.73 (s, 2H), 9.11 (s, 2H).

Embodiment 16 Synthesis of 2-(((2-(quinoline-3-yl)-9-methyl-6-morpholine-9H-purine-8-yl))methyl(methyl)amino)-N-hydroxyl pyrimidine-5-formamide (Compound CLJ-14)

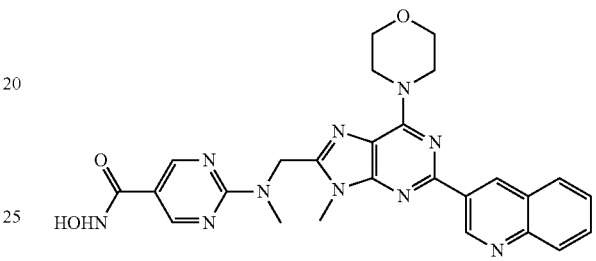

The synthesis method is the same as that of Embodiment 3, except that 6-methoxypyridine-3-boronic acid is replaced by quinolone-3-boronic acid; the sum yield of the two steps is 37%.

LCMS: 527.5 [M+1]$^+$. $^1$H-NMR (400 MHz, DMSO-d6) δ: 3.21 (s, 3H), 3.76 (s, 4H), 3.82 (s, 3H), 4.30 (s, 4H), 5.19 (s, 2H), 7.65 (t, 1H, J=7.6 Hz), 7.80 (t, 1H, J=7.6 Hz), 8.07 (d, 1H, J=8.4 Hz), 8.16 (d, 1H, J=8.0 Hz), 8.71 (s, 2H), 9.21 (s, 1H), 9.87 (s, 1H).

Embodiment 17 Synthesis of 2-(((2-(1H-indazole-5-yl)-9-methyl-6-morpholine-9H-purine-8-yl))methyl(methyl)amino)-N-hydroxyl pyrimidine-5-formamide (Compound CLJ-15)

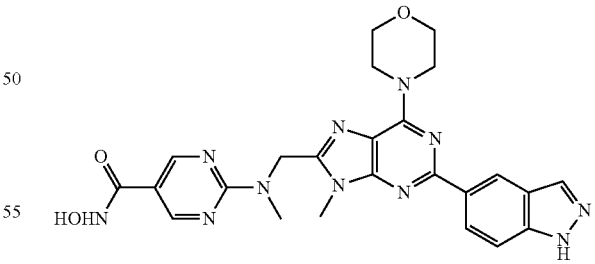

The synthesis method is the same as that of Embodiment 3, except that 6-methoxypyridine-3-boronic acid is replaced by 1H-indazole-5-boronic acid; the sum yield of the two steps is 45%.

LCMS: 516.3[M+1]$^+$. $^1$H-NMR (400 MHz, DMSO-d6) δ: 3.24 (s, 3H), 3.75 (s, 4H), 3.84 (s, 3H), 4.18-4.36 (br, 4H), 5.21 (s, 2H), 7.46 (s, 1H), 7.65 (s, 1H), 8.21 (s, 1H), 8.74 (s, 2H), 8.91 (s, 1H), 13.21 (s, 1H).

Embodiment 18 Synthesis of N-hydroxy-2-(((2-(1H-indazole-5-yl)-9-methyl-6-morpholine-9H-purine-8-yl))methyl(propyl)amino)pyrimidine-5-formamide (Compound CLJ-16)

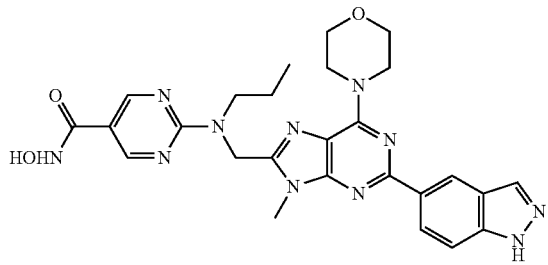

The synthesis method is the same as that of Embodiment 3, except that 6-methoxypyridine-3-boronic acid is replaced by 1H-indazole-5-boronic acid and meanwhile methylamine is replaced by propylamine in step 9 of the reaction; the sum yield of the final two steps is 27%.

LCMS: 544.3[M+1]$^+$. $^1$H-NMR (400 MHz, CDCl$_3$) δ: 0.90 (t, 4.8 Hz, 3H), 1.57-1.64 (m, 2H), 2.24 (s, 1H), 3.49 (t, 2H, J=4.8 Hz), 3.73-3.84 (m, 4H), 3.77 (s, 3H), 4.25 (s, 4H), 5.20 (s, 2H), 7.77 (s, 1H), 8.12 (s, 1H), 8.24 (s, 2H), 8.64 (s, 2H).

Embodiment 19 Synthesis of N-hydroxy-2-(((2-(1H-indazole-5-yl)-9-methyl-6-morpholine-9H-purine-8-yl))methyl(butyl)amino)pyrimidine-5-formamide (Compound CLJ-17)

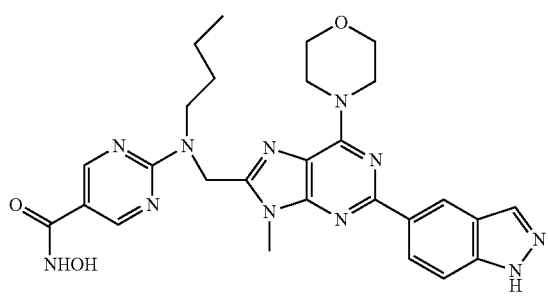

The synthesis method is the same as that of Embodiment 3, except that 6-methoxypyridine-3-boronic acid is replaced by 1H-indazole-5-boronic acid and meanwhile methylamine is replaced by butyl in step 9 of the reaction; the sum yield of the final two steps is 42%.

LCMS: 558.3[M+1]$^+$. $^1$H-NMR (400 MHz, CDCl$_3$) δ: 0.90 (t, 3H, J=4.8 Hz), 1.37-1.45 (m, 2H), 1.49-1.54 (m, 2H), 2.24 (s, 1H), 3.49 (t, 2H, J=4.8 Hz), 3.73-3.78 (m, 4H), 3.77 (s, 3H), 4.25 (s, 4H), 5.20 (s, 2H), 7.77 (s, 1H), 8.12 (s, 1H), 8.24 (s, 2H), 8.64 (s, 2H).

Embodiment 20 Synthesis of 2-(((2-(2-thienyl)-9-methyl-6-morpholine-9H-purine-8-yl))methyl(methyl)amino)-N-hydroxyl pyrimidine-5-formamide (Compound CLJ-18)

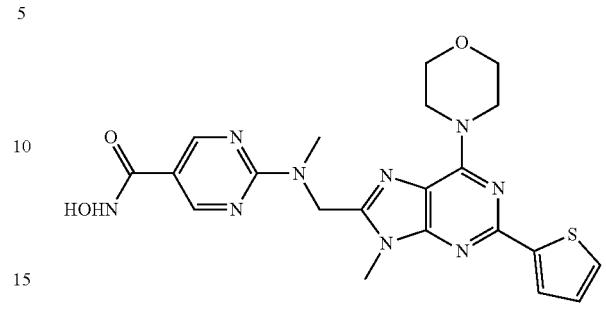

The synthesis method is the same as that of Embodiment 3, except that 6-methoxypyridine-3-boronic acid is replaced by thiophene-2-boronic acid; the sum yield of the two steps is 28%.

LCMS: 481.3[M+1]$^+$. $^1$H-NMR (400 MHz, DMSO-d6) δ: 3.18 (s, 3H), 3.72 (s, 7H), 4.22 (s, 4H), 5.15 (s, 2H), 7.54-7.61 (m, 1H), 7.80 (d, 1H, J=4.8 Hz), 8.23 (s, 1H), 8.68 (s, 2H).

Embodiment 21 Synthesis of 2-(((2-(3-methyl-2-thienyl)-9-methyl-6-morpholine-9H-purine-8-yl))methyl(methyl)amino)-N-hydroxyl pyrimidine-5-formamide (Compound CLJ-19)

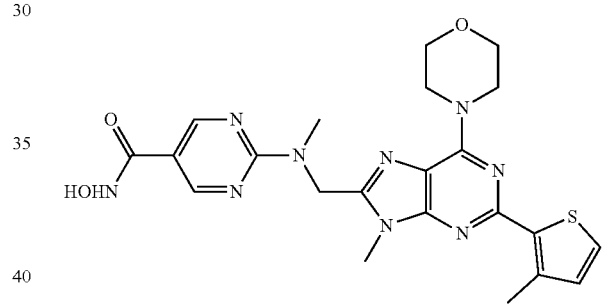

The operation is the same as that of Embodiment 3, except that the 6-methoxypyridine-3-boronic acid is replaced by (3-methyl-2-thienyl)boronic acid in step 12; the sum yield of the final two steps is 53%.

LCMS: 496.1[M+1]$^+$. $^1$H-NMR (400 MHz, DMSO-d6) δ: 2.34 (s, 3H), 3.16 (s, 3H), 3.73-3.79 (br, 7H), 4.22 (s, 4H), 5.18 (s, 2H), 7.82 (d, 1H, J=4.4 Hz), 8.20 (s, 1H), 8.72 (s, 2H).

Embodiment 22 Synthesis of 2-(((2-(5-carboxyl-2-thienyl)-9-methyl-6-morpholine-9H-purine-8-yl))methyl(methyl)amino)-N-hydroxyl pyrimidine-5-formamide (Compound CLJ-20)

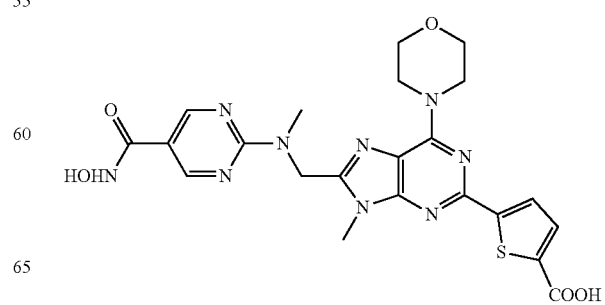

The operation is the same as that of Embodiment 3, except that the 6-methoxypyridine-3-boronic acid is replaced by (5-carboxyl-2-thienyl)boronic acid in step 12; the sum yield of the final two steps is 48%.

LCMS: 526.1[M+1]⁺. ¹H-NMR (400 MHz, DMSO-d6) δ: 3.16 (s, 3H), 3.72-3.82 (br, 7H), 4.26 (s, 4H), 5.22 (s, 2H), 7.88 (d, 1H, J=4.4 Hz), 8.25 (s, 1H), 8.73 (s, 2H).

Embodiment 23 Synthesis of 2-(((2-(5-n-butyl-2-thienyl)-9-methyl-6-morpholine-9H-purine-8-yl))methyl(methyl)amino)-N-hydroxyl pyrimidine-5-formamide (Compound CLJ-21)

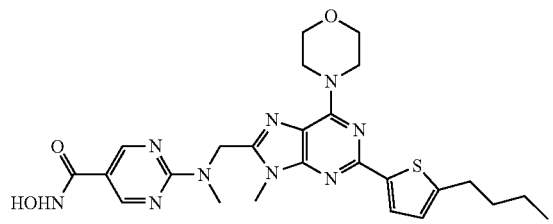

The operation is the same as that of Embodiment 3, except that the 6-methoxypyridine-3-boronic acid is replaced by (5-carboxyl-2-thienyl)boronic acid in step 12; the sum yield of the final two steps is 48%.

LCMS: 538.3[M+1]⁺. ¹H-NMR (400 MHz, DMSO-d6) δ: 0.9 (t, 3H, J=7.2 Hz), 1.33-1.51 (m, 4H), 2.36 (t, 2H, J=7.6 Hz), 3.18 (s, 3H), 3.71 (s, 7H), 4.16-4.30 (br, 4H), 5.16 (s, 2H), 7.15 (t, 1H, J=3.6 Hz), 7.58 (d, 1H, J=4.4 Hz), 8.72 (s, 2H).

Embodiment 24 Synthesis of 2-(((2-(3-thienyl)-9-methyl-6-morpholine-9H-purine-8-yl))methyl(methyl)amino)-N-hydroxyl pyrimidine-5-formamide (Compound CLJ-22)

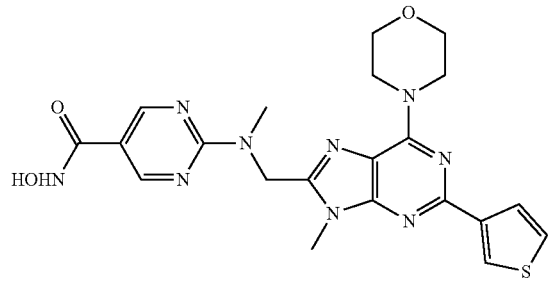

The synthesis method is the same as that of Embodiment 3, except that 6-methoxypyridine-3-boronic acid is replaced by pyrrole-2-boronic acid; the sum yield of the two steps is 43%.

LCMS: 482.2[M+1]⁺. ¹H-NMR (400 MHz, DMSO-d6) δ: 3.19 (s, 3H), 3.71 (s, 7H), 4.12-4.30 (br, 4H), 5.15 (s, 2H), 7.13 (t, 1H, J=3.2 Hz), 7.61 (d, 1H, J=4.4 Hz), 7.83 (d, 1H, J=2.8 Hz), 8.70 (s, 2H).

Embodiment 25 Synthesis of 2-(((2-(3-methyl-3-thienyl)-9-methyl-6-morpholine-9H-purine-8-yl))methyl(methyl)amino)-N-hydroxyl pyrimidine-5-formamide (Compound CLJ-23)

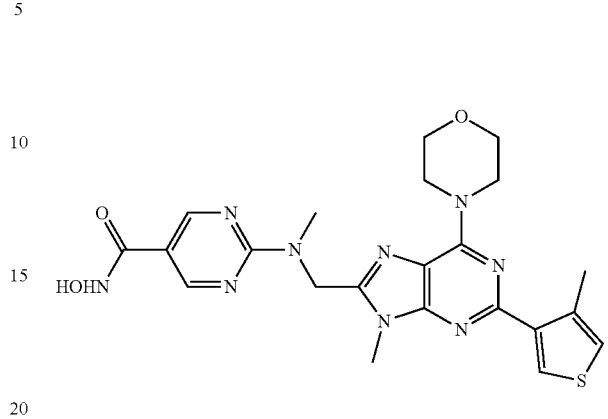

The operation is the same as that of Embodiment 3, except that the 6-methoxypyridine-3-boronic acid is replaced by (3-methyl-3-thienyl)boronic acid in step 12; the sum yield of the final two steps is 56%.

LCMS: 496.1[M+1]⁺. ¹H-NMR (400 MHz, DMSO-d6) δ: 2.38 (s, 3H), 3.16 (s, 3H), 3.71-3.77 (br, 7H), 4.18-4.32 (br, 4H), 5.17 (s, 2H), 7.12 (t, 1H, J=3.2 Hz), 7.58 (d, 1H, J=4.4 Hz), 8.72 (s, 2H).

Embodiment 26 Synthesis of 2-(((2-(1H-2-pyrrolyl)-9-methyl-6-morpholine-9H-purine-8-yl))methyl(methyl)amino)-N-hydroxyl pyrimidine-5-formamide (Compound CLJ-24)

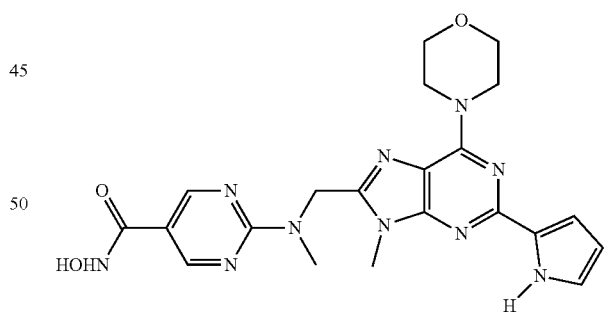

The operation is the same as that of Embodiment 3, except that the 6-methoxypyridine-3-boronic acid is replaced by (1(1H)-2-pyrrolyl)boronic acid in step 12; the sum yield of the final two steps is 49%.

LCMS: 565.1[M+1]⁺. ¹H-NMR (400 MHz, DMSO-d6) δ: 3.16 (s, 3H), 3.71 (s, 7H), 4.22-4.28 (br, 4H), 5.18 (s, 2H), 7.54-7.61 (m, 1H), 7.82 (d, 1H, J=4.4 Hz), 8.17 (s, 1H), 8.72 (s, 2H), 11.43 (s, 1H).

Embodiment 27 Synthesis of 2-(((1-(2-(dimethylamino)ethyl)-1H-4-pyrazolyl)-9-methyl-6-morpholine-9H-purine-8-yl))methyl(methyl)amino)-N-hydroxyl pyrimidine-5-formamide (Compound CLJ-25)

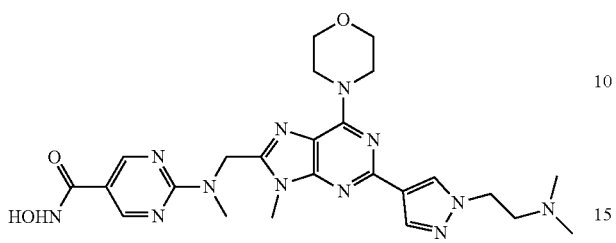

The operation is the same as that of Embodiment 3, except that the 6-methoxypyridine-3-boronic acid is replaced by (1-(2-(dimethylamino)ethyl)-1H-4-pyrazolyl)boronic acid in step 12; the sum yield of the final two steps is 52%.

LCMS: 537.1[M+1]+. 1H-NMR (400 MHz, DMSO-d6) δ: 2.88 (s, 6H), 3.16 (s, 3H), 3.71-3.76 (m, 9H), 4.22-4.26 (br, 4H), 5.18 (s, 2H), 5.46 (t, 2H, J=7.6 Hz), 7.94 (s, 1H), 7.97 (s, 1H), 8.70 (s, 2H).

Embodiment 28 Synthesis of 2-(((2-(2-furyl)-9-methyl-6-morpholine-9H-purine-8-yl))methyl(methyl)amino)-N-hydroxyl pyrimidine-5-formamide (Compound CLJ-26)

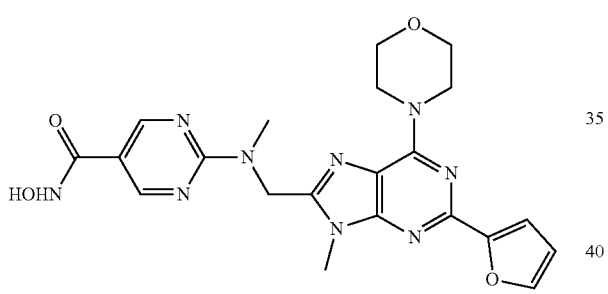

The operation is the same as that of Embodiment 3, except that the 6-methoxypyridine-3-boronic acid is replaced by 2-furan boronic acid in step 12; the sum yield of the final two steps is 46%.

LCMS: 466.1[M+1]+. 1H-NMR (400 MHz, DMSO-d6) δ: 3.21 (s, 3H), 3.63-3.77 (m, 7H), 4.11-4.29 (br, 4H), 5.16 (s, 2H), 6.61 (s, 1H), 7.14 (d, 1H, J=2.8 Hz), 7.80 (s, 1H), 8.72 (s, 2H).

Embodiment 29 Synthesis of 2-(((2-(3-hydroxyphenyl)-9-methyl-6-morpholine-9H-purine-8-yl))methyl(methyl)amino)-N-hydroxyl pyrimidine-5-formamide (Compound CLJ-27)

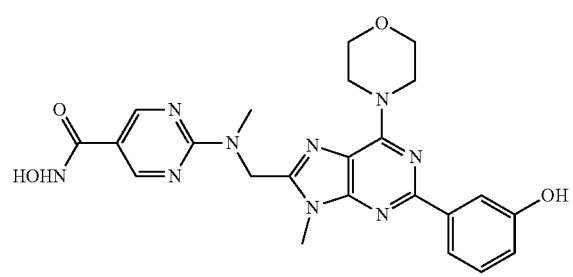

The operation is the same as that of Embodiment 3, except that 6-methoxypyridine-3-boronic acid is replaced by 3-hydroxy phenylboronic acid; the sum yield of the two steps is 37%.

LCMS: 492.2[M+1]+. 1H-NMR (400 MHz, DMSO-d6) δ: 3.22 (s, 3H), 3.73-3.79 (br, 4H), 3.75 (s, 3H), 4.23-4.29 (br, 4H), 5.18 (s, 2H), 6.82 (s, 1H), 7.24-7.28 (m, 1H), 7.84-7.92 (m, 2H), 8.73 (s, 2H).

Embodiment 30 Synthesis of 2-(((2-(4-hydroxyphenyl)-9-methyl-6-morpholine-9H-purine-8-yl))methyl(methyl)amino)-N-hydroxyl pyrimidine-5-formamide (Compound CLJ-28)

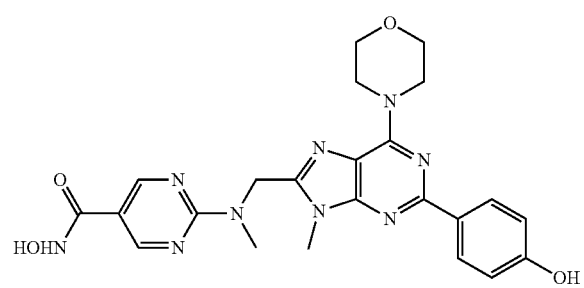

The synthesis method is the same as that of Embodiment 3, except that 6-methoxypyridine-3-boric acid is replaced by p-hydroxy phenylboronic acid; the sum yield of the two steps is 53%.

LCMS: 492.3[M+1]+. 1H-NMR (400 MHz, DMSO) δ: 3.18 (s, 3H), 3.66-3.74 (m, 4H), 3.77 (s, 3H), 4.27 (s, 4H), 5.16 (s, 2H), 7.82 (d, 2H, J=8.8 Hz), 8.58 (d, 2H, J=8.8 Hz), 8.64 (s, 2H).

Embodiment 31 Synthesis of 2-(((2-(4-methoxyphenyl)-9-methyl-6-morpholine-9H-purine-8-yl))methyl(methyl)amino)-N-hydroxyl pyrimidine-5-formamide (Compound CLJ-29)

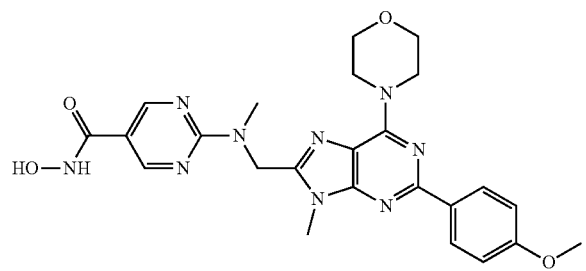 [SMILES: COc1ccc(-c2nc(N3CCOCC3)c3nc(CN(C)c4ncc(C(=O)NO)cn4)n(C)c3n2)cc1]

The synthesis method is the same as that of Embodiment 3, except that 6-methoxypyridine-3-boric acid is replaced by p-methoxy phenylboronic acid; the sum yield of the two steps is 22%.

LCMS: 506.2[M+1]+. 1H-NMR (400 MHz, DMSO-d6) δ: 3.23 (s, 3H), 3.72-3.78 (m, 4H), 3.75 (s, 3H), 3.81 (s, 3H), 4.22-4.28 (br, 4H), 5.17 (s, 2H), 7.01 (d, 2H, J=8.8 Hz), 8.33 (d, 2H, J=8.8 Hz), 8.72 (s, 2H), 9.03 (s, 1H), 11.09 (s, 1H).

Embodiment 32 Synthesis of 2-((9-ethyl-2(4-methoxyphenyl)-6-morpholino-9H-purine-8-yl)methyl)(methyl)amino-N-hydroxyl pyrimidine-5-formamide (Compound CLJ-30)

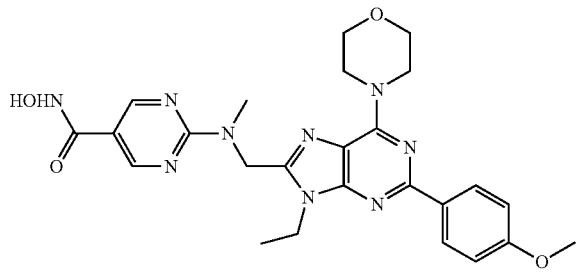

The synthesis method is the same as that of Embodiment 3, except that 6-methoxypyridine-3-boric acid is replaced by p-methoxy phenylboronic acid and meanwhile methyl iodide is replaced by ethyl iodide in step 5 of the reaction; the sum yield of the final two steps is 46%.

LCMS: 520.3[M+1]$^+$. $^1$H-NMR (400 MHz, DMSO-d6) δ: 1.29 (t, 2H, J=7.0 Hz), 3.64-3.72 (m, 4H), 3.75 (s, 3H), 3.81 (s, 3H), 4.12 (q, 3H, J=7.2 Hz), 4.22-4.30 (br, 4H), 5.17 (s, 2H), 7.01 (d, 2H, J=8.8 Hz), 8.33 (d, 2H, J=8.8 Hz), 8.72 (s, 2H), 9.03 (s, 1H), 11.10 (s, 1H).

Embodiment 33 Synthesis of 2-(((9-isopropyl-2-(6-metoxybenzene)-6-morpholino-9H-purine-8-yl)methyl)(methyl)amino-N-hydroxyl pyrimidine-5-formamide (Compound CLJ-31)

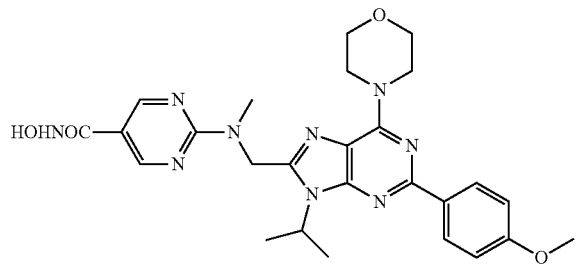

The synthesis method is the same as that of Embodiment 3, except that methyl iodide is replaced by 2-iodopropane in step 5 and 6-methoxy-3-pyridine boronic acid is replaced by 6-methoxy boronic acid in step 12 of the reaction; the sum yield of the final two steps is 38%.

LCMS: 534.3 [M+1]$^+$. $^1$H-NMR (400 MHz, DMSO-d6) δ:1.62 (d, 6H, J=6.4 Hz), 3.19 (s, 1H), 3.67-3.75 (m, 4H), 3.81 (s, 3H), 4.18-4.28 (br, 4H), 4.78-4.84 (m, 1H), 5.18 (s, 2H), 7.01 (d, 2H, J=8.8 Hz), 8.30 (d, 2H, J=8.8 Hz), 8.73 (s, 2H), 9.05 (s, 1H), 11.06 (s, 1H).

Embodiment 34 Synthesis of 2-(((9-cyclopentyl-2(4-methoxyphenyl)-6-morpholine-9H-purine-8-yl)methyl)(methyl)amino)-N-hydroxyl pyrimidine-5-formamide (Compound CLJ-32)

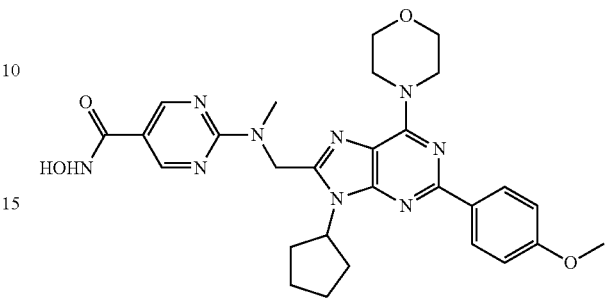

The synthesis method is the same as that of Embodiment 3, except that 6-methoxypyridine-3-boronic acid is replaced by p-methoxy phenylboronic acid and meanwhile methyl iodide is replaced by cyclopentane in step 5 of the reaction; the sum yield of the final two steps is 39%.

LCMS: 562.3[M+1]$^+$. $^1$H-NMR (400 MHz, DMSO-d6) δ: 1.56-1.64 (m, 4H), 1.83-1.92 (m, 4H), 3.23 (s, 3H), 3.61-3.70 (m, 2H), 3.72-3.76 (m, 4H), 3.81 (s, 3H), 4.22-4.30 (br, 4H), 5.17 (s, 2H), 7.01 (d, 2H, J=8.8 Hz), 8.33 (d, 2H, J=8.8 Hz), 8.72 (s, 2H), 9.03 (s, 1H), 11.09 (s, 1H).

Embodiment 35 Synthesis of N-hydroxy-2-(((2-(4-methoxyphenyl)-6-morpholino-9-butyl-9H-purine-8-yl)methyl)(methyl)amino)pyrimidine-5-formamide (Compound CLJ-33)

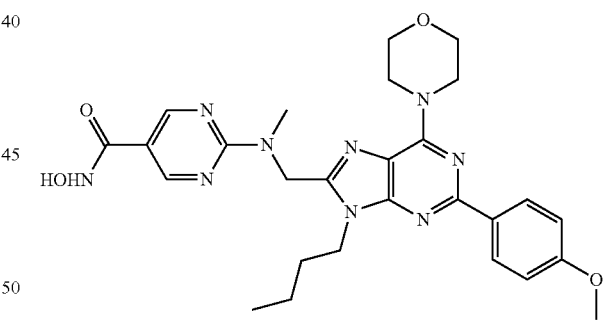

The synthesis method is the same as that of Embodiment 3, except that 6-methoxypyridine-3-boronic acid is replaced by p-methoxy phenylboronic acid and meanwhile methyl iodide is replaced by butyl iodide in step 5 of the reaction; the sum yield of the final two steps is 36%.

LCMS: 548.4[M+1]$^+$. $^1$H-NMR (400 MHz, DMSO-d6) δ: 0.90 (t, 3H, J=5.2 Hz), 1.29 (t, 2H, J=7.0 Hz), 1.97-2.04 (m, 2H), 3.68-3.72 (m, 4H), 3.75 (s, 3H), 3.81 (s, 3H), 4.12 (q, 3H, J=7.0 Hz), 4.22-4.28 (br, 4H), 5.17 (s, 2H), 7.01 (d, 2H, J=8.8 Hz), 8.33 (d, 2H, J=8.8 Hz), 8.72 (s, 2H), 9.03 (s, 1H), 11.10 (s, 1H).

Embodiment 36 Synthesis of N-hydroxy-2-(((2-(4-methoxyphenyl)-9-methyl-6-morpholine-9H-purine-8-yl)methyl)amino)pyrimidine-5-formamide (Compound CLJ-34)

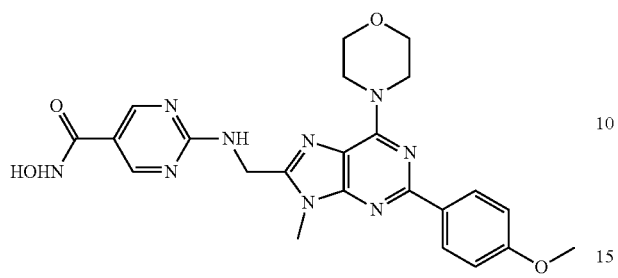

The synthesis method is the same as that of Embodiment 3, except that 6-methoxypyridine-3-boronic acid is replaced by p-methoxy phenylboronic acid and meanwhile methylamine is replaced by ammonia in step 9 of the reaction; the sum yield of the final two steps is 37%.

LCMS: 492.2[M+1]$^+$. $^1$H-NMR (400 MHz, DMSO-d6) δ: 3.68-3.72 (m, 4H), 3.75 (s, 3H), 3.81 (s, 3H), 4.22-4.30 (br, 4H), 5.17 (s, 2H), 7.01 (d, 2H, J=8.8 Hz), 8.33 (d, 2H, J=8.8 Hz), 8.72 (s, 2H), 9.03 (s, 1H), 10.01 (s, 1H), 11.09 (s, 1H).

Embodiment 37 Synthesis of 2-(((2-(3,4,5-trimetoxyphenyl)-9-methyl-6-morpholine-9H-purine-8-yl))methyl(methyl)amino)-N-hydroxyl pyrimidine-5-formamide (Compound CLJ-35)

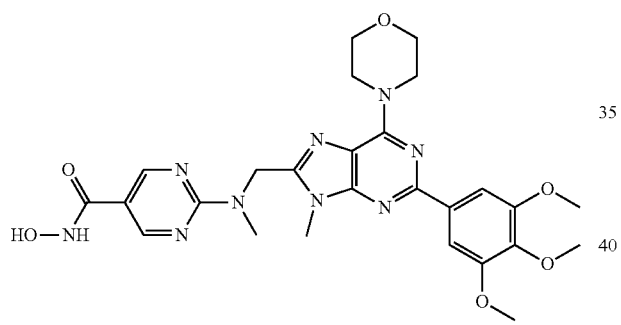

The synthesis method is the same as that of Embodiment 3, except that 6-methoxypyridine-3-boronic acid is replaced by 3,4,5-trimetoxyphenylboronic acid; the sum yield of the two steps is 29%.

LCMS: 551.2[M+1]$^+$. $^1$H-NMR (400 MHz, DMSO-d6) δ: 3.21 (s, 3H), 3.69-3.76 (br, 7H), 3.77 (s, 3H), 3.87 (s, 6H), 4.18-4.31 (br, 4H), 5.16 (s, 2H), 7.72 (s, 2H), 8.70 (s, 2H).

Embodiment 38 Synthesis of 2-(((2-(benzo[d][1,3]dioxole-5-yl)-9-methyl-6-morpholine-9H-purine-8-yl))methyl(methyl)amino)-N-hydroxyl pyrimidine-5-formamide (Compound CLJ-36)

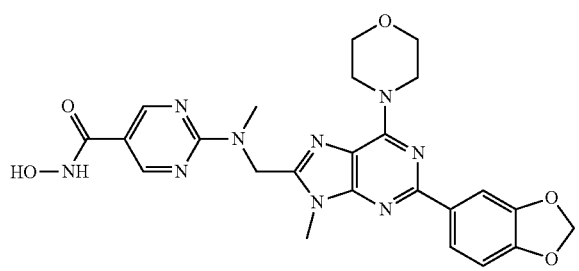 [SMILES: CN(Cc1nc2c(N3CCOCC3)nc(-c3ccc4c(c3)OCO4)nc2n1C)c1ncc(C(=O)NO)cn1]

The synthesis method is the same as that of Embodiment 3, except that 6-methoxypyridine-3-boronic acid is replaced by benzo 1,3 dioxolane-5-boronic acid; the sum yield of the two steps is 45%.

LCMS: 520.3[M+1]$^+$. $^1$H-NMR (400 MHz, DMSO-d6) δ: 3.21 (s, 3H), 3.64-3.72 (m, 4H), 3.74 (s, 3H), 4.22 (s, 4H), 5.16 (s, 2H), 6.08 (s, 2H), 6.90 (d, 1H, J=8.4 Hz), 7.87 (s, 1H), 7.99 (d, 1H, J=8.4 Hz), 8.71 (d, 2H, J=4.4 Hz).

Embodiment 39 Synthesis of 2-(((2-(benzo[d][1.4]dioxy heterocyclic hexylene-6-yl)-9-methyl-6-morpholine-9H-purine-8-yl))methyl(methyl)amino)-N-hydroxyl pyrimidine-5-formamide (Compound CLJ-37)

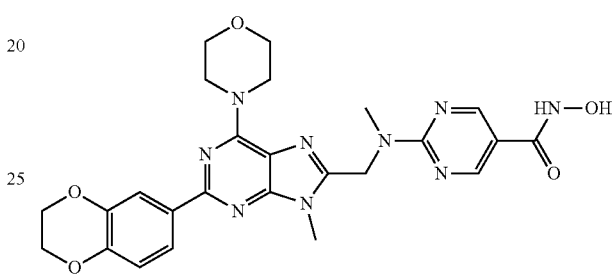

The synthesis method is the same as that of Embodiment 3, except that 6-methoxypyridine-3-boronic acid is replaced by benzo 1,4 dioxane-6-boronic acid in step 12; the sum yield of the two steps is 41%.

LCMS: 533.7 [M+1]$^+$. $^1$H-NMR (400 MHz, DMSO-d6) δ: 3.22 (s, 3H), 3.70 (s, 4H), 3.74 (s, 3H), 4.15-4.25 (br, 4H), 4.28 (s, 2H), 5.17 (s, 2H), 6.92 (d, 1H, J=8.4 Hz), 7.80-7.90 (m, 2H), 8.72 (s, 2H), 9.04 (s, 1H), 11.11 (s, 1H).

Embodiment 40 Synthesis of 2-(((2-(2-methoxy-5-trifluoromethylphenyl)-9-methyl-6-morpholine-9H-purine-8-yl))methyl(methyl)amino)-N-hydroxyl pyrimidine-5-formamide (Compound CLJ-38)

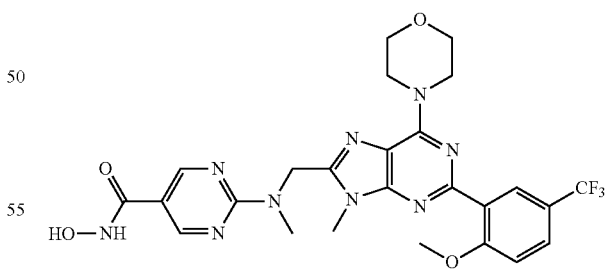

The synthesis method is the same as that of Embodiment 3, except that 6-methoxypyridine-3-boronic acid is replaced by 2-methoxy-5-trifluoromethyl phenylboronic acid; the sum yield of the two steps is 31%.

LCMS: 574.3[M+1]$^+$. $^1$H-NMR (400 MHz, DMSO-d6) δ: 3.22 (s, 3H), 3.58-3.64 (m, 4H), 3.70 (s, 3H), 3.84 (s, 3H), 4.15 (s, 4H), 5.18 (s, 2H), 7.30 (d, 1H, J=8.8 Hz), 7.76 (d, 1H, J=8.4 Hz), 7.80 (s, 1H), 8.71 (s, 2H).

Embodiment 41 Synthesis of 2-(((2-(2-(3-(1-hydroxyethyl)2-phenyl)-9-methyl-6-morpholine-9H-purine-8-yl))methyl(methyl)amino)-N-hydroxyl pyrimidine-5-formamide (Compound CLJ-39)

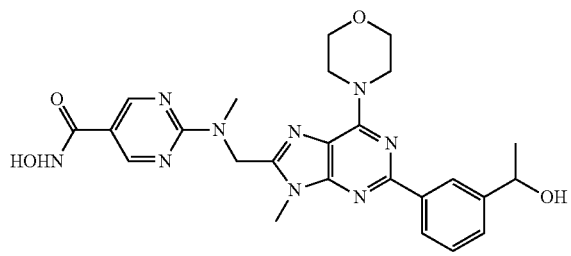

The synthesis method is the same as that of Embodiment 3, except that 6-methoxypyridine-3-boronic acid is replaced by 3-(1-hydroxyethyl) phenylboronic acid; the sum yield of the two steps is 33%.

LCMS: 536.3[M+1]$^+$. $^1$H-NMR (400 MHz, CDCl$_3$) δ: 1.59 (s, 3H), 2.11 (s, 1H), 2.17 (s, 1H), 3.16 (s, 3H), 3.64-3.72 (m, 4H), 3.80 (s, 4H), 3.93 (s, 3H), 4.51 (s, 1H), 4.58 (s, 1H), 4.71 (s, 1H), 6.86 (s, 1H), 7.36 (s, 1H), 7.50 (s, 1H), 7.81 (s, 1H), 8.03 (s, 1H), 8.48 (s, 2H).

Embodiment 42 Synthesis of 2-(((2-(3-(hydroxymethyl)phenyl)-9-methyl-6-morpholine-9H-purine-8-yl))methyl(methyl)amino)-N-hydroxyl pyrimidine-5-formamide (Compound CLJ-40)

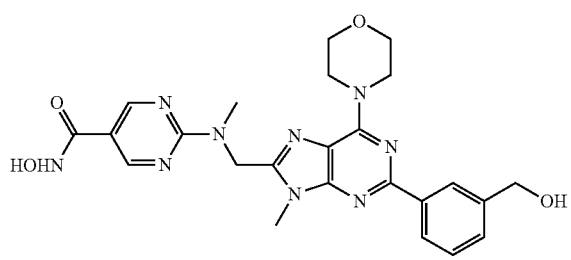

The synthesis method is the same as that of Embodiment 3, except that 6-methoxypyridine-3-boronic acid is replaced by 3-hydroxymethyl phenylboronic acid; the sum yield of the two steps is 36%.

LCMS: 506.3[M+1]$^+$. $^1$H-NMR (400 MHz, DMSO-d6) δ: 2.17 (d, 2H, J=9.2 Hz), 3.14 (s, 3H), 3.73-3.79 (br, 4H), 3.91 (s, 3H), 4.25 (s, 4H), 4.59 (d, 4H, J=13.2 Hz), 6.86 (s, 1H), 7.49 (d, 2H, J=14.0 Hz), 7.80 (s, 1H), 8.03 (s, 1H), 8.48 (s, 2H).

Embodiment 43 Synthesis of 2-(((2-(3-(2-hydroxylethyoxyl)phenyl)-9-methyl-6-morpholine-9H-purine-8-yl))methyl(methyl)amino)-N-hydroxyl pyrimidine-5-formamide (Compound CLJ-41)

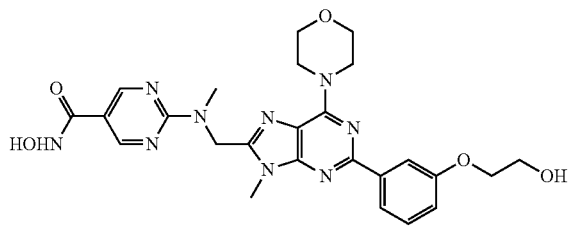

The synthesis method is the same as that of Embodiment 3, except that 6-methoxypyridine-3-boronic acid is replaced by (3-(2-hydroxylethyoxyl) phenylboronic acid; the sum yield of the two steps is 32%.

LCMS: 536.3[M+1]$^+$. $^1$H-NMR (400 MHz, CDCl$_3$) δ: 3.23 (s, 3H), 3.73-3.79 (m, 6H), 3.75 (s, 3H), 4.23-4.29 (br, 4H), 4.33 (m, 2H), 5.18 (s, 2H), 6.82 (s, 1H), 7.24-7.28 (m, 1H), 7.84-7.92 (m, 2H), 8.73 (s, 2H).

Embodiment 44 Synthesis of 2-(((2-(4-((2-hydroxycaproyl)sulfydryl)phenyl)-9-methyl-6-morpholine-9H-purine-8-yl))methyl(methyl)amino)-N-hydroxyl pyrimidine-5-formamide (Compound CLJ-42)

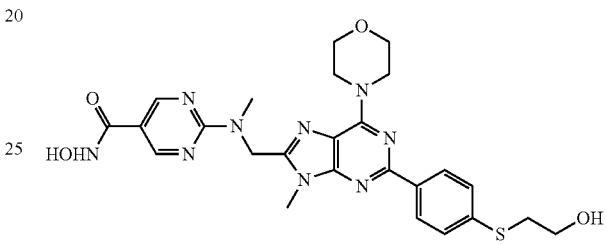

The operation is the same as that of Embodiment 3, except that 6-methoxypyridine-3-boronic acid is replaced by (4-((2-hydroxycaproyl)sulfydryl)phenyl)boronic acid in step 12; the sum yield of the final two steps is 42%.

LCMS: 536.3[M+1]$^+$. $^1$HNMR (400 MHz, DMSO-d6) δ: 3.22 (s, 3H), 3.72-3.78 (m, 6H), 3.76 (s, 3H), 4.23-4.31 (br, 4H), 4.33 (m, 2H), 5.16 (s, 2H), 5.56 (s, 1H), 6.82 (d, 2H, J=8.8 Hz), 8.18 (d, 2H, J=8.8 Hz), 8.73 (s, 2H), 9.01 (s, 1H), 11.03 (s, 1H).

Embodiment 45 Synthesis of 2-(((2-(4-isobutoxyphenyl)-9-methyl-6-morpholine-9H-purine-8-yl))methyl(methyl)amino)-N-hydroxyl pyrimidine-5-formamide (Compound CLJ-43)

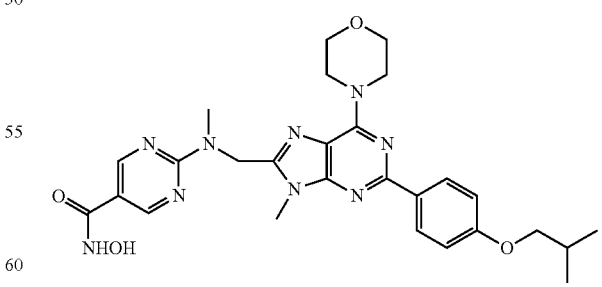

The operation is the same as that of Embodiment 3, except that 6-methoxypyridine-3-boronic acid is replaced by isobutoxy phenylboronic acid in step 12; the sum yield of the final two steps is 49%.

LCMS: 548.3[M+1]$^+$. $^1$H-NMR (400 MHz, DMSO-d6) δ: 0.91 (s, 6H), 1.88 (m, 1H), 3.22 (s, 3H), 3.71-3.79 (m, 4H), 3.75 (s, 3H), 3.88 (m, 2H), 4.22-4.28 (br, 4H), 5.16 (s, 2H), 7.11 (d, 2H, J=8.8 Hz), 8.34 (d, 2H, J=8.8 Hz), 8.73 (s, 2H), 9.03 (s, 1H), 11.09 (s, 1H).

Embodiment 46 Synthesis of 2-(((2-p-aminophenyl)-9-methyl-6-morpholine-9H-purine-8-yl))methyl(methyl)amino)-N-hydroxyl pyrimidine-5-formamide (Compound CLJ-44)

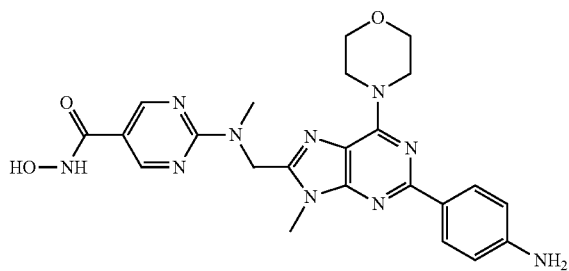 [SMILES: CN(Cc1nc2c(N3CCOCC3)nc(-c3ccc(N)cc3)nc2n1C)c1ncc(C(=O)NO)cn1]

The synthesis method is the same as that of Embodiment 3, except that 6-methoxypyridine-3-boronic acid is replaced by p-amino phenylboronic acid; the sum yield of the two steps is 34%.

LCMS: 491.3[M+1]$^+$. $^1$H-NMR (400 MHz, DMSO-d6) δ: 3.17 (s, 3H), 3.64-3.72 (m, 7H), 4.20 (s, 4H), 5.13 (s, 2H), 5.44 (s, 2H), 6.59 (d, 2H, J=8.4 Hz), 8.09 (d, 2H, J=8.4 Hz), 8.70 (s, 2H).

Embodiment 47 Synthesis of N-hydroxy-2-(((2-(4-aminophenyl)-6-morpholino-9-propyl-9H-purine-8-yl)methyl)(methyl)amino)pyrimidine-5-formamide (Compound CLJ-45)

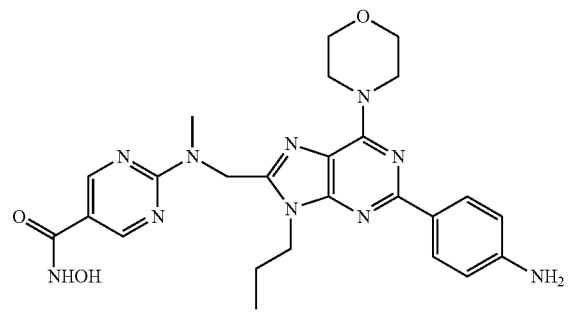

The synthesis method is the same as that of Embodiment 3, except that 6-methoxypyridine-3-boronic acid is replaced by p-amino phenylboronic acid and meanwhile methyl iodide is replaced by iodopropane in step 5 of the reaction; the sum yield of the final two steps is 42%.

LCMS: 519.4[M+1]$^+$. $^1$H-NMR (400 MHz, DMSO-d6) δ: 0.9 (t, J=5.2 Hz, 3H), 1.74-1.81 (m, 2H), 3.12 (s, 3H), 3.74-3.80 (br, 4H), 4.16 (t, 2H, J=10.0 Hz), 4.27 (s, 4H), 5.16 (s, 2H), 7.03 (s, 2H), 7.82 (d, 2H, J=8.4 Hz), 8.58 (d, 2H, J=8.4 Hz), 8.64 (s, 2H).

Embodiment 48 Synthesis of 2-(((2-(4-N,N-(hydroxymethyl)dimethyl phenyl)-9-methyl-6-morpholine-9H-purine-8-yl))methyl(methyl)amino)-N-hydroxyl pyrimidine-5-formamide (Compound CLJ-46)

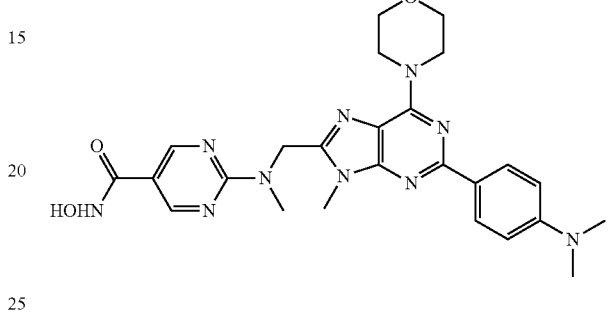

The synthesis method is the same as that of Embodiment 3, except that 6-methoxypyridine-3-boronic acid is replaced by 4-N,N-dimethyl phenylboronic acid; the sum yield of the two steps is 50%.

LCMS: 519.2[M+1]$^+$. $^1$H-NMR (400 MHz, DMSO-d6) δ: 3.06 (s, 6H), 3.16 (s, 3H), 3.74-3.80 (br, 4H), 3.77 (s, 3H), 4.27 (s, 4H), 5.16 (s, 2H), 7.82 (d, 2H, J=8.4 Hz), 8.58 (d, 2H, J=8.4 Hz), 8.64 (s, 2H).

Embodiment 49 Synthesis of N-hydroxy-2-(((2-(4-methylamino phenyl)-9-methyl-6-morpholine-9H-purine-8-yl)methyl)(butyl)amino)pyrimidine-5-formamide (Compound CLJ-47)

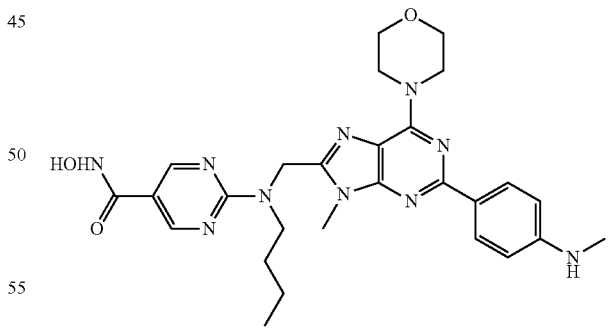

The synthesis method is the same as that of Embodiment 3, except that 6-methoxypyridine-3-boronic acid is replaced by p-methylamino boronic acid and meanwhile methylamine is replaced by butyl amine in step 9 of the reaction; the sum yield of the final two steps is 21%.

LCMS: 547.3[M+1]$^+$. $^1$H-NMR (400 MHz, CDCl$_3$) δ: 0.90 (t, 3H, J=4.8 Hz), 1.37-1.43 (m, 2H), 1.49-1.58 (m,

2H), 2.68 (s, 3H), 3.49 (t, 2H, J=4.8 Hz), 3.73-3.84 (m, 4H), 3.77 (s, 3H), 4.25 (s, 4H), 5.20 (s, 2H), 7.77 (s, 1H), 8.12 (d, 2H, J=8.4 Hz), 8.24 (d, 2H, J=8.4 Hz), 8.64 (s, 2H).

Embodiment 50 Synthesis of 2-(((9-methyl-2(p-aminoethyl benzene)-6-morpholino-9H-purine-8-yl)methyl)(methyl)amino-N-hydroxyl pyrimidine-5-formamide (Compound CLJ-48)

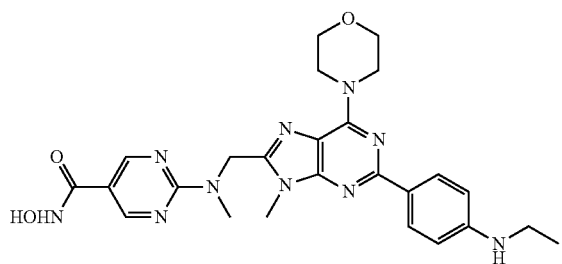

The synthesis method is the same as that of Embodiment 3, except that 6-methoxy-3-pyridine boronic acid is replaced by p-aminoethyl phenylboronic acid in step 12 of the reaction; the sum yield of the final two steps is 37%.

LCMS: 519.3 [M+1]$^+$. $^1$H-NMR (400 MHz, DMSO-d6) δ: 1.18 (t, 3H, J=7.2 Hz), 3.05-3.12 (m, 2H), 3.21 (s, 3H), 3.67-3.75 (br, 7H), 4.15-4.26 (br, 4H), 5.16 (s, 2H), 5.53-5.66 (t, 1H, J=5.2 Hz), 6.59 (d, 2H, J=8.8 Hz), 8.14 (d, 2H, J=8.8 Hz), 8.72 (s, 2H), 9.05 (s, 1H), 11.11 (s, 1H).

Embodiment 51 Synthesis of 2-(((9-methyl-2(p-N,N-diisopentenyl phenylamino)-6-morpholino-9H-purine-8-yl)methyl)(methyl)amino-N-hydroxyl pyrimidine-5-formamide (Compound CLJ-49)

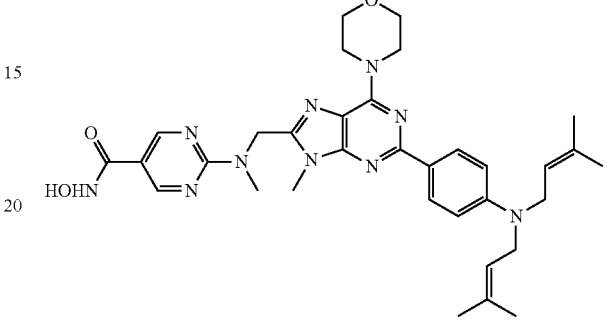

The synthesis method is the same as that of Embodiment 3, except that 6-methoxy-3-pyridine boronic acid is replaced by 4-N,N-diisopentenyl phenylboronic acid in step 12 of the reaction; the sum yield of the final two steps is 38%.

LCMS: 627.5 [M+1]$^+$. $^1$H-NMR (400 MHz, DMSO-d6) δ: 1.70 (d, J=3.6 Hz, 12H), 3.21 (s, 3H), 3.67-3.76 (br, 7H), 3.92 (d, J=5.6 Hz, 4H), 414-4.26 (br, 4H), 5.16 (s, 4H), 6.68 (d, J=8.8 Hz, 2H), 8.18 (d, J=8.8 Hz, 2H), 8.73 (s, 2H), 9.05 (s, 1H), 11.10 (s, 1H).

Embodiment 52 Synthesis of 2-(((2-(3-(2-chloroethyl sulfonamide)phenyl)-9-methyl-6-morpholine-9H-purine-8-yl))methyl(methyl)amino)-N-hydroxyl pyrimidine-5-formamide (Compound CLJ-50)

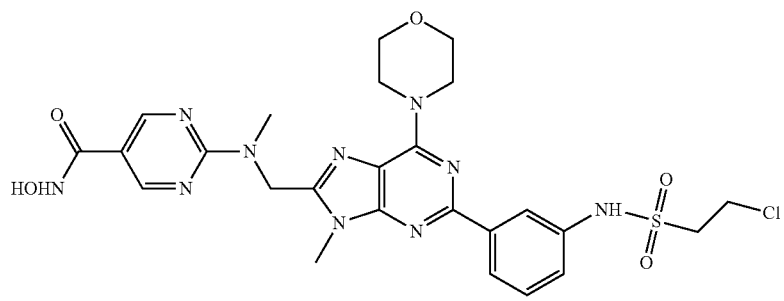

The operation is the same as that of Embodiment 3, except that 6-methoxypyridine-3-boronic acid is replaced by (3-(2-chloroethyl sulfonamido)phenyl)boronic acid in step 12; the sum yield of the final two steps is 38%.

LCMS: 617.4 [M+1]+. 1H-NMR (400 MHz, DMSO-d6) δ: 3.22 (s, 3H), 3.73-3.78 (m, 6H), 3.79 (s, 3H), 3.94 (m, 2H), 4.23-4.31 (br, 4H), 5.16 (s, 2H), 6.84 (s, 1H), 7.24-7.28 (m, 1H), 7.82-7.92 (m, 2H), 8.73 (s, 2H), 9.43 (s, 1H).

Embodiment 53 Synthesis of 2-(((2-(3-(2-chloro-propyl sulfonamide)phenyl)-9-methyl-6-morpholine-9H-purine-8-yl))methyl(methyl)amino)-N-hydroxyl pyrimidine-5-formamide (Compound CLJ-51)

The operation is the same as that of Embodiment 3, except that the 6-methoxypyridine-3-boronic acid is replaced by (4-amino t-butyloxycarboryl phenylboronic acid in step 12; the sum yield of the final two steps is 32%.

LCMS: 591.3 [M+1]+. 1H-NMR (400 MHz, DMSO-d6) δ: 1.34 (s, 9H), 3.18 (s, 3H), 3.64-3.72 (m, 7H), 4.22 (s, 4H), 5.16 (s, 2H), 7.11 (d, 2H, J=8.4 Hz), 8.09 (d, 2H, J=8.4 Hz), 8.81 (s, 2H), 9.41 (s, 1H).

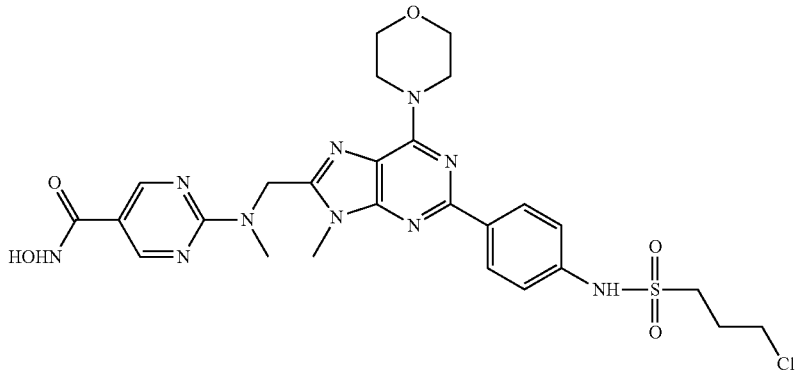

The operation is the same as that of Embodiment 3, except that 6-methoxypyridine-3-boronic acid is replaced by (4-(2-chloropropyl sulfonamido)phenyl)boronic acid in step 12; the sum yield of the final two steps is 42%.

LCMS: 631.2 [M+1]+. 1H-NMR (400 MHz, DMSO-d6) δ: 2.28 (m, 2H), 3.10 (t, 2H, J=2.4 Hz), 3.23 (s, 3H), 3.70-3.78 (m, 6H), 3.80 (s, 1H), 3.98 (m, 2H), 4.21-4.31 (br, 4H), 5.18 (s, 2H), 7.24 (d, 2H, J=8.4 Hz), 7.82 (d, 2H, J=8.4 Hz), 8.78 (s, 2H), 9.03 (s, 1H), 9.44 (s, 1H), 11.09 (s, 1H).

Embodiment 54 Synthesis of 2-(((2-(4-t-butyloxy-carboryl amino)phenyl)-9-methyl-6-morpholine-9H-purine-8-yl))methyl(methyl)amino)-N-hydroxyl pyrimidine-5-formamide (Compound CLJ-52)

Embodiment 55 Synthesis of 2-(((2-(2-methanesul-fonamide)phenyl)-9-methyl-6-morpholine-9H-purine-8-yl))methyl(methyl)amino)-N-hydroxyl pyrimidine-5-formamide (Compound CLJ-53)

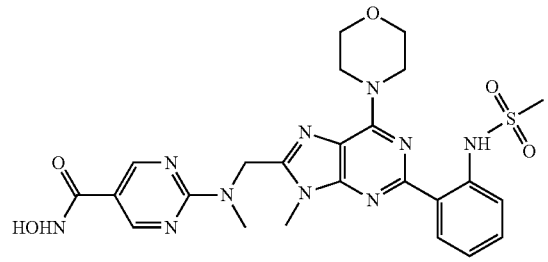

The operation is the same as that of Embodiment 3, except that 6-methoxypyridine-3-boric acid is replaced by 2-methanesulfonamide phenylboronic acid in step 12; the sum yield of the final two steps is 39%.

LCMS: 569.2 [M+1]+. 1H-NMR (400 MHz, DMSO-d6) δ: 3.21 (s, 3H), 3.25 (s, 3H), 3.63-3.72 (m, 7H), 4.42-4.46 (br, 4H), 5.16 (s, 2H), 7.01-7.10 (m, 2H), 7.28 (s, 1H), 7.60 (s, 1H), 8.70 (s, 2H).

Embodiment 56 Synthesis of 2-(((2-(-4-chlorine-3-trifluoromethylphenyl)-9-methyl-6-morpholine-9H-purine-8-yl))methyl(methyl)amino)-N-hydroxyl pyrimidine-5-formamide (Compound CLJ-54)

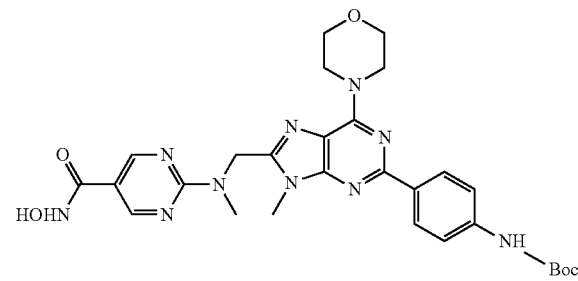

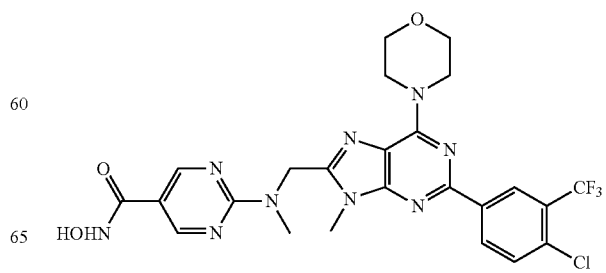

The synthesis method is the same as that of Embodiment 3, except that 6-methoxypyridine-3-boronic acid is replaced by 4-chlorine-3-trifluoromethyl phenylboronic acid; the sum yield of the two steps is 25%.

LCMS: 578.2[M+1]+. 1H-NMR (400 MHz, CDCl3) δ: 3.30 (s, 3H), 3.81 (s, 3H), 3.87 (s, 4H), 4.35 (s, 4H), 7.55 (d, 1H, J=8.4 Hz), 8.54 (d, 1H, J=8.4 Hz), 8.77 (s, 2H), 8.95 (s, 1H).

Embodiment 57 Synthesis of 2-(((2-p-trifluoromethylphenyl)-9-methyl-6-morpholine-9H-purine-8-yl)) methyl(methyl)amino)-N-hydroxyl pyrimidine-5-formamide (Compound CLJ-55)

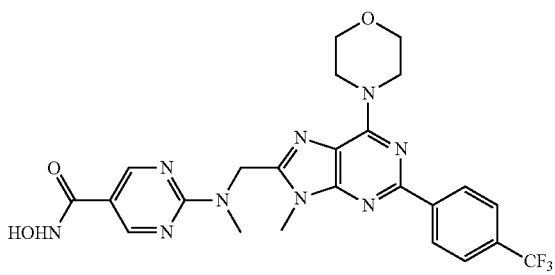

The synthesis method is the same as that of Embodiment 3, except that 6-methoxypyridine-3-boronic acid is replaced by p-trifluoromethyl phenylboronic acid; the sum yield of the two steps is 41%.

LCMS: 544.2[M+1]+. 1H-NMR (400 MHz, DMSO-d6) δ: 3.16 (s, 3H), 3.70-3.76 (br, 4H), 3.77 (s, 3H), 4.27 (s, 4H), 5.16 (s, 2H), 7.82 (d, 2H, J=8.4 Hz), 8.58 (d, 2H, J=8.4 Hz), 8.64 (s, 2H).

Embodiment 58 Synthesis of 2-(((2-3,5-ditrifluoromethylphenyl)-9-methyl-6-morpholine-9H-purine-8-yl))methyl(methyl)amino)-N-hydroxyl pyrimidine-5-formamide (Compound CLJ-56)

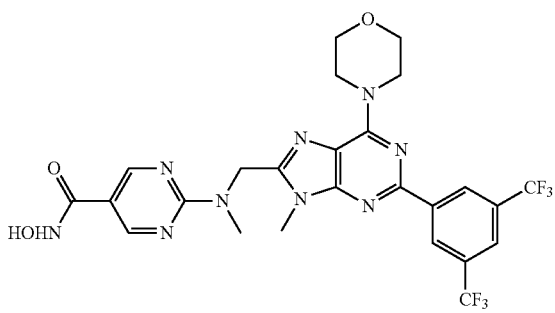

The synthesis method is the same as that of Embodiment 3, except that 6-methoxypyridine-3-boronic acid is replaced by 3,5-ditrifluoromethyl phenylboronic acid; the sum yield of the two steps is 40%.

LCMS: 612.3[M+1]+. 1H-NMR (400 MHz, DMSO-d6) δ: 3.25 (s, 3H), 3.63-3.74 (m, 4H), 3.82 (s, 3H), 4.24-2.30 (br, 4H), 5.20 (s, 2H), 8.21 (s, 1H), 8.72 (s, 2H), 8.90 (s, 2H).

Embodiment 59 Synthesis of 2-(((2-(4-methylsulphonylphenyl)-9-methyl-6-morpholine-9H-purine-8-yl))methyl(methyl)amino)-N-hydroxyl pyrimidine-5-formamide (Compound CLJ-57)

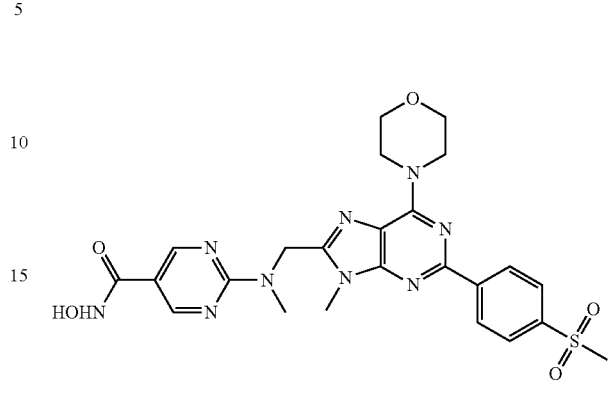

The synthesis method is the same as that of Embodiment 3, except that 6-methoxypyridine-3-boronic acid is replaced by p-methylsulphonyl phenylboronic acid; the sum yield of the two steps is 21%.

LCMS: 554.2[M+1]+. 1H-NMR (400 MHz, DMSO-d6) δ: 3.25 (s, 6H), 3.73 (s, 4H), 3.79 (s, 3H), 4.25 (s, 4H), 5.20 (s, 2H), 8.02 (d, 2H, J=7.8 Hz), 8.61 (d, 2H, J=8.0 Hz), 8.73 (s, 2H).

Embodiment 60 Synthesis of 2-(((2-(4-(N-(3-chloropropyl)sulfonamide)phenyl)-9-methyl-6-morpholine-9H-purine-8-yl))methyl(methyl)amino)-N-hydroxyl pyrimidine-5-formamide (Compound CLJ-58)

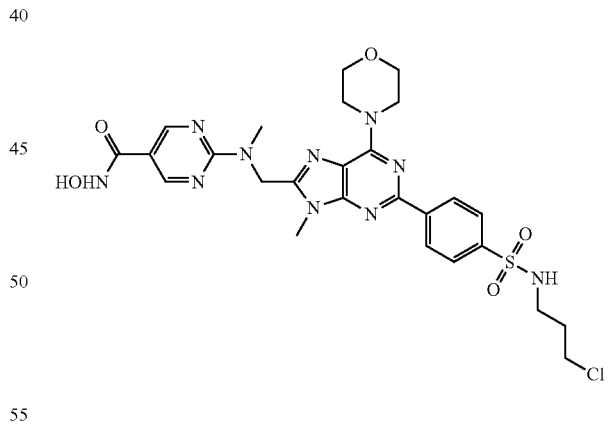

The operation is the same as that of Embodiment 3, except that 6-methoxypyridine-3-boronic acid is replaced by (4-(N-(3-chloropropyl)sulfonamide)phenyl)boronic acid in step 12; the sum yield of the final two steps is 41%.

LCMS: 631.3 [M+1]+. 1H-NMR (400 MHz, DMSO-d6) δ: 2.21 (m, 2H), 3.12 (t, 2H, J=2.0 Hz), 3.22 (s, 3H), 3.70-3.78 (m, 6H), 3.82 (s, 1H), 3.98 (m, 2H), 4.21-4.29 (br, 4H), 5.16 (s, 2H), 7.26 (d, 2H, J=8.4 Hz), 7.80 (d, 2H, J=8.4 Hz), 8.70 (s, 2H), 9.01 (s, 1H), 9.44 (s, 1H), 11.08 (s, 1H).

Embodiment 61 Synthesis of 2-(((2-(3-(N-(hydroxymethyl)sulfonamide)phenyl)-9-methyl-6-morpholine-9H-purine-8-yl))methyl(methyl)amino)-N-hydroxyl pyrimidine-5-formamide (Compound CLJ-59)

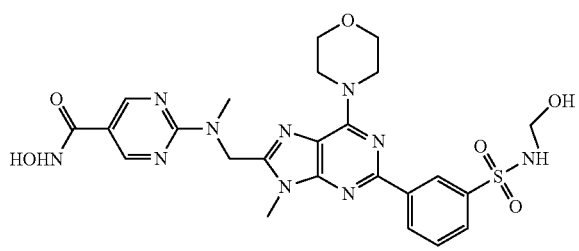

The operation is the same as that of Embodiment 3, except that 6-methoxypyridine-3-boronic acid is replaced by (3-(N-(hydroxymethyl)sulfonyl)phenyl)boronic acid in step 12; the sum yield of the final two steps is 48%.

LCMS: 584.2 [M+1]$^+$. $^1$H-NMR (400 MHz, DMSO-d6) δ: 3.18 (s, 3H), 3.73-3.79 (br, 4H), 3.75 (s, 3H), 4.20-4.28 (br, 4H), 5.16 (s, 2H), 5.48 (m, 2H), 6.81 (s, 1H), 7.21-7.27 (m, 2H), 7.84-7.88 (m, 1H), 8.70 (s, 2H), 9.03 (s, 1H), 10.08 (s, 1H).

Embodiment 62 Synthesis of 2-(((2-(p-methyl benzene)-9-methyl-6-morpholine-9H-purine-8-yl))methyl(methyl)amino)-N-hydroxyl pyrimidine-5-formamide (Compound CLJ-60)

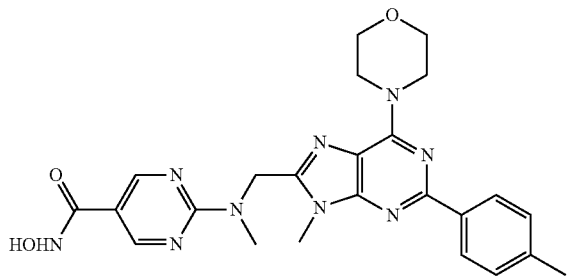

The synthesis method is the same as that of Embodiment 3, except that 6-methoxypyridine-3-boronic acid is replaced by p-methyl phenylboronic acid; the sum yield of the final two steps is 59%.

LCMS: 490.5 [M+1]$^+$. $^1$H-NMR (400 MHz, DMSO-d6) δ: 2.36 (s, 3H), 3.21 (s, 3H), 3.72 (s, 4H), 3.75 (s, 3H), 4.18-4.30 (br, 4H), 5.17 (s, 2H), 7.27 (d, 2H, J=8.0 Hz), 8.29 (d, 2H, J=8.0 Hz), 8.71 (s, 2H).

Embodiment 63 Synthesis of 2-(((2-(4-ethylphenyl)-9-methyl-6-morpholine-9H-purine-8-yl))methyl(methyl)amino)-N-hydroxyl pyrimidine-5-formamide (Compound CLJ-61)

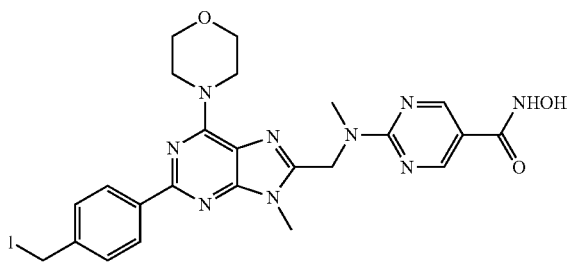

The operation is the same as that of Embodiment 3, except that 6-methoxypyridine-3-boronic acid is replaced by 4-ethyl phenylboronic acid in step 12; the sum yield of the final two steps is 44%.

LCMS: 503.8[M+1]$^+$. $^1$H-NMR (400 MHz, DMSO-d6) δ: 1.21 (t, 3H, J=7.2 Hz), 2.66 (q, 2H, J=7.2 Hz), 3.23 (s, 3H), 3.76 (s, 4H), 4.23 (s, 4H), 5.18 (s, 2H), 7.30 (d, 2H, J=7.2 Hz), 8.30 (d, 2H, J=7.6 Hz), 8.73 (s, 2H), 9.06 (s, 1H), 11.12 (s, 1H).

Embodiment 64 Synthesis of 2-(((2-(4-propylphenyl)-9-methyl-6-morpholine-9H-purine-8-yl))methyl(methyl)amino)-N-hydroxyl pyrimidine-5-formamide (Compound CLJ-62)

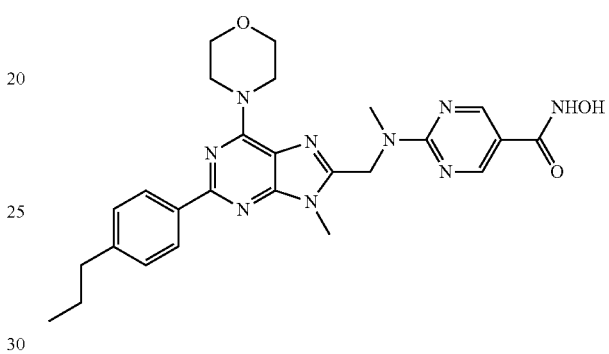

The operation is the same as that of Embodiment 3, except that 6-methoxypyridine-3-boronic acid is replaced by 4-propyl phenylboronic acid in step 12; the sum yield of the final two steps is 42%.

LCMS: 517.0 [M+1]$^+$. $^1$H-NMR (400 MHz, DMSO-d6) δ: 0.92 (t, 3H, J=7.2 Hz), 1.62 (m, 2H), 2.60 (t, 2H, J=7.6 Hz), 3.22 (s, 3H), 3.72 (m, 4H), 3.76 (s, 3H), 4.23 (m, 4H), 5.18 (s, 2H), 7.28 (d, 2H, J=8.0 Hz), 8.29 (d, 2H, J=8.0 Hz), 8.72 (s, 2H).

Embodiment 65 Synthesis of 2-(((9-methyl-2(4-t-butylphenyl)-6-morpholino-9H-purine-8-yl)methyl)(methyl)amino-N-hydroxyl pyrimidine-5-formamide (Compound CLJ-63)

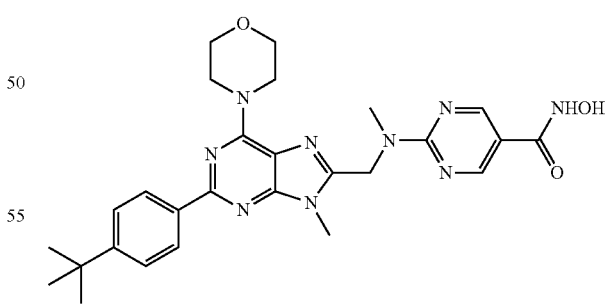

The synthesis method is the same as that of Embodiment 3, except that 6-methoxy-3-pyridine boronic acid is replaced by p-tertiary butyl boronic acid in step 12 of the reaction; the sum yield of the final two steps is 42%.

LCMS: 532.3[M+1]$^+$. $^1$H-NMR (400 MHz, DMSO-d6) δ: 1.32 (s, 9H), 3.23 (s, 3H), 3.67-3.75 (m, 4H), 3.76 (s, 3H), 4.17-4.29 (br, 4H), 5.18 (s, 2H), 7.48 (d, 2H, J=8.4 Hz), 8.29 (d, 2H, J=8.4 Hz), 8.73 (s, 2H), 9.06 (s, 1H), 11.12 (s, 1H).

Embodiment 66 Synthesis of 2-(((2-(3-carbamoyl-phenyl)-9-methyl-6-morpholine-9H-purine-8-yl))methyl(methyl)amino)-N-hydroxyl pyrimidine-5-formamide (Compound CLJ-64)

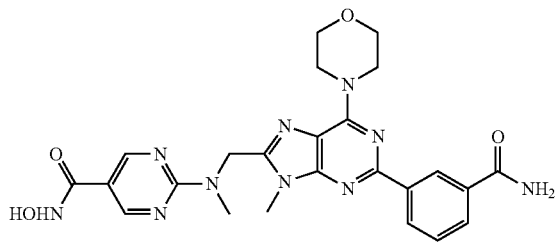

The operation is the same as that of Embodiment 3, except that 6-methoxypyridine-3-boronic acid is replaced by 3-carbamoyl phenylboronic acid in step 12; the sum yield of the final two steps is 47%.

LCMS: 519.2[M+1]⁺. ¹H-NMR (400 MHz, DMSO-d6) δ: 3.23 (s, 3H), 3.73-3.79 (br, 4H), 3.75 (s, 3H), 4.23-4.29 (br, 4H), 5.16 (s, 2H), 6.76 (s, 1H), 7.24-7.32 (m, 2H), 7.84-7.88 (m, 1H), 8.70 (s, 2H), 8.88 (s, 2H), 9.03 (s, 1H), 11.09 (s, H).

Embodiment 67 Synthesis of 2-(((2-(3-(N-(hydroxyethyl)acylamino)phenyl)-9-methyl-6-morpholine-9H-purine-8-yl))methyl(methyl)amino)-N-hydroxyl pyrimidine-5-formamide (Compound CLJ-65)

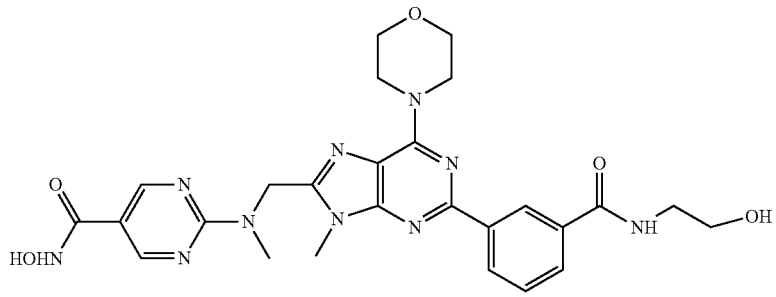

The operation is the same as that of Embodiment 3, except that 6-methoxypyridine-3-boronic acid is replaced by (3-(N-(hydroxyethyl)acylamino)phenyl)boronic acid in step 12; the sum yield of the final two steps is 47%.

LCMS: 563.2 [M+1]⁺. ¹H-NMR (400 MHz, DMSO-d6) δ: 3.18 (s, 3H), 3.30 (m, 2H), 3.60-3.65 (m, 2H), 3.71-3.77 (br, 4H), 3.76 (s, 3H), 4.20-4.28 (br, 4H), 5.16 (s, 2H), 6.88 (s, 1H), 7.20-7.26 (m, 1H), 7.84-7.92 (m, 2H), 8.72 (s, 2H), 8.88 (s, 1H), 9.03 (s, 1H), 9.44 (s, 1H), 11.09 (s, 1H).

Embodiment 68 Synthesis of 2-(((2-(3-(4-(hydroxymethyl)piperazine-1-carbonyl)phenyl)-9-methyl-6-morpholine-9H-purine-8-yl))methyl(methyl)amino)-N-hydroxyl pyrimidine-5-formamide (Compound CLJ-66)

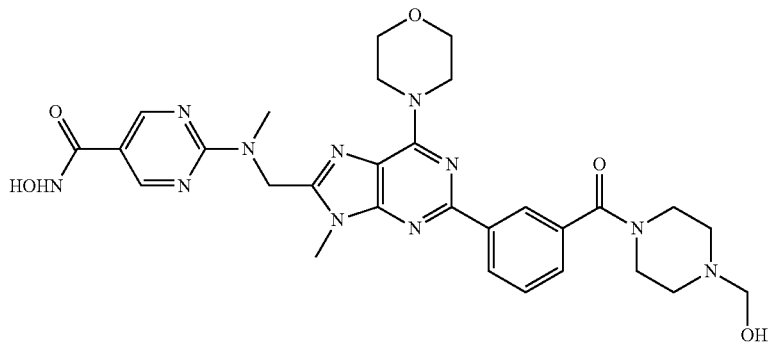

The operation is the same as that of Embodiment 3, except that 6-methoxypyridine-3-boronic acid is replaced by (3-(4-(hydroxymethyl)piperazine-1-carbonyl)phenyl)boronic acid in step 12; the sum yield of the final two steps is 49%.

LCMS: 618.3 [M+1]+. 1H-NMR (400 MHz, DMSO-d6) δ: 2.55-2.63 (br, 4H), 3.23 (s, 3H), 3.44-3.52 (m, 4H), 3.72-3.78 (br, 4H), 3.76 (s, 3H), 4.22-4.28 (br, 4H), 4.60 (s, 2H), 5.16 (s, 2H), 6.83 (s, 1H), 7.06 (s, 1H), 7.24-728 (m, 2H), 7.84-7.90 (m, 1H), 8.72 (s, 2H), 9.03 (s, 1H), 11.09 (s, 1H).

Embodiment 69 Synthesis of 2-(((2-(4-((4-morpholinylmethy)phenyl)-9-methyl-6-morpholine-9H-purine-8-yl))methyl(methyl)amino)-N-hydroxyl pyrimidine-5-formamide (Compound CLJ-67)

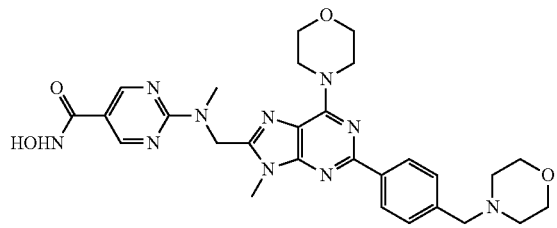

The operation is the same as that of Embodiment 3, except that 6-methoxypyridine-3-boronic acid is replaced by 4-(4-morpholinylmethy) phenylboronic acid in step 12; the sum yield of the final two steps is 52%.

LCMS: 575.3[M+1]+. 1H-NMR (400 MHz, DMSO-d6) δ: 2.50-2.58 (br, 4H), 3.23 (s, 3H), 3.72-3.78 (br, 11H), 4.18-4.32 (br, 4H), 5.18 (s, 2H), 5.20 (s, 2H), 7.06 (d, 2H, J=8.4 Hz), 8.10 (d, 2H, J=8.4 Hz).

Embodiment 70 Synthesis of 2-(((2-(4-chlorine)-9-methyl-6-morpholino-9H-purine-8-yl)methyl (methyl)amino)-N-hydroxyl pyrimidine-5-formamide (Compound CLJ-68)

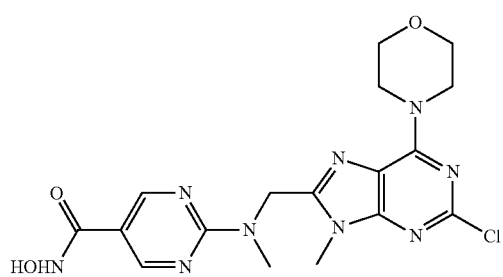

The synthesis method is the same as that of Embodiment 3, except that step 12 of the reaction is omitted; the target compound is obtained by midbody 13 through step 14; the yield of the last step is 86%.

LCMS: 433.6 [M+1]+. 1H-NMR (400 MHz, DMSO-d6) δ: 3.20 (s, 3H), 3.65 (s, 7H), 3.91-4.31 (br, 4H), 5.14 (s, 2H), 8.70 (s, 2H).

Embodiment 71 Synthesis of N-hydroxy-2-(((2-(4-methoxyphenyl)-9-methyl-6-(piperazine-1-yl)-9H-purine-8-yl)methyl)(methyl)amino)pyrimidine-5-formamide (Compound CLJ-69)

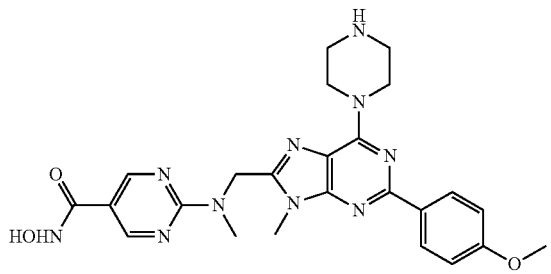

The synthesis method is the same as that of Embodiment 3, except that 6-methoxypyridine-3-boronic acid is replaced by p-methoxy phenylboronic acid and meanwhile morpholine ring is replaced by piperazine ring in step 6 of the reaction; the sum yield of the final two steps is 20%.

LCMS: 505.3[M+1]+. 1H-NMR (400 MHz, DMSO-d6) δ: 2.78-2.86 (br, 4H), 3.17 (s, 4H), 3.23 (s, 3H), 3.75 (s, 3H), 3.81 (s, 3H), 5.17 (s, 2H), 7.01 (d, 2H, J=8.8 Hz), 8.33 (d, 2H, J=8.8 Hz), 8.72 (s, 2H), 9.03 (s, 1H), 10.01 (s, 1H), 11.09 (s, 1H).

Embodiment 72 Synthesis of N-hydroxy-2-(((2-(4-methoxyphenyl)-9-methyl-6-(4-(2-hydroxyethyl piperazine)-1-yl)-9H-purine-8-yl)methyl)(methyl) amino)pyrimidine-5-formamide (Compound CLJ-70)

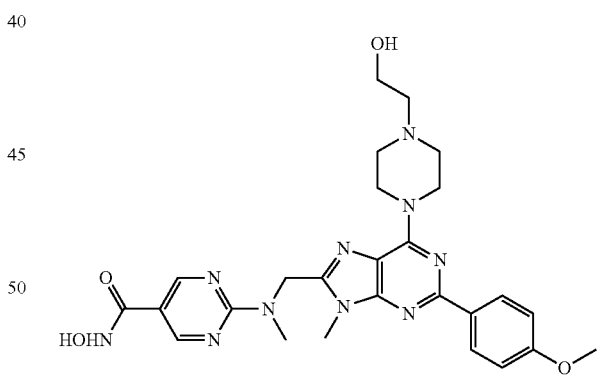

The synthesis method is the same as that of Embodiment 3, except that 6-methoxypyridine-3-boronic acid is replaced by p-methoxy phenylboronic acid and meanwhile morpholine ring is replaced by 4-(2-hydroxyethyl piperazine) in step 6 of the reaction; the sum yield of the final two steps is 27%.

LCMS: 549.3[M+1]+. 1H-NMR (400 MHz, DMSO-d6) δ: 2.53 (t, 2H, J=5, 2 Hz), 3.45 (t, 2H, J=5.2 Hz), 3.2 (s, 3H), 3.47 (s, 4H), 3.62-3.70 (br, 4H), 3.78 (s, 3H), 3.81 (s, 3H), 4.65 (s, 1H), 5.17 (s, 2H), 7.01 (d, 2H, J=8.8 Hz), 8.33 (d, 2H, J=8.8 Hz), 8.72 (s, 2H), 9.03 (s, 1H), 10.01 (s, 1H), 11.10 (s, 1H).

Embodiment 73 Determination of the Inhibition Capability of the Compound to the Activities of Histone Deacetylase of Subtype I (HDAC1) and Phosphoinositol 3-Kinase of all Subtypes The following tests are used for determining the inhibition values $IC_{50}$ of the small molecule compound of the Invention and the control compounds CUDC907 and LBH589 for inhibiting HDAC kinases, PI3K kinases and mTOR.

a) In vitro test for determining the inhibition capability of the compound to the enzymatic activity of HDAC1:

Determining the inhibition capability to HDAC activity through the substrate method of fluorophore 4-amino-7-coumarin coupled Ac-peptide (Lys-Ac-AMC). HDAC1 protein is purchased from BPS Bioscience Company; the reaction buffer system is a modified tris(hydroxymethyl) aminomethane (TRIS) buffer (pH7.0). All small molecule compounds are prepared and dissolved by 100% DMSO (dimethyl sulfoxide). HDAC is prepared into the buffer as per certain concentration to be served as the enzyme solution; trypsin and the fluorophore 4-amino-7-coumarin coupled Ac-peptide substrate are prepared into the buffer as per certain concentration to be served as the substrate solution. Adding the compound into the reaction wells of the 384 well plate at the designed concentration, then adding 15 µL HDAC solution into the reaction wells (adding 15 µL blank buffer into the control well 0) for incubation under ambient temperature for 15 min; then adding 10 µL substrate solution to start reaction; during the reaction, the final concentration of HDAC1 protein is 6 nM, trypsin 0.05 µM and Ac-peptide 8 µM. Keeping the 384 well plate in dark place for incubation under ambient temperature for 1 h, then determining the fluorescence intensity with a microplate reader (emission wavelength: 355 nm, absorption wavelength: 460 nm) and analyzing the result data with the software GraphPad Prism.

Calculating the value of $IC_{50}$ as per the formula:

$$Y=\text{background data}+(\text{top data}-\text{background data})/(1+10^{((\text{Log IC50}-X)*\text{rate of curve})})$$

Where, Y refers to the inhibition ratio (%) and X refers to the compound concentration.

b) In vitro test for determining the inhibition capability of the compound to PI3Kα and PI3Kδ activities:

Detecting the inhibition capability of the compound to PI3Kα and PI3Kδ activities with Kinase-Glo (purchased from Promege Company; Catalog No.: V3771). PI3Kα protein is purchased from Invitrogen Company (Catalog No.: PV4788) and PI3Kδ protein is purchased from Millipore Company (Catalog No.: 14-604-K). The reaction system also comprises substrates as $PIP_2$ (4, 5-diphosphoinositide, purchased from Life Technologies Company) and ATP (triphosadenine, purchased from Sigma Company). The reaction buffer system comprises 50 mM HEPES (4-hydroxyethylpiperazine ethane sulfonic acid), 3 mM $MgCl_2$, 1 mM EGTA (ethylene glycol bis(2-amino ethylether) quadrol), 100 mM NaCl, 0.03% CHAPS (3-[3-(cholamidopropyl)dimethylamino]-1-propanesulfonic acid), 2 mM DTT (dithiothreitol). The pH value of the reaction buffer is 7.5. Preparing 10 µL reaction system in corresponding wells of the 384 well plate, which contains the compositions as: the compound with designed concentration (or blank control), protein kinases (PI3Kα, with the concentration of 1.65 nM in PI3Kα test and PI3Kδ, with the concentration of 5.7 nM in PI3Kδ test) and substrates ($PIP_2$, with the concentration of 50 µM and ATP, with the concentration of 25 µM). Mixing the system evenly for incubation under ambient temperature (for 1 h in PI3Kα test and for 2 h in PI3Kδ test). After incubation, adding 10 µL Kinase-Glo which has been preheated to ambient temperature into each reaction well to terminate the reaction; shaking it in dark place for 15 min after it is mixed evenly, then measuring the fluorescence intensity with a microplate reader and analyzing the result data with the software GraphPad Prism.

Calculating the value of $IC_{50}$ as per the formula:

$$Y=\text{background data}+(\text{top data}-\text{background data})/(1+10^{((\text{Log IC50}-X)*\text{rate of curve})})$$

Where, Y refers to the inhibition ratio (%) and X refers to the compound concentration.

c) In vitro test for determining the inhibition capability of the compound to PI3Kβ and PI3Kγ activities:

Detecting the inhibition capability of the compound to PI3Kβ and PI3Kγ activities with ADP-Glo (purchased from Promege Company; Catalog No.: v9102/3). PI3Kβ protein is purchased from Millipore Company (Catalog No.: 14-603-K) and PI3Kγ protein is purchased from Invitrogen Company (Catalog No.: PR8641C). The reaction system also comprises substrates as $PIP_2$ and ATP. The reaction buffer system comprises 50 mM HEPES, 3 mM $MgCl_2$, 1 mM EGTA, 100 mM NaCl, 0.03% CHAPS and 2 mM DTT. The pH value of the reaction buffer is 7.5. Preparing 10 µL reaction system in corresponding wells of the 384 well plate, which contains the compositions as: the compound with designed concentration (or blank control), protein kinases (PI3Kβ, with the concentration of 4.8 nM in PI3Kβ test and PI3Kγ, with the concentration of 7.6 nM in PI3Kγ test) and substrates ($PIP_2$, with the concentration of 50 µM and ATP, with the concentration of 25 µM). Mixing the system evenly for incubation under ambient temperature for 1 h; getting a new 384 well plate and transferring 5 µL reaction liquid from the each well of original 384 well plate to the corresponding wells of the new 384 well plate; adding 5 µL ADP-Glo which has been preheated to ambient temperature into each new reaction well to terminate the reaction; oscillating it slowly in dark place for 40 min's incubation after it is mixed evenly; adding 10 µL testing liquid in each reaction well, oscillating it for 1 min to mix evenly and incubating it for 1 h, then measuring the fluorescence intensity with a microplate reader and analyzing the result data with the software GraphPad Prism.

Calculating the value of $IC_{50}$ as per the formula:

$$Y=\text{background data}+(\text{top data}-\text{background data})/(1+10^{((\text{Log IC50}-X)*\text{rate of curve})})$$

Where, Y refers to the inhibition ratio (%) and X refers to the compound concentration.

d) In vitro test for determining the inhibition capability of the compound to mTOR activity:

mTOR protein is purchased from Millipore Company (Catalog No.: 14-770). The reaction buffer system comprises 50 mM HEPES, 10 mM $MgCl_2$, 1 mM EGTA, 3 mM MnCl, 0.01% Tween-20 (purchased from Chengdu Kelong Chemical Regent Factory) and 2 mM DTT. The pH value of the reaction buffer is 7.5. Preparing 10 µL reaction system in corresponding wells of the 384 well plate, which contains the compositions as: the compound with designed concentration (or blank control), mTOR protein (with the concentration of 2.5 nM), ULight-4E-BP1 (containing the $37^{th}$ and the $46^{th}$ threonine residues, Thr37/46) peptide (purchased from PE Company, Catalog No.: TRF0128-M) and ATP substrates (ULight-4E-BP1 peptide, with the concentration of 50 nM and ATP, with the concentration of 10.81 µmM). Mixing it evenly for incubation under ambient temperature for 1 h; adding 10 µL testing liquid containing EDTA (ethylenediaminetetraacetic acid) and Eu-anti-phosphorylation-4E-BP1 (Thr37/46) antibody (purchased from PE Company, Catalog No.: TRF0216-M) into the reaction wells (after the testing liquid is added, the concentration of EDTA is 8 mM and the concentration of Eu-phosphorylation-4E-BP1 antibody is 2 nM); mixing it evenly and incubating it for 1 h under ambient temperature, then measuring the fluorescence intensity with a microplate reader and analyzing the result data with the software GraphPad Prism.

Calculating the value of $IC_{50}$ as per the formula:

$$Y = \text{background data} + (\text{top data} - \text{background data})/(1 + 10^{((\log IC50 - X) \ast \text{rate of curve})})$$

Where, Y refers to the inhibition ratio (%) and X refers to the compound concentration.

The compounds of the Invention and the testing results of inhibition capability thereof to the activities of histone deacetylase of subtype I (HDAC1), phosphoinositol 3-kinase of all subtypes (4 subtypes in total) and sirolimus of the receptor in mammal system are listed in the following Table 1. The values of $IC_{50}$ of the results are expressed through the grading as: A>10 µM, 10 µM>B>1 µM, 1 µM>C>0.1 µM, 0.1 µM>D>nM and E<1 nM. The reference compound CUDC907 is synthesized as per the method[1] in the literature; LBH589 is purchased from Selleck Company. The structures are:

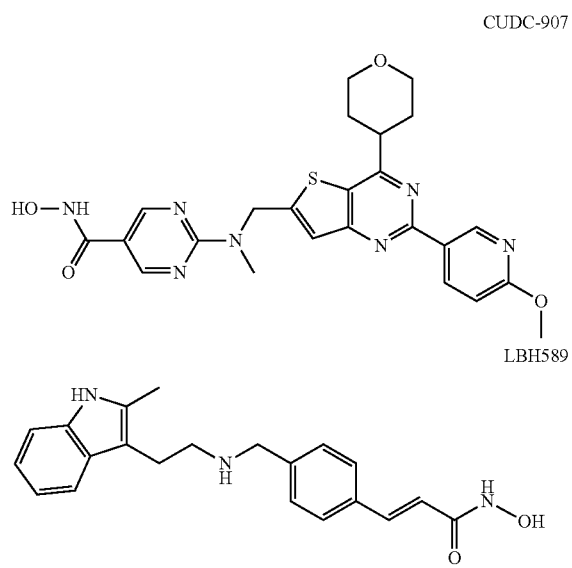

CUDC-907

LBH589

TABLE 1

Testing results of activity inhibition capability of the compound of the Invention

| Compound No. | HDAC1 | PI3Kα | PI3Kβ | PI3Kδ | PI3Kγ | mTOR |
|---|---|---|---|---|---|---|
| CLJ-1 | D | B | B | C | C | B |
| CLJ-2 | D | B | | | | |
| CLJ-3 | D | B | | | | |
| CLJ-4 | D | B | | | | |
| CLJ-5 | C | D | C | C | C | C |
| CLJ-6 | C | A | A | A | A | A |
| CLJ-7 | D | A | | | | |
| CLJ-8 | E | B | | | | |
| CLJ-9 | E | A | | | | |

TABLE 1-continued

Testing results of activity inhibition capability of the compound of the Invention

| Compound No. | HDAC1 | PI3Kα | PI3Kβ | PI3Kδ | PI3Kγ | mTOR |
|---|---|---|---|---|---|---|
| CLJ-10 | D | D | | | | |
| CLJ-11 | D | D | C | C | C | C |
| CLJ-12 | D | D | C | C | C | C |
| CLJ-13 | D | D | C | C | C | C |
| CLJ-14 | D | A | A | A | A | A |
| CLJ-15 | E | B | A | A | A | A |
| CLJ-16 | C | A | | | | |
| CLJ-17 | C | A | | | | |
| CLJ-18 | D | A | | | | |
| CLJ-19 | D | A | | | | |
| CLJ-20 | D | A | | | | |
| CLJ-21 | D | A | | | | |
| CLJ-22 | E | A | | | | |
| CLJ-23 | D | A | | | | |
| CLJ-24 | E | B | | | | |
| CLJ-25 | D | B | | | | |
| CLJ-26 | E | A | | | | |
| CLJ-27 | E | A | | | | |
| CLJ-28 | C | A | | | | |
| CLJ-29 | E | A | | | | |
| CLJ-30 | D | A | | | | |
| CLJ-31 | C | A | | | | |
| CLJ-32 | C | A | | | | |
| CLJ-33 | C | A | | | | |
| CLJ-34 | D | A | | | | |
| CLJ-35 | D | A | | | | |
| CLJ-36 | E | A | | | | |
| CLJ-37 | E | A | | | | |
| CLJ-38 | D | A | | | | |
| CLJ-39 | D | A | | | | |
| CLJ-40 | D | A | | | | |
| CLJ-41 | C | C | | | | |
| CLJ-42 | D | A | | | | |
| CLJ-43 | D | A | | | | |
| CLJ-44 | E | B | | | | |
| CLJ-45 | B | A | | | | |
| CLJ-46 | E | A | | | | |
| CLJ-47 | B | A | | | | |
| CLJ-48 | D | A | | | | |
| CLJ-49 | D | A | | | | |
| CLJ-50 | D | A | | | | |
| CLJ-51 | D | A | | | | |
| CLJ-52 | D | A | | | | |
| CLJ-53 | D | A | | | | |
| CLJ-54 | D | A | | | | |
| CLJ-55 | D | A | | | | |
| CLJ-56 | D | A | | | | |
| CLJ-57 | E | A | | | | |
| CLJ-58 | D | A | | | | |
| CLJ-59 | D | A | | | | |
| CLJ-60 | D | A | | | | |
| CLJ-61 | D | A | | | | |
| CLJ-62 | D | A | | | | |
| CLJ-63 | D | A | | | | |
| CLJ-64 | D | A | | | | |
| CLJ-65 | D | A | | | | |
| CLJ-66 | D | A | | | | |
| CLJ-67 | E | A | | | | |
| CLJ-68 | D | A | | | | |
| CLJ-69 | D | A | | | | |
| CLJ-70 | D | A | | | | |
| CUDC907 | D | D | D | D | C | B |
| LBH589 | D | | | | | |

The results show that, most of above compounds have the ability to inhibit HDAC1 activity, while the inhibition value $IC_{50}$ of nitrogen-containing six-membered heterocyclic compound to the activity of kinase PI3Kα is less than 0.1M; as the inhibition values $IC_{50}$ of the compounds CLJ-5 and CLJ-10-CLJ-13 to the activities of HDAC1 and PI3Kα are all less than 0.1 µM, these compounds are typical bifunctional compounds. Partial compounds have no obvious inhibitory effect to PI3Kα activity, but favorable inhibitory effect to HDAC activity; the inhibition values $IC_{50}$ of the compounds as CLJ-8, CLJ-9, CLJ-15, CLJ-22, CLJ-24, CLJ-26, CLJ-27, CLJ-29, CLJ-36, CLJ-37, CLJ-44, CLJ-46, CLJ-57 and CLJ-67 to the activity of HDAC1 are less than 1 nM, therefore, they can be used as the HDAC inhibitors with high activity. The inhibition value $IC_{50}$ of CLJ-5 to PI3Kα activity is less than 0. μM; meanwhile, CLJ-5 has favorable inhibitory effect to activities of PI3Kβ, PI3Kδ, PI3Kγ and mTOR, therefore it is a single functional compound of PI3K.

Embodiment 74 Determination of Inhibition Capability of Compound to Cell Proliferation Activity The following test is used for determining the inhibition values $IC_{50}$ of the small molecule compound of the Invention and the reference compounds as SAHA, LBH589 and chidamide to proliferation of tumor cell lines cultured in vitro.

The tumor cell lines are purchased from American Type Culture Collection (ATCC) and cultivated to the status of logarithmic growth as per the cultural method recommended by ATCC. The cells in logarithmic phase are spread on a 96 well plate as per 2000-3000/well; as for anchorage-dependent cells, the compound should be added in the test wells at certain concentration for incubation for 96 h after cell adherence. Determining cell proliferation activities with method MTT for tumor cells representing solid tumor model and with method cck-8 for tumor cells representing hematologic tumor model, and analyzing the result data with the software GraphPad Prism.

Calculating the value of $IC_{50}$ as per the formula:

$$Y = \text{background data} + (\text{top data} - \text{background data})/(1 + 10^{((\log IC_{50} - X)*\text{rate of curve})})$$

Where, Y refers to the inhibition ratio (%) and X refers to the compound concentration.

The compounds of the Invention and the inhibition capability thereof to cell proliferation activity of the tumor cell lines cultured in vitro are listed in the following Table 2. The values of $IC_{50}$ of the results are expressed through the grading as: A>1 μM, 1 μM>B>100 nM, 100 nM>C>10 nM and 10 nM>D>0.1 nM. Wherein, the positive drug SAHA is purchased from Dalian Meilun Biotech Co., Ltd; LBH589 is purchased from Selleck Company and chidamide is provided by ChipScreen Company; the structural formulas of SAHA and chidamide are as follows:

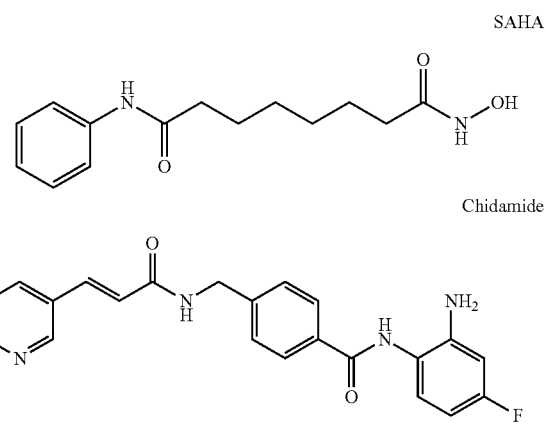

SAHA

Chidamide

TABLE 2

Proliferation activity inhibition capability of the compounds of the Invention

| Compound | Acute myeloid leukemia MV4-11 | Colon cancer hct116 | Ovarian cancer A2780s |
| --- | --- | --- | --- |
| CLJ-1 | D | C | D |
| CLJ-2 | B | B | B |
| CLJ-3 | A | A | A |
| CLJ-4 | A | A | A |
| CLJ-5 | B | B | B |
| CLJ-6 | A | A | A |
| CLJ-7 | D | B | C |
| CLJ-8 | D | C | D |
| CLJ-9 | D | C | C |
| CLJ-10 | C | C | B |
| CLJ-11 | D | C | C |
| CLJ-12 | D | D | D |
| CLJ-13 | D | D | D |
| CLJ-14 | D | C | D |
| CLJ-15 | C | C | C |
| CLJ-16 | A | A | A |
| CLJ-17 | A | A | A |
| CLJ-18 | D | D | C |
| CLJ-19 | D | D | C |
| CLJ-20 | D | D | C |
| CLJ-21 | D | D | D |
| CLJ-22 | D | D | D |
| CLJ-23 | D | D | D |
| CLJ-24 | D | D | D |
| CLJ-25 | D | D | D |
| CLJ-27 | D | C | C |
| CLJ-29 | D | D | D |
| CLJ-30 | D | C | C |
| CLJ-31 | A | A | A |
| CLJ-32 | A | A | A |
| CLJ-35 | D | C | C |
| CLJ-36 | D | D | D |
| CLJ-38 | D | B | C |
| CLJ-44 | D | C | D |
| CLJ-48 | D | D | D |
| CLJ-49 | C | B | C |
| CLJ-54 | B | B | B |
| CLJ-55 | D | C | C |
| CLJ-56 | C | B | B |
| CLJ-57 | D | C | D |
| CLJ-60 | D | C | D |
| CLJ-68 | C | C | C |
| SAHA | B | B | A |
| LBH589 | D | D | D |
| Chidamide | B | A | A |

It is shown from the above table that the above compounds all have favorable inhibitory effect to the proliferation activities of the tested tumor cell lines; such inhibitory effect is obviously better than that of positive drugs as SAHA and chidamide and some compounds even have the same inhibitory effect with LBH589. The values $IC_{50}$ of most compounds are 5 less than 1 μM; the compounds with the highest inhibitory effect are CLJ-12, CLJ-13, CLJ-21-CLJ-25, CLJ-29, CLJ-36 and CLJ-48, the inhibition values $IC_{50}$ of which to proliferation activities of three types of tumor cell lines are between 0.1 nM and 10 nM; meanwhile, CLJ-7 and CLJ-38 show a selective anti-tumor potential as the values of $IC_{50}$ to MV4-11 cells representing acute myeloid leukemia are less than 10 nM, while the values of $IC_{50}$ to hct116 cells representing colon cancer are more than 100 nM, indicating that they may have strong inhibition capability to the activities of the tumors of specific type.

Embodiment 75 Determination of Influence of the Compounds of the Invention on Marker Protein Acetylation Level of Tumor Cells Selecting 5 compounds CLJ-1, CLJ-8, CLJ-11, CLJ-29 and CLJ-44 as the preferred compounds in combination with the results of Embodiments 73 and 74. The following tests are used for determining the $EC_{50}$ of several preferred small molecule compounds of the Invention and the reference compounds as SAHA, LBH589 and CUDC907 for inducing marker protein $H_3$ and α-tubulin acetylation in tumor cells.

Test scheme: A2780s cells from American Type Culture Collection (ATCC) are spread on a 96 well plate as per 5000 cells/well; after cell adherence, treating the cells for 6 h with the compounds or the positive reference compounds as SAHA, LBH589 and CUDC907 at the concentration of 1.6, 8, 40, 200 and 1000 nM respectively; then testing the protein levels of the acetylated histone $H_3(Ac-H_3)$ and the acetylated Ac-α-tubulin with the method of cytoblot. Specific operation: After the treatment, washing each well once with 50-100 μl of cold TBS buffer [with the composition as 20 mM Tris (trismetyl aminomethane), pH7.5] and fixing it with 100 μL of 4% pre-cooled paraformaldehyde at 4° C. for 1 h; after paraformaldehyde is washed off, adding 50 μL of pre-cooled methyl alcohol in each well and evenly spreading at 4° C. for 5 min; after methyl alcohol is washed off, washing it once with the TBS buffer containing 3% skim milk powder and adding 50 μL of antibody fluid, oscillating it slightly at 4° C. and incubating overnight. For determination of Ac—$H_3$, the antibody fluid is prepared by diluting Ac—$H_3$ antibody and horseradish peroxide coupled secondary antibody to a same system with the TBS buffer containing 3% skim milk powder (Ac—$H_3$ antibody is purchased from Santa Cruz Company and diluted at a ratio of 1:100; horseradish peroxide coupled secondary antibody is purchased from Jackson Company and diluted at a ratio of 1:2000); for determination of acetylated Ac-α-tubulin, the antibody fluid is prepared by diluting Ac-α-tubulin antibody and horseradish peroxide coupled secondary antibody to a same system with the TBS buffer containing 3% skim milk powder (Ac-α-tubulin antibody is purchased from Santa Cruz Company and diluted at a ratio of 1:100; horseradish peroxide coupled secondary antibody is purchased from Jackson Company and diluted at a ratio of 1:2000). Discarding the antibody fluid in the next day and washing it twice with TBS buffer; then adding enhanced chemiluminescence (ECL) liquid (which is purchased from Abbkine Company), determining the chemiluminescence intensity with a microplate reader, and analyzing the result data with the software GraphPad Prism.

Calculating the value of $IC_{50}$ as per the formula:

$$Y = \text{background data} + (\text{top data} - \text{background data})/(1 + 10^{((\text{Log } EC50 - X)*\text{rate of curve})})$$

Where, Y refers to the activating rate (%) and X refers to the compound concentration.

Several preferred compounds of the Invention and their abilities to promote the acetylation activities of histones $H_3$ and α-tubulin in tumor cell A2780s are listed in the following table 3. The values of $EC_{50}$ of the results are expressed through the grading as: A>200 nM, 200 nM>B>100 nM and C<100 nM. Wherein, the positive drug SAHA is purchased from Dalian Meilun Biotech Co., Ltd.; LBH589 is purchased from Selleck Company and CUDC907 is synthesized as per the method[1] in the literature.

TABLE 3

Abilities of the compounds of the Invention to promote the acetylation activities of histones $H_3$ and α-tubulin in tumor cells

| Compound | Ac-Tub | Ac-$H_3$ |
| --- | --- | --- |
| CLJ-1 | B | B |
| CLJ-8 | B | B |
| CLJ-11 | B | B |
| CLJ-29 | A | C |

TABLE 3-continued

Abilities of the compounds of the Invention to promote the acetylation activities of histones $H_3$ and α-tubulin in tumor cells

| Compound | Ac-Tub | Ac-$H_3$ |
| --- | --- | --- |
| CLJ-44 | A | B |
| LBH-589 | B | B |
| CUDC907 | A | B |
| SAHA | A | A |

It is shown from Table 3 that through the determination of the ability of the five preferred compounds in inducing acetylation activity of marker proteins, their inhibition capability to the activity of HDAC enzyme can be verified. The abilities of the five preferred compounds in inducing acetylation activity of marker proteins are superior to that of positive drug SAHA and equal to those of LBH589 and CUDC907.

Embodiment 76 Determination of Inhibition Capability of the Compounds of the Invention to the Activities of HDAC Enzymes of all Subtypes and Phosphoinositol 3-Kinase of all Subtypes In Vitro The following tests are used for determining the $IC_{50}$ of several preferred small molecule compounds of the Invention and the control compounds CUDC907 and LBH589 for inhibiting HDAC1-11 enzymes of subtypes and PI3K kinases.

Determining the inhibition capability of HDAC through the substrate method of fluorophore coupled acetylized peptide fragment (Lys-Ac-AMC). HDAC2-11 proteins of subtypes are purchased from BPS Bioscience Company with the Art. No. as: HDAC2, 50002; HDAC3, 50003; HDAC4, 50004; HDAC5, 50005; HDAC6, 50006; HDAC7, 50007; HDAC8, 50008; HDAC9, 50009; HDAC10, 50060; HDAC11, 50011. The reaction buffer system is a modified Tris buffer (pH7.0). The small molecule compounds are prepared and dissolved with 100% DMSO. HDAC is prepared into the buffer as per certain concentration to be served as the enzyme solution; in the tests for HDAC1, 2, 3, 4, 5, 6, 7 and 9 subtypes, trypsin and the fluorophore 4-amino-7-coumarin coupled Ac-peptide substrate are prepared into the buffer as per certain concentration to be served as the substrate solution; in the tests for HDAC8, 10 and 11 subtypes, the fluorophore 4-amino-7-coumarin coupled Ac-peptide substrate is prepared into the buffer as per certain concentration to be served as the substrate solution and in addition the trypsin fluid with certain concentration is prepared. Adding the compound into the reaction wells of the 384 well plate at the designed concentration, then adding 15 μL HDAC enzyme solution into the reaction wells (adding 15 μL blank buffer into the control well 0) for incubation under ambient temperature for 15 min; then adding 10 μL substrate solution to start reaction. Keeping the 384 well plate in dark place for incubation under ambient temperature for 1 h for the tests of HDAC1, 2, 3, 4, 5, 6, 7 and 9 subtypes, then determining the fluorescence intensity with a microplate reader (emission wavelength: 355 nm, absorption wavelength: 460 nm); or incubation for 3 h for the tests of HDAC8, 10 and 11 subtypes, adding trypsin fluid into the reaction well for another 2 h's incubation in dark place and then determining the fluorescence intensity with a microplate reader. The final concentrations of the specific protease, trypsin and Ac-peptide in the test of each HDAC subtype are respectively as follows: For HDAC2, the concentration of protease is 4 nM, Ac-peptide 10 μM and trypsin 0.05 μM; for HDAC3, the concentration of protease is 7 nM, Ac-peptide 5 μM and trypsin 0.05 μM; for HDAC4, the concentration of protease is 0.05 nM, Ac-peptide 20 μM and trypsin 0.05 μM; for HDAC5, the concentration of protease is 1.5 nM, Ac-peptide 20 μM and trypsin 0.05 μM; for HDAC6, the concentration of protease is 8 nM, Ac-peptide 11 μM and trypsin 0.01 μM; for HDAC7, the concentration of protease is 0.05 nM, Ac-peptide 20 μM and trypsin 0.05 μM; for HDAC8, the concentration of protease is 150 nM, Ac-peptide 10 μM and trypsin 50 μM; for HDAC9, the concentration of protease is 0.5 nM, Ac-peptide 20 μM and trypsin 0.05 μM; for HDAC10, the concentration of protease is 13 nM, Ac-peptide 4 μM and trypsin 0.05 μM and for HDAC11, the concentration of protease is 5 nM, Ac-peptide 10 μM and trypsin 50 μM.

The method for determining the inhibition capability to the activities of phosphoinositide-3-kinase of all subtypes is as described in part b) and part c) in Embodiment 73.

Analyzing the result data with the software GraphPad Prism and calculating the value of $IC_{50}$ as per the formula:

$$Y = \text{background data} + (\text{top data} - \text{background data})/(1 + 10^{((\log IC_{50} - X) \cdot \text{rate of curve})})$$

Where, Y refers to the inhibition ratio (%) and X refers to the compound concentration.

Several preferred compounds of the Invention and the inhibition capability thereof to the activities of histone deacetylase of 11 subtypes (HDAC1-11) and phosphoinositol 3-kinase of all subtypes are listed in the following Table 4. The values of $IC_{50}$ of the results are expressed through the grading as: A>10 μM, 10 μM>B>1 μM, 1 μM>C>0.1 μM, 0.1 μM>D>1 nM and E<1 nM. Wherein, the positive drug SAHA is purchased from Dalian Meilun Biotech Co., Ltd.; LBH589 is purchased from Selleck Company and CUDC907 is synthesized as per the method[1] in the literature.

TABLE 4

Inhibition capability of the compound of the Invention to the activities of HDAC1-11 and PI3K kinases

| Enzyme subtypes | CLJ-1 | CLJ-8 | CLJ-11 | CLJ-29 | CLJ-44 | CUDC-907 | LBH-589 |
|---|---|---|---|---|---|---|---|
| HDAC1 | D | E | D | E | E | D | D |
| HDAC2 | D | D | D | D | D | D | D |
| HDAC3 | D | D | D | D | D | D | D |
| HDAC4 | B | B | C | B | B | C | C |
| HDAC5 | B | B | C | B | C | C | C |
| HDAC6 | D | D | D | D | D | D | D |
| HDAC7 | B | C | C | B | B | C | B |
| HDAC8 | C | D | D | D | D | C | D |
| HDAC9 | B | B | B | B | B | C | C |
| HDAC10 | D | E | D | D | D | D | D |
| HDAC11 | B | C | B | B | B | D | B |
| PI3Kα | B | B | D | A | B | D | A |
| PI3Kβ | B | A | D | A | A | D | A |
| PI3Kγ | C | A | D | A | A | C | A |
| PI3Kδ | C | A | D | A | A | D | A |

It is shown from Table 4 that compounds CLJ-1, CLJ-8, CLJ-29 and CLJ-44 have the same inhibition capability with the positive compounds CUDC-907 and LBH589 to the activities of HDAC1, HDAC2, HDAC3 and HDAC6, HDAC8 and HDAC10; wherein, compounds CLJ-1 and CLJ-11 show a same inhibition capability with CUDC-907 to the double activities of HDAC1 and PI3K kinases.

Embodiment 77 Model Tests of the Compounds of the Invention for Treating MV4-11 Subcutaneous Tumor in Animals Test scheme: Inoculating MV4-11 cells subcutaneously to 54 NOD/SCID female mice with the inoculation amount of $10^7$ cells per mouse; when the inoculated tumor grows to 100 mm$^3$, selecting 36 mice with uniform gross tumor volume and dividing them into 6 groups randomly. Injecting the treatment group intravenously (i.v.) with a dose of 10 mg/kg of five compounds as CLJ-1, CLJ-8, CLJ-11, CLJ-29 and CLJ-44; giving SAHA, the drug available on the market intraperitoneally (i.p.) to the positive control group with a dose of 50 mg/kg; giving the control group with equal amount of blank solvent; conducting the drug administration once per two days for 22 days' treatment. During drug administration, measuring the weight and gross tumor volume of the mice per 2 days and keeping a record. The calculation formula is as $V = \pi/6 \times A^2 \times B$, where, where, V=gross tumor volume (mm$^3$), A=tumor width (mm) and B=tumor length (mm). Observing and keeping a record for the survival condition of the tested animals. After drug discontinuance, killing the mice through cervical dislocation and peeling off their tumors as per the operation specification of animal experiment. Evaluating the inhibition capability of the compounds to tumor activities by calculating the tumor inhibitory rate with the formula as: tumor inhibitory rate=(1−tumor weight of treatment group/tumor weight of control group)×100%. Analyzing and comparing the difference between each treatment group and control group with the method of t-test. The grading of significance level of difference is: *, P<0.001; , P<0.01; *, P<0.05; no statistical significance (ns), P>0.05.

Several preferred compounds and the results of the model tests thereof for treating MV4-11 subcutaneous tumor in animals are listed in the following Table 5. The parameters showing the results are tumor inhibitory rate, statistic difference and final survival condition. Wherein, the positive drug SAHA is purchased from Dalian Meilun Biotech Co., Ltd.

TABLE 5

Effects of the models of the compounds of the Invention for treating MV4-11 subcutaneous tumor in animals

| Compound | Dosage (mg/kg) | Tumor inhibitory rate (%) | Statistic difference | Final survival condition (survived individuals/total individuals) |
|---|---|---|---|---|
| CLJ-1 | 10 | 63.4 | *** | 5/6 |
| CLJ-8 | 10 | 64.3 | *** | 5/6 |
| CLJ-11 | 10 | 45.1 | ** | 4/6 |
| CLJ-29 | 10 | 65.3 | *** | 4/6 |
| CLJ-44 | 10 | 65.6 | *** | 6/6 |
| SAHA | 50 | 0 | ns | 6/6 |

It is shown from Table 5 that the five preferred compounds can inhibit the growth activity of the subcutaneous tumor MV4-11; wherein, the tumor inhibitory rates of four compounds as CLJ-1, CLJ-8, CLJ-29 and CLJ-44 are more than 60% under the dosage of 10 mg/kg, while the positive drug SAHA has no tumor inhibitory effect. Meanwhile, 6 tested animals in group compound CLJ-44 are all survived, indicating that the compound has no obvious toxic and side effect and it is probably a most potential compound.

Embodiment 78 Tests for Inhibition Capability of the Compounds of the Invention to the Proliferation Activity of Multiple Hematological Tumor Cells At present, the preferred development direction of HDAC inhibitors in tumor therapy is to treat hematological tumor.

The following test is used for determining the inhibition values $IC_{50}$ of several preferred compounds of the Invention and the reference compound LBH589 to proliferation of multiple hematological tumor cell lines cultured in vitro.

The tumor cells of human multiple myeloma model as U266 and RPMI-8226 and the tumor cells of human B-cell lymphoma model as ramos and SUDHL-4 are purchased from ATCC and cultivated to the status of logarithmic growth as per the cultural method recommended by ATCC; the tumor cell of human multiple myeloma model as MM1S is provided by Hematology Department of West China Hospital of Sichuan University and cultivated to the status of logarithmic growth as per the cultural method recommended by the Department; the tumor cell of human B-cell lymphoma model as OCI-LY1 is purchased from DSMZ and cultivated to the status of logarithmic growth as per the cultural method recommended by DSMZ; the tumor cell of human B-cell lymphoma model as HBL-1 is purchased from RIKEN and cultivated to the status of logarithmic growth as per the cultural method recommended by RIKEN. The cells in logarithmic phase are spread on a 96 well plate as per 7,500-10,000/well; then adding the compound into the test wells at certain concentration for incubation for 96 h and determining cell proliferation activities with method cck-8, and analyzing the result data with the software GraphPad Prism.

Calculating the value of $IC_{50}$ as per the formula:

$$Y=\text{background data}+(\text{top data}-\text{background data})/(1+10^{((\text{Log IC50}-X)*\text{rate of curve}))}.$$

Where, Y refers to the inhibition ratio (%) and X refers to the compound concentration.

Several preferred compounds of the Invention and the inhibitory effect thereof to the proliferation activity of multiple hematological tumor cells cultured in vitro are listed in the following Table 6. The values of $IC_{50}$ of the results are expressed through the grading as: 1 μM>A>100 nM, 100 nM>B>10 nM, 10 nM>C>1 nM and 1 nM>D>0.1 nM. The positive compound LBH589 is purchased from Selleck Company.

TABLE 6

Inhibition capability of the compounds of the Invention to the proliferation activity of multiple hematological tumor cells

| Compound | CLJ-1 | CLJ-8 | CLJ-11 | CLJ-29 | CLJ-44 | LBH589 |
|---|---|---|---|---|---|---|
| U266 | D | C | B | D | C | C |
| RPMI-8226 | C | C | B | D | D | C |
| MM1S | D | D | C | D | C | C |
| OCI-LY1 | B | C | A | C | B | B |
| HBL-1 | C | C | B | C | C | C |
| Ramos | D | D | B | C | C | D |
| SUDHL-4 | C | C | B | D | C | C |

It is shown from Table 6 that the 5 preferred compounds have inhibitory effect to proliferation activities of a few tumor cell lines of human multiple myeloma and human B-cell lymphoma; the value of $IC_{50}$ is of level nM. Wherein, the four compounds as CLJ-1, CLJ-8, CLJ-29 and CLJ-44 have equal or superior activity to positive drug LBH589.

Embodiment 79 Investigation on Inhibition Capability of Compound CLJ-44 to Activities of Multiple Animal Subcutaneous Solid Tumor Models The solid tumor model comprises human colon cancer hct116, human breast cancer MCF-7 and MDA-MB-231; the hematological tumor model comprises human multiple myeloma MM1S and human B-cell lymphoma Raji.

1) Laboratory animal: positive drug LBH589 purchased from Selleck Company; SPF female nude mice BALB/c (Balb/C nu/nu), 4-6 weeks old, 18-22 g and NOD/SCID female mice, 6-8 weeks old, purchased from Beijing Huafukang Biotechnology Co., Ltd. Production Permit No.: SCXK (J) 2014-0012. Test condition: SPF animal room; Laboratory Animal Usage License No.: SYXK (J) 2015-0023

2) Cell source and culture

Human colon cancer hct116, human breast cancer MCF-7 and MDA-MB-231 and human B-cell lymphoma Raji are purchased from ATCC, the breed of which is conserved in the State Key Laboratory of Biotherapy, Sichuan University; human multiple myeloma cell strain MM1S is provided by Hematology Department of West China Hospital of Sichuan University and subcultured in the State Key Laboratory of Biotherapy, Sichuan University. Cell MM1S is cultured in RPMI1640 medium (HyClone) which contains 10% fetal calf serum (Hohhot Caoyuan Lvye Bioengineering Material Co., Ltd.) and 100 U/mL penicillin and streptomycin (Beyotime).

3) Inoculation, grouping and treatment: collecting cells in logarithmic phase under aseptic conditions and counting; diluting the single cell suspension with the medium containing neither fetal calf serum nor antibiotics to $1 \times 10^7$-8 cell/mL for standby. Mixing the cell suspension; injecting 100 μL of cell suspension ($5 \times 10^6$-$2 \times 10^7$ cells) subcutaneously with a 1 mL injector on the right side of the back of animals. Weeding out the animals with oversized and undersized tumor when the tumor grows to an average volume of about 120 mm$^3$ and grouping the qualified animals for treatment and drug administration. Refer to Table 7 for each grouping model and drug administration frequency. Measuring the weight of each model per 2 days and measuring the length and width of the tumor with a vernier caliper; killing the tested animals through cervical dislocation and peeling off their tumors for weight measuring and photographing. Then calculating the tumor inhibition ratio (%) and evaluating the inhibition intensity to tumor with such tumor inhibition ratio. The treatment effect of the compound CLJ-44 to each model is listed in the following Table 7.

TABLE 7

Summary of treatment effects of the compound CLJ-44 to various tumor models

| Tumor model | Compound | Method of administration | | | Death | Inhibitory rate (%) |
|---|---|---|---|---|---|---|
| | | Dosage (mg/kg) | Frequency | Approach | | |
| hct116 | Blank control | — | Once per 2 days | Intravenous administration | 0/6 | — |
| | CLJ-44 | 2.5 | Once per 2 days | Intravenous administration | 0/6 | 49.4 |
| | CLJ-44 | 5 | Once per 2 days | Intravenous administration | 0/6 | 53.3 |

TABLE 7-continued

Summary of treatment effects of the compound CLJ-44 to various tumor models

| Tumor model | Compound | Dosage (mg/kg) | Frequency | Approach | Death | Inhibitory rate (%) |
|---|---|---|---|---|---|---|
| | CLJ-44 | 10 | Once per 2 days | Intravenous administration | 0/6 | 68.2 |
| | SAHA | 50 | Once per 2 days | Intraperitoneal administration | 0/6 | 32.4 |
| MCF-7 | Blank control | — | Once per 2 days | Intravenous administration | 0/6 | — |
| | CLJ-44 | 2.5 | Once per 2 days | Intravenous administration | 0/6 | 69.58 |
| | CLJ-44 | 5 | Once per 2 days | Intravenous administration | 0/6 | 77.58 |
| | CLJ-44 | 10 | Once per 2 days | Intravenous administration | 0/6 | 82.24 |
| | Paclitaxel | 30 | Once per 7 days | Intraperitoneal administration | 0/6 | 77.73 |
| | LBH589 | 10 | Once per 2 days | Intraperitoneal administration | 0/6 | 75.69 |
| MDA-MB-231 | Blank control | — | Once per 2 days | Intravenous administration | 0/6 | NA |
| | CLJ-44 | 2.5 | Once per 2 days | Intravenous administration | 0/6 | 72.1 |
| | CLJ-44 | 5 | Once per 2 days | Intravenous administration | 0/6 | 83.9 |
| | CLJ-44 | 10 | Once per 2 days | Intravenous administration | 0/6 | 86.9 |
| | Paclitaxel | 30 | Once per 7 days | Intraperitoneal administration | 0/6 | 59.19 |
| | LBH589 | 10 | Once per 2 days | Intraperitoneal administration | 0/6 | 77.95 |
| MM1S | Blank control | — | Once per 2 days | Intravenous administration | 0/7 | |
| | CLJ-44 | 2.5 | Once per 2 days | Intravenous administration | 0/7 | 45.09 |
| | CLJ-44 | 5 | Once per 2 days | Intravenous administration | 0/7 | 69.65 |
| | CLJ-44 | 10 | Once per 2 days | Intravenous administration | 0/7 | 71.94 |
| | LBH589 | 10 | Once per 2 days | Intraperitoneal administration | 0/7 | 47.33 |
| Raji | Blank control | — | Once per 2 days | | 0/6 | NA |
| | CLJ-44 | 5 | Once per 2 days | Intraperitoneal administration | 0/6 | 76.96 |
| | CLJ-44 | 10 | Once per 2 days | Intraperitoneal administration | 0/6 | 97.34 |
| | CLJ-44 | 20 | Once per 2 days | Intraperitoneal administration | 0/6 | 99.29 |
| | LBH589 | 10 | Once per 2 days | Intraperitoneal administration | 0/6 | 54.93 |

It is shown from Table 7 that, the compound CLJ-44 has favorable inhibitory effect to the tumor activities of various human subcutaneous transplantation tumor models (including colon cancer, breast cancer, multiple myeloma and B-cell lymphoma). It has good interdependence between dosage and tumor inhibitory rate in each model and the inhibition capability to tumor activity is obviously better than the reference drugs SAHA and LBH589.

REFERENCES

[1] Qian, C., et al., Cancer network disruption by a single molecule inhibitor targeting both histone deacetylase activity and phosphatidylinositol 3-kinase signaling. *Clin Cancer Res*, 2012. 18(15): p. 4104-13.

The invention claimed is:
1. A compound of Formula I:

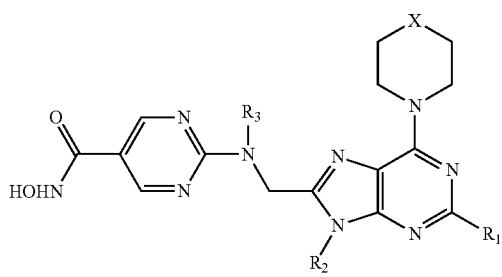

Formula I wherein, X is O or N—R'; R' is —H, $C_1$-$C_4$ alkyl, $C_1$-$C_4$ alkoxy or an alkyl substituted by $C_1$-$C_4$ hydroxy; $R_1$ is $C_1$-$C_4$ alkyl, $C_1$-$C_4$ alkoxy, —OH, halogen, $C_3$-$C_8$ cycloalkyl, —$NH_2$,

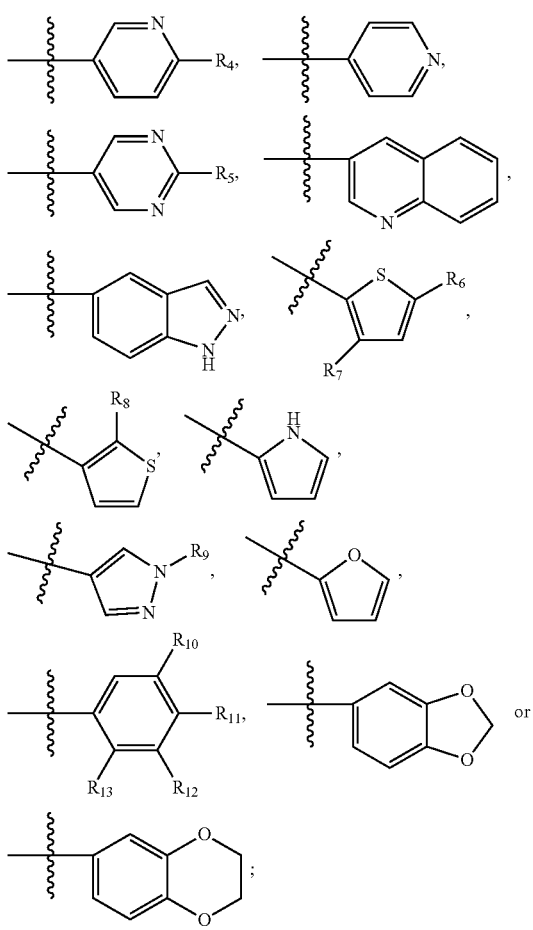

$R_2$ and $R_3$ are independently —H, $C_1$-$C_4$ alkyl, $C_1$-$C_4$ alkoxy, —OH, halogen or $C_3$-$C_8$ cycloalkyl;

$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

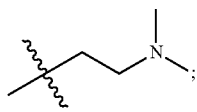;

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

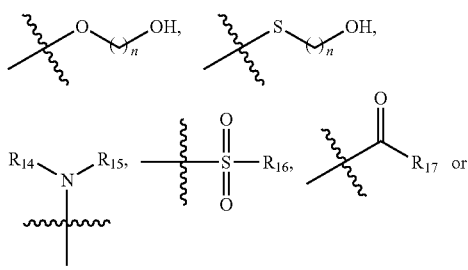

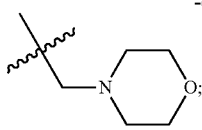

n=1-4; $R_{14}$ and $R_{15}$ are independently —H, $C_1$-$C_4$ alkyl, $C_1$-$C_6$ alkenyl,

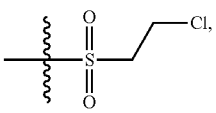

t-butyloxycarboryl,

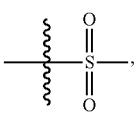

$C_1$-$C_4$ alkoxy or halogen;

$R_{16}$ is $C_1$-$C_4$ alkyl, $C_1$-$C_4$ alkoxy, halogen,

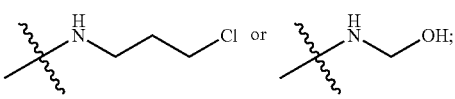

$R_{17}$ is —NH$_2$,

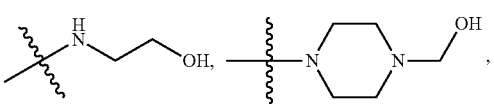

—OH or halogen; or a pharmaceutically acceptable salt thereof.

2. The compound according to claim 1, wherein:

X is O or N—R'; R' is —H or an alkyl substituted by $C_1$-$C_4$ hydroxy; $R_1$ is $C_1$-$C_4$ alkyl, $C_1$-$C_4$ alkoxy, —OH, halogen, $C_3$-$C_8$ cycloalkyl, —NH$_2$,

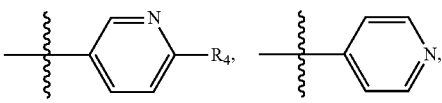

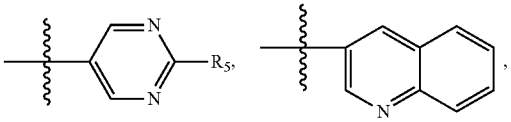

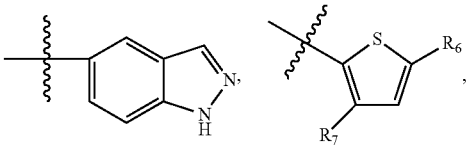

-continued

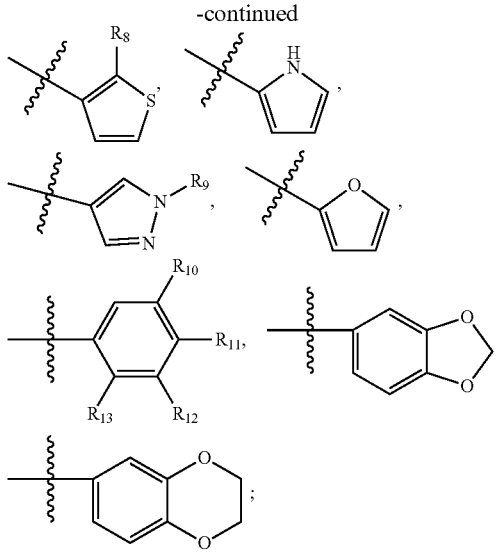

R₂ and R₃ are independently —H, C₁-C₄ alkyl, C₁-C₄ alkoxy, —OH, halogen or C₃-C₈ cycloalkyl;
R₄-R₉ are independently —H, C₁-C₄ alkyl, C₁-C₄ alkoxy, —OH, halogen, C₃-C₈ cycloalkyl, —NH₂, —COOH, C₁-C₄ alkyl amino or

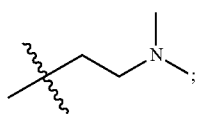

R₁₀-R₁₃ are independently -H, C₁-C₄ alkyl, C₁-C₄ alkoxy, —OH, —CF₃, halogen, C₃-C₈ cycloalkyl, —NH₂, an alkyl substituted by C₁-C₄ hydroxy,

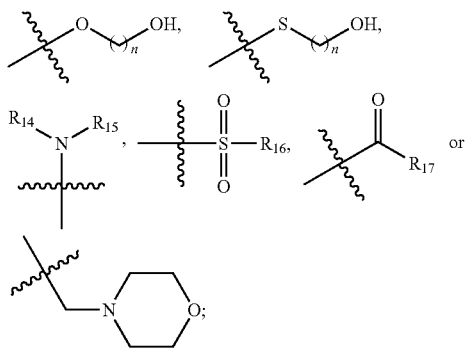

n=1-4; R₁₄ and R₁₅ are independently —H, C₁-C₄ alkyl, C₁-C₆ alkenyl,

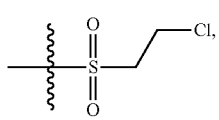

t-butyloxycarboryl,

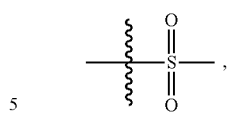

C₁-C₄ alkoxy or halogen; R₁₆ is C₁-C₄ alkyl, C₁-C₄ alkoxy, halogen,

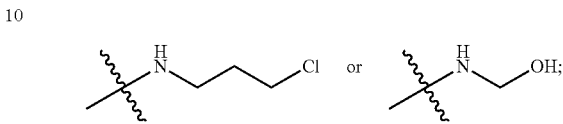

R₁₇ is —NH₂,

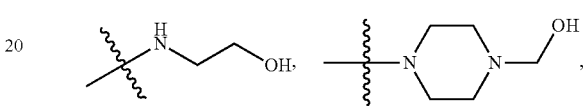

—OH or halogen.

3. The compound according to claim 2, wherein: R₁ is halogen, C₃-C₈ cycloalkyl, —NH₂,

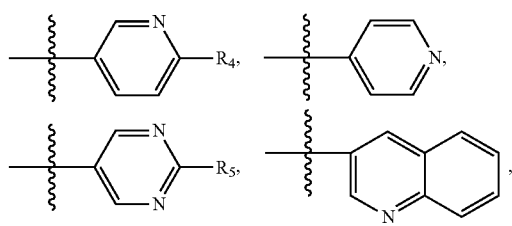

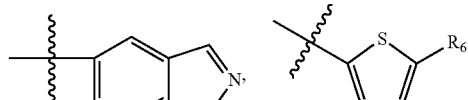

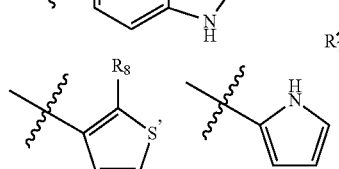

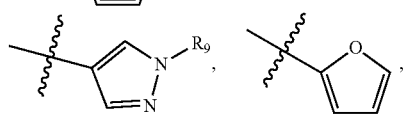

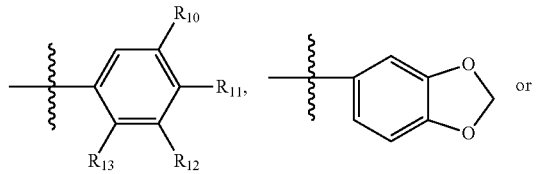

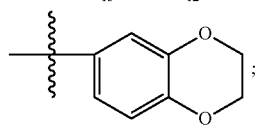

X is O or N—R'; R' is —H or an alkyl substituted by C₁-C₄ hydroxy; R₂ and R₃ are independently —H, C₁-C₄ alkyl, C₁-C₄ alkoxy, —OH, halogen or C₃-C₈ cycloalkyl; R₄-R₉ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

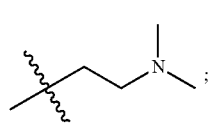

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

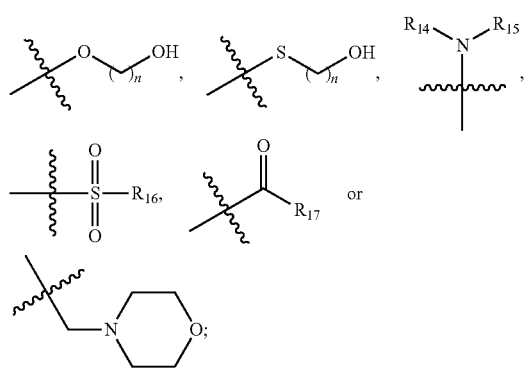

n=1-4; $R_{14}$ and $R_{15}$ are independently —H, $C_1$-$C_4$ alkyl, $C_1$-$C_6$ alkenyl,

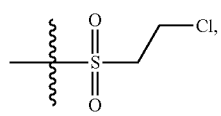 [SMILES: *S(=O)(=O)CCCl]

t-butyloxycarboryl,

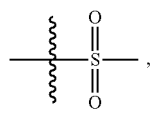 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

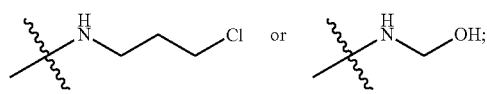

$R_{17}$ is —NH$_2$,

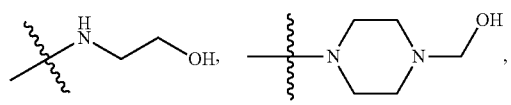

—OH or halogen.

4. The compound according to claim 3, wherein: $R_1$ is halogen,

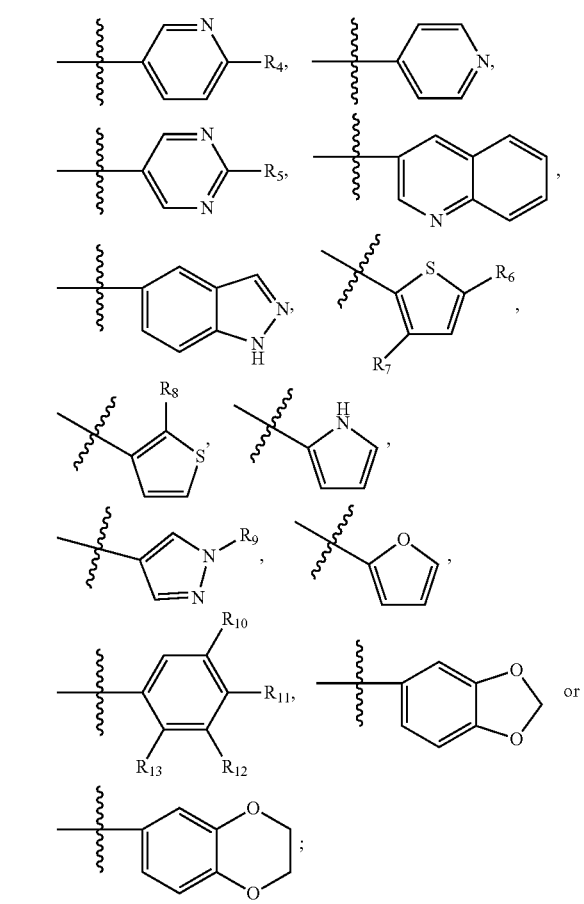

X is O or N—R'; R' is —H or an alkyl substituted by $C_1$-$C_4$ hydroxy; $R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

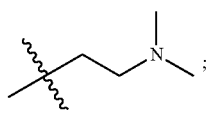

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

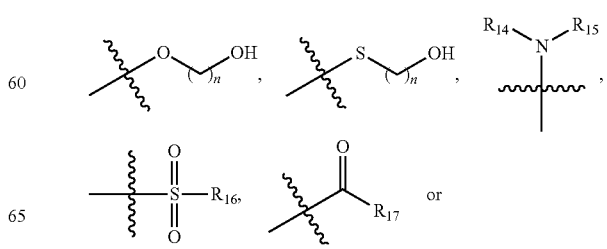

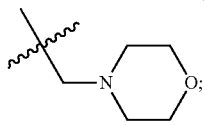

n=1-4; $R_{14}$ and $R_{15}$ are independently —H, $C_1$-$C_4$ alkyl, $C_1$-$C_6$ alkenyl,

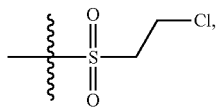 [SMILES: *S(=O)(=O)CCCl]

t-butyloxycarboryl,

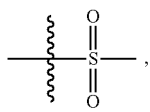 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

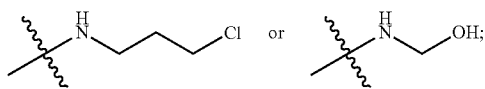

$R_{17}$ is —$NH_2$,

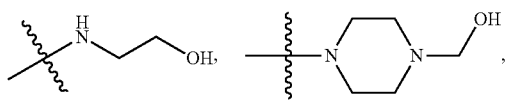

—OH or halogen.

5. The compound according to claim 4, wherein: $R_1$ is —Cl,

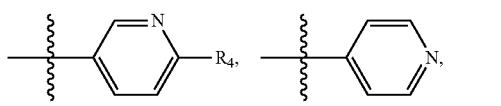

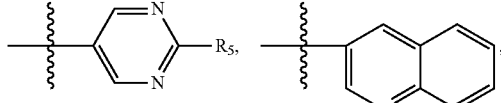

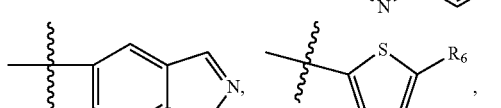

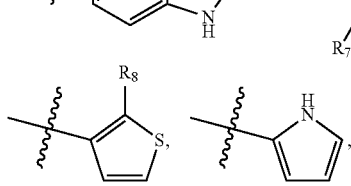

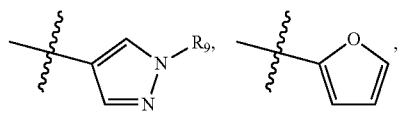

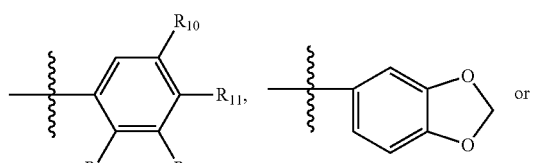

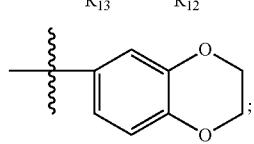

X is O or N—R'; R' is —H or an alkyl substituted by $C_1$-$C_4$ hydroxy; $R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

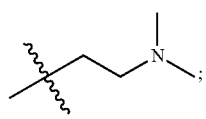 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

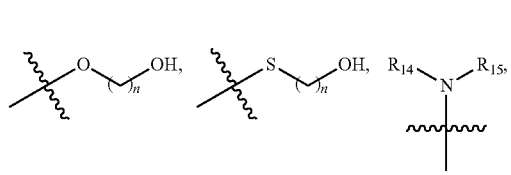

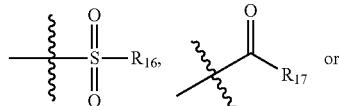

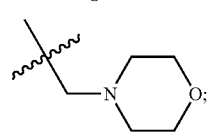

n=1-4; $R_{14}$ and $R_{15}$ are independently —H, $C_1$-$C_4$ alkyl, $C_1$-$C_6$ alkenyl,

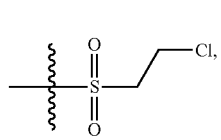 [SMILES: *S(=O)(=O)CCCl]

t-butyloxycarboryl,

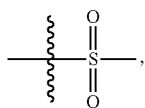 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

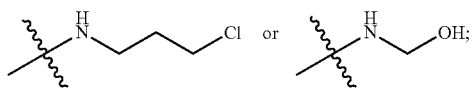

$R_{17}$ is —$NH_2$,

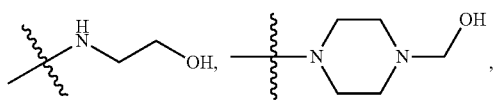

—OH or halogen.

6. The compound according to claim 2, wherein: $R_2$ and $R_3$ are independently —H, $C_1$-$C_4$ alkyl, $C_1$-$C_4$ alkoxy or $C_3$-$C_8$ cycloalkyl; X is O or N—R'; R' is —H or an alkyl substituted by $C_1$-$C_4$ hydroxy; $R_1$ is halogen,

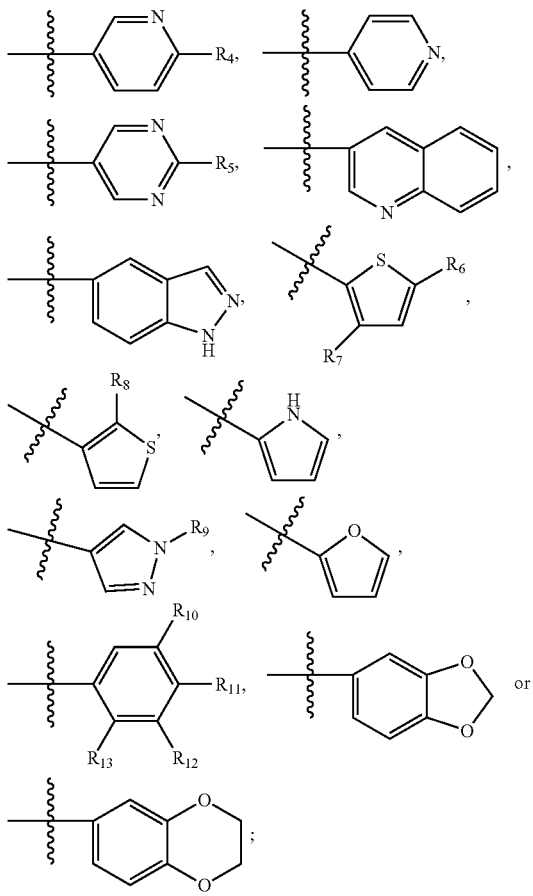

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

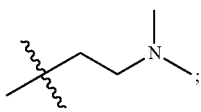 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

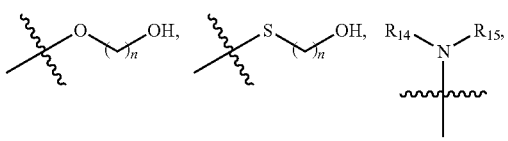

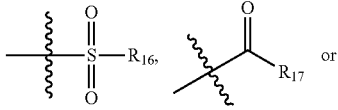

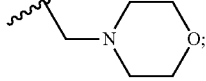

n=1-4; $R_{14}$ and $R_{15}$ are independently —H, $C_1$-$C_4$ alkyl, $C_1$-$C_6$ alkenyl,

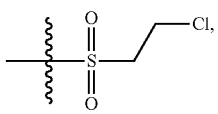

t-butyloxycarboryl,

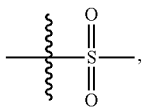 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

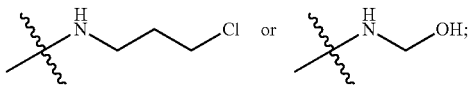

$R_{17}$ is —$NH_2$,

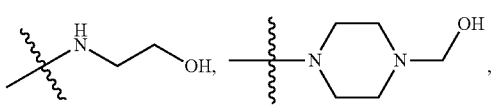 [SMILES: *NCCO ; *N1CCN(CO)CC1]

—OH or halogen.

7. The compound according to claim 6, wherein: $R_2$ and $R_3$ are independently —H, $C_1$-$C_4$ alkyl or $C_3$-$C_8$ cycloalkyl; X is O or N—R'; R' is —H or an alkyl substituted by $C_1$-$C_4$ hydroxy; $R_1$ is halogen,

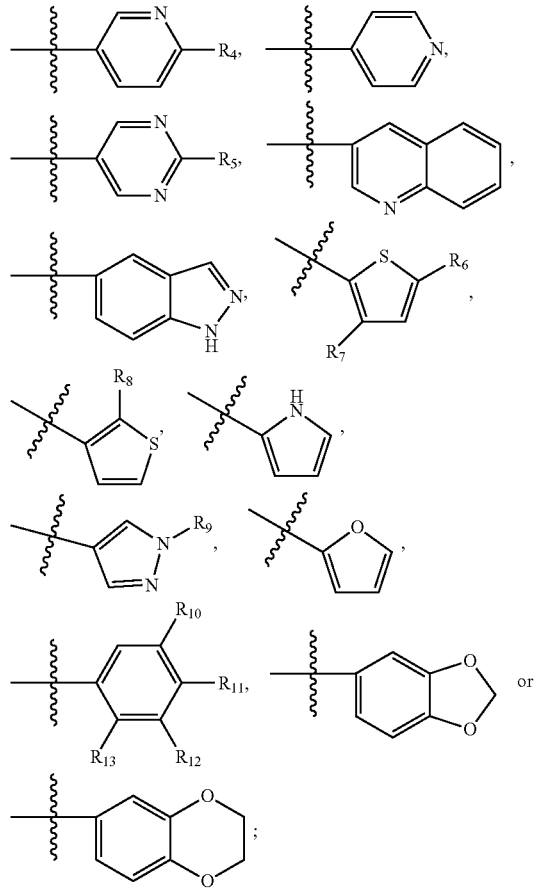

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

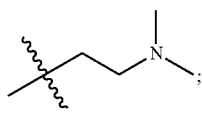

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

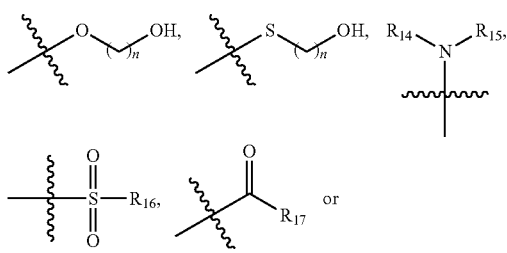

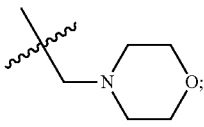

n=1-4; $R_{14}$ and $R_{15}$ are independently —H, $C_1$-$C_4$ alkyl, $C_1$-$C_6$ alkenyl,

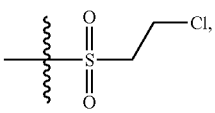 [SMILES: *S(=O)(=O)CCCl]

t-butyloxycarboryl,

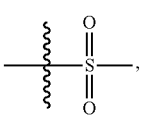 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

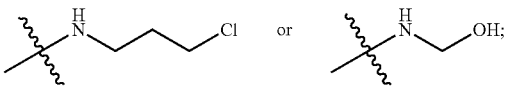

$R_{17}$ is —$NH_2$,

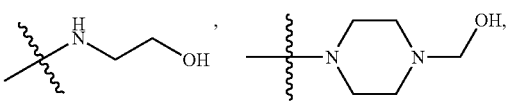

—OH or halogen.

8. The compound according to claim 7, wherein: $R_2$ and $R_3$ are independently —H, $C_1$-$C_4$ alkyl or cyclopentyl alkyl; X is O or N—R'; R' is —H or an alkyl substituted by $C_1$-$C_4$ hydroxy; $R_1$ is halogen,

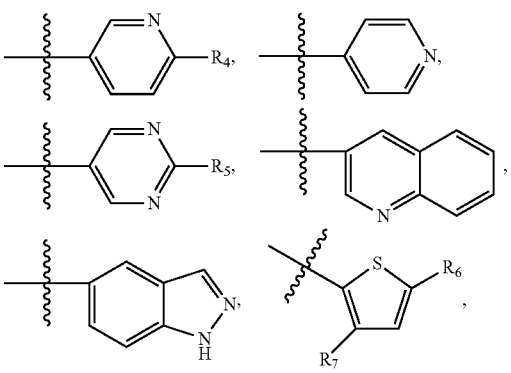

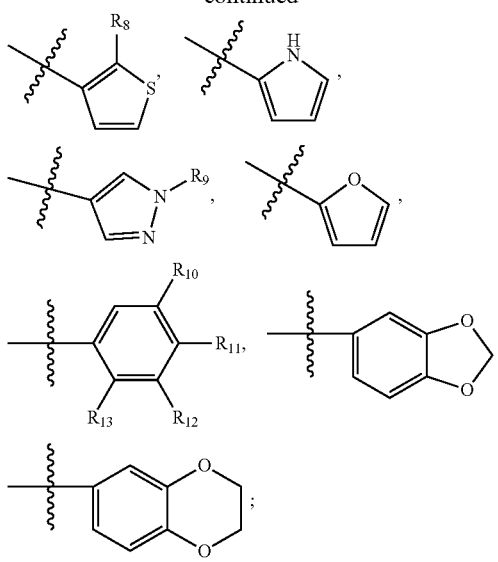

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

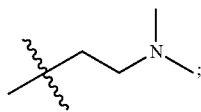 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

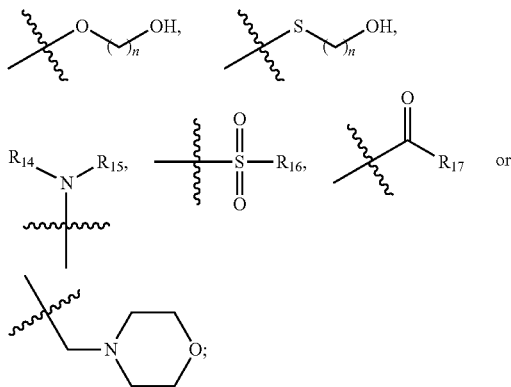

n=1-4; $R_{14}$ and $R_{15}$ are independently —H, $C_1$-$C_4$ alkyl, $C_1$-$C_6$ alkenyl,

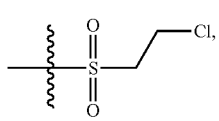 [SMILES: *S(=O)(=O)CCCl]

t-butyloxycarboryl,

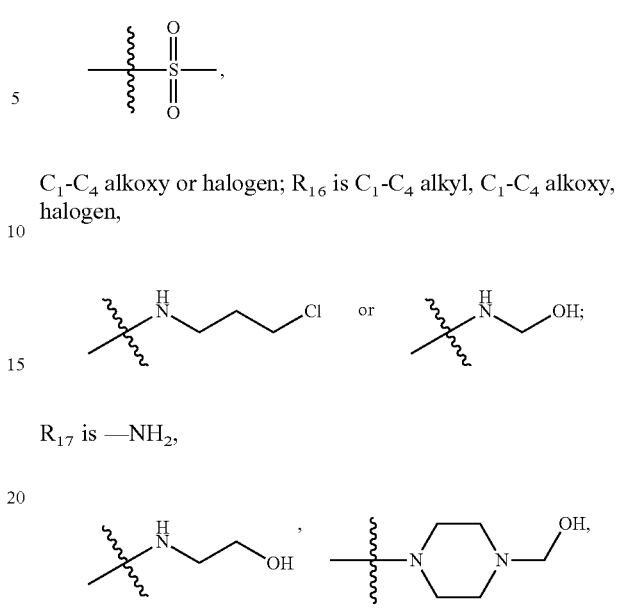

$C_1$-$C_4$ alkoxy or halogen; $R_{16}$ is $C_1$-$C_4$ alkyl, $C_1$-$C_4$ alkoxy, halogen, $R_{17}$ is —$NH_2$, —OH or halogen.

9. The compound according to claim 2, wherein: $R_4$-$R_9$ are independently —H, $C_1$-$C_4$ alkyl, $C_1$-$C_4$ alkoxy, $C_3$-$C_8$ cycloalkyl, —$NH_2$, —COOH, $C_1$-$C_4$ alkyl amino or

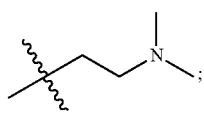 [SMILES: *CCN(C)C]

X is O or N—R'; R' is —H or an alkyl substituted by $C_1$-$C_4$ hydroxy; $R_1$ is halogen,

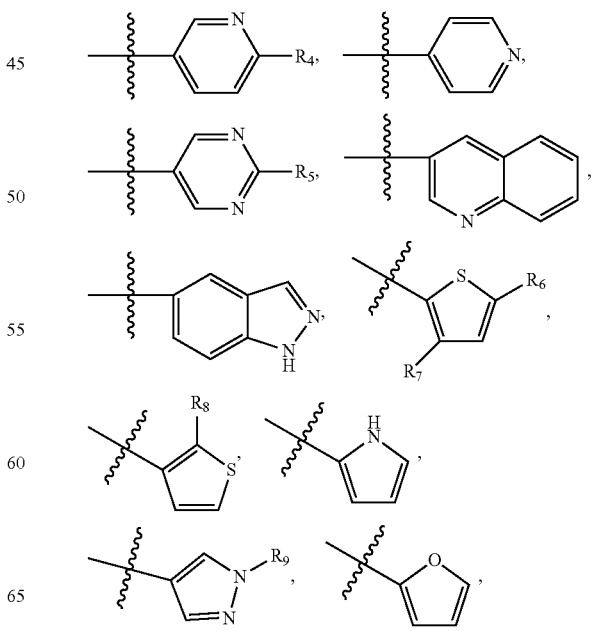

-continued

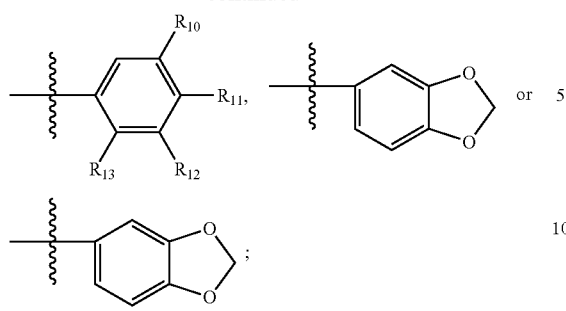

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

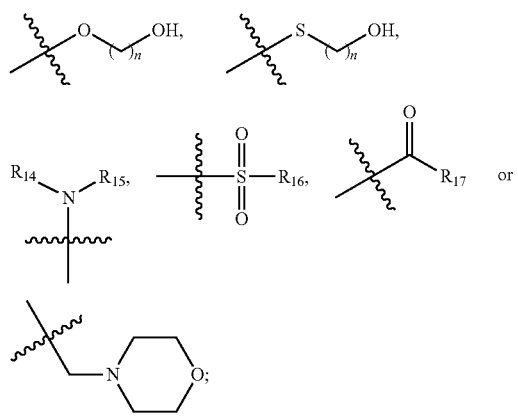

n=1-4; $R_{14}$ and $R_{15}$ are independently —H, $C_1$-$C_4$ alkyl, $C_1$-$C_6$ alkenyl,

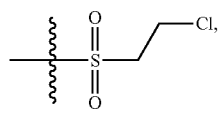

t-butyloxycarboryl,

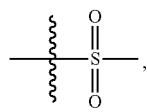 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

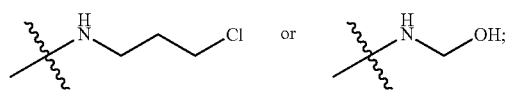

$R_{17}$ is —$NH_2$,

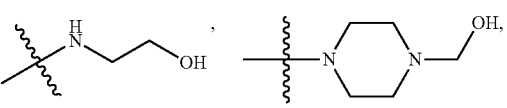

—OH or halogen.

10. The compound according to claim 9, wherein: $R_4$-$R_9$ are independently —H, $C_1$-$C_4$ alkyl, $C_1$-$C_4$ alkoxy, —$NH_2$, —COOH, $C_1$-$C_4$ alkyl amino or

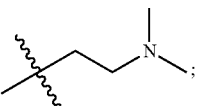 [SMILES: *CCN(C)C]

X is O or N—R'; R' is —H or an alkyl substituted by $C_1$-$C_4$ hydroxy; $R_1$ is halogen,

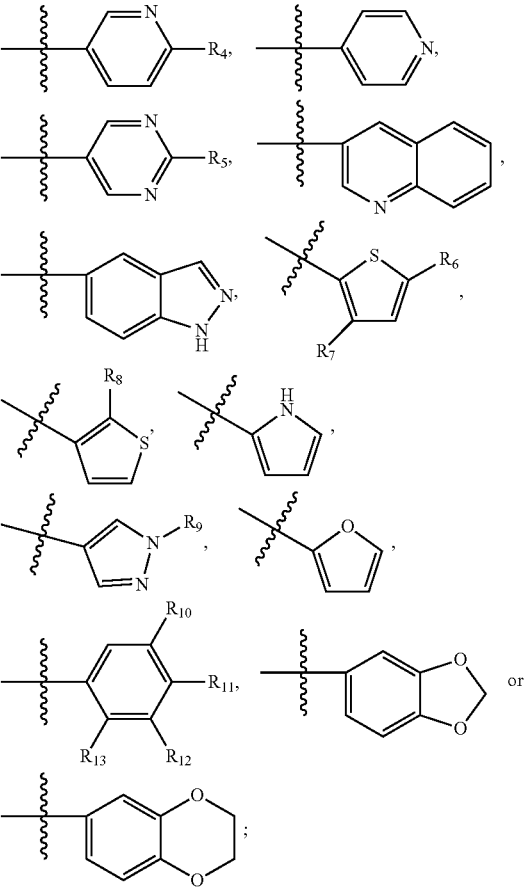

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

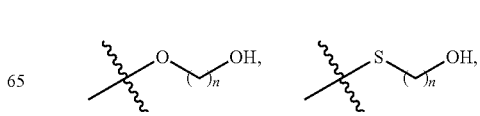

-continued

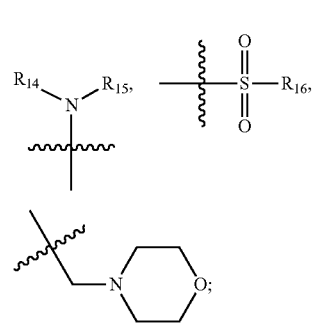

n=1-4; R$_{14}$ and R$_{15}$ are independently —H, C$_1$-C$_4$ alkyl, C$_1$-C$_6$ alkenyl,

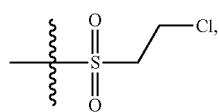 [SMILES: *S(=O)(=O)CCCl]

t-butyloxycarboryl,

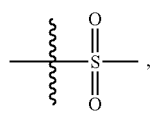 [SMILES: *S(C)(=O)=O]

C$_1$-C$_4$ alkoxy or halogen; R$_{16}$ is C$_1$-C$_4$ alkyl, C$_1$-C$_4$ alkoxy, halogen,

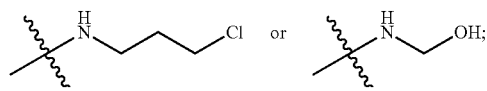

R$_{17}$ is —NH$_2$,

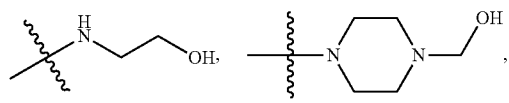

—OH or halogen.

11. The compound according to claim 10, wherein: R$_4$-R$_9$ are independently —H, C$_1$-C$_4$ alkyl, methoxyl, —NH$_2$, —COOH, methylamino or

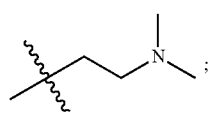

X is O or N—R'; R' is —H or an alkyl substituted by C$_1$-C$_4$ hydroxy; R$_1$ is halogen,

R$_2$ and R$_3$ are independently —H, C$_1$-C$_4$ alkyl or C$_3$-C$_8$ cycloalkyl; R$_{10}$-R$_{13}$ are independently —H, C$_1$-C$_4$ alkyl, C$_1$-C$_4$ alkoxy, —OH, —CF$_3$, halogen, C$_3$-C$_8$ cycloalkyl, —NH$_2$, an alkyl substituted by C$_1$-C$_4$ hydroxy,

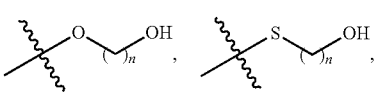

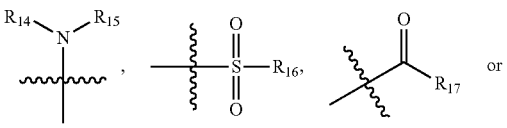

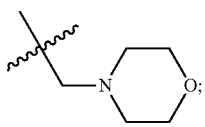

n=1-4; R$_{14}$ and R$_{15}$ are independently —H, C$_1$-C$_4$ alkyl, C$_1$-C$_6$ alkenyl,

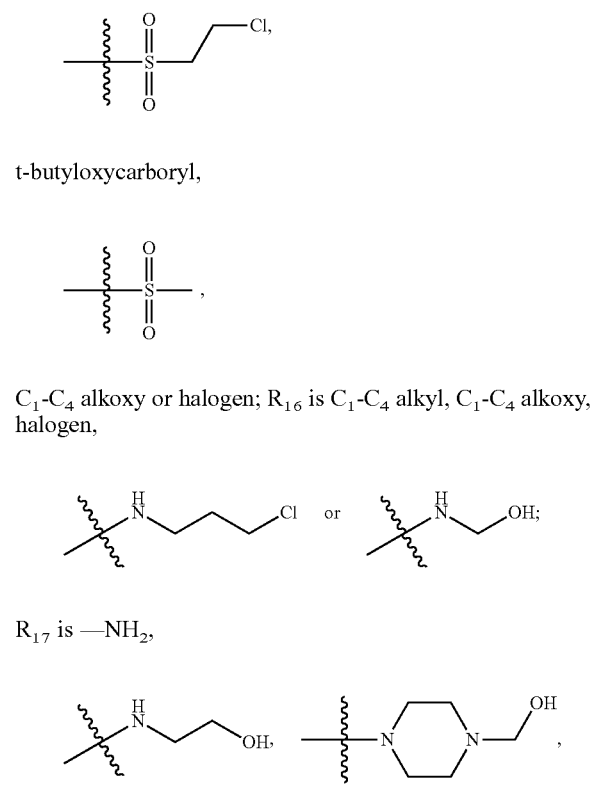

t-butyloxycarboryl, $C_1$-$C_4$ alkoxy or halogen; $R_{16}$ is $C_1$-$C_4$ alkyl, $C_1$-$C_4$ alkoxy, halogen,

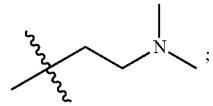 [SMILES: *CCN(C)C]

$R_{17}$ is —$NH_2$,

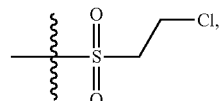

—OH or halogen.

12. The compound according to claim 2, wherein: $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

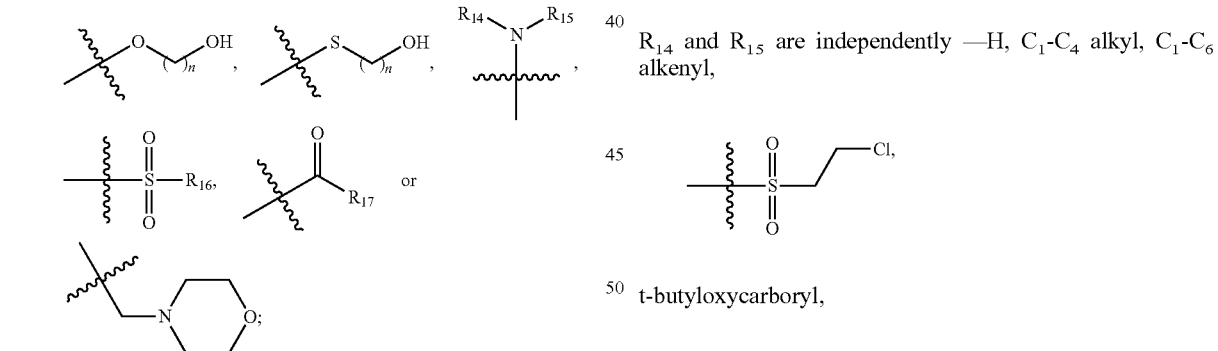

n=1-4; X is O or N—R'; R' is —H or an alkyl substituted by $C_1$-$C_4$ hydroxy $R_1$ is halogen,

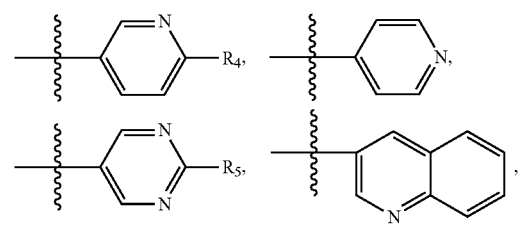

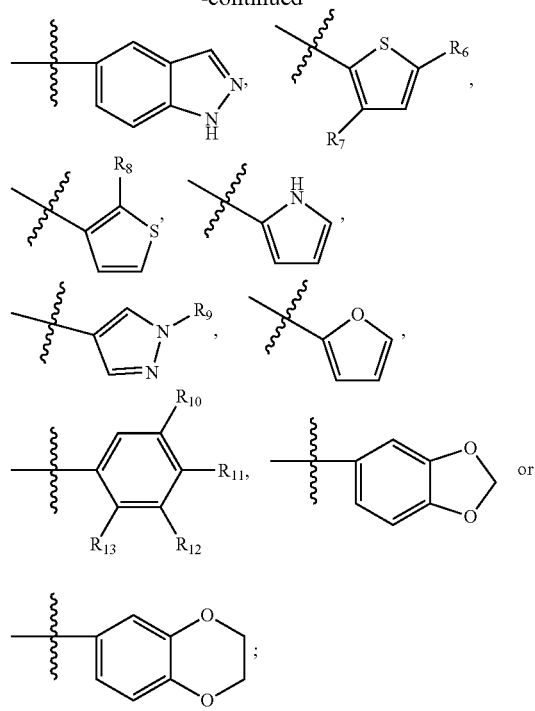

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

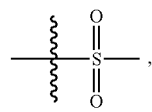

$R_{14}$ and $R_{15}$ are independently —H, $C_1$-$C_4$ alkyl, $C_1$-$C_6$ alkenyl,

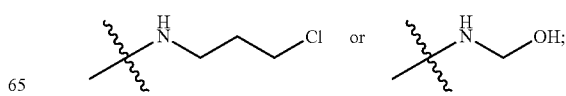

t-butyloxycarboryl, $C_1$-$C_4$ alkoxy or halogen; $R_{16}$ is $C_1$-$C_4$ alkyl, $C_1$-$C_4$ alkoxy, halogen,

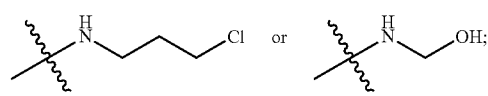

$R_{17}$ is —$NH_2$,

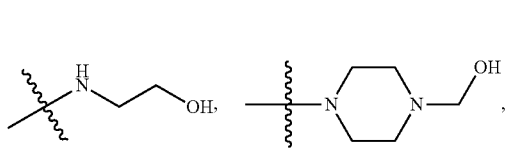

—OH or halogen.

13. The compound according to claim 12, wherein: $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

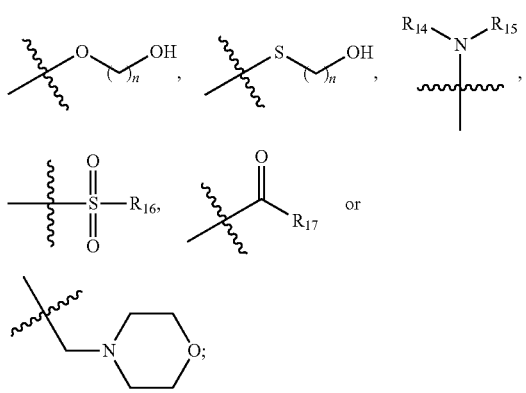

n=1 or 2; X is O or N—R'; R' is —H or an alkyl substituted by $C_1$-$C_4$ hydroxy; $R_1$ is halogen,

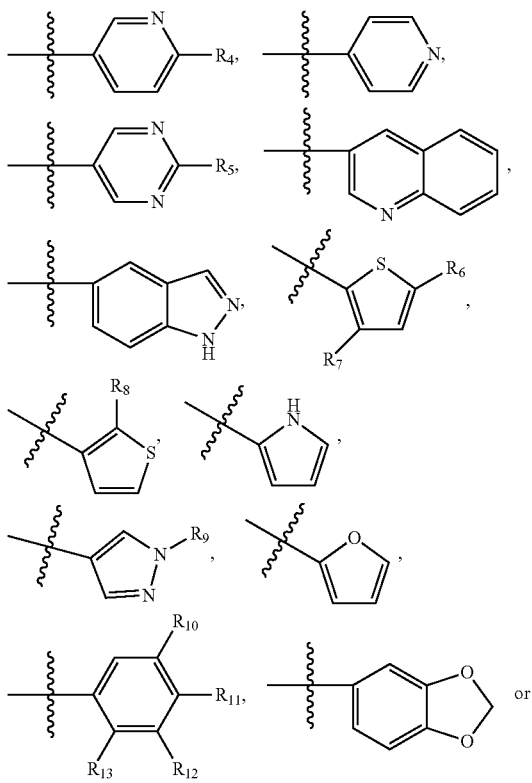

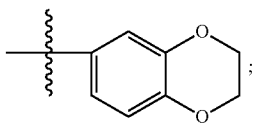

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

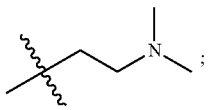

$R_{14}$ and $R_{15}$ are independently —H, $C_1$-$C_4$ alkyl, $C_1$-$C_6$ alkenyl,

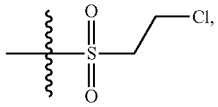 [SMILES: *S(=O)(=O)CCCl]

t-butyloxycarboryl,

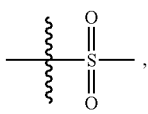

$C_1$-$C_4$ alkoxy or halogen; $R_{16}$ is $C_1$-$C_4$ alkyl, $C_1$-$C_4$ alkoxy, halogen,

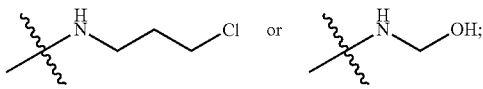

$R_{17}$ is —$NH_2$,

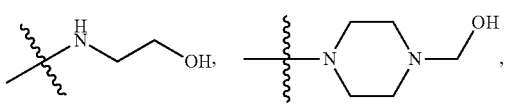

—OH or halogen.

14. The compound according to claim 2, wherein: $R_{14}$ and $R_{15}$ are independently —H, $C_1$-$C_4$ alkyl, $C_1$-$C_6$ alkenyl,

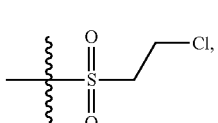

t-butyloxycarboryl,

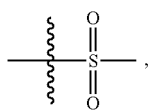 [SMILES: *S(C)(=O)=O]

$C_1$-$C_4$ alkoxy or halogen; X is O or N—R'; R' is —H or an alkyl substituted by $C_1$-$C_4$ hydroxy; $R_1$ is halogen,

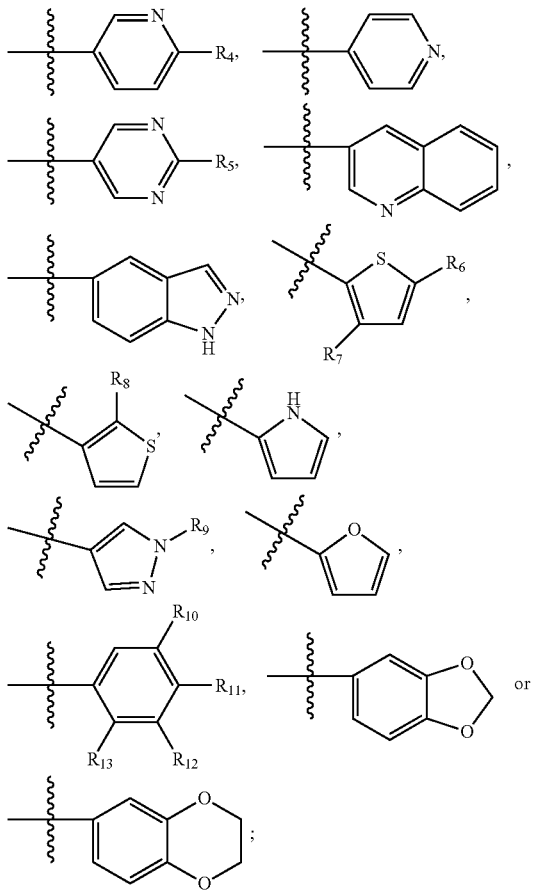

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —NH$_2$, —COOH, $C_1$-$C_4$ alkyl amino or

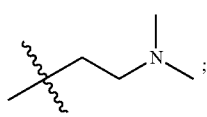 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, —NH$_2$, an alkyl substituted by $C_1$-$C_4$ hydroxy,

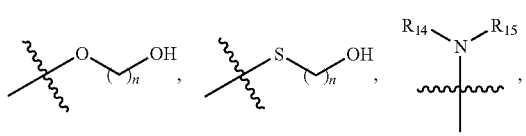

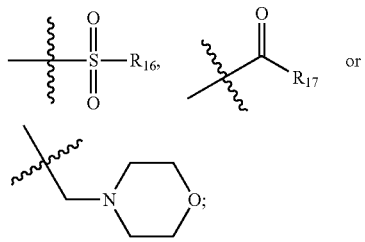

n=1-4; $R_{16}$ is $C_1$-$C_4$ alkyl, $C_1$-$C_4$ alkoxy, halogen,

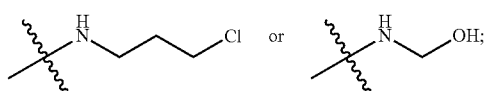

$R_{17}$ is —NH$_2$,

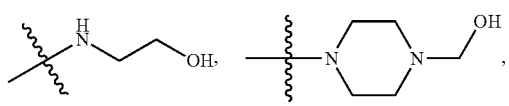 [SMILES: *NCCO ; *N1CCN(CO)CC1]

—OH or halogen.

15. The compound according to claim 14, wherein: $R_{14}$ and $R_{15}$ are independently —H, $C_1$-$C_4$ alkyl, $C_1$-$C_6$ alkenyl,

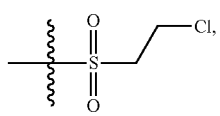 [SMILES: *S(=O)(=O)CCCl]

t-butyloxycarboryl or

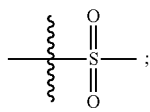 [SMILES: *S(C)(=O)=O]

X is O or N—R'; R' is —H or an alkyl substituted by $C_1$-$C_4$ hydroxy; $R_1$ is halogen,

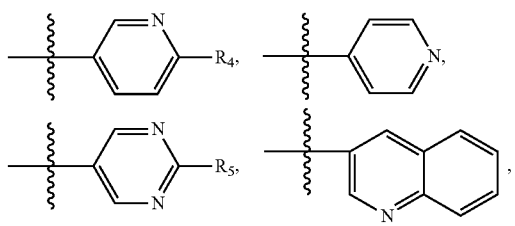

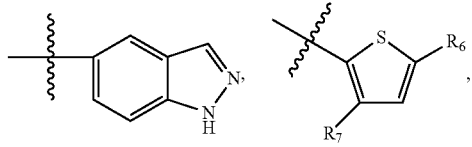

-continued

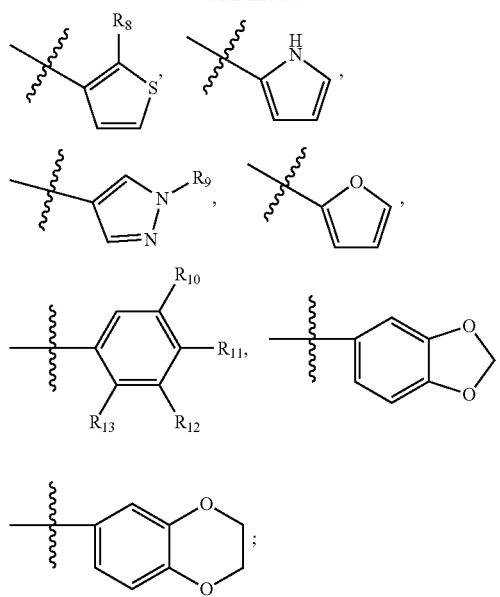

R₂ and R₃ are independently —H, $C_1$-$C_4$ alkyl or $C_3$-$C_8$ cycloalkyl; R₄-R₉ are independently —H, $C_1$-$C_4$ alkyl, $C_1$-$C_4$ alkoxy, —NH₂, —COOH, $C_1$-$C_4$ alkyl amino or

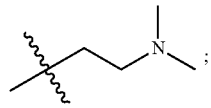

R₁₀-R₁₃ are independently —H, $C_1$-$C_4$ alkyl, $C_1$-$C_4$ alkoxy, —OH, —CF₃, halogen, —NH₂, an alkyl substituted by $C_1$-$C_4$ hydroxy,

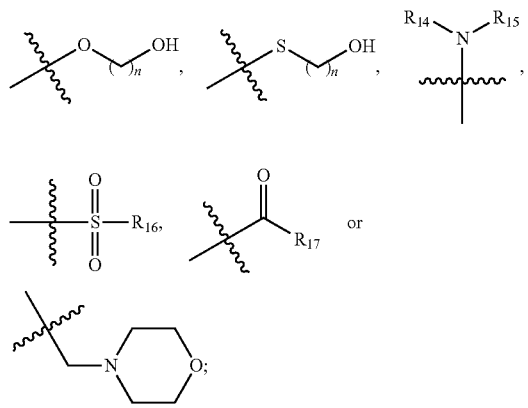

n=1-4; R₁₆ is $C_1$-$C_4$ alkyl, $C_1$-$C_4$ alkoxy, halogen,

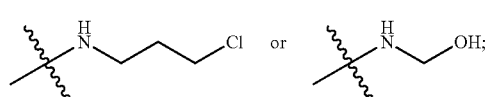

R₁₇ is —NH₂,

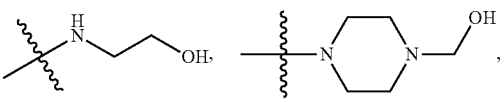

OH or halogen.

16. The compound according to claim 2, wherein: R₁₆ is $C_1$-$C_4$ alkyl,

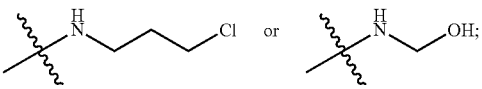

X is O or N—R'; R' is —H or an alkyl substituted by $C_1$-$C_4$ hydroxy; R₁ is halogen,

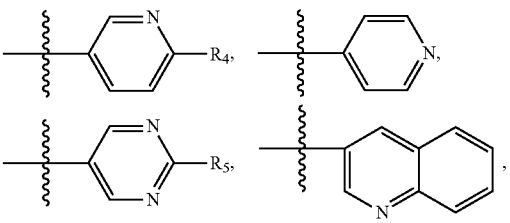

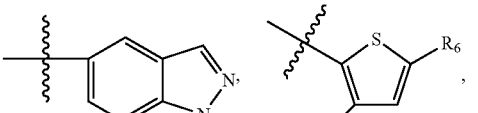

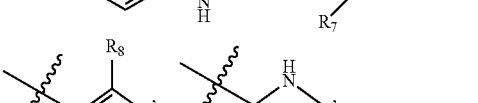

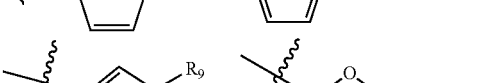

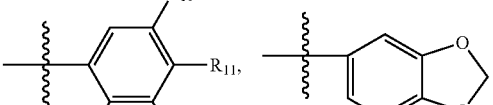

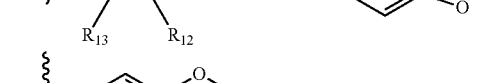

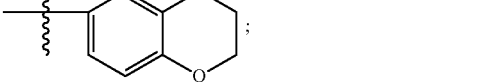

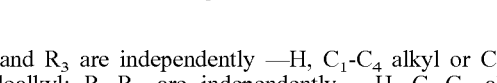

R₂ and R₃ are independently —H, $C_1$-$C_4$ alkyl or $C_3$-$C_8$ cycloalkyl; R₄-R₉ are independently —H, $C_1$-$C_4$ alkyl, $C_1$-$C_4$ alkoxy, —NH₂, —COOH, $C_1$-$C_4$ alkyl amino or

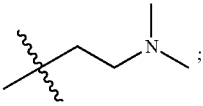

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

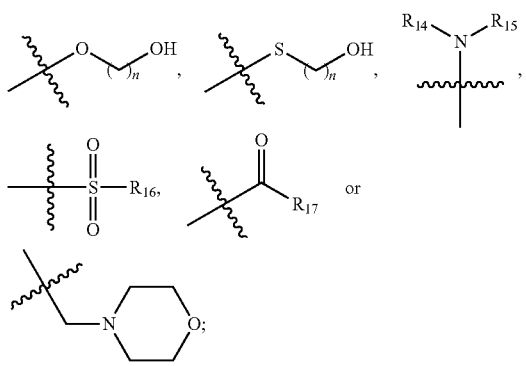

n=1-4; $R_{14}$ and $R_{15}$ are independently —H, $C_1$-$C_4$ alkyl, $C_1$-$C_6$ alkenyl,

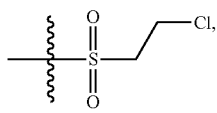 [SMILES: *S(=O)(=O)CCCl]

t-butyloxycarboryl or

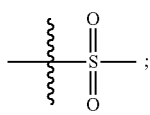 [SMILES: *S(C)(=O)=O]

$R_{17}$ is —$NH_2$,

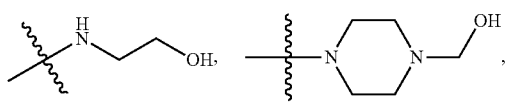

—OH or halogen.

17. The compound according to claim 16, wherein: X is O or N—R'; R' is —H or an alkyl substituted by $C_1$-$C_4$ hydroxy; $R_1$ is halogen,

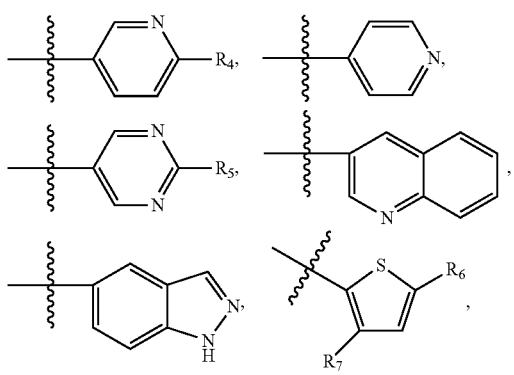

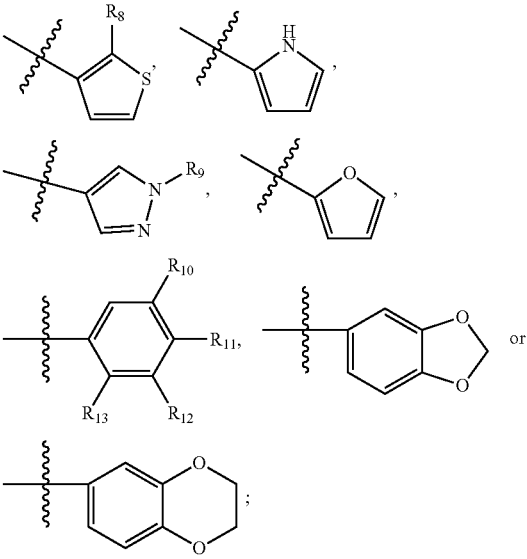

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

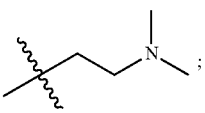 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

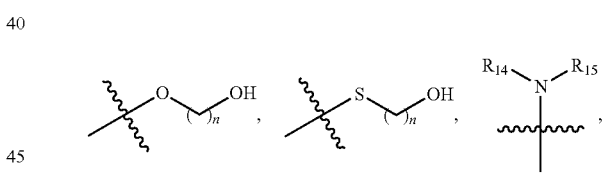

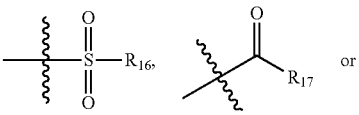

n=1-4; $R_{14}$ and $R_{15}$ are independently —H, $C_1$-$C_4$ alkyl, $C_1$-$C_6$ alkenyl,

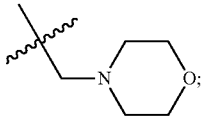

t-butyloxycarboryl or

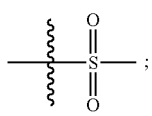 [SMILES: *S(C)(=O)=O]

$R_{16}$ is $C_1$-$C_4$ alkyl,

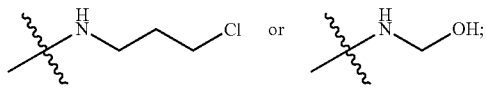

$R_{17}$ is —$NH_2$,

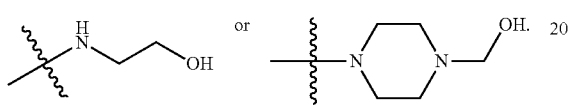

18. The compound according to claim 2, wherein: X is O or N—R'; R' is —H or hydroxy ethyl; $R_1$ is —Cl,

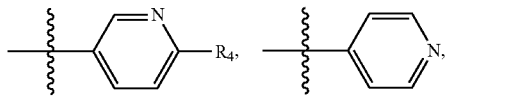

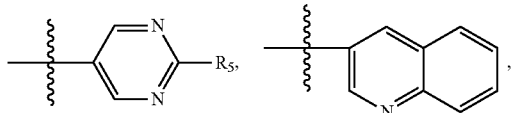

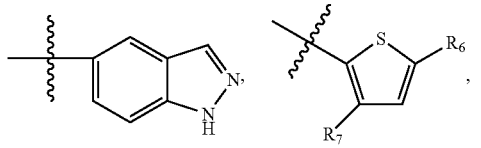

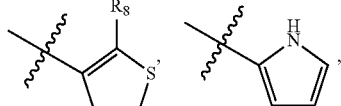

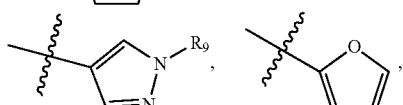

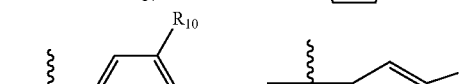

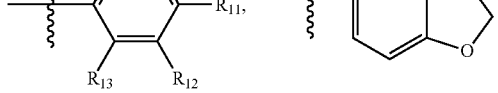

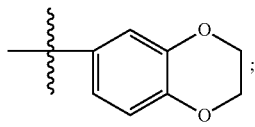

$R_2$ and $R_3$ are independently —H, $C_1$-$C_4$ alkyl or cyclopentyl alkyl; $R_4$-$R_9$ are independently —H, $C_1$-$C_4$ alkyl, methoxy, —$NH_2$, —COOH, methylamino or

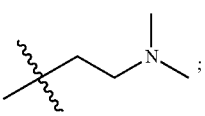

$R_{10}$-$R_{13}$ are independently —H, $C_1$-$C_4$ alkyl, methoxy, —OH, —$CF_3$, —Cl, —$NH_2$, an alkyl substituted by $C_1$-$C_4$ hydroxy,

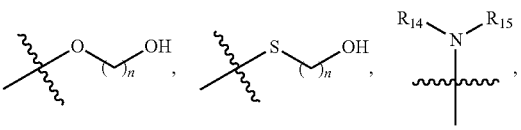

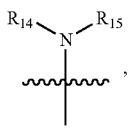

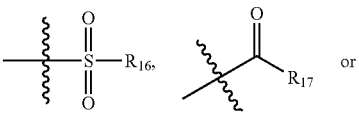

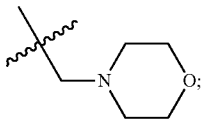

n=1 or 2; $R_{14}$ and $R_{15}$ are independently —H, $C_1$-$C_4$ alkyl, $C_1$-$C_6$ alkenyl,

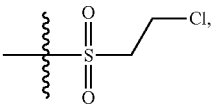 [SMILES: *S(=O)(=O)CCCl]

t-butyloxycarboryl or

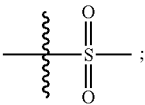 [SMILES: *S(C)(=O)=O]

$R_{16}$ is $C_1$-$C_4$ alkyl,

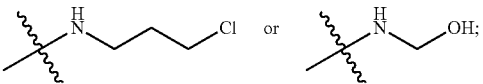

$R_{17}$ is —$NH_2$,

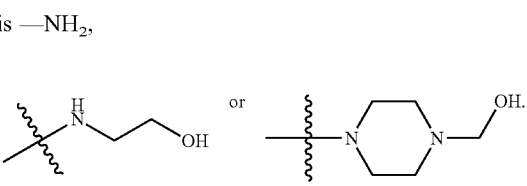

19. The compound according to claim 1, wherein: when X is O, the structure of which is as shown in Formula II:

Formula II

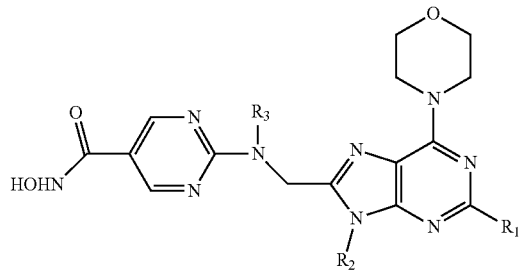

wherein, $R_1$ is $C_1$-$C_4$ alkyl, $C_1$-$C_4$ alkoxy, —OH, halogen, $C_3$-$C_8$ cycloalkyl, —NH$_2$,

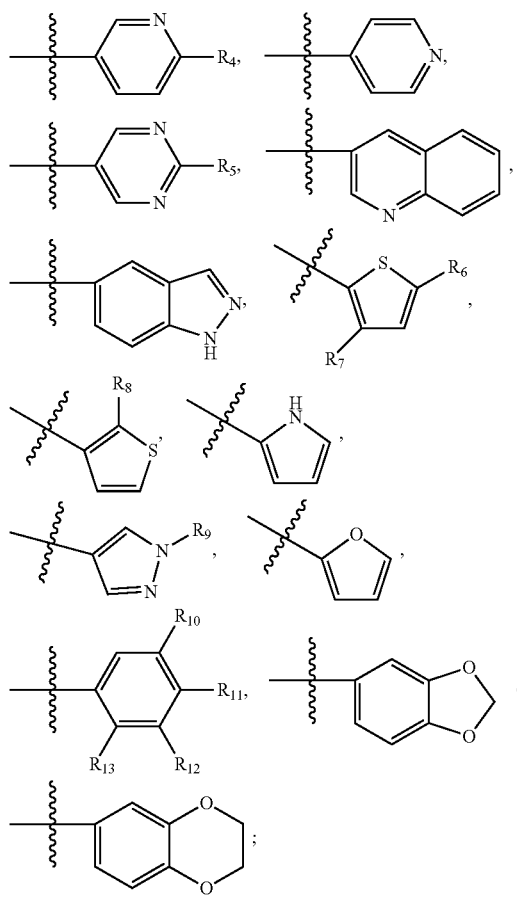

$R_2$ and $R_3$ are independently —H, $C_1$-$C_4$ alkyl, $C_1$-$C_4$ alkoxy, —OH, halogen or $C_3$-$C_8$ cycloalkyl;
$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

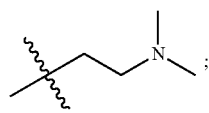 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

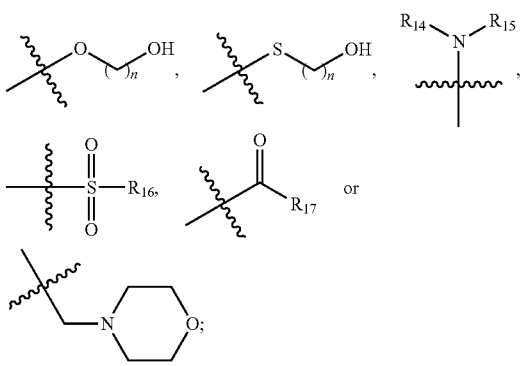

$n$=1-4;
$R_{14}$ and $R_{15}$ are independently —H, $C_1$-$C_4$ alkyl, $C_1$-$C_6$ alkenyl,

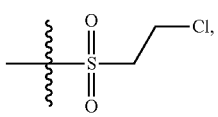

t-butyloxycarboryl,

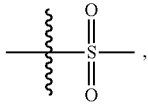 [SMILES: *S(C)(=O)=O]

$C_1$-$C_4$ alkoxy or halogen;
$R_{16}$ is $C_1$-$C_4$ alkyl, $C_1$-$C_4$ alkoxy, halogen,

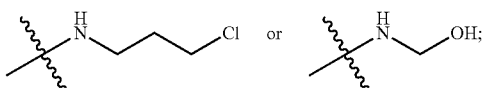

$R_{17}$ is —NH$_2$,

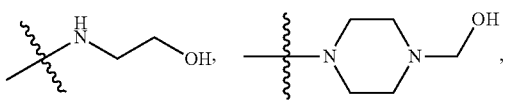

—OH or halogen.

20. The compound according to claim 19, wherein: $R_1$ is halogen, $C_3$-$C_8$ cycloalkyl, —NH$_2$,

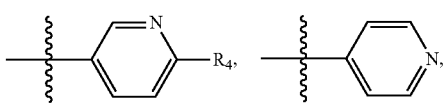

-continued

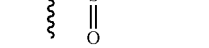

$R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

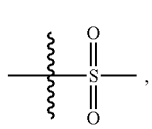 [SMILES: *S(C)(=O)=O]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

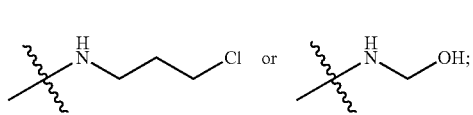

n=1-4; $R_{14}$ and $R_{15}$ are independently —H, $C_1$-$C_4$ alkyl, $C_1$-$C_6$ alkenyl, t-butyloxycarboryl, $C_1$-$C_4$ alkoxy or halogen; $R_{16}$ is $C_1$-$C_4$ alkyl, $C_1$-$C_4$ alkoxy, halogen, $R_{17}$ is —NH$_2$, —OH or halogen.

21. The compound according to claim 20, wherein: $R_1$ is halogen,

-continued

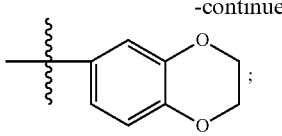

$R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

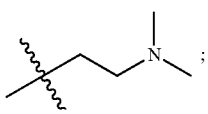

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

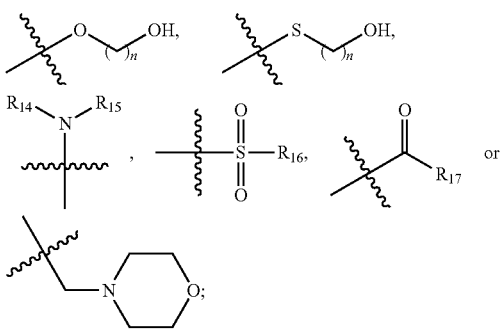

n=1-4; $R_{14}$ and $R_{15}$ are independently —H, $C_1$-$C_4$ alkyl, $C_1$-$C_6$ alkenyl,

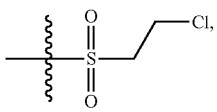 [SMILES: *S(=O)(=O)CCCl]

t-butyloxycarboryl,

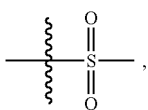 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

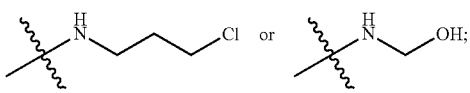

$R_{17}$ is —NH$_2$,

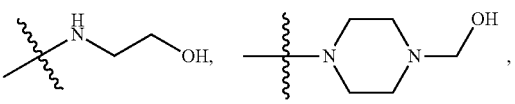 [SMILES: *NCCO ; *N1CCN(CO)CC1]

—OH or halogen.

22. The compound according to claim 21, wherein: $R_1$ is —Cl,

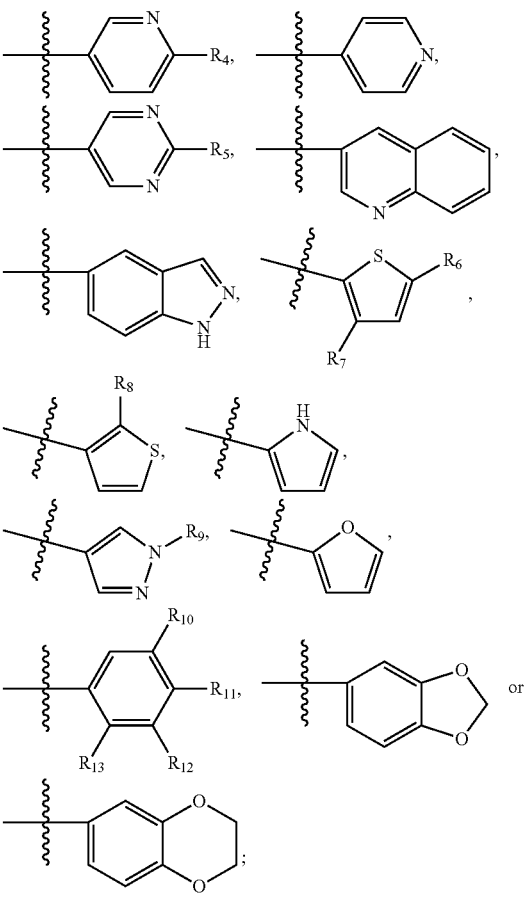

$R_2$ and $R_3$ are independently —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

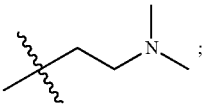 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

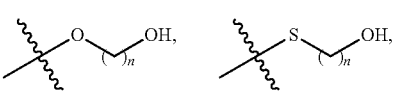

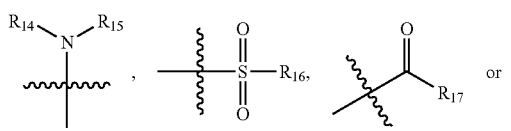

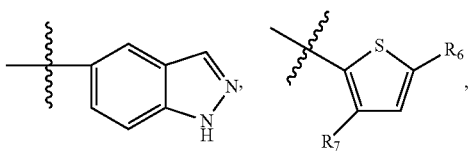

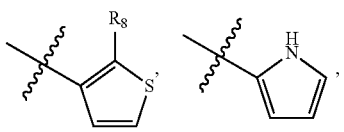

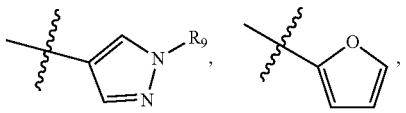

n=1-4; $R_{14}$ and $R_{15}$ are independently —H, $C_1$-$C_4$ alkyl, $C_1$-$C_6$ alkenyl,

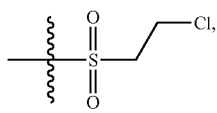 [SMILES: *S(=O)(=O)CCCl]

t-butyloxycarboryl,

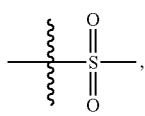 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

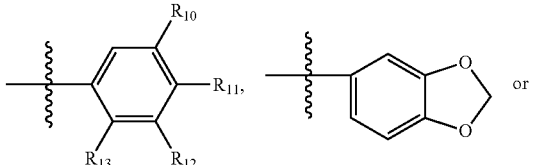

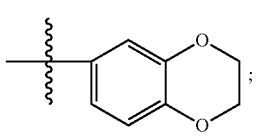

$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or $R_{17}$ is —NH$_2$,

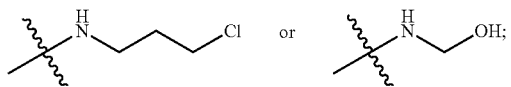

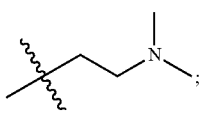

—OH or halogen.

23. The compound according to claim 19, wherein: $R_2$ and $R_3$ are independently —H, $C_1$-$C_4$ alkyl, $C_1$-$C_4$ alkoxy or $C_3$-$C_8$ cycloalkyl; $R_1$ is halogen,

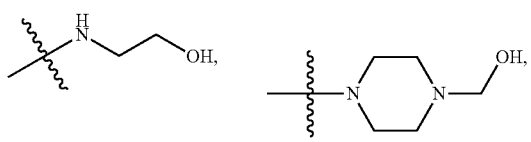 [SMILES: *NCCO ; *N1CCN(CO)CC1]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

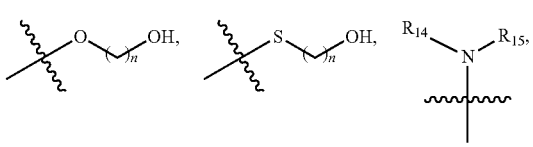

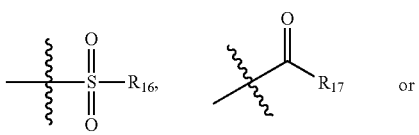

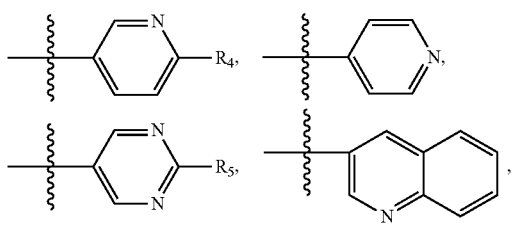

n=1-4; $R_{14}$ and $R_{15}$ are independently —H, $C_1$-$C_4$ alkyl, $C_1$-$C_6$ alkenyl,

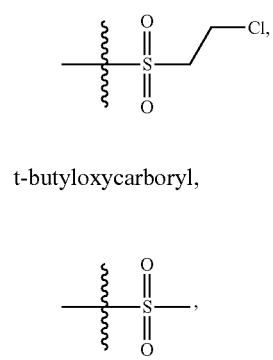

t-butyloxycarboryl,

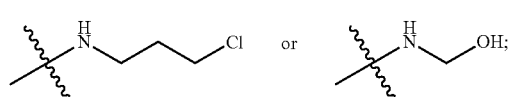

$C_1$-$C_4$ alkoxy or halogen; $R_{16}$ is $C_1$-$C_4$ alkyl, $C_1$-$C_4$ alkoxy, halogen,

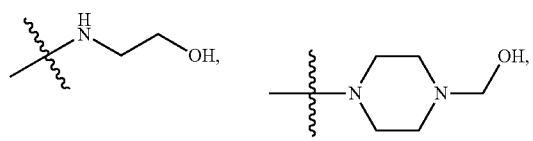 [SMILES: *NCCO ; *N1CCN(CO)CC1]

$R_{17}$ is —$NH_2$,

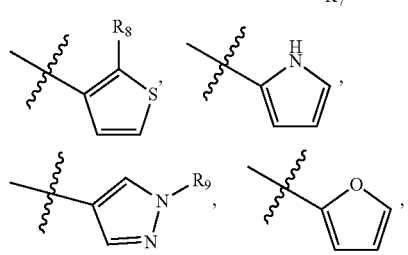

—OH or halogen.

24. The compound according to claim 23, wherein: $R_2$ and $R_3$ are independently —H, $C_1$-$C_4$ alkyl or $C_3$-$C_8$ cycloalkyl; $R_1$ is halogen,

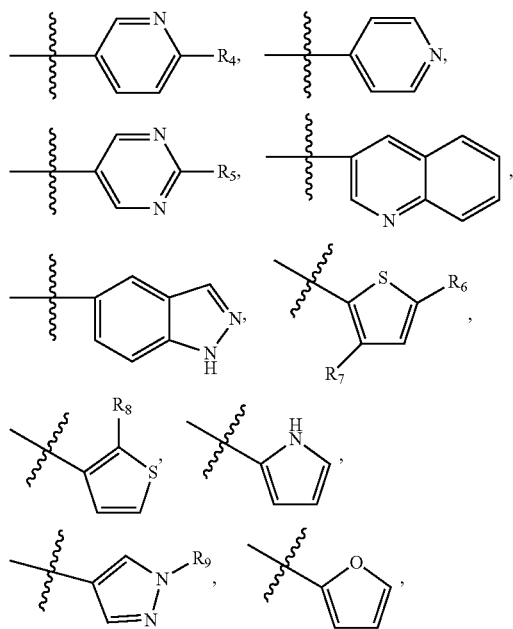

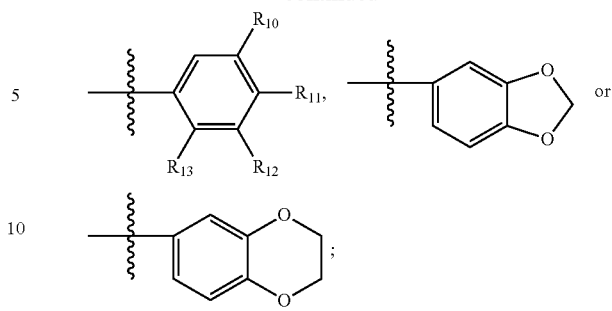

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

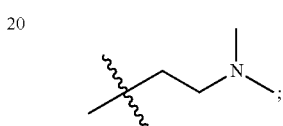

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

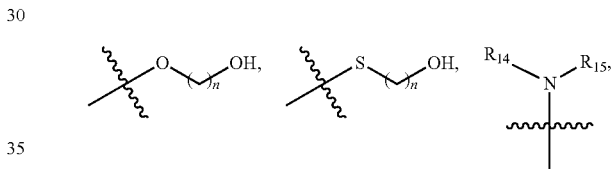

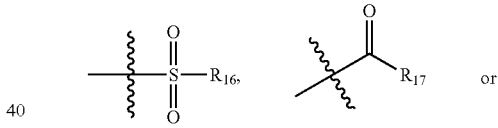

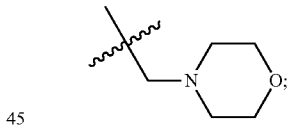

n=1-4; $R_{14}$ and $R_{15}$ are independently —H, $C_1$-$C_4$ alkyl, $C_1$-$C_6$ alkenyl,

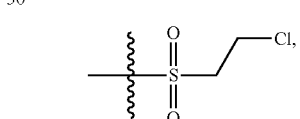

t-butyloxycarboryl,

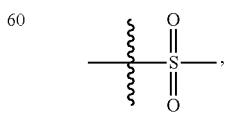

$C_1$-$C_4$ alkoxy or halogen; $R_{16}$ is $C_1$-$C_4$ alkyl, $C_1$-$C_4$ alkoxy, halogen,

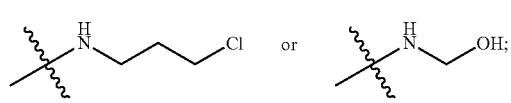

$R_{17}$ is —$NH_2$,

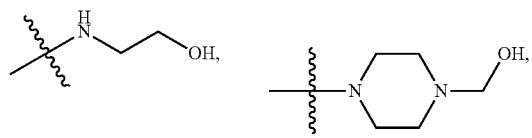

—OH or halogen.

25. The compound according to claim 24, wherein: $R_2$ and $R_3$ are independently —H, $C_1$-$C_4$ alkyl or cyclopentyl alkyl; $R_1$ is halogen,

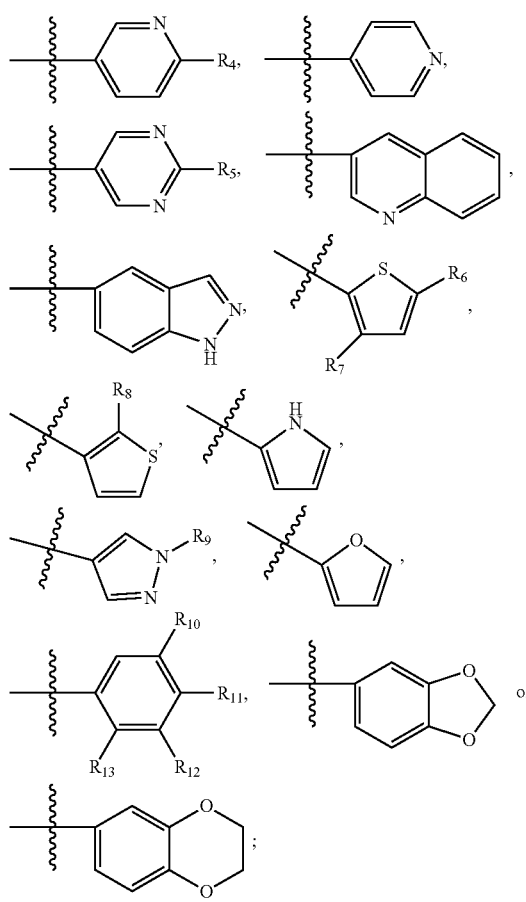

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

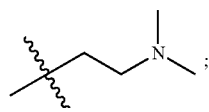 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

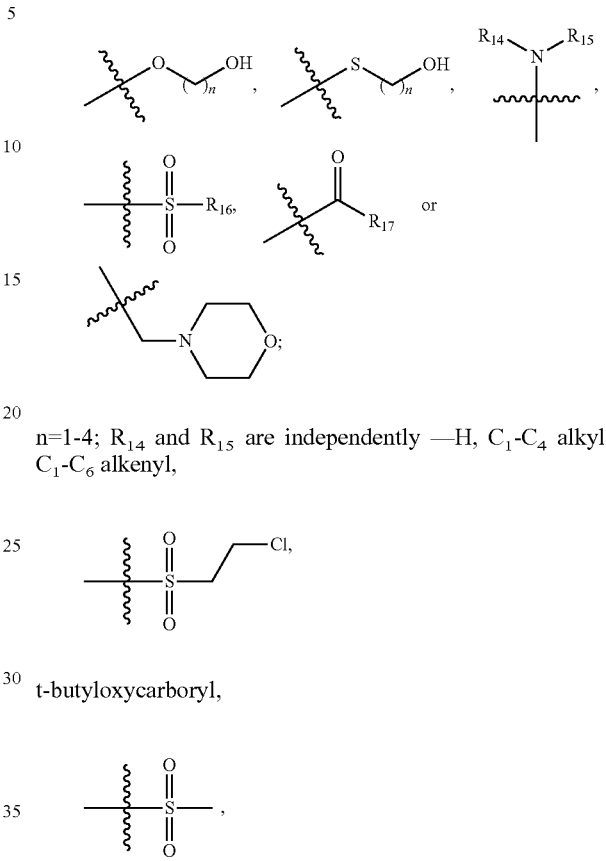

n=1-4; $R_{14}$ and $R_{15}$ are independently —H, $C_1$-$C_4$ alkyl, $C_1$-$C_6$ alkenyl,

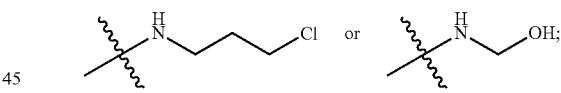

t-butyloxycarboryl,

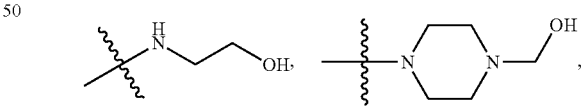

$C_1$-$C_4$ alkoxy or halogen; $R_{16}$ is $C_1$-$C_4$ alkyl, $C_1$-$C_4$ alkoxy, halogen,

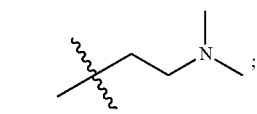 [SMILES: *CCN(C)C]

$R_{17}$ is —$NH_2$,

—OH or halogen.

26. The compound according to claim 19, wherein: $R_4$-$R_9$ are independently —H, $C_1$-$C_4$ alkyl, $C_1$-$C_4$ alkoxy, $C_3$-$C_8$ cycloalkyl, —$NH_2$, —COOH, $C_1$-$C_4$ alkyl amino or R₁ is halogen,

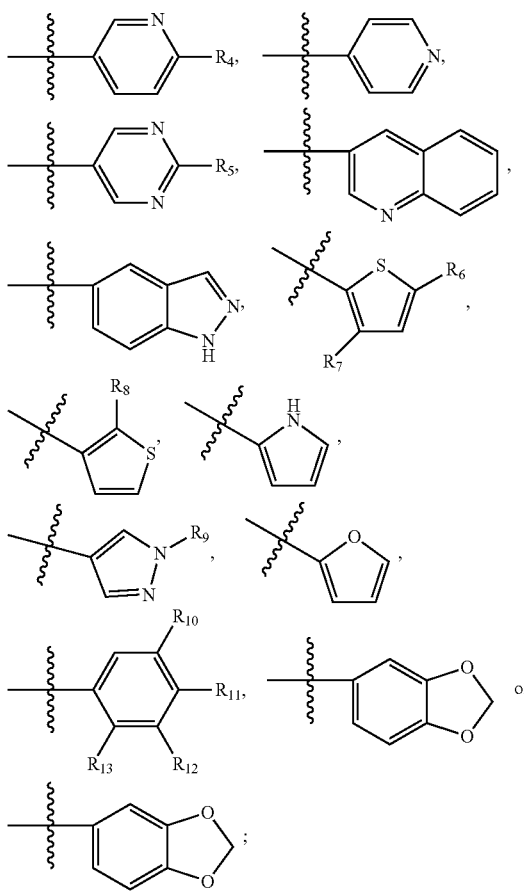

R₂ and R₃ are independently —H, C₁-C₄ alkyl or C₃-C₈ cycloalkyl; R₁₀-R₁₃ are independently —H, C₁-C₄ alkyl, C₁-C₄ alkoxy, —OH, —CF₃, halogen, C₃-C₈ cycloalkyl, —NH₂, an alkyl substituted by C₁-C₄ hydroxy,

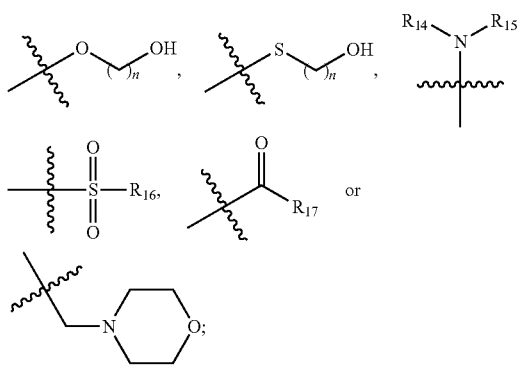

n=1-4; R₁₄ and R₁₅ are independently —H, C₁-C₄ alkyl, C₁-C₆ alkenyl,

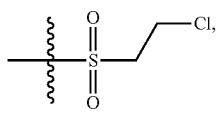

t-butyloxycarboryl,

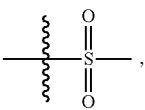 [SMILES: *S(C)(=O)=O]

C₁-C₄ alkoxy or halogen; R₁₆ is C₁-C₄ alkyl, C₁-C₄ alkoxy, halogen,

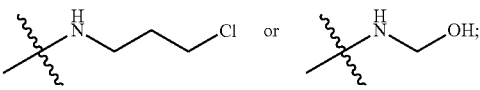

R₁₇ is —NH₂,

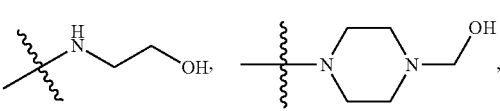 [SMILES: *NCCO ; *N1CCN(CO)CC1]

—OH or halogen.

27. The compound according to claim 26, wherein: R₄-R₉ are independently —H, C₁-C₄ alkyl, C₁-C₄ alkoxy, —NH₂, —COOH, C₁-C₄ alkyl amino or

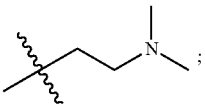

R₁ is halogen,

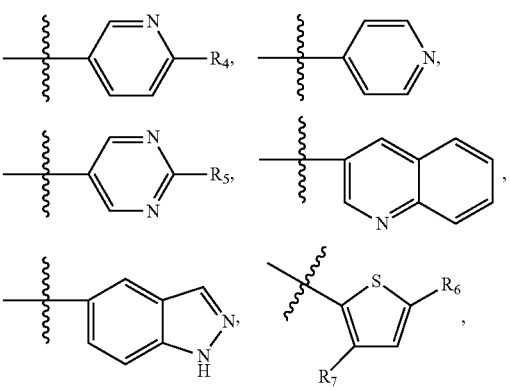

-continued

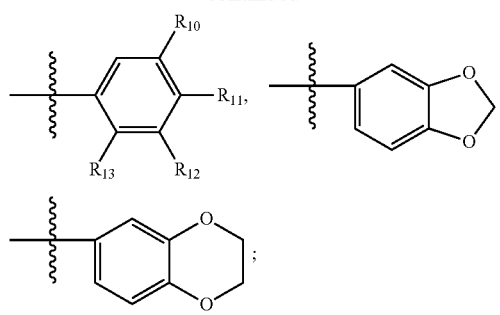

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

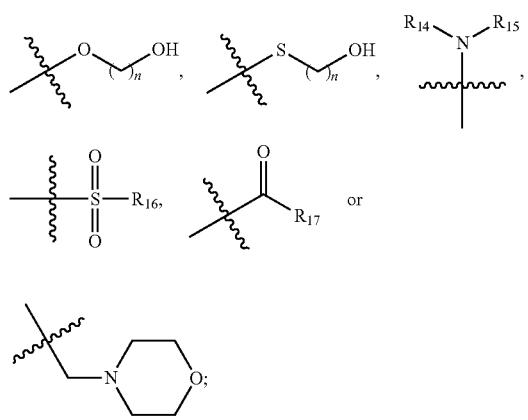

n=1-4; $R_{14}$ and $R_{15}$ are independently —H, $C_1$-$C_4$ alkyl, $C_1$-$C_6$ alkenyl,

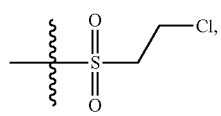 [SMILES: *S(=O)(=O)CCCl]

t-butyloxycarboryl,

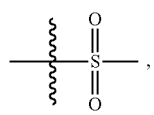 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

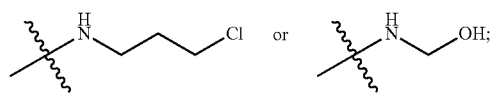

$R_{17}$ is —NH$_2$,

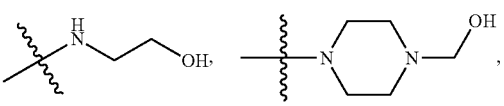

—OH or halogen.

28. The compound according to claim 27, wherein: $R_4$-$R_9$ are independently —H, $C_1$-$C_4$ alkyl, methoxy, —NH$_2$, —COOH, methylamino or

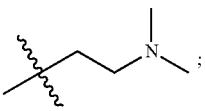

$R_1$ is halogen,

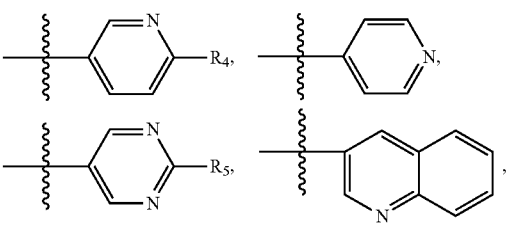

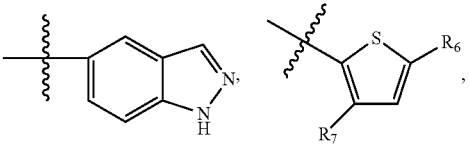

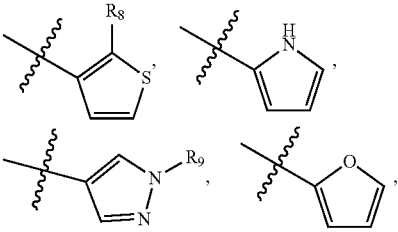

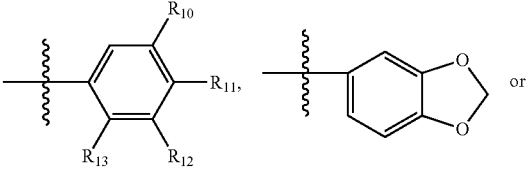

$R_2$ and $R_3$ are independently —H, $C_1$-$C_4$ alkyl or $C_3$-$C_8$ cycloalkyl; $R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

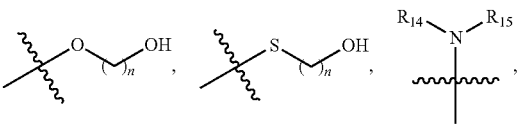

-continued

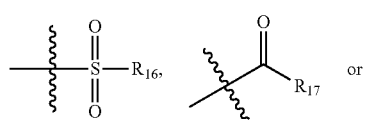

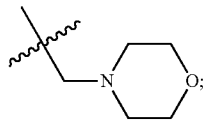

n=1-4; $R_{14}$ and $R_{15}$ are independently —H, $C_1$-$C_4$ alkyl, $C_1$-$C_6$ alkenyl,

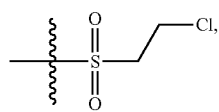

t-butyloxycarboryl,

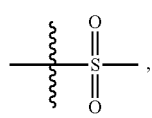

$C_1$-$C_4$ alkoxy or halogen; $R_{16}$ is $C_1$-$C_4$ alkyl, $C_1$-$C_4$ alkoxy, halogen,

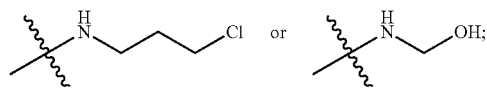

$R_{17}$ is —NH$_2$,

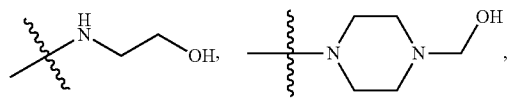 [SMILES: *NCCO ; *N1CCN(CO)CC1]

—OH or halogen.

29. The compound according to claim 19, wherein: $R_{10}$-$R_{13}$ are independently —H, $C_1$-$C_4$ alkyl, $C_1$-$C_4$ alkoxy, —OH, —CF$_3$, halogen, —NH$_2$, an alkyl substituted by $C_1$-$C_4$ hydroxy,

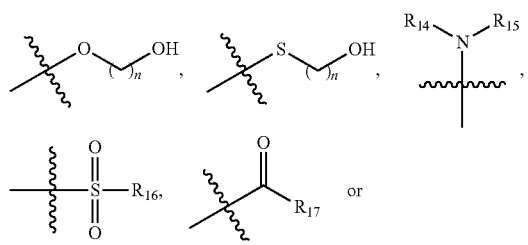

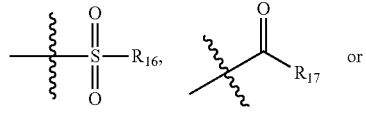

-continued

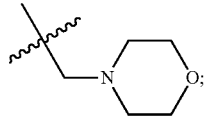

n=1-4; $R_1$ is halogen,

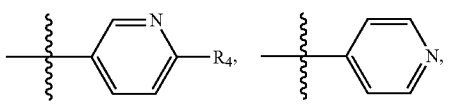

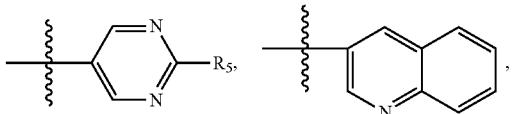

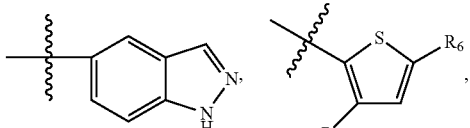

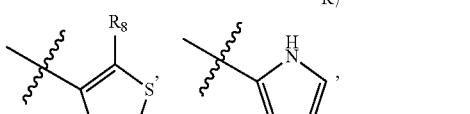

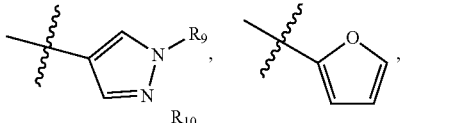

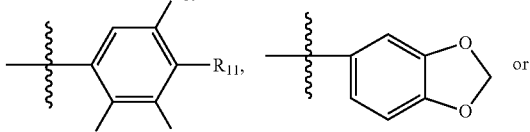

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —NH$_2$, —COOH, $C_1$-$C_4$ alkyl amino or

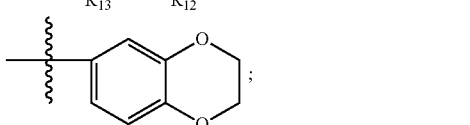

$R_{14}$ and $R_{15}$ are independently —H, $C_1$-$C_4$ alkyl, $C_1$-$C_6$ alkenyl,

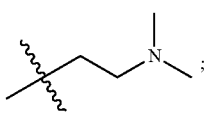 [SMILES: *CCN(C)C]

t-butyloxycarboryl,

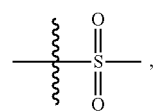 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

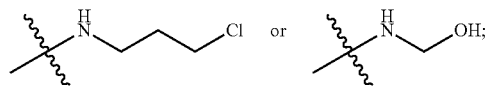

$R_{17}$ is —$NH_2$,

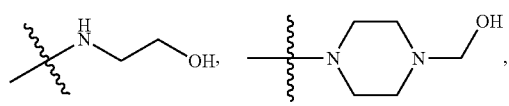

—OH or halogen.

30. The compound according to claim 29, wherein: $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

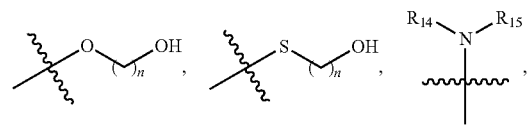

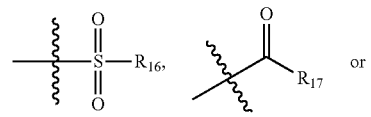

n=1 or 2; $R_1$ is halogen,

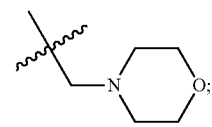

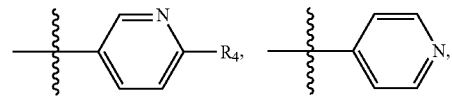

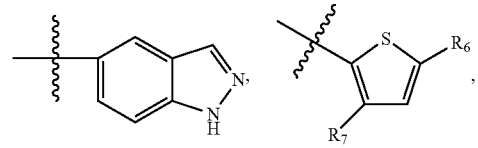

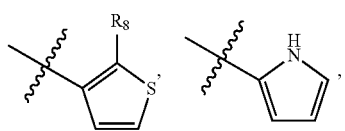

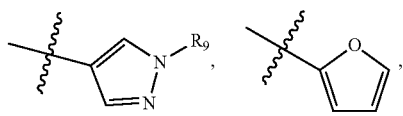

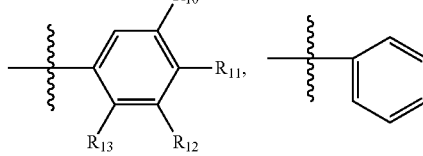

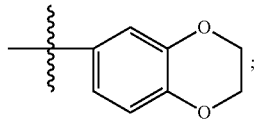

$R_2$ and $R_3$ are independently $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

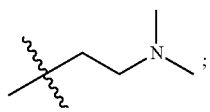 [SMILES: *CCN(C)C]

$R_{14}$ and $R_{15}$ are independently —H, $C_1$-$C_4$ alkyl, $C_1$-$C_6$ alkenyl,

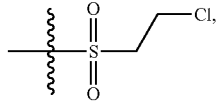 [SMILES: *S(=O)(=O)CCCl]

t-butyloxycarboryl,

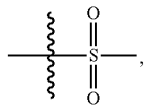

$C_1$-$C_4$ alkoxy or halogen; $R_{16}$ is $C_1$-$C_4$ alkyl, $C_1$-$C_4$ alkoxy, halogen,

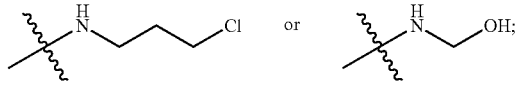

$R_{17}$ is —$NH_2$,

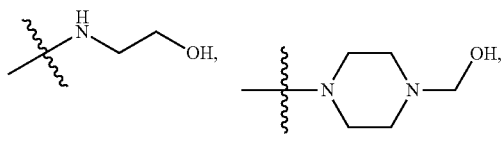 [SMILES: *NCCO ; *N1CCN(CO)CC1]

—OH or halogen.

31. The compound according to claim 19, wherein: $R_{14}$ and $R_{15}$ are independently —H, $C_1$-$C_4$ alkyl, $C_1$-$C_6$ alkenyl,

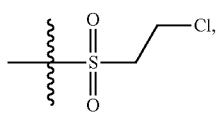 [SMILES: *S(=O)(=O)CCCl]

t-butyloxycarboryl,

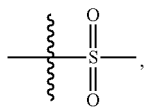 [SMILES: *S(C)(=O)=O]

$C_1$-$C_4$ alkoxy or halogen; $R_1$ is halogen,

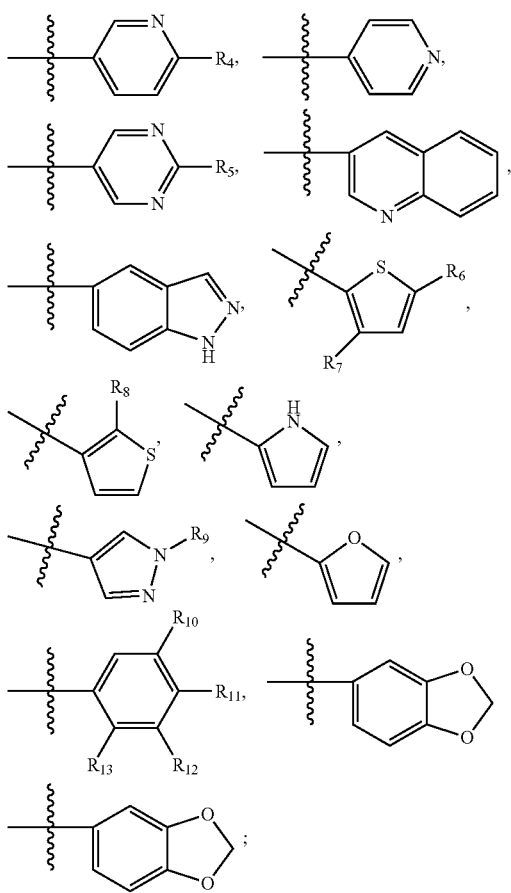

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

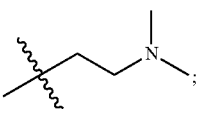 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

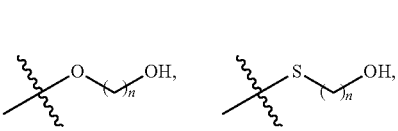

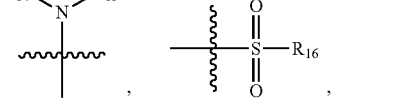

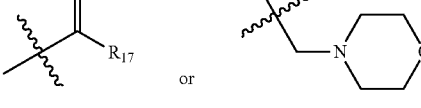

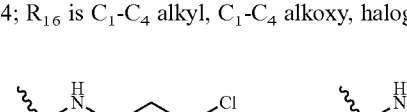
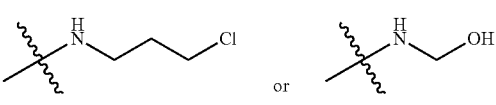

n=1-4; $R_{16}$ is $C_1$-$C_4$ alkyl, $C_1$-$C_4$ alkoxy, halogen,

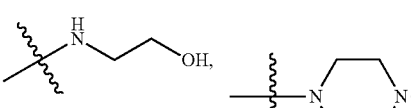

$R_{17}$ is —$NH_2$,

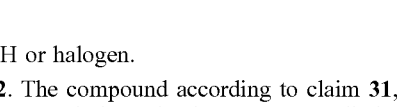

—OH or halogen.

32. The compound according to claim 31, wherein: $R_{14}$ and $R_{15}$ are independently —H, $C_1$-$C_4$ alkyl, $C_1$-$C_6$ alkenyl,

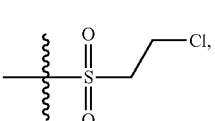

t-butyloxycarboryl or

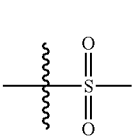

$R_1$ is halogen,

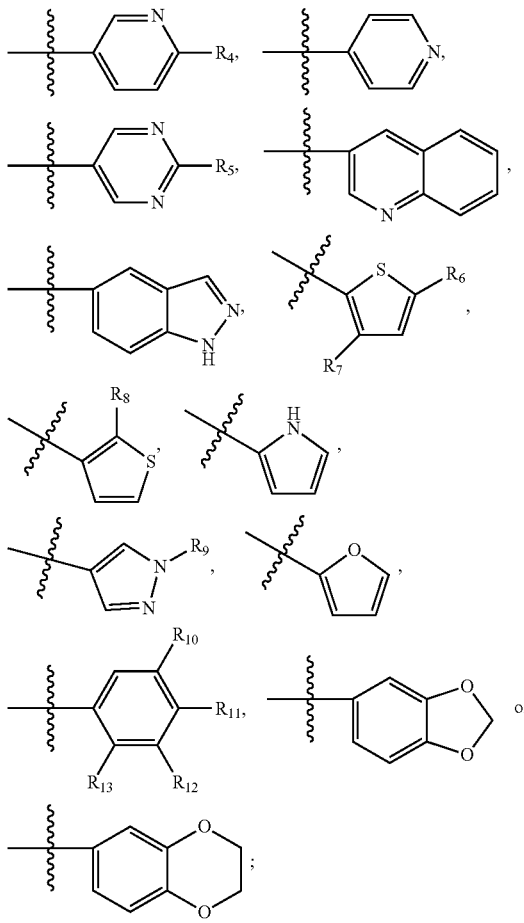

$R_2$ and $R_3$ are independently —H, $C_1$-$C_4$ alkyl or $C_3$-$C_8$ cycloalkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

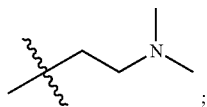 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

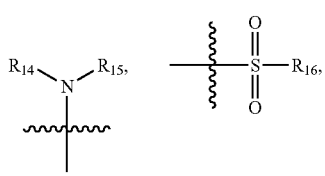

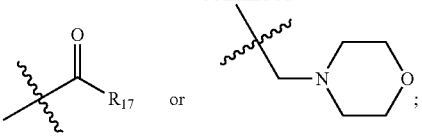

n=1-4; $R_{16}$ is $C_1$-$C_4$ alkyl, $C_1$-$C_4$ alkoxy, halogen,

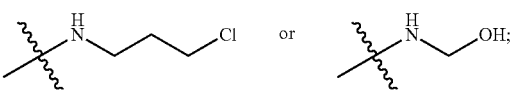

$R_{17}$ is —$NH_2$,

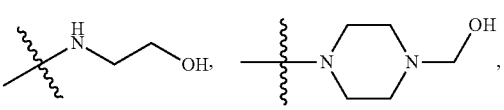 [SMILES: *NCCO ; *N1CCN(CO)CC1]

—OH or halogen.

33. The compound according to claim 19, wherein: $R_{16}$ is $C_1$-$C_4$ alkyl,

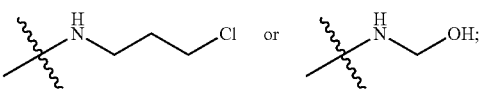

$R_1$ is halogen,

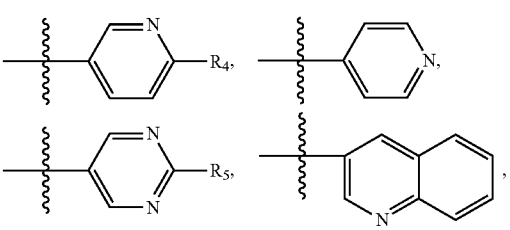

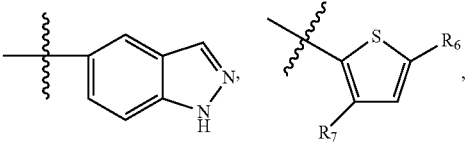

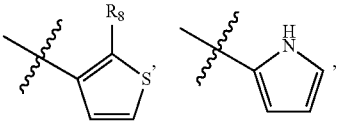

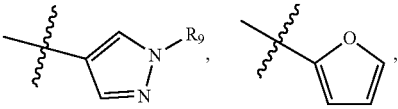

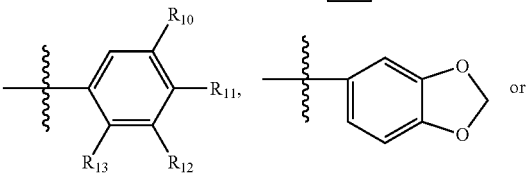

-continued

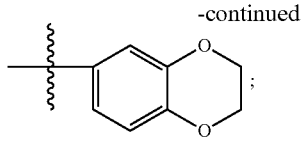

R$_2$ and R$_3$ are independently —H, C$_1$-C$_4$ alkyl or C$_3$-C$_8$ cycloalkyl; R$_4$-R$_9$ are independently —H, C$_1$-C$_4$ alkyl, C$_1$-C$_4$ alkoxy, —NH$_2$, —COOH, C$_1$-C$_4$ alkyl amino or

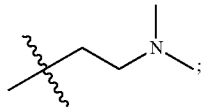 [SMILES: *CCN(C)C]

R$_{10}$-R$_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

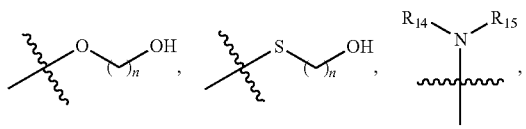

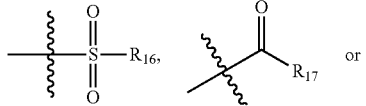

n=1-4; R$_{14}$ and R$_{15}$ are independently —H, C$_1$-C$_4$ alkyl, C$_1$-C$_6$ alkenyl,

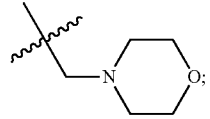

t-butyloxycarboryl or

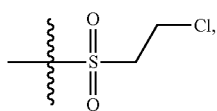

R$_{17}$ is —NH$_2$,

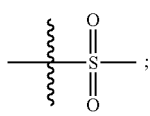 [SMILES: *S(C)(=O)=O]

—OH or halogen.

34. The compound according to claim 19, wherein: R$_1$ is halogen,

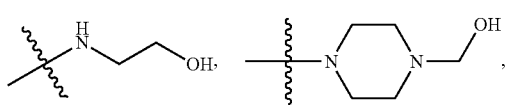

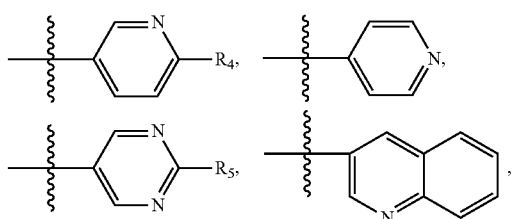

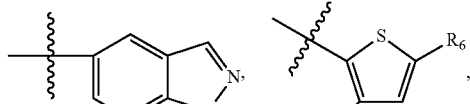

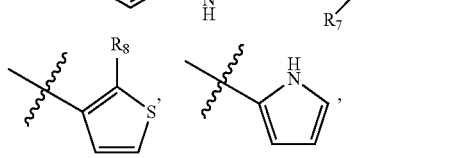

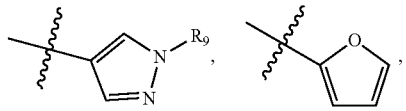

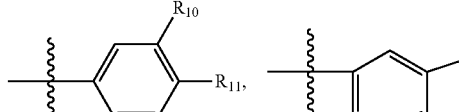

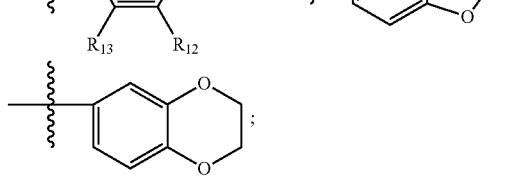

R$_2$ and R$_3$ are independently —H, C$_1$-C$_4$ alkyl or C$_3$-C$_8$ cycloalkyl; R$_4$-R$_9$ are independently —H, C$_1$-C$_4$ alkyl, C$_1$-C$_4$ alkoxy, —NH$_2$, —COOH, C$_1$-C$_4$ alkyl amino or

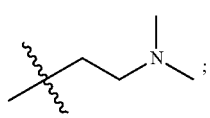

R$_{10}$-R$_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

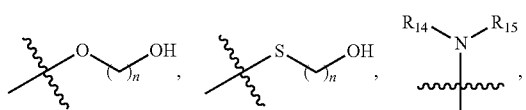

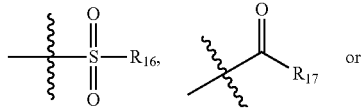

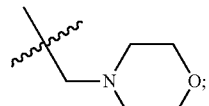

n=1-4;

$R_{14}$ and $R_{15}$ are independently —H, $C_1$-$C_4$ alkyl, $C_1$-$C_6$ alkenyl,

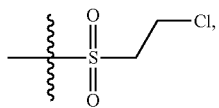 [SMILES: *S(=O)(=O)CCCl]

t-butyloxycarboryl or

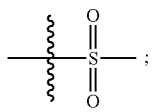

$R_{16}$ is $C_1$-$C_4$ alkyl,

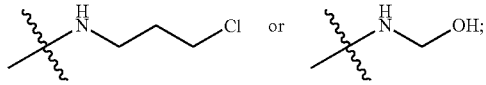

$R_{17}$ is —NH$_2$,

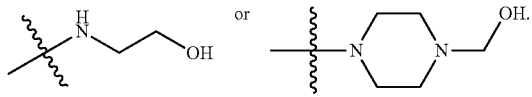 [SMILES: *NCCO ; "or" ; *N1CCN(CO)CC1]

35. The compound according to claim 34, wherein: preferably, $R_1$ is —Cl,

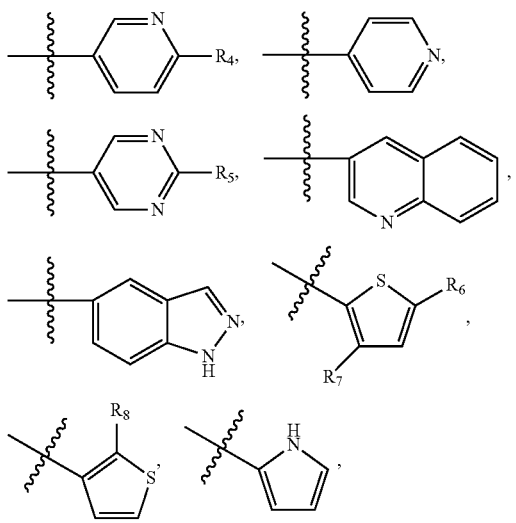

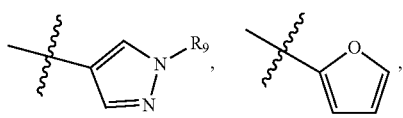

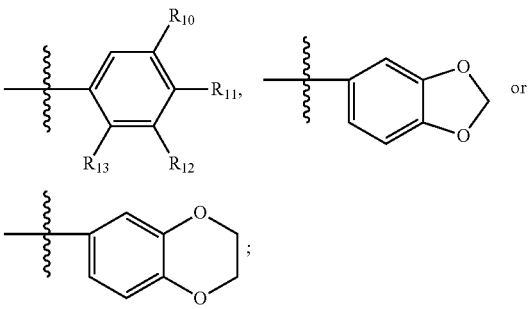

$R_2$ and $R_3$ are independently —H, $C_1$-$C_4$ alkyl or cyclopentyl alkyl; $R_4$-$R_9$ are independently —H, $C_1$-$C_4$ alkyl, methoxy, —NH$_2$, —COOH, methylamino or

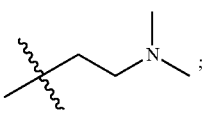

$R_{10}$-$R_{13}$ are independently —H, $C_1$-$C_4$ alkyl, methoxy, —OH, —CF$_3$, —Cl, —NH$_2$, an alkyl substituted by $C_1$-$C_4$ hydroxy,

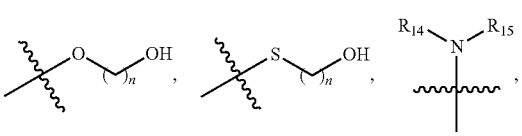

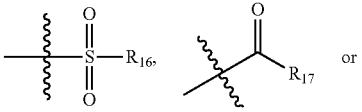

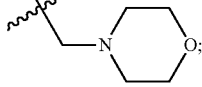

n=1 or 2; $R_{14}$ and $R_{15}$ are independently —H, $C_1$-$C_4$ alkyl, $C_1$-$C_6$ alkenyl,

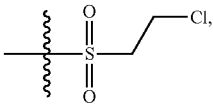 [SMILES: *S(=O)(=O)CCCl]

t-butyloxycarboryl or

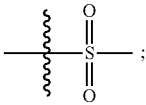 [SMILES: *S(C)(=O)=O]

$R_{16}$ is $C_1$-$C_4$ alkyl,

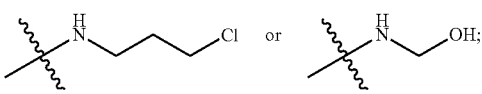 or 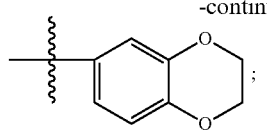

$R_{17}$ is —$NH_2$,

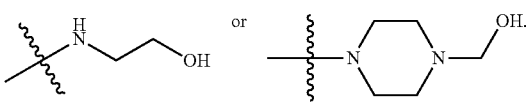

36. The compound according to claim 19, wherein: when $R_2$ is methyl, the structure of which is as shown in Formula III:

Formula III

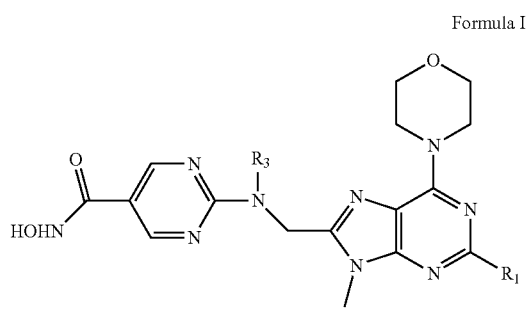

wherein, $R_1$ is $C_1$-$C_4$ alkyl, $C_1$-$C_4$ alkoxy, —OH, halogen, $C_3$-$C_8$ cycloalkyl, —$NH_2$,

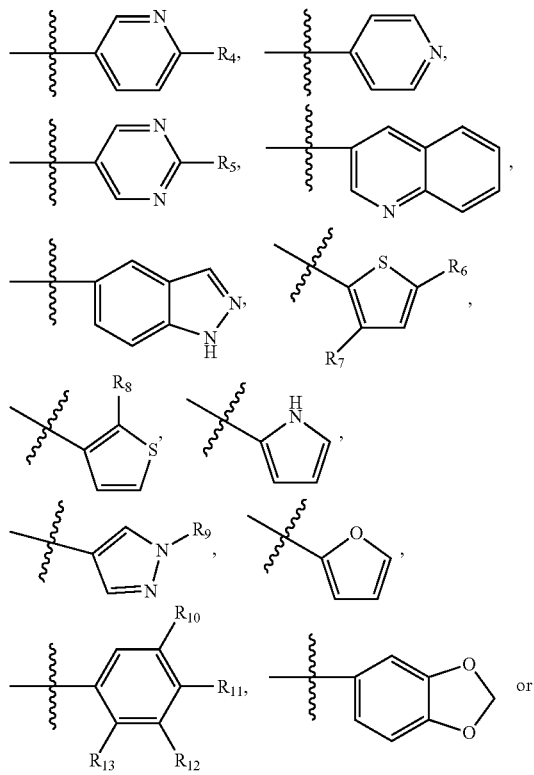

$R_3$ is —H, $C_1$-$C_4$ alkyl, $C_1$-$C_4$ alkoxy, —OH, halogen or $C_3$-$C_8$ cycloalkyl;

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

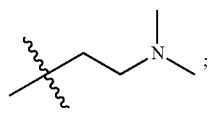 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

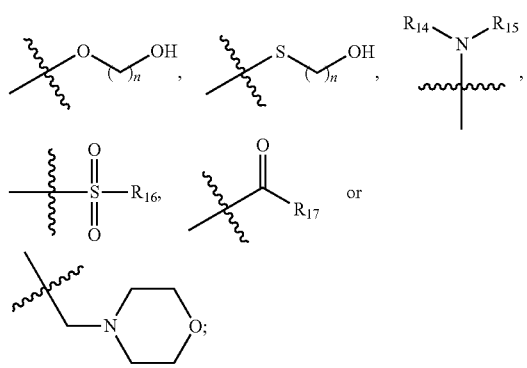

$n=1$-$4$;

$R_{14}$ and $R_{15}$ are independently —H, $C_1$-$C_4$ alkyl, $C_1$-$C_6$ alkenyl,

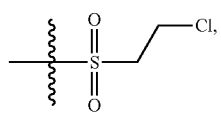

t-butyloxycarboryl,

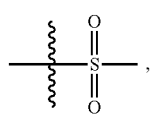 [SMILES: *S(C)(=O)=O]

$C_1$-$C_4$ alkoxy or halogen;

$R_{16}$ is $C_1$-$C_4$ alkyl, $C_1$-$C_4$ alkoxy, halogen,

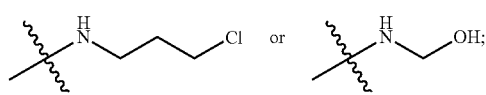

$R_{17}$ is —$NH_2$,

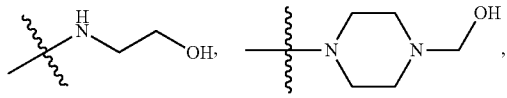

—OH or halogen.

37. The compound according to claim 36, wherein: $R_1$ is halogen, $C_3$-$C_8$ cycloalkyl, —$NH_2$,

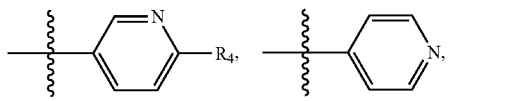

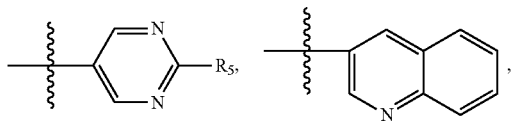

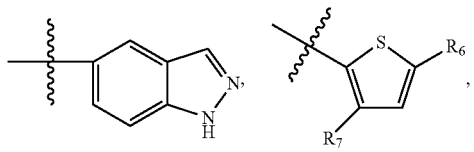

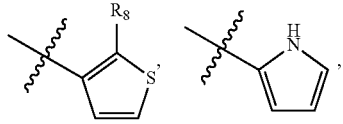

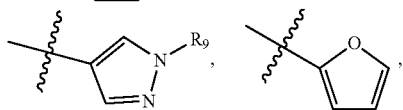

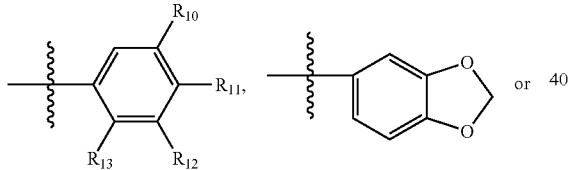

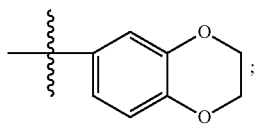

$R_3$ is —H, $C_1$-$C_4$ alkyl, $C_1$-$C_4$ alkoxy, —OH, halogen or $C_3$-$C_8$ cycloalkyl; $R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

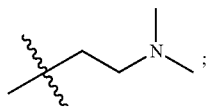 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

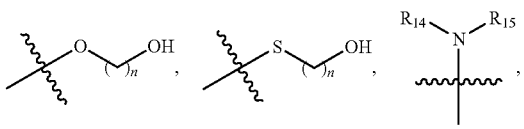

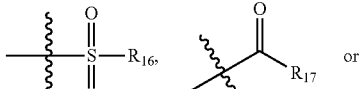

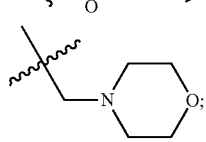

n=1-4; $R_{14}$ and $R_{15}$ are independently —H, $C_1$-$C_4$ alkyl, $C_1$-$C_6$ alkenyl,

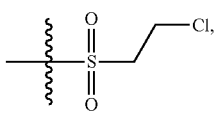

t-butyloxycarboryl,

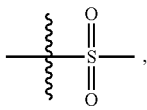

$C_1$-$C_4$ alkoxy or halogen; $R_{16}$ is $C_1$-$C_4$ alkyl, $C_1$-$C_4$ alkoxy, halogen,

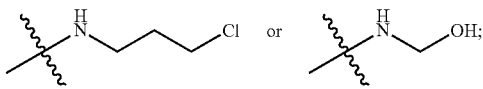

$R_{17}$ is —$NH_2$,

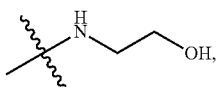 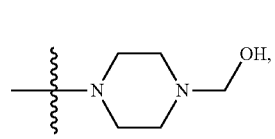

—OH or halogen.

38. The compound according to claim 37, wherein: $R_1$ is halogen,

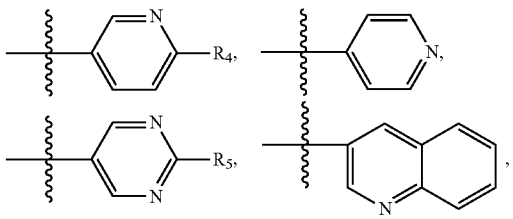

-continued

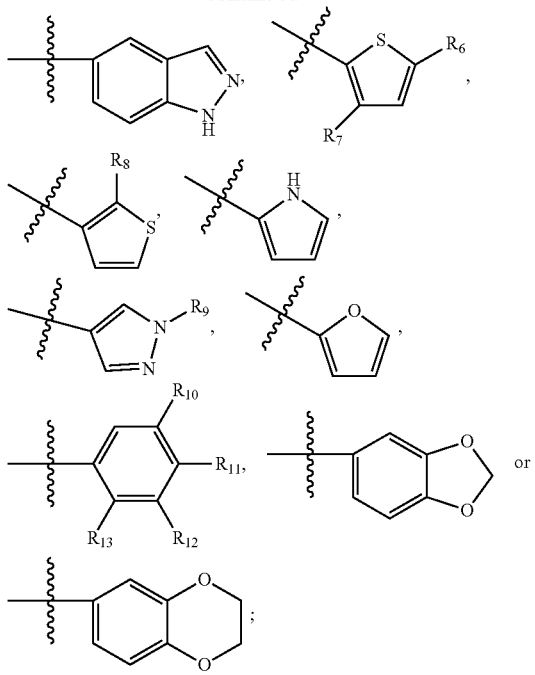

R$_3$ is —H, C$_1$-C$_4$ alkyl, C$_1$-C$_4$ alkoxy, —OH, halogen or C$_3$-C$_8$ cycloalkyl; R$_4$-R$_9$ are independently —H, C$_1$-C$_4$ alkyl, C$_1$-C$_4$ alkoxy, —OH, halogen, C$_3$-C$_8$ cycloalkyl, —NH$_2$, —COOH, C$_1$-C$_4$ alkyl amino or

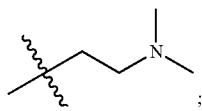 [SMILES: *CCN(C)C]

;

R$_{10}$-R$_{13}$ are independently —H, C$_1$-C$_4$ alkyl, C$_1$-C$_4$ alkoxy, —OH, —CF$_3$, halogen, C$_3$-C$_8$ cycloalkyl, —NH$_2$, an alkyl substituted by C$_1$-C$_4$ hydroxy,

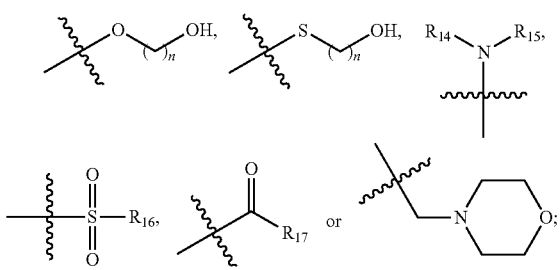

n=1-4; R$_{14}$ and R$_{15}$ are independently —H, C$_1$-C$_4$ alkyl, C$_1$-C$_6$ alkenyl,

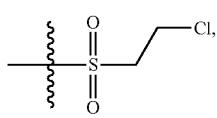 [SMILES: *S(=O)(=O)CCCl]

t-butyloxycarboryl,

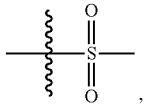 [SMILES: *S(C)(=O)=O]

C$_1$-C$_4$ alkoxy or halogen; R$_{16}$ is C$_1$-C$_4$ alkyl, C$_1$-C$_4$ alkoxy, halogen,

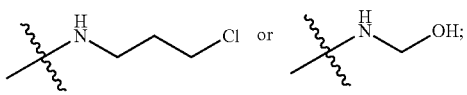

R$_{17}$ is —NH$_2$,

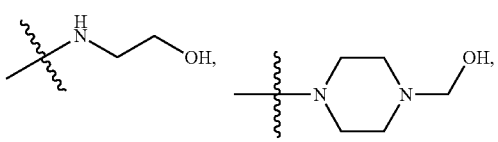 [SMILES: *NCCO ; *N1CCN(CO)CC1]

—OH or halogen.

39. The compound according to claim 38, wherein: R$_1$ is —Cl,

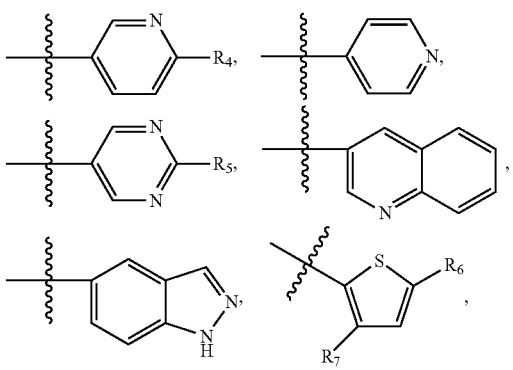

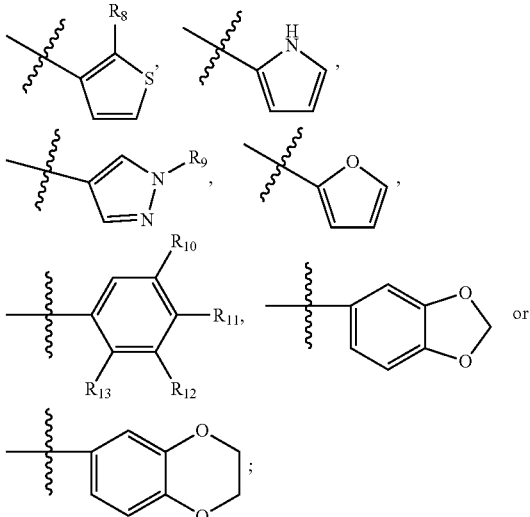

R$_3$ is —H, C$_1$-C$_4$ alkyl, C$_1$-C$_4$ alkoxy, —OH, halogen or C$_3$-C$_8$ cycloalkyl; R$_4$-R$_9$ are independently —H, C$_1$-C$_4$ alkyl, $C_1$-$C_4$ alkoxy, —OH, halogen, $C_3$-$C_8$ cycloalkyl, —NH$_2$, —COOH, $C_1$-$C_4$ alkyl amino or

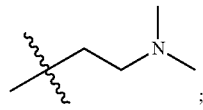 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

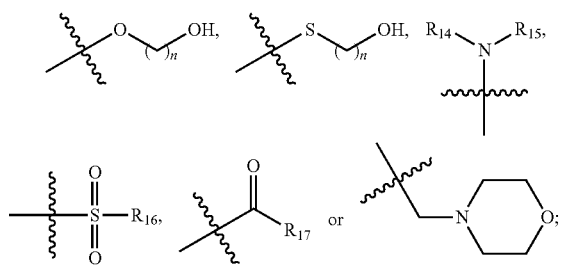

n=1-4; $R_{14}$ and $R_{15}$ are independently —H, $C_1$-$C_4$ alkyl, $C_1$-$C_6$ alkenyl,

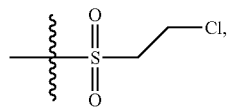 [SMILES: *S(=O)(=O)CCCl]

t-butyloxycarboryl,

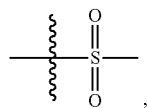 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

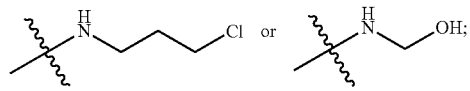

$R_{17}$ is —NH$_2$,

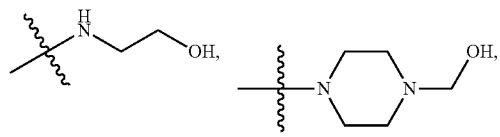 [SMILES: *NCCO ; *N1CCN(CO)CC1]

—OH or halogen.

40. The compound according to claim 36, wherein: $R_3$ is —H, $C_1$-$C_4$ alkyl, $C_1$-$C_4$ alkoxy or $C_3$-$C_8$ cycloalkyl; $R_1$ is halogen,

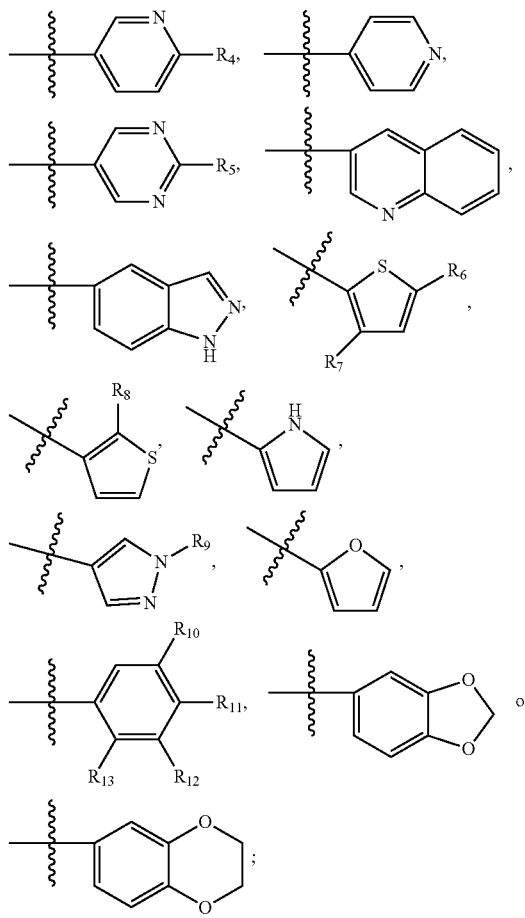

$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

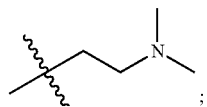 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

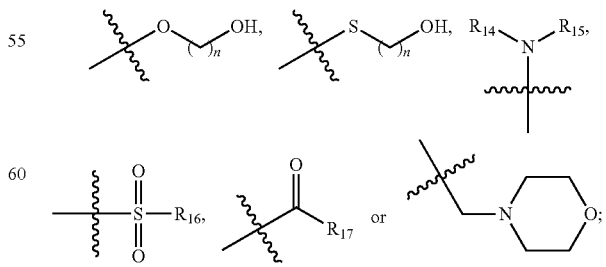

n=1-4; $R_{14}$ and $R_{15}$ are independently —H, $C_1$-$C_4$ alkyl, $C_1$-$C_6$ alkenyl,

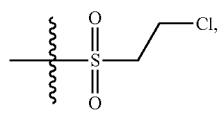 [SMILES: *S(=O)(=O)CCCl]

t-butyloxycarboryl,

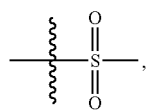 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

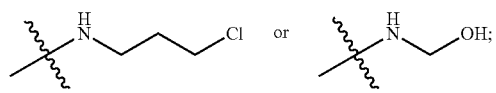

$R_{17}$ is —$NH_2$,

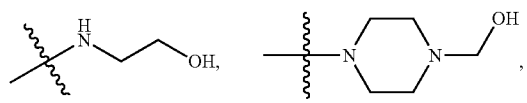

—OH or halogen.

41. The compound according to claim 40, wherein: $R_3$ is —H, $C_1$-$C_4$ alkyl or $C_3$-$C_8$ cycloalkyl; $R_1$ is halogen,

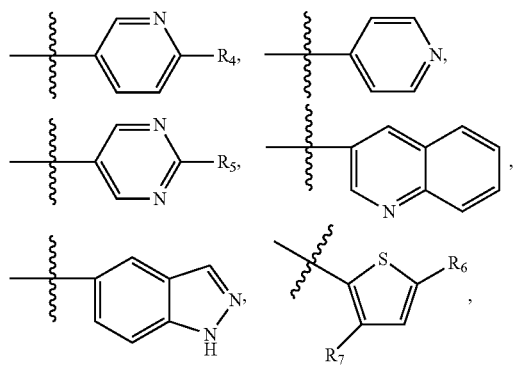

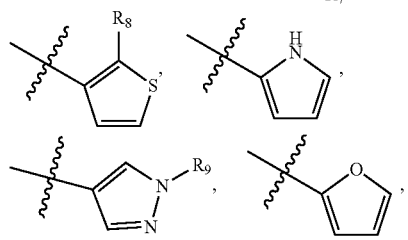

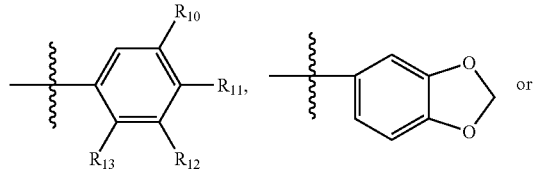

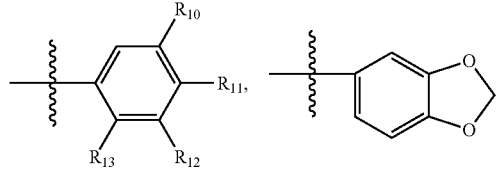

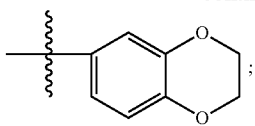

$R_4$-$R_9$ are independently —H, $C_1$-$C_4$ alkyl, $C_1$-$C_4$ alkoxy, —OH, halogen, $C_3$-$C_8$ cycloalkyl, —$NH_2$, —COOH, $C_1$-$C_4$ alkyl amino or

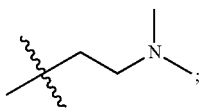

$R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

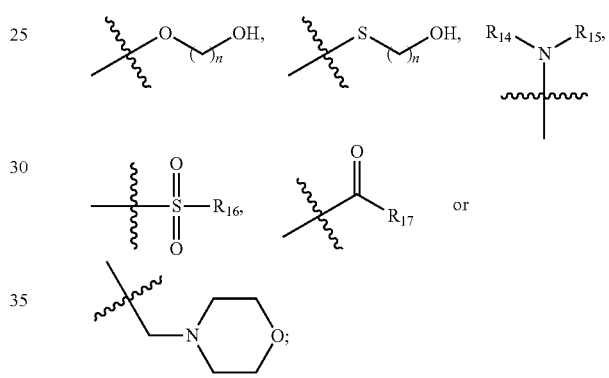

n=1-4; $R_{14}$ and $R_{15}$ are independently —H, $C_1$-$C_4$ alkyl, $C_1$-$C_6$ alkenyl,

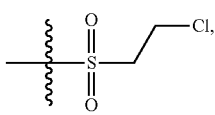

t-butyloxycarboryl,

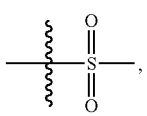

$C_1$-$C_4$ alkoxy or halogen; $R_{16}$ is $C_1$-$C_4$ alkyl, $C_1$-$C_4$ alkoxy, halogen, $R_{17}$ is —NH$_2$,

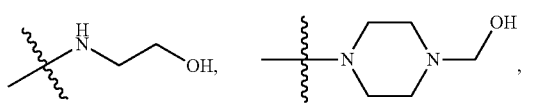 [SMILES: *NCCO ; *N1CCN(CO)CC1 ; ","]

—OH or halogen.

42. The compound according to claim 41, wherein: $R_3$ is —H or $C_1$-$C_4$ alkyl; $R_1$ is halogen,

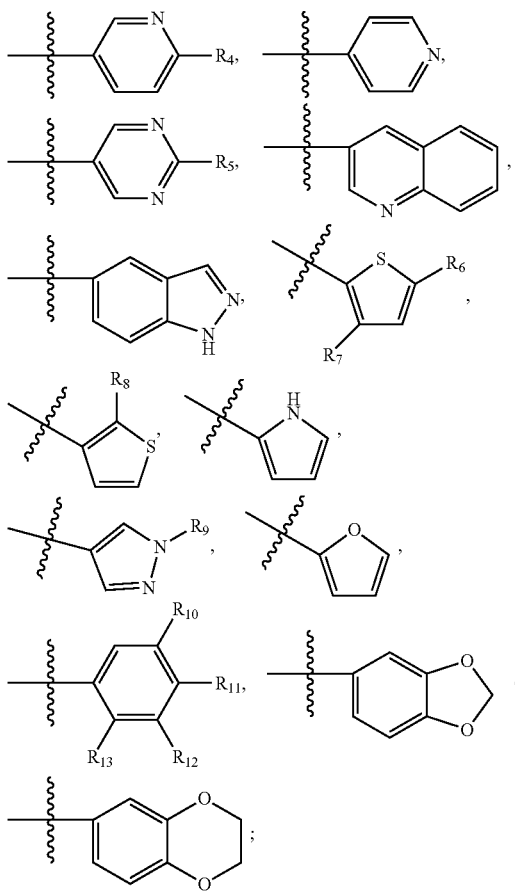

$R_4$-$R_9$ are independently —H, $C_1$-$C_4$ alkyl, $C_1$-$C_4$ alkoxy, —OH, halogen, $C_3$-$C_8$ cycloalkyl, —NH$_2$, —COOH, $C_1$-$C_4$ alkyl amino or

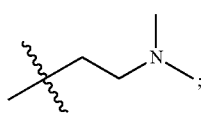 [SMILES: *CCN(C)C]

$R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

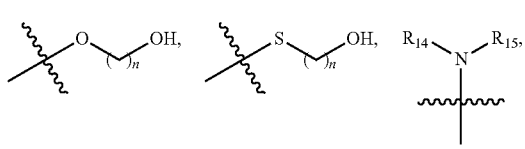

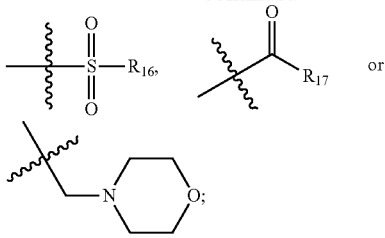

n=1-4; $R_{14}$ and $R_{15}$ are independently —H, $C_1$-$C_4$ alkyl, $C_1$-$C_6$ alkenyl,

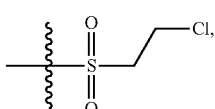

t-butyloxycarboryl,

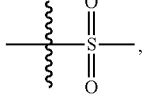

$C_1$-$C_4$ alkoxy or halogen; $R_{16}$ is $C_1$-$C_4$ alkyl, $C_1$-$C_4$ alkoxy, halogen,

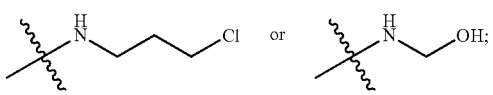

$R_{17}$ is —NH$_2$,

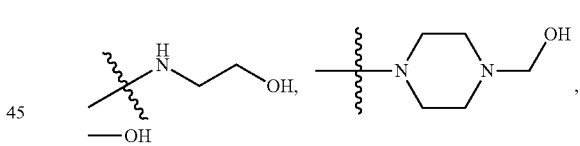

—OH or halogen.

43. The compound according to claim 36, wherein: $R_4$-$R_9$ are independently —H, $C_1$-$C_4$ alkyl, $C_1$-$C_4$ alkoxy, $C_3$-$C_8$ cycloalkyl, —NH$_2$, —COOH, $C_1$-$C_4$ alkyl amino or

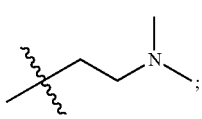 [SMILES: *CCN(C)C]

$R_1$ is halogen,

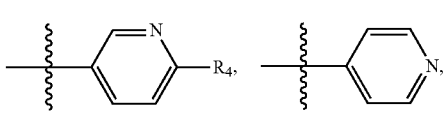

-continued

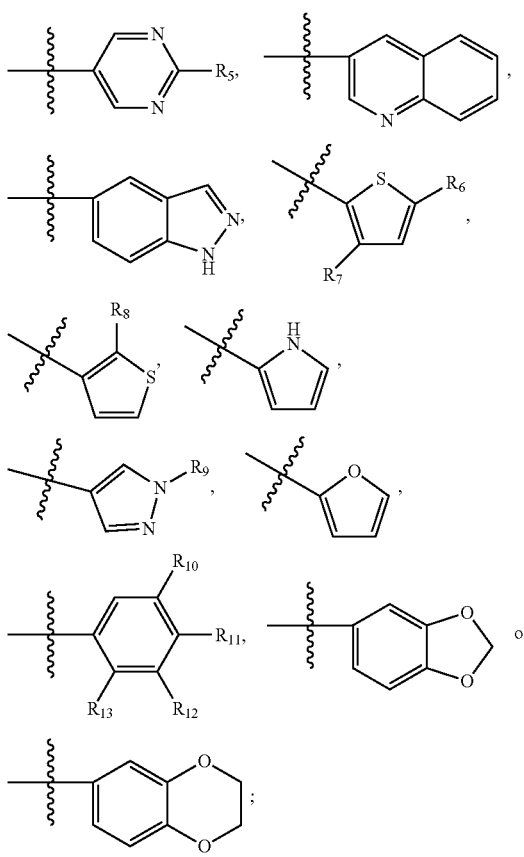

$R_3$ is —H or $C_1$-$C_4$ alkyl; $R_{10}$-$R_{13}$ are independently —H, $C_1$-$C_4$ alkyl, $C_1$-$C_4$ alkoxy, —OH, —$CF_3$, halogen, $C_3$-$C_8$ cycloalkyl, —$NH_2$, an alkyl substituted by $C_1$-$C_4$ hydroxy,

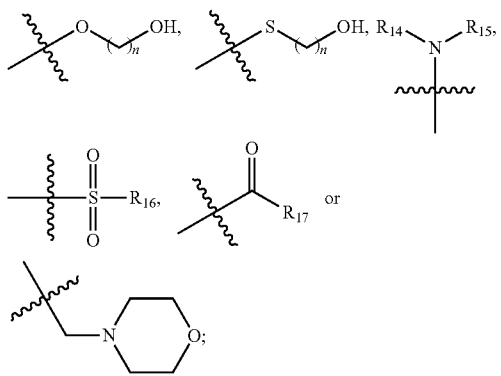

n=1-4; $R_{14}$ and $R_{15}$ are independently —H, $C_1$-$C_4$ alkyl, $C_1$-$C_6$ alkenyl,

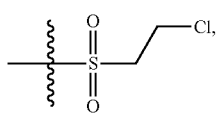 [SMILES: *S(=O)(=O)CCCl]

t-butyloxycarboryl,

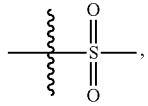

$C_1$-$C_4$ alkoxy or halogen; $R_{16}$ is $C_1$-$C_4$ alkyl, $C_1$-$C_4$ alkoxy, halogen,

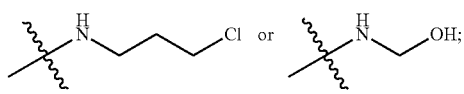

$R_{17}$ is —$NH_2$,

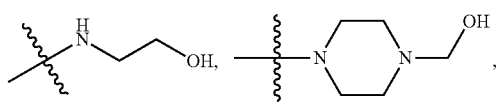

—OH or halogen.

44. The compound according to claim 43, wherein: $R_4$-$R_9$ are independently —H, $C_1$-$C_4$ alkyl, $C_1$-$C_4$ alkoxy, —$NH_2$, —COOH, $C_1$-$C_4$ alkyl amino or

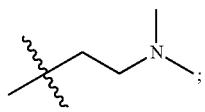 [SMILES: *CCN(C)C]

$R_1$ is halogen,

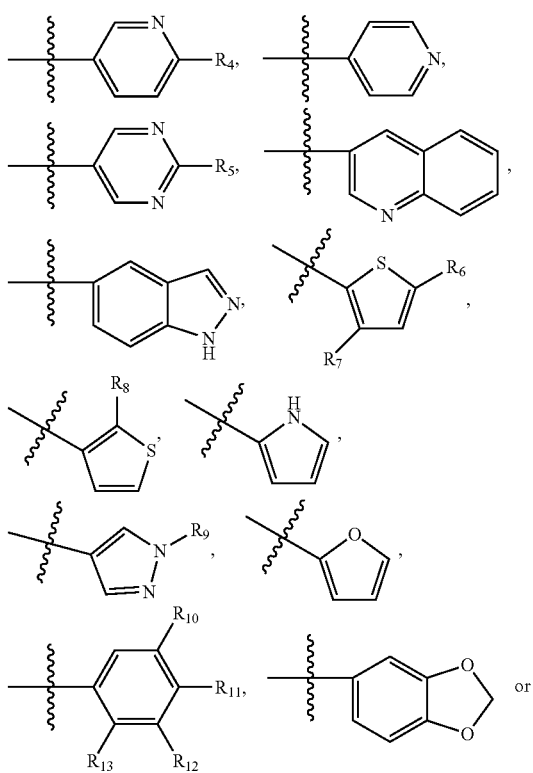

-continued

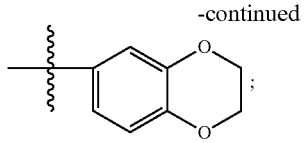

$R_3$ is —H or $C_1$-$C_4$ alkyl; $R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

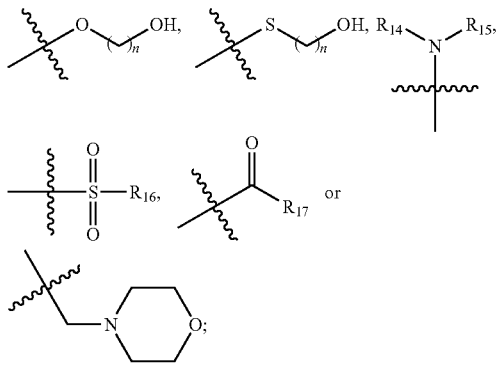

n=1-4; $R_{14}$ and $R_{15}$ are independently —H, $C_1$-$C_4$ alkyl, $C_1$-$C_6$ alkenyl,

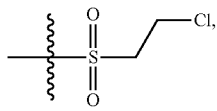 [SMILES: *S(=O)(=O)CCCl]

t-butyloxycarboryl,

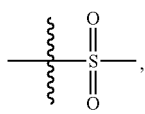 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

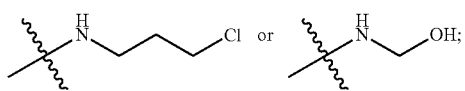

$R_{17}$ is —NH$_2$,

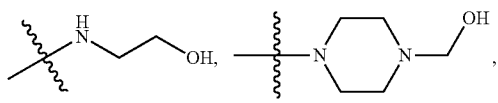

—OH or halogen.

45. The compound according to claim 44, wherein: $R_4$-$R_9$ are independently —H, $C_1$-$C_4$ alkyl, methoxy, —NH$_2$, —COOH, methylamino or

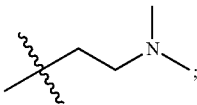 [SMILES: *CCN(C)C]

$R_1$ is halogen,

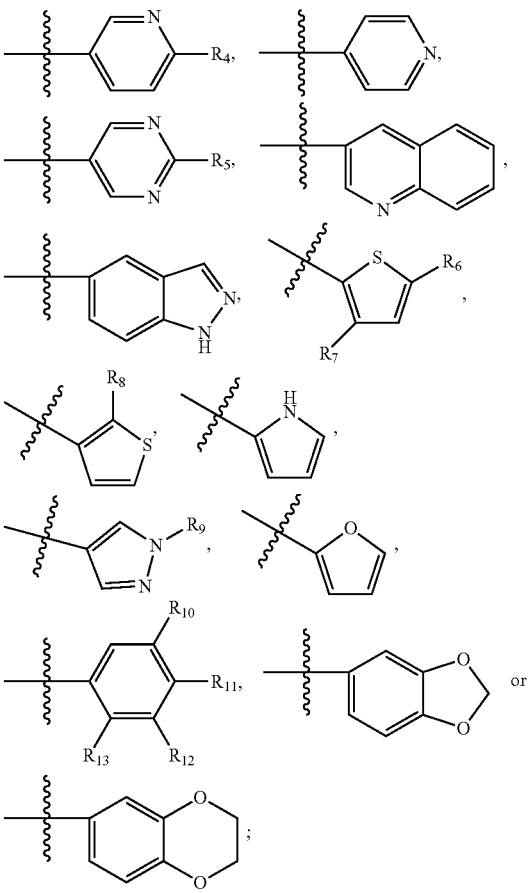

$R_3$ is —H or $C_1$-$C_4$ alkyl; $R_{10}$-$R_{13}$ are independently —H, $C_1$-$C_4$ alkyl, $C_1$-$C_4$ alkoxy, —OH, —CF$_3$, halogen, $C_3$-$C_8$ cycloalkyl, —NH$_2$, an alkyl substituted by $C_1$-$C_4$ hydroxy,

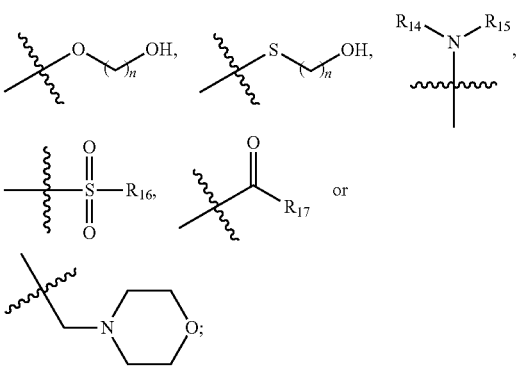

n=1-4; $R_{14}$ and $R_{15}$ are independently —H, $C_1$-$C_4$ alkyl, $C_1$-$C_6$ alkenyl,

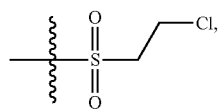 [SMILES: *S(=O)(=O)CCCl]

t-butyloxycarboryl,

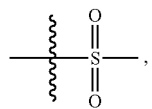

$C_1$-$C_4$ alkoxy or halogen; $R_{16}$ is $C_1$-$C_4$ alkyl, $C_1$-$C_4$ alkoxy, halogen,

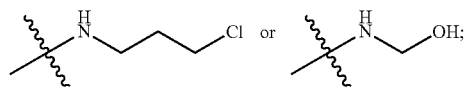

$R_{17}$ is —$NH_2$,

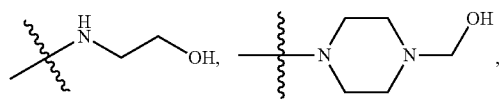 [SMILES: *NCCO ; *N1CCN(CO)CC1 ; ","]

—OH or halogen.

46. The compound according to claim 36, wherein: $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

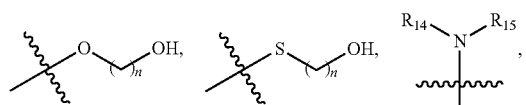

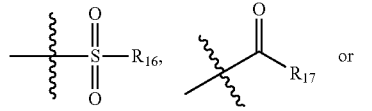

n=1-4; $R_1$ is halogen,

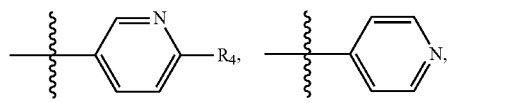

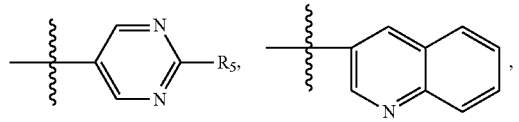

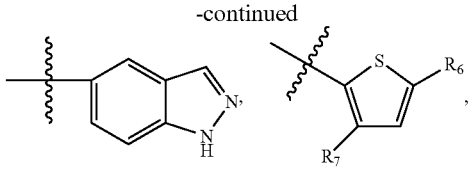

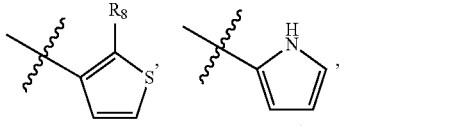

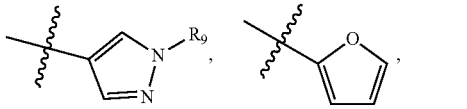

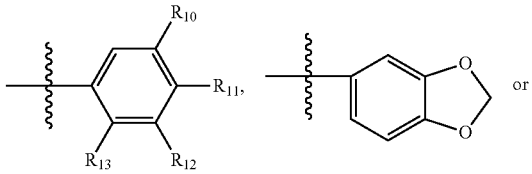

$R_3$ is —H or $C_1$-$C_4$ alkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

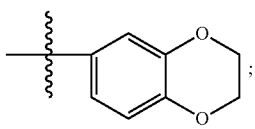

$R_{14}$ and $R_{15}$ are independently —H, $C_1$-$C_4$ alkyl, $C_1$-$C_6$ alkenyl,

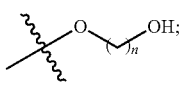

t-butyloxycarboryl,

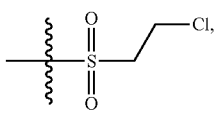 [SMILES: *S(=O)(=O)CCCl]

$C_1$-$C_4$ alkoxy or halogen; $R_{16}$ is $C_1$-$C_4$ alkyl, $C_1$-$C_4$ alkoxy, halogen,

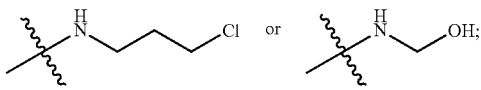

$R_{17}$ is —$NH_2$,

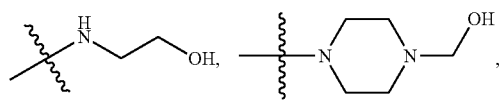 [SMILES: *NCCO ; *N1CCN(CO)CC1 ; ","]

—OH or halogen.

47. The compound according to claim 46, wherein: $R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

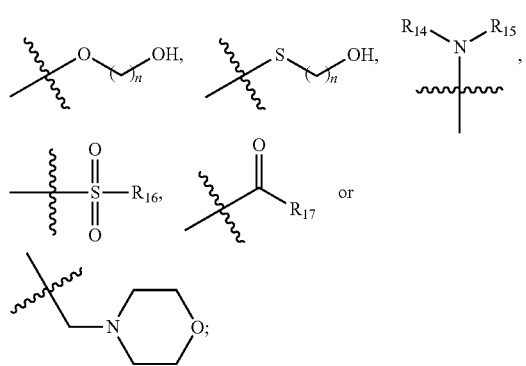

n=1 or 2; $R_1$ is halogen,

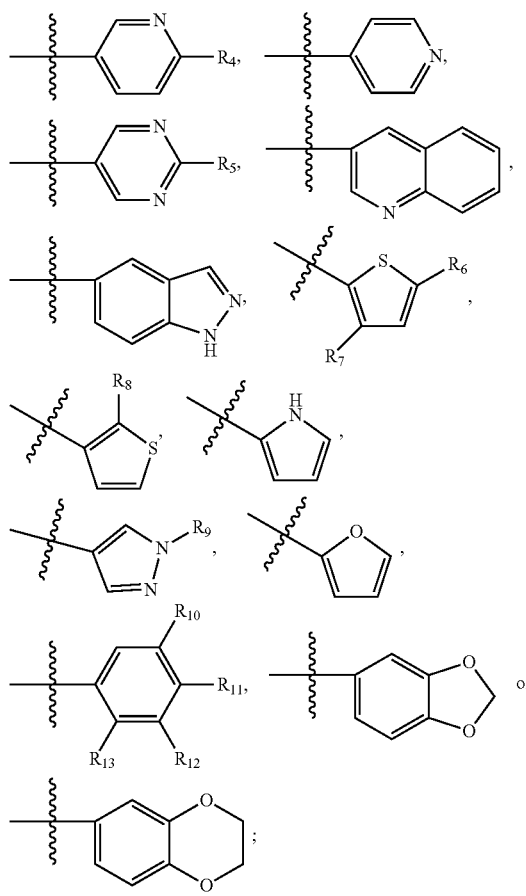

$R_3$ is —H or $C_1$-$C_4$ alkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

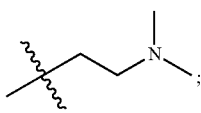 [SMILES: *CCN(C)C]

$R_{14}$ and $R_{15}$ are independently —H, $C_1$-$C_4$ alkyl, $C_1$-$C_6$ alkenyl,

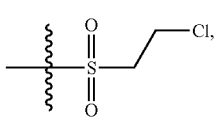 [SMILES: *S(=O)(=O)CCCl]

t-butyloxycarboryl,

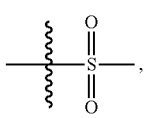 [SMILES: *S(C)(=O)=O]

$C_1$-$C_4$ alkoxy or halogen; $R_{16}$ is $C_1$-$C_4$ alkyl, $C_1$-$C_4$ alkoxy, halogen,

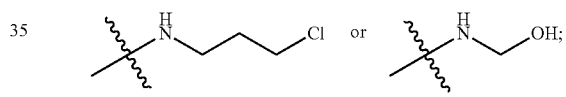

$R_{17}$ is —$NH_2$,

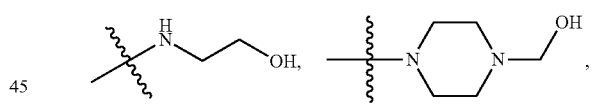

—OH or halogen.

48. The compound according to claim 36, wherein: $R_{14}$ and $R_{15}$ are independently —H, $C_1$-$C_4$ alkyl, $C_1$-$C_6$ alkenyl,

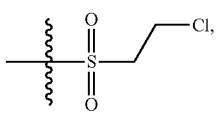 [SMILES: *S(=O)(=O)CCCl]

t-butyloxycarboryl,

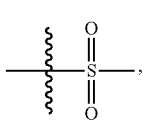 [SMILES: *S(C)(=O)=O]

$C_1$-$C_4$ alkoxy or halogen; $R_1$ is halogen,

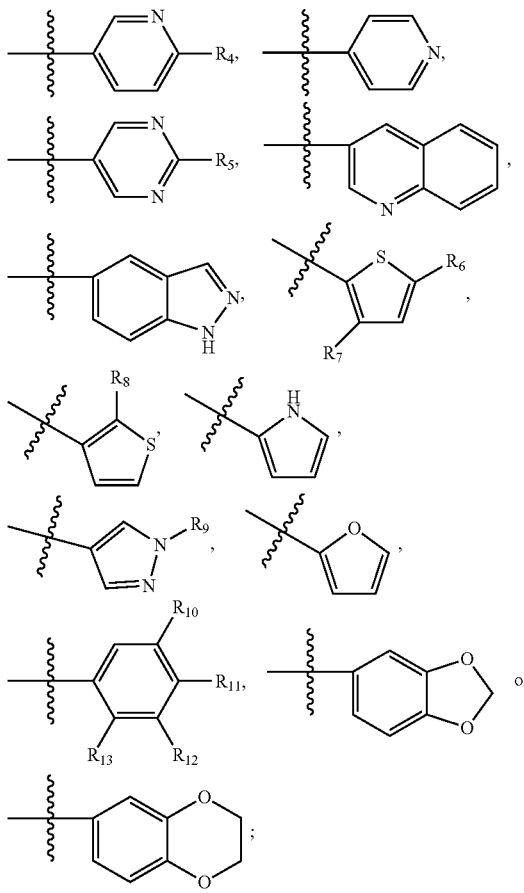

$R_3$ is —H or $C_1$-$C_4$ alkyl; $R_4$-$R_9$ are independently —H, $C_1$-$C_4$ alkyl, $C_1$-$C_4$ alkoxy, —$NH_2$, —COOH, $C_1$-$C_4$ alkyl amino or

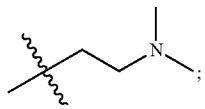 [SMILES: *CCN(C)C]

$R_{10}$-$R_{13}$ are independently —H, $C_1$-$C_4$ alkyl, $C_1$-$C_4$ alkoxy, —OH, —$CF_3$, halogen, —$NH_2$, an alkyl substituted by $C_1$-$C_4$ hydroxy,

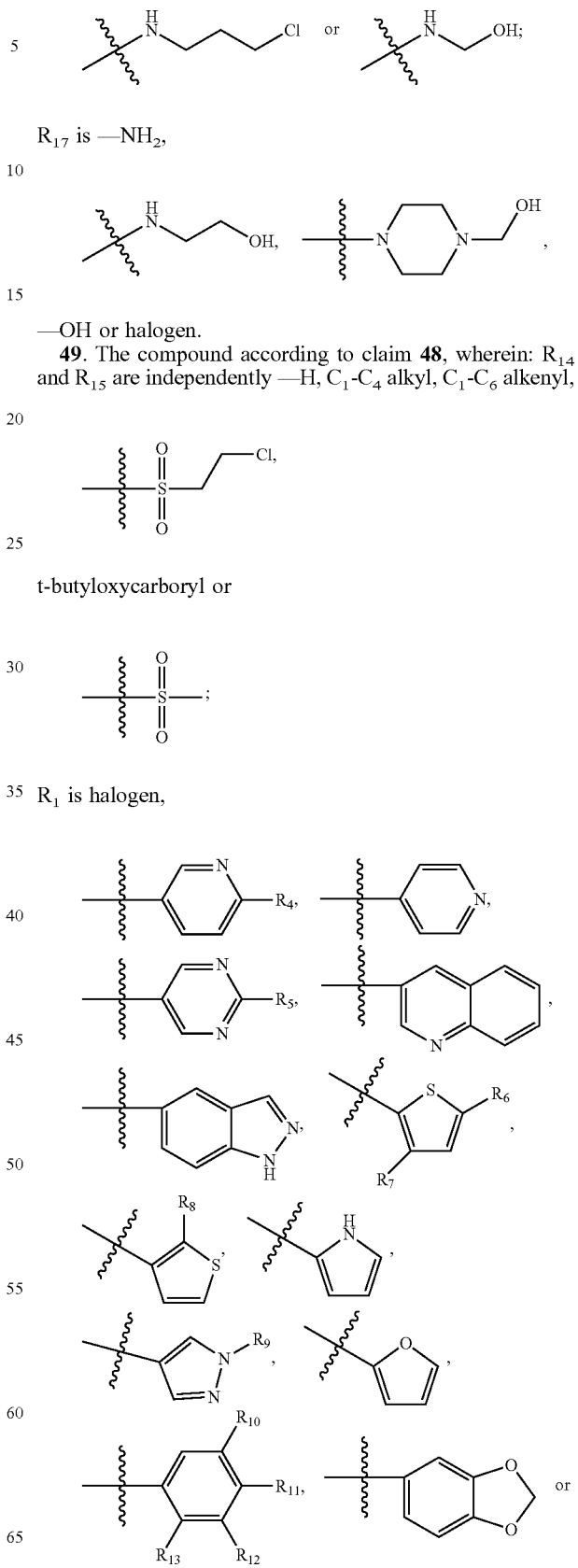

n=1-4; $R_{16}$ is $C_1$-$C_4$ alkyl, $C_1$-$C_4$ alkoxy, halogen,

—OH or halogen.

49. The compound according to claim 48, wherein: $R_{14}$ and $R_{15}$ are independently —H, $C_1$-$C_4$ alkyl, $C_1$-$C_6$ alkenyl, t-butyloxycarboryl or $R_1$ is halogen, -continued

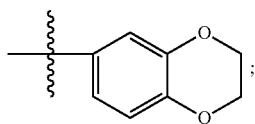

R$_3$ is —H or C$_1$-C$_4$ alkyl; R$_4$-R$_9$ are independently —H, C$_1$-C$_4$ alkyl, C$_1$-C$_4$ alkoxy, —NH$_2$, —COOH, C$_1$-C$_4$ alkyl amino or

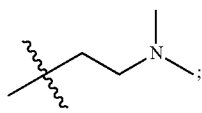

R$_{10}$-R$_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

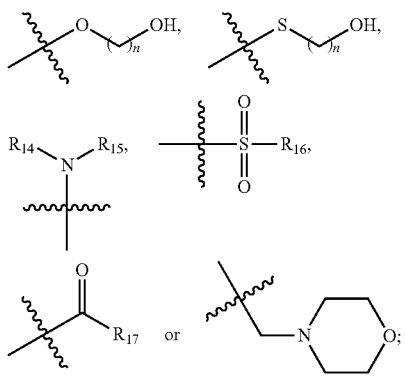

n=1-4; R$_{16}$ is C$_1$-C$_4$ alkyl, C$_1$-C$_4$ alkoxy, halogen,

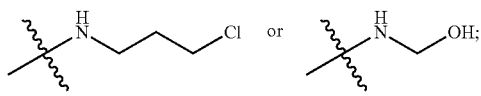

R$_{17}$ is —NH$_2$,

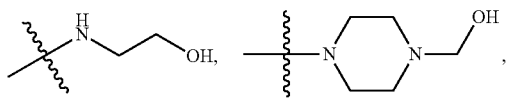 [SMILES: *NCCO ; *N1CCN(CO)CC1]

—OH or halogen.

50. The compound according to claim 36, wherein: R$_{16}$ is C$_1$-C$_4$ alkyl,

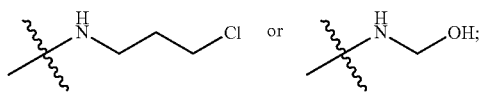

R$_1$ is halogen,

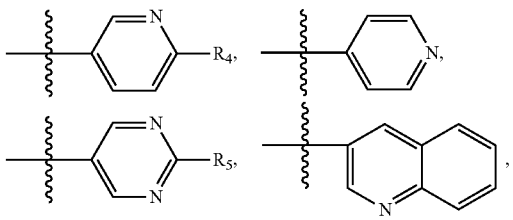

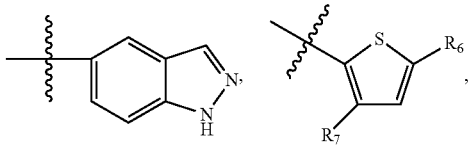

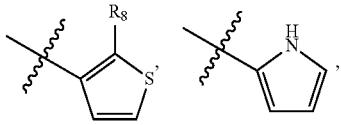

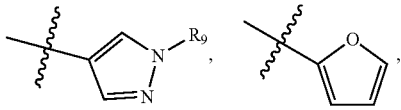

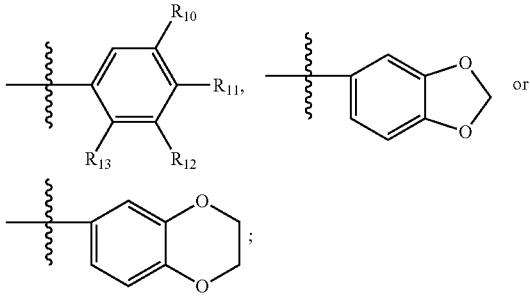

R$_3$ is —H or C$_1$-C$_4$ alkyl; R$_4$-R$_9$ are independently —H, C$_1$-C$_4$ alkyl, C$_1$-C$_4$ alkoxy, —NH$_2$, —COOH, C$_1$-C$_4$ alkyl amino or

R$_{10}$-R$_{13}$ are independently —H, C$_1$-C$_4$ alkyl, C$_1$-C$_4$ alkoxy, —OH, —CF$_3$, halogen, —NH$_2$, an alkyl substituted by C$_1$-C$_4$ hydroxy,

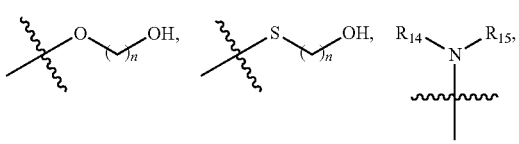

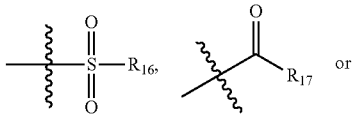

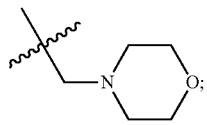

n=1-4; $R_{14}$ and $R_{15}$ are independently —H, $C_1$-$C_4$ alkyl, $C_1$-$C_6$ alkenyl,

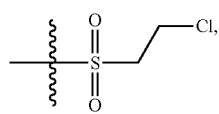 [SMILES: *S(=O)(=O)CCCl]

t-butyloxycarboryl or

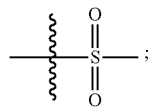 [SMILES: *S(C)(=O)=O]

$R_{17}$ is —NH$_2$,

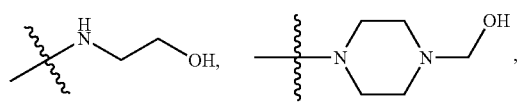

—OH or halogen.

51. The compound according to claim 36, wherein: $R_1$ is halogen,

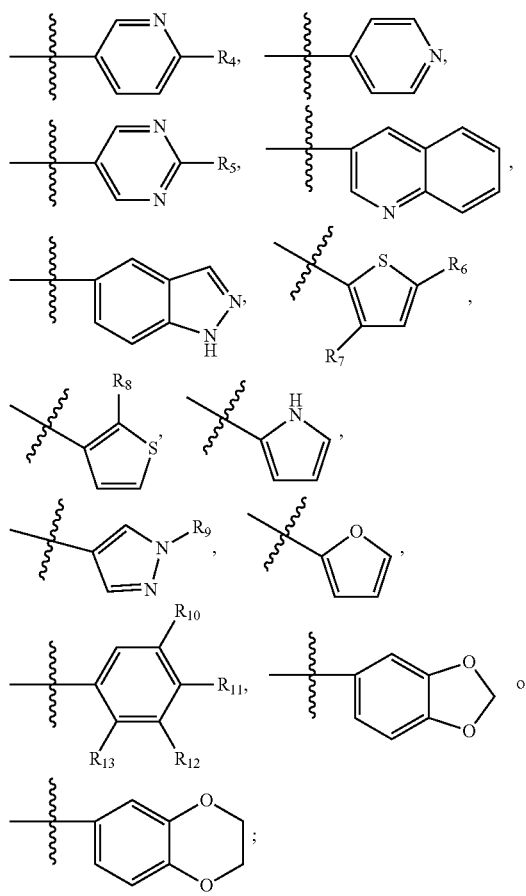

$R_3$ is —H or $C_1$-$C_4$ alkyl; $R_4$-$R_9$ are independently —H, $C_1$-$C_4$ alkyl, $C_1$-$C_4$ alkoxy, —NH$_2$, —COOH, $C_1$-$C_4$ alkyl amino or

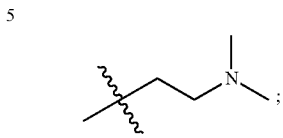

$R_{10}$-$R_{13}$ are independently —H, $C_1$-$C_4$ alkyl, $C_1$-$C_4$ alkoxy, —OH, —CF$_3$, halogen, —NH$_2$, an alkyl substituted by $C_1$-$C_4$ hydroxy,

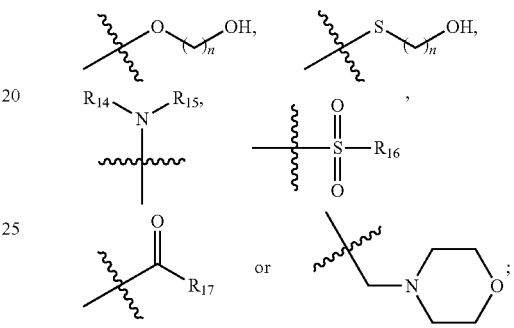

n=1-4; $R_{14}$ and $R_{15}$ are independently —H, $C_1$-$C_4$ alkyl, $C_1$-$C_6$ alkenyl,

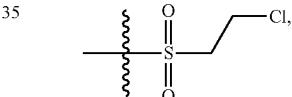

t-butyloxycarboryl or

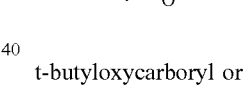

$R_{16}$ is $C_1$-$C_4$ alkyl,

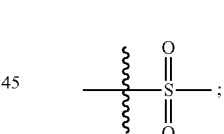

$R_{17}$ is —NH$_2$,

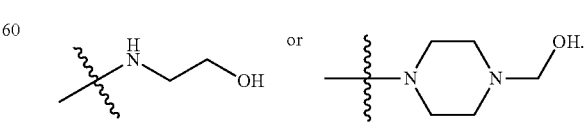

52. The compound according to claim 36, wherein: $R_1$ is —Cl,

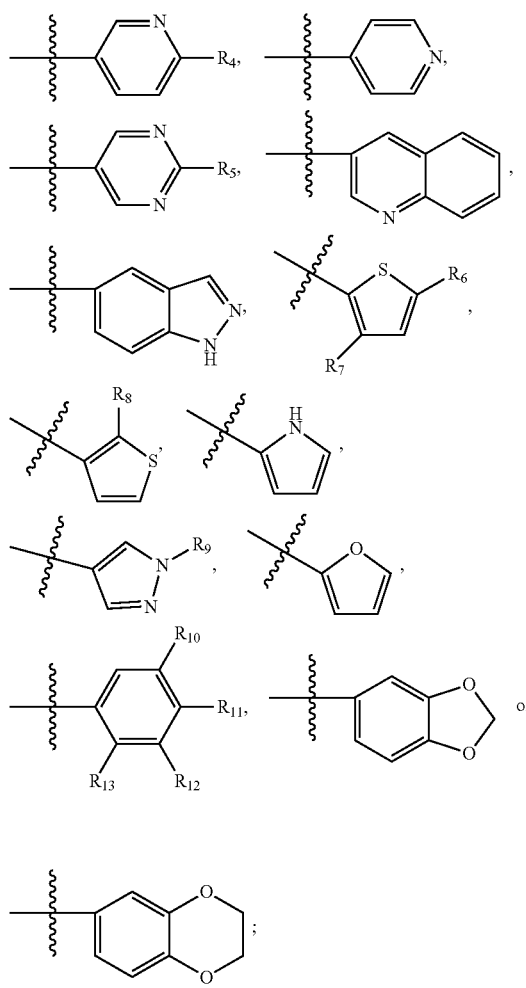
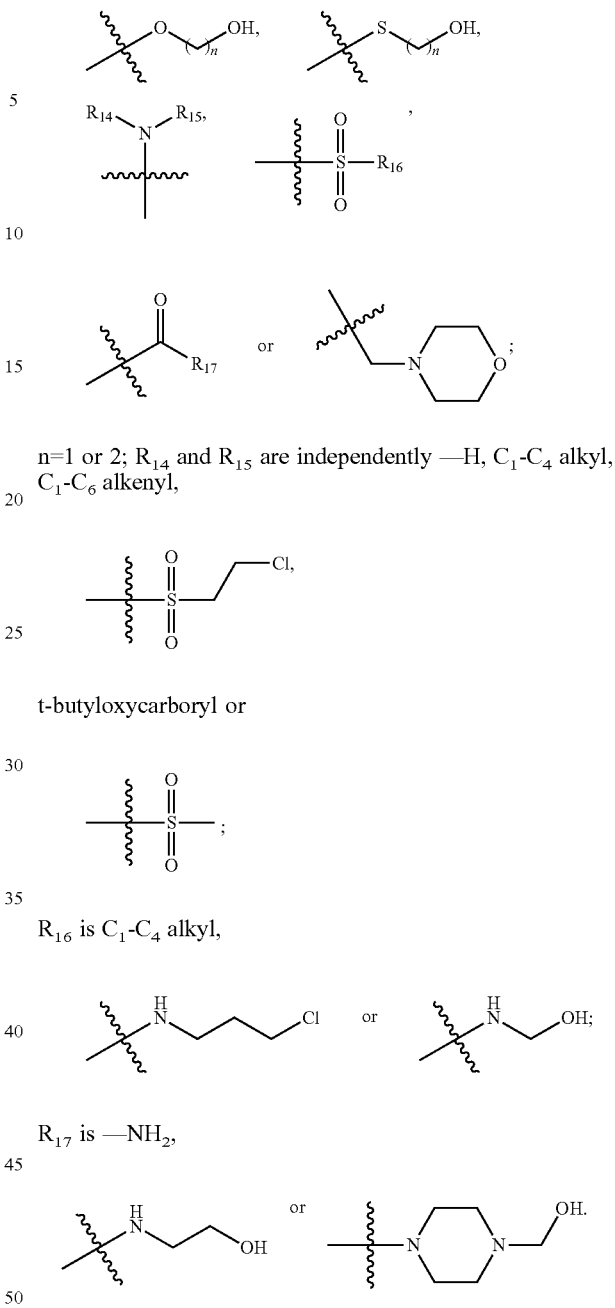
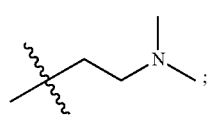 [SMILES: *CCN(C)C]
$R_{10}$-$R_{13}$ are independently —H, $C_1$-$C_4$ alkyl, methoxy, —OH, —$CF_3$, —Cl, —$NH_2$, an alkyl substituted by $C_1$-$C_4$ hydroxy,
n=1 or 2; $R_{14}$ and $R_{15}$ are independently —H, $C_1$-$C_4$ alkyl, $C_1$-$C_6$ alkenyl,
t-butyloxycarboryl or
$R_{16}$ is $C_1$-$C_4$ alkyl,
$R_{17}$ is —$NH_2$,
53. The compound according to claim 1, having a structure selected from the following group:
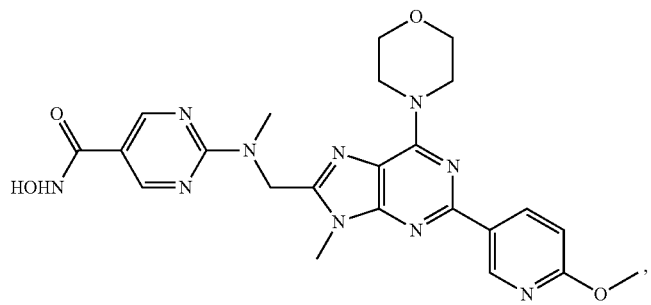

-continued
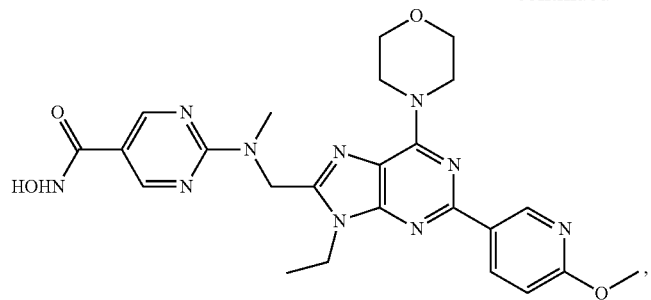
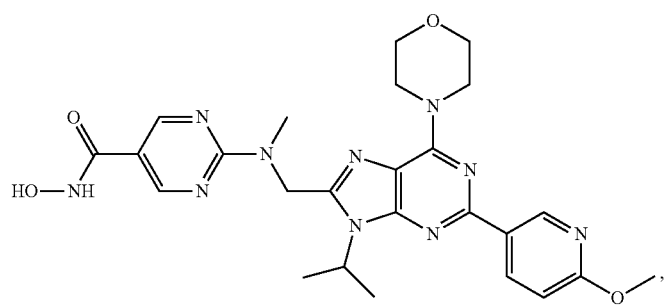
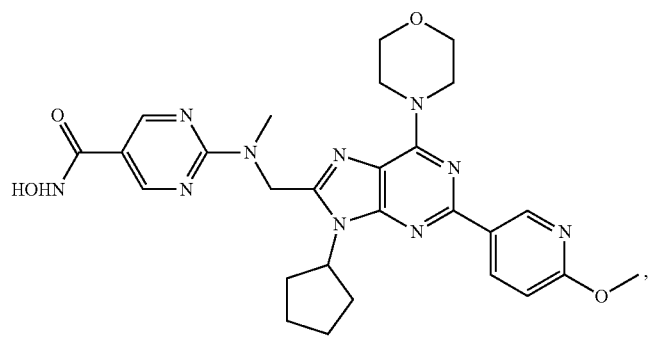
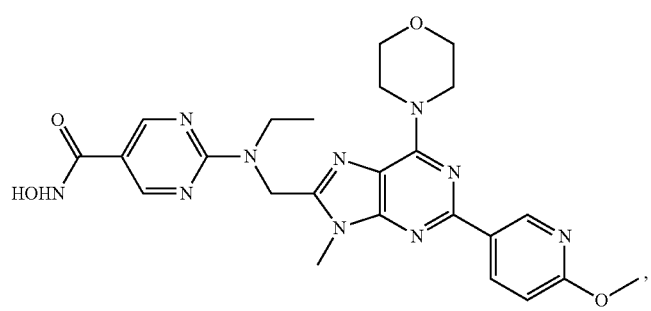
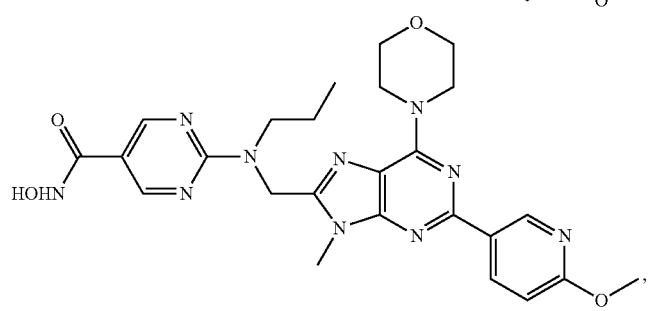

-continued
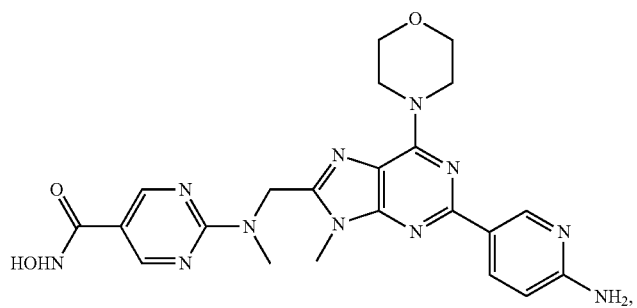
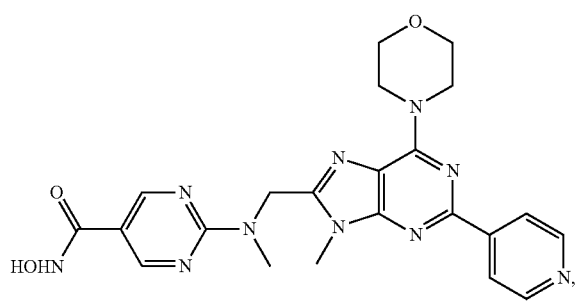
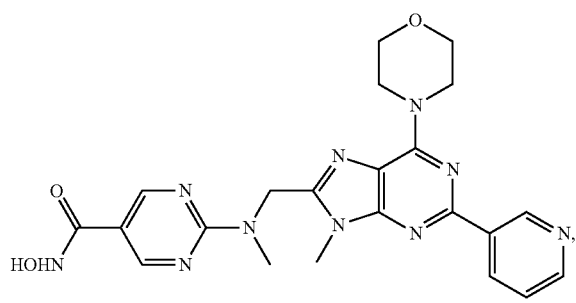
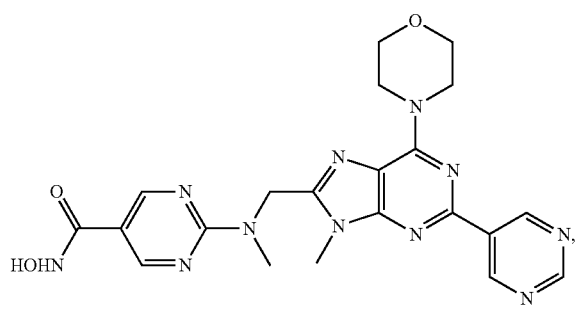
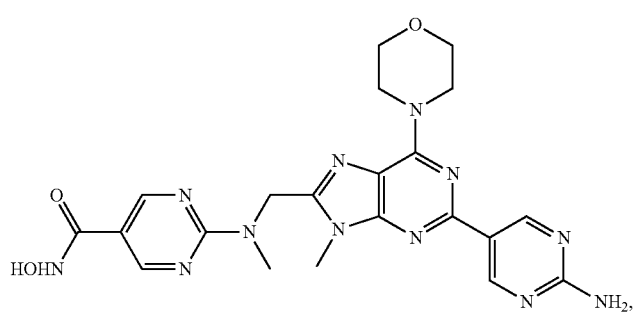

-continued
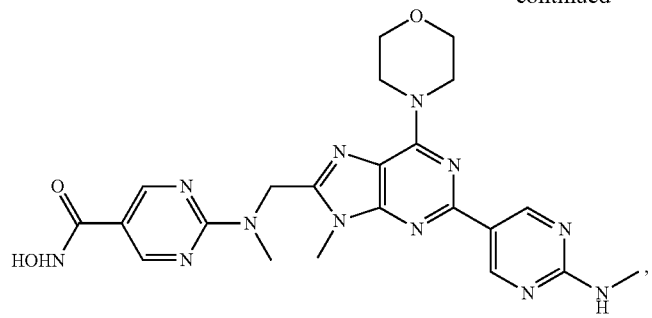
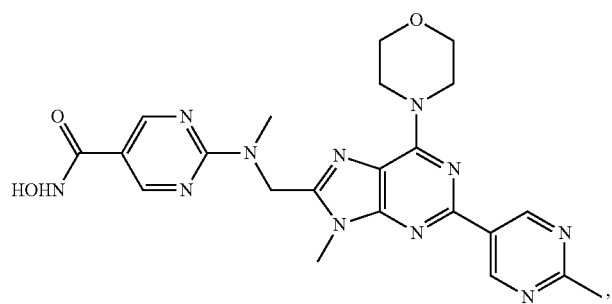
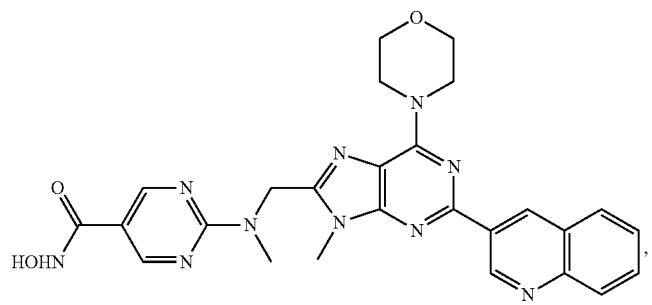
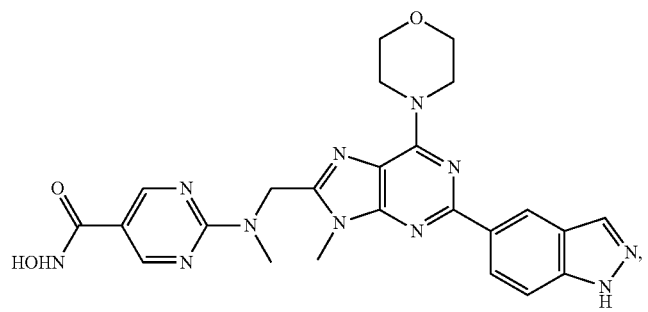
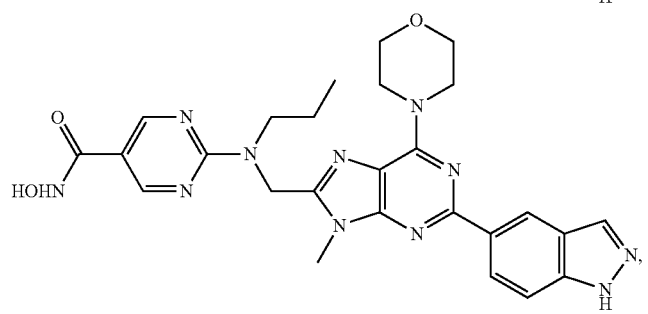

-continued
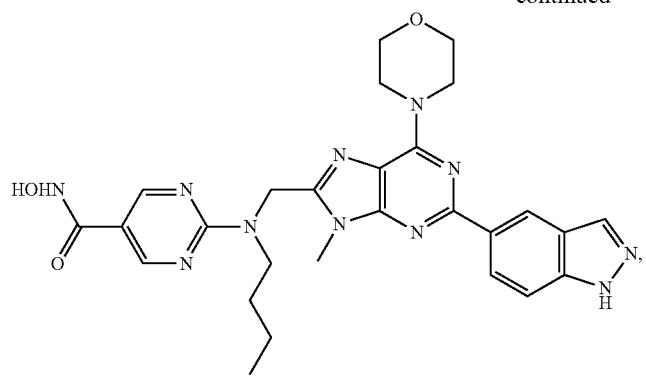
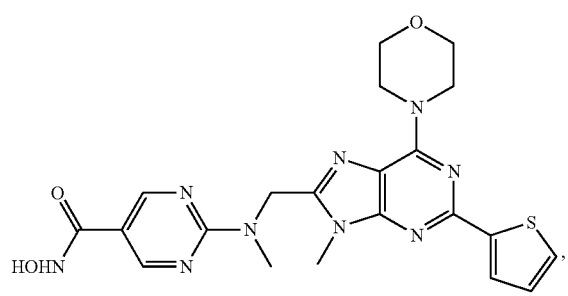
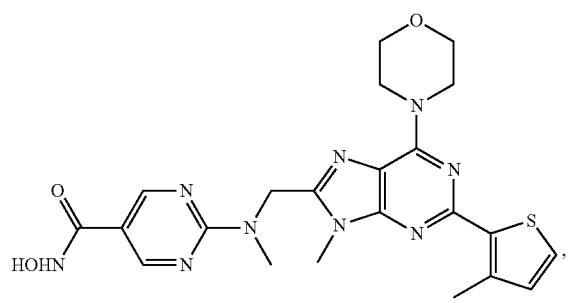
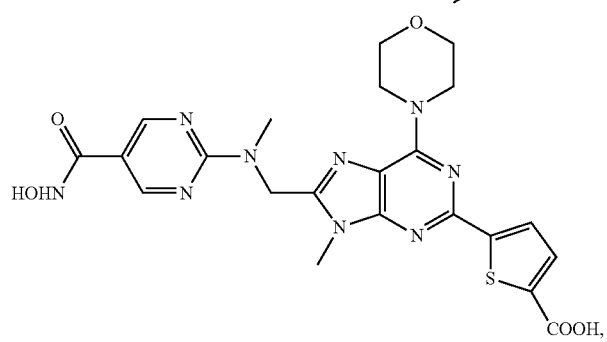
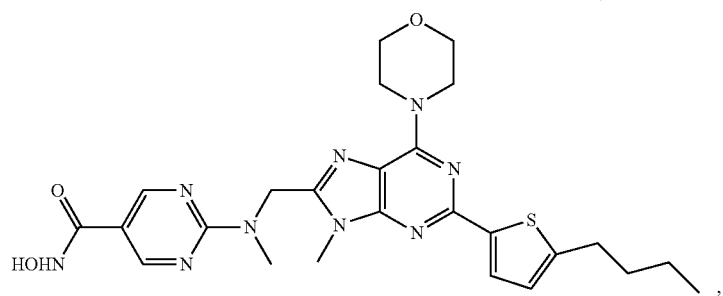

265 266
-continued
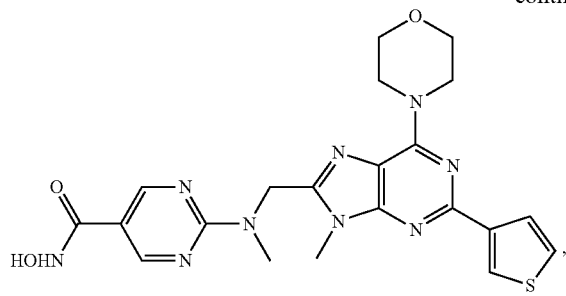
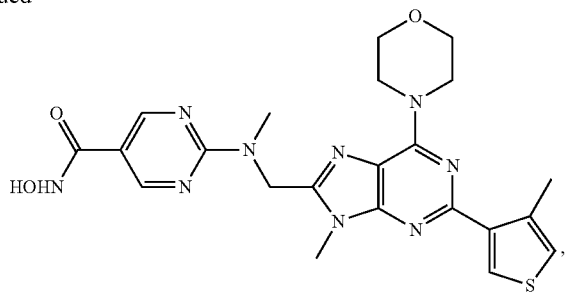
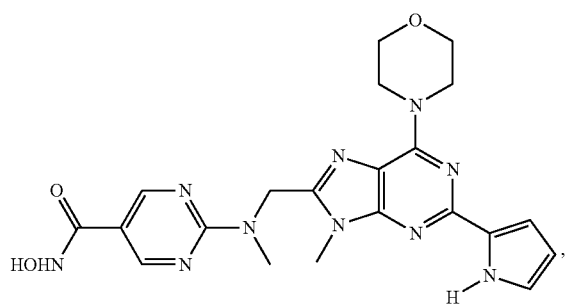
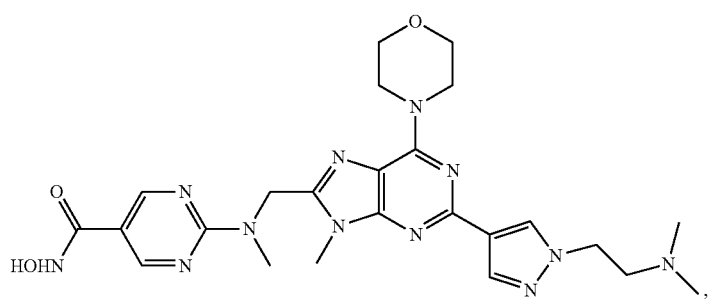
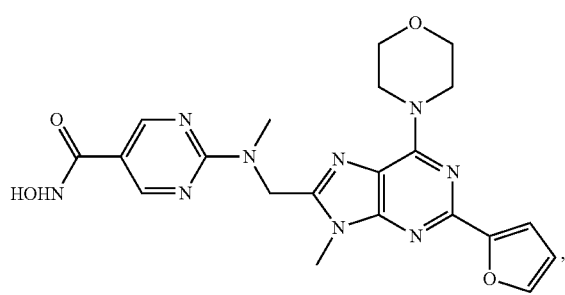
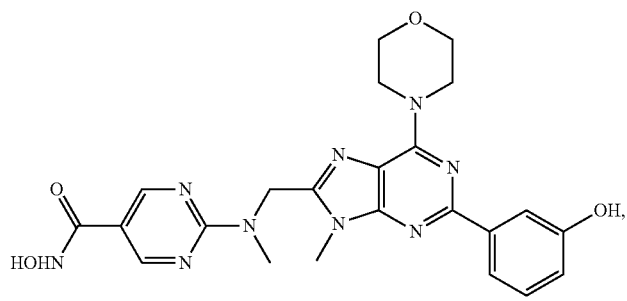

-continued
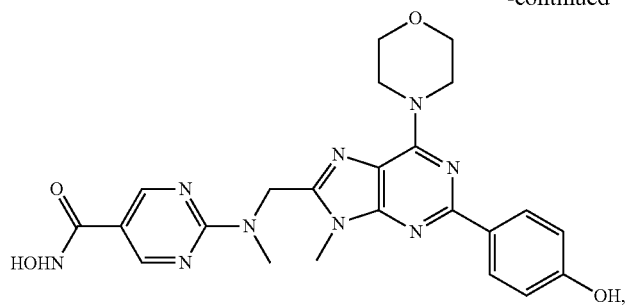
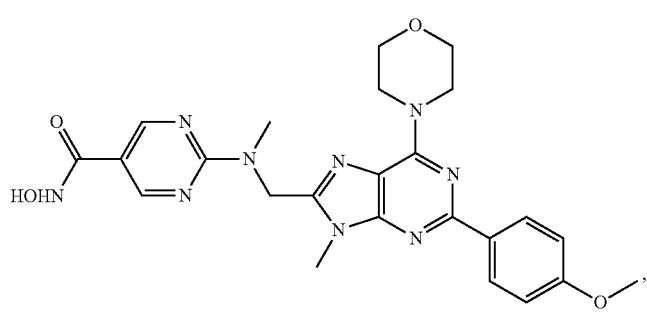
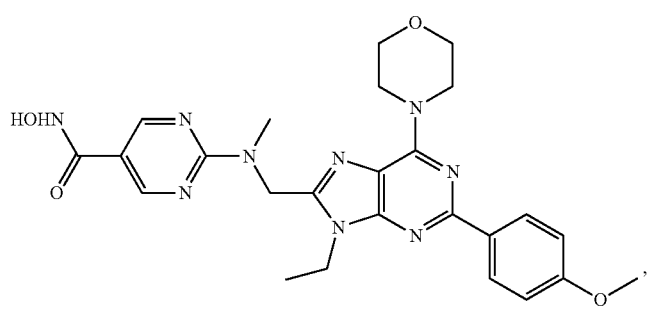
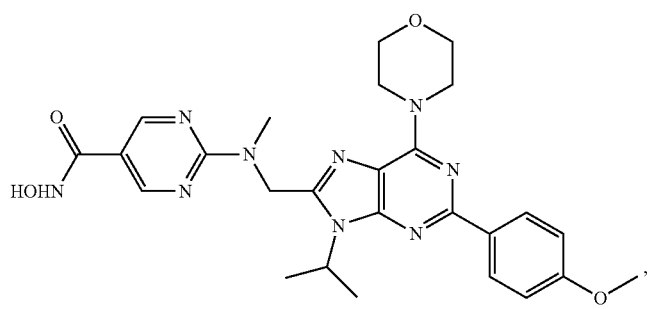
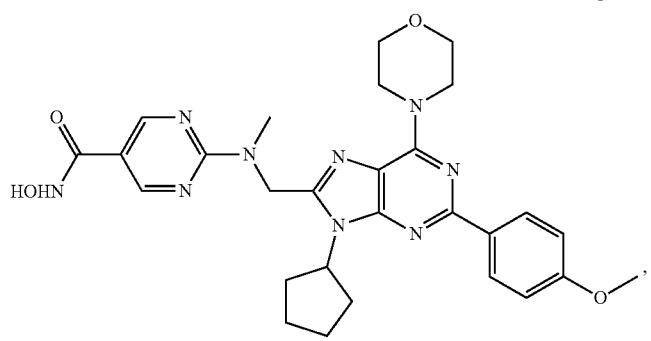

-continued
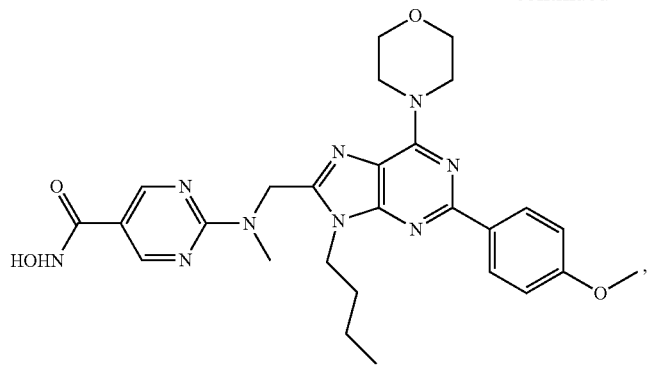
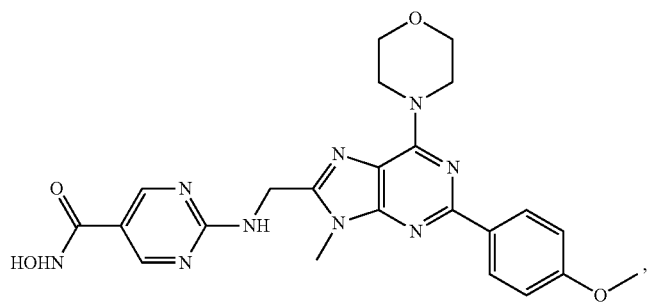
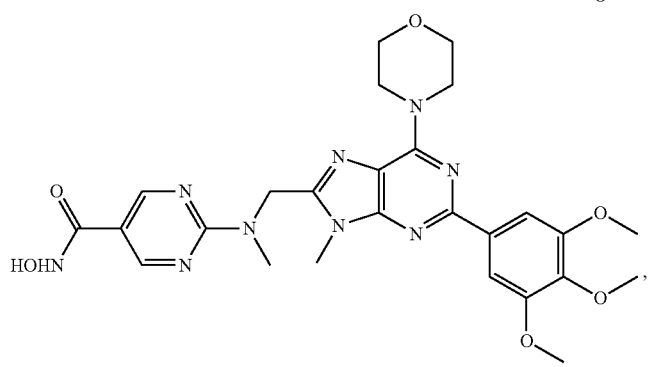
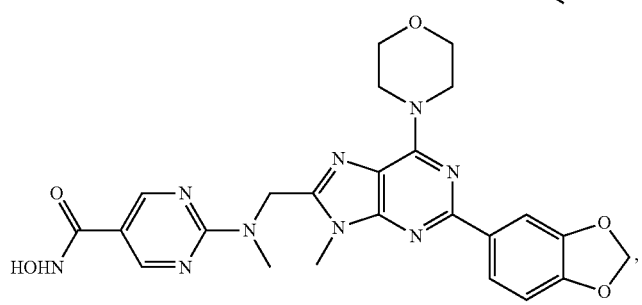
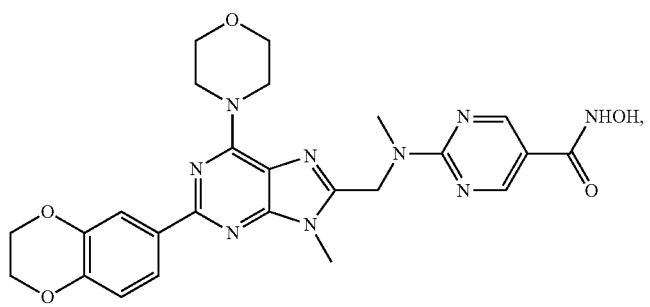

-continued
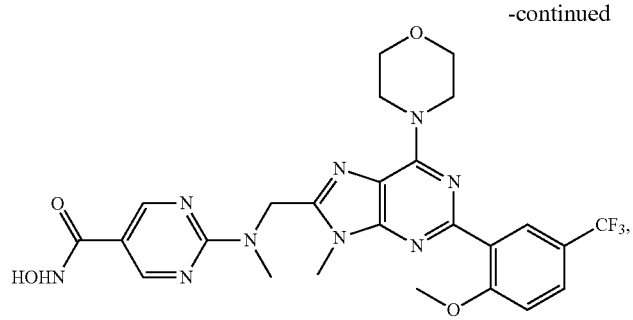
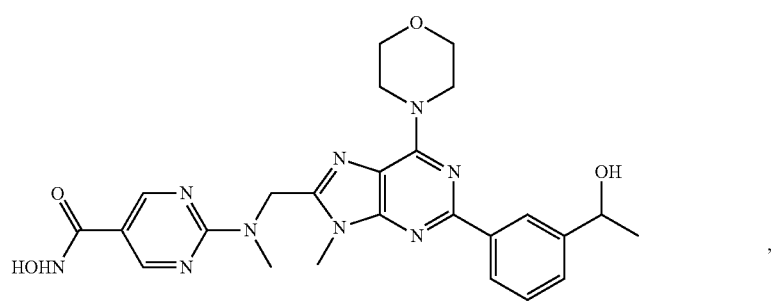
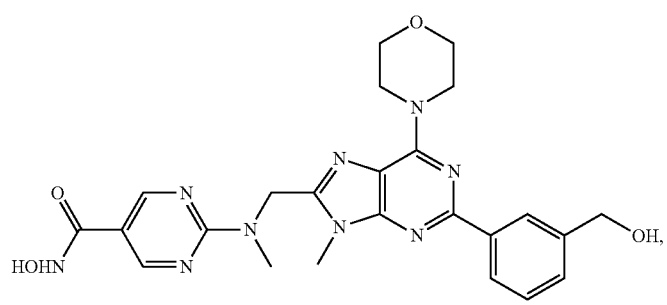
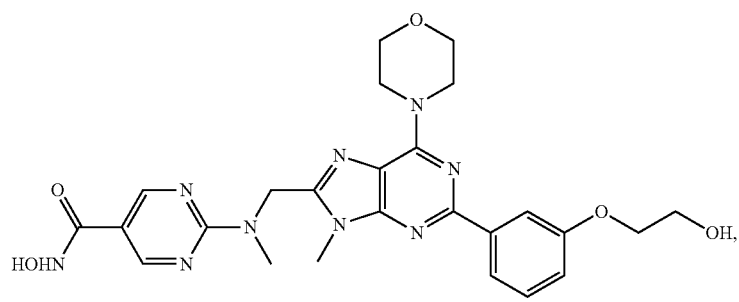
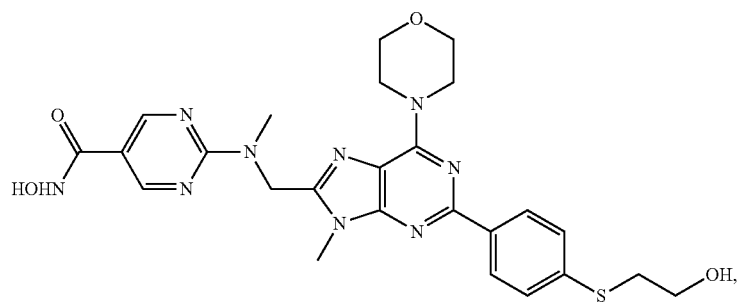

-continued
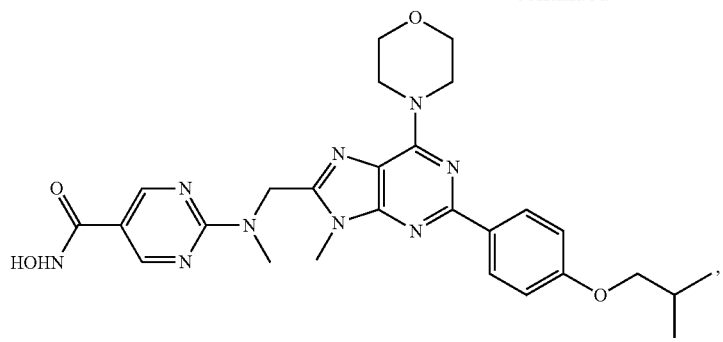
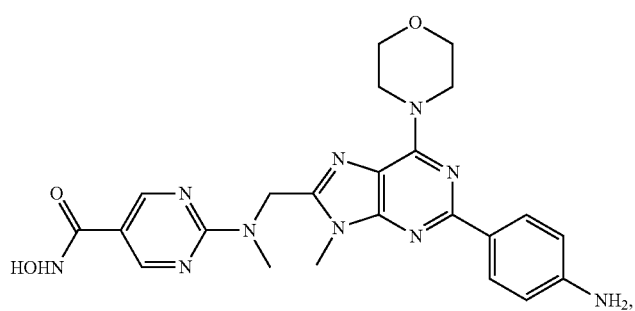
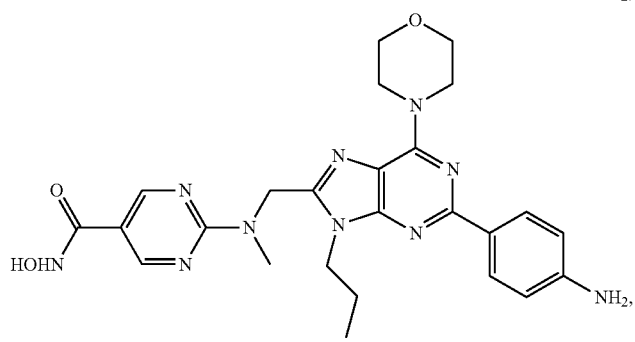
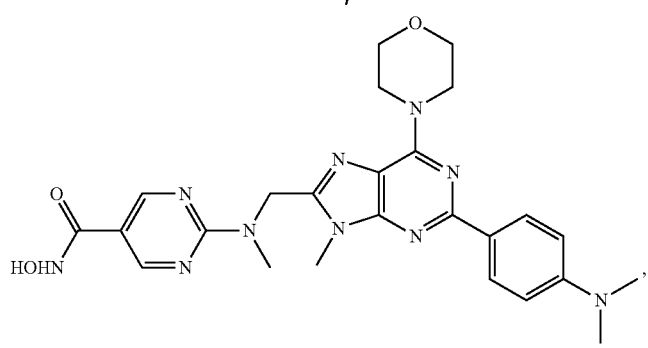
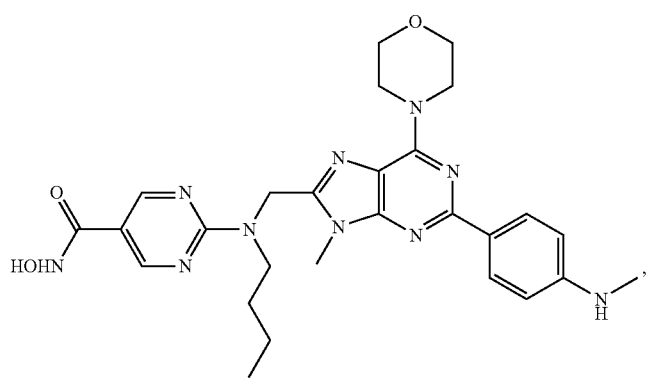

-continued
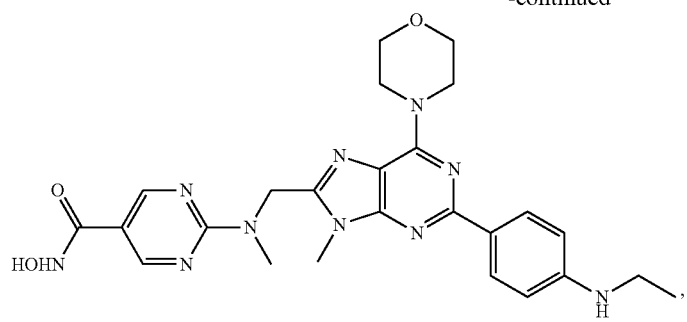
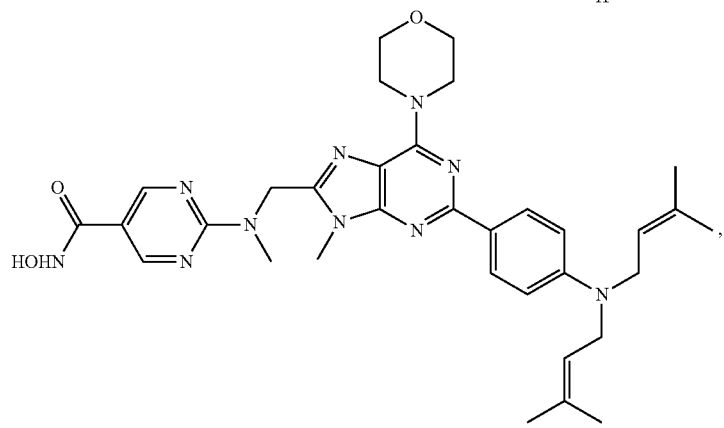
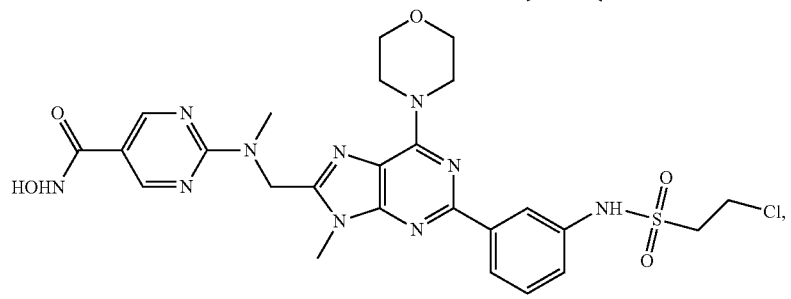
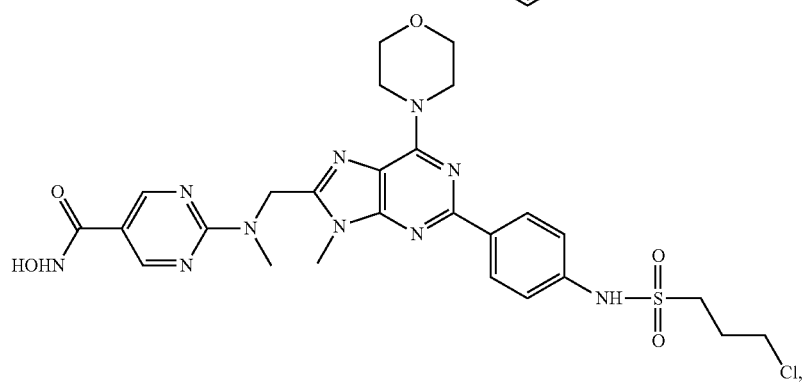
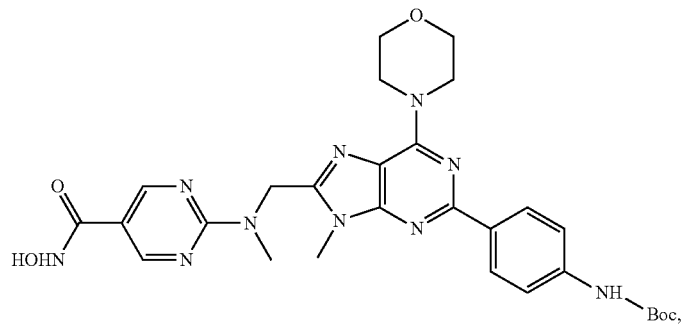

-continued
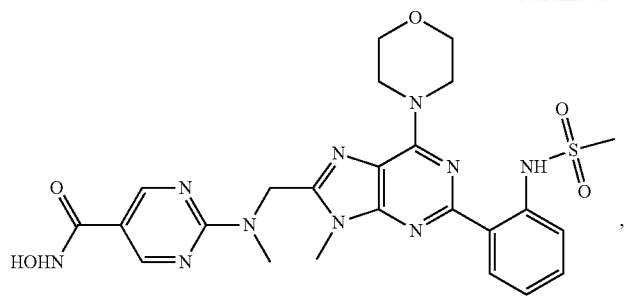
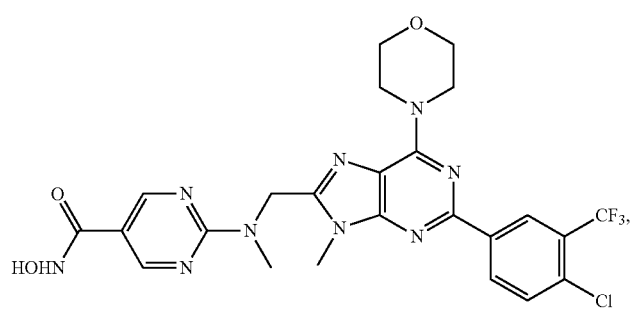
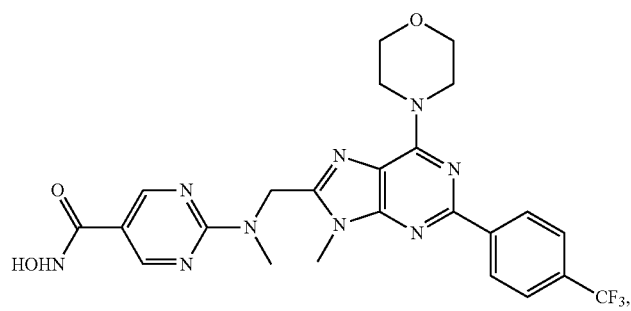
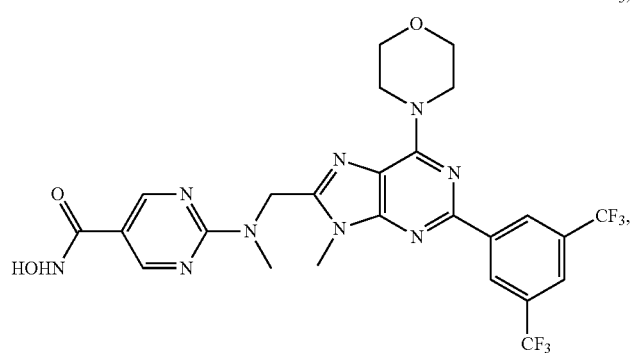
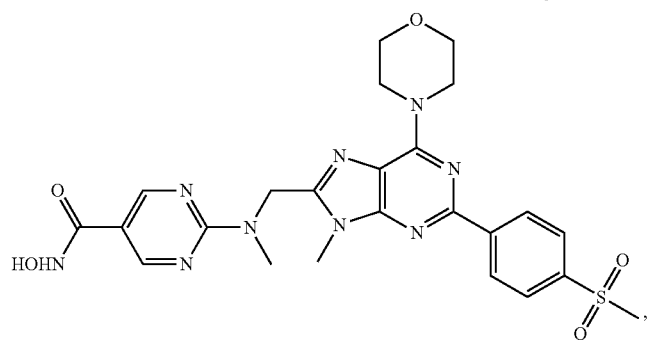

-continued
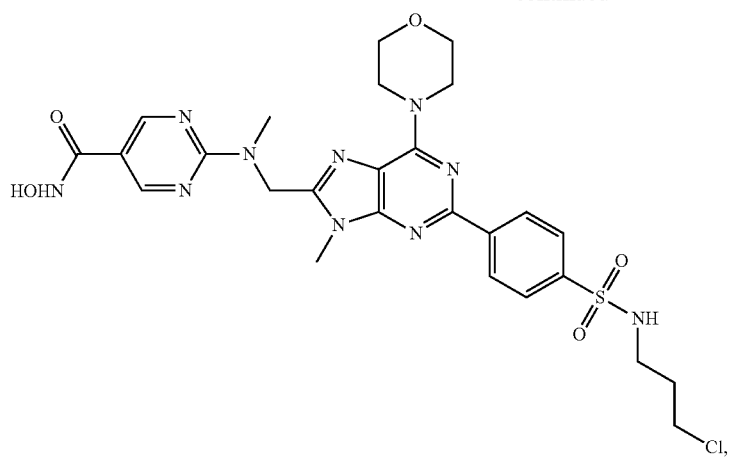
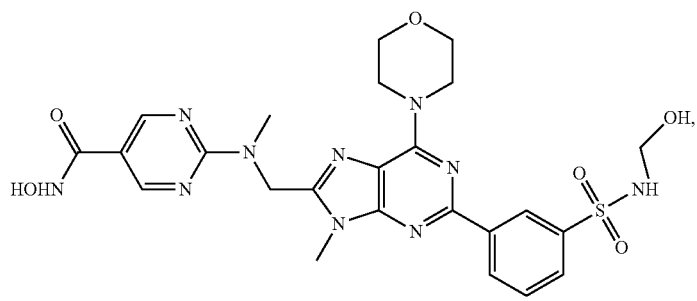
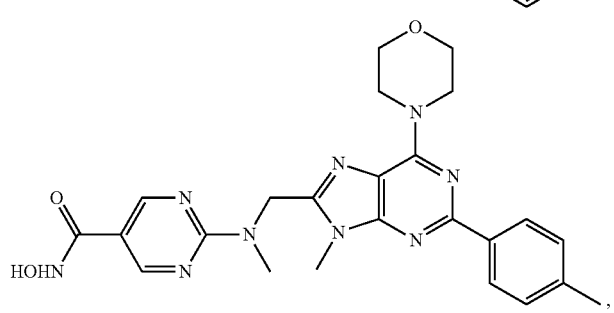
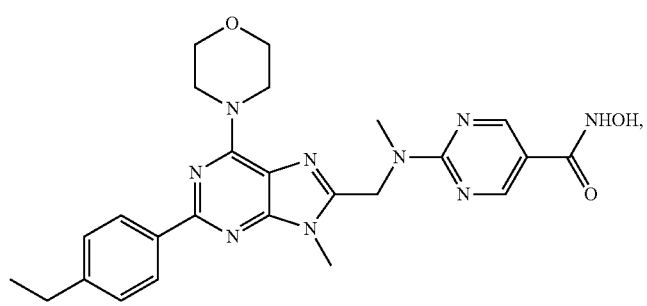
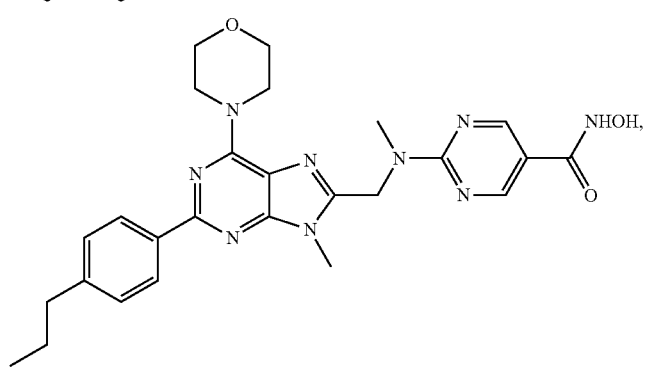

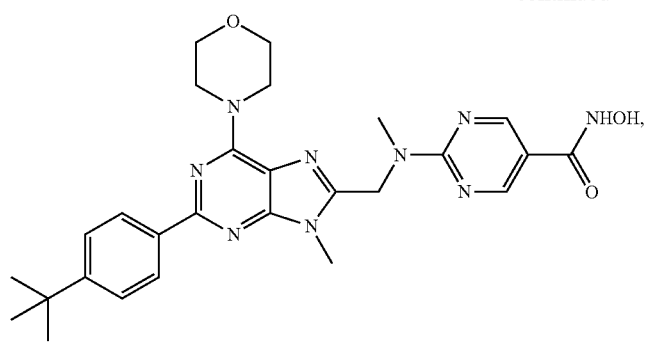
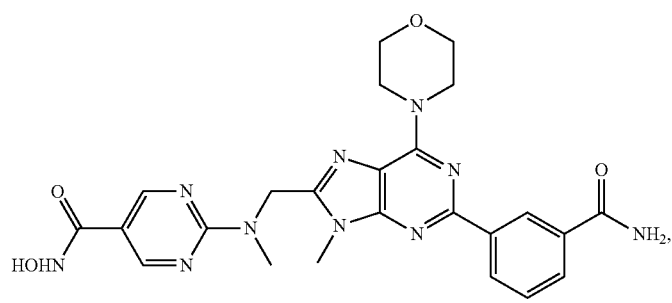
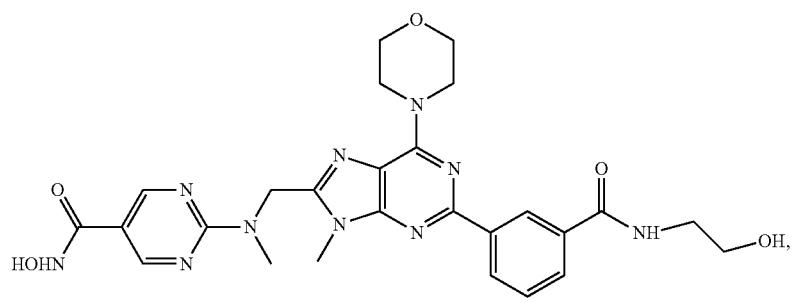
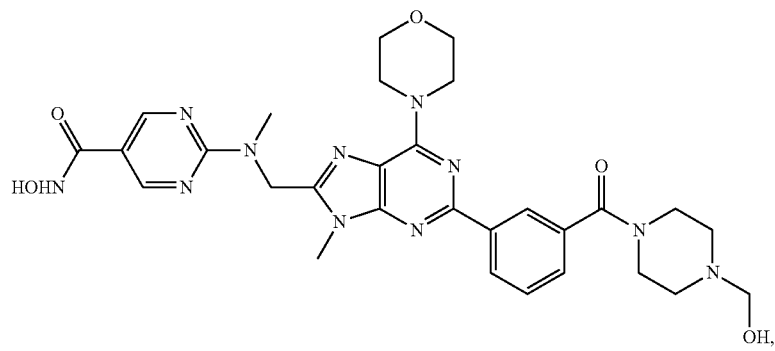
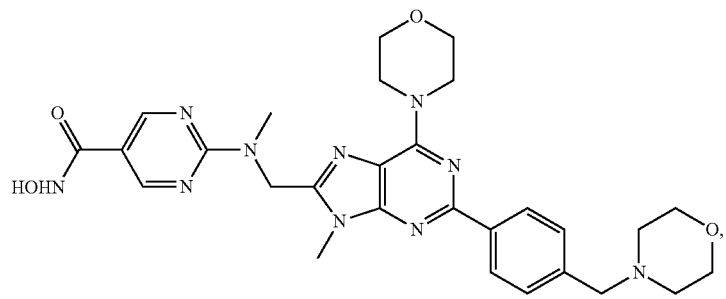

-continued

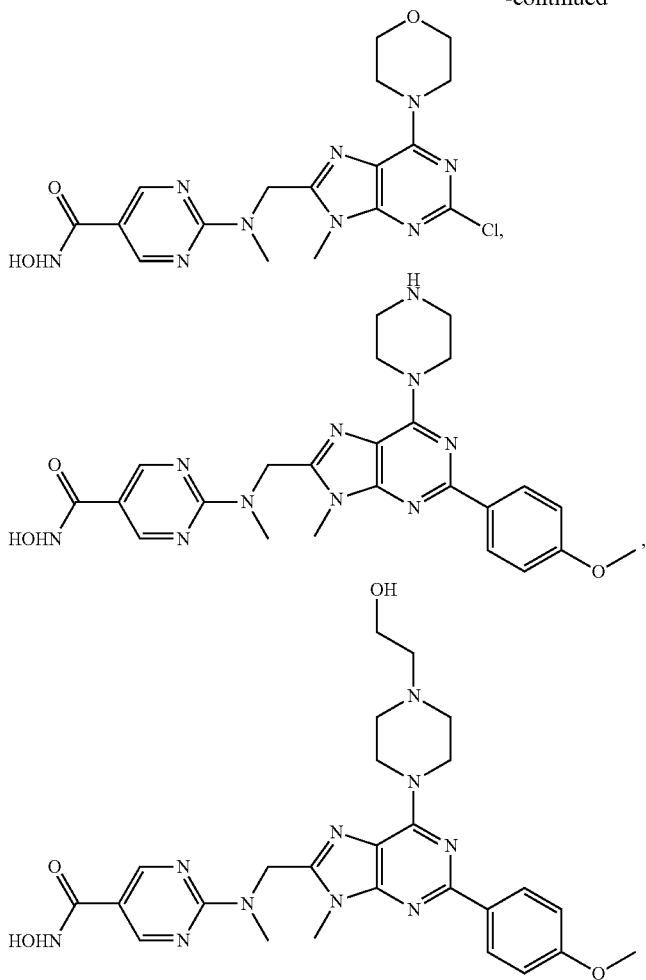

or a pharmaceutically acceptable salt thereof.

54. A pharmaceutical composition comprising pharmaceutically acceptable auxiliary ingredients and the compound according to claim 1 or a pharmaceutically acceptable salt thereof.

55. The pharmaceutical composition of claim 54, which is provided in a form of an oral preparation or an intravenous injection preparation.

* * * * *

UNITED STATES PATENT AND TRADEMARK OFFICE
CERTIFICATE OF CORRECTION

Page 1 of 1

PATENT NO. : 10,227,347 B2
APPLICATION NO. : 15/568506
DATED : March 12, 2019
INVENTOR(S) : Lijuan Chen and Yuquan Wei It is certified that error appears in the above-identified patent and that said Letters Patent is hereby corrected as shown below:

At (30) Foreign Application Priority Data, the application number:
"(CN) ...................... 2015 1 0189476"

Should read:
-- (CN) ...................... 2015 1 0189476.9 --.

Signed and Sealed this
First Day of June, 2021

Drew Hirshfeld
*Performing the Functions and Duties of the
Under Secretary of Commerce for Intellectual Property and
Director of the United States Patent and Trademark Office*